(12) United States Patent
Lo et al.

(10) Patent No.: US 6,277,974 B1
(45) Date of Patent: Aug. 21, 2001

(54) COMPOSITIONS AND METHODS FOR DIAGNOSING AND TREATING CONDITIONS, DISORDERS, OR DISEASES INVOLVING CELL DEATH

(75) Inventors: Donald C. Lo, Chapel Hill; Shawn Barney, Apex; Mary Beth Thomas, Chapel Hill; Stuart D. Portbury, Durham; Kasturi Puranam, Durham; Lawrence C. Katz, Durham, all of NC (US)

(73) Assignee: Cogent Neuroscience, Inc., Durham, NC (US)

( * ) Notice: Subject to any disclaimer, the term of this patent is extended or adjusted under 35 U.S.C. 154(b) by 0 days.

(21) Appl. No.: 09/461,697

(22) Filed: Dec. 14, 1999

(51) Int. Cl.$^7$ .................................................... C07H 21/02
(52) U.S. Cl. ...................... 536/23.1; 536/23.1; 536/23.5; 424/93.2; 424/93.1; 424/93.21; 435/69.1; 435/325; 435/352; 435/320.1; 530/300; 530/350
(58) Field of Search ................................. 536/23.1, 23.4; 435/320.1, 325, 69.1; 530/300, 350; 424/93.2, 93.21, 93.1

(56) References Cited

U.S. PATENT DOCUMENTS

| | | |
|---|---|---|
| 5,786,173 | 7/1998 | Alnemri et al. . |
| 5,856,171 | 1/1999 | Korsmeyer . |
| 5,858,715 | 1/1999 | Hillman et al. . |
| 5,925,640 | 7/1999 | Nakai et al. . |

FOREIGN PATENT DOCUMENTS

| | | |
|---|---|---|
| WO 88/09810 | 12/1988 | (WO) . |
| WO 89/10134 | 11/1989 | (WO) . |
| WO 99/59615 | 11/1999 | (WO) . |

OTHER PUBLICATIONS

Adams and Cory, 1998, "The Bcl–2 Protein Family: Arbiters of Cell Survival," *Science* 281(5381):1322–1326.

Baumgartner et al., 1999, "Assessing the Impact of Cerebral Injury After Cardiac Surgery: Will Determining the Mechanism Reduce This Injury," *Ann Thorac Surg* 67(6):1871–1873.

Behl et al., 1993, "BCL–2 Prevents Killing of Neuronal Cells by Glutamate but Not by Amyloid Beta Protein," *Biochem Biophys Res Commun* 197(2):949–956.

Caroni, 1997, "Overexpression of growth–associated proteins in the neurons of adult transgenic mice," *J Neurosci. Meth.* 71:3–9.

Charriaut–Marlangue and Ben–Ari, 1998, "Apoptosis and Programmed Cell Death: Role in Ischemic Injury," *Cerebrovascular Disease: Pathophysiology, Diagnosis, and Management*, Blackwell Science, pp 597–608.

Choi et al., 1999, "Two Distinct Mechanism Are Involved in 6–Hydroxydopamine– and MPP$^+$–Induced Dopaminergic Neuronal Cell Death: Role of Caspases, ROS, and JNK," *J Neurosci Res* 57(1):86–94.

Forss–Petter et al., 1990, "Transgenic Mice Expressing β–Galactosidase in Mature Neurons under Neuron–Specific Enolase Promoter Control," *Neuron* 5:187–197.

Fujikawa et al., 1999, "Lithium–pilocarpine–induced status epilepticus produces necrotic neurons with internucleosomal DNA fragmentation in adult rats," *Eur J Neurosci* 11(5):1605–1614.

Fukuda et al., 1999, "Novel non–apoptotic morphological changes in neurons of the mouse hippocampus following transient hypoxic–ischemia," *Neurosci Res* 33(1):49–55.

Guégan et al., 1999, "Reduction of Ischemic Damage in NGF–Transgenic Mice: Correlation with Enhancement of Antioxidant Enzyme Activities," *Neurobiol Dis* 6(3):180–189.

(List continued on next page.)

*Primary Examiner*—Christopher S. F. Low
*Assistant Examiner*—Patricia Robinson

(57) ABSTRACT

The present invention relates to compositions and methods for the treatment and diagnosis of conditions, disorders, or diseases involving cell death. The invention encompasses protective nucleic acids which, when introduced into a cell predisposed to undergo cell death or in the process of undergoing cell death, prevent, delay, or rescue the cell from death relative to a corresponding cell into which no exogenous nucleic acids have been introduced. The invention encompasses nucleic acids of the protective sequence, host cell expression systems of the protective sequence, and hosts that have been transformed by these expression systems, including transgenic animals. The invention also encompasses novel protective sequence products, including proteins, polypeptides and peptides containing amino acid sequences of the proteins, fusion proteins of proteins, polypeptides and peptides, and antibodies directed against such gene products. The invention further relates to target sequences, including upstream and downstream regulatory sequences or complete gene sequences, antibodies, antisense molecules or sequences, ribozyme molecules, and other inhibitors or modulators directed against such protective sequences, protective sequence products, genes, gene products, and/or their regulatory elements involved in cell death. The present invention also relates to methods and compositions for the diagnosis and treatment of conditions, disorders, or diseases, involving cell death, including, but not limited to, treatment of the types of conditions, disorders, or diseases, which can be prevented, delayed or rescued from cell death and include, but are not limited to, those associated with the central nervous system, including neurological and psychiatric conditions, disorders, or diseases, and those of the peripheral nervous system. Further, the invention relates to methods of using the protective sequence, protective sequence products, and/or their regulatory elements for the identification of compounds that modulate the expression of the protective sequence and/or the activity of the protective sequence product. Such compounds can be useful as therapeutic agents in the treatment of various conditions, disorders, or diseases involving cell death.

12 Claims, 92 Drawing Sheets

OTHER PUBLICATIONS

Figure 2:
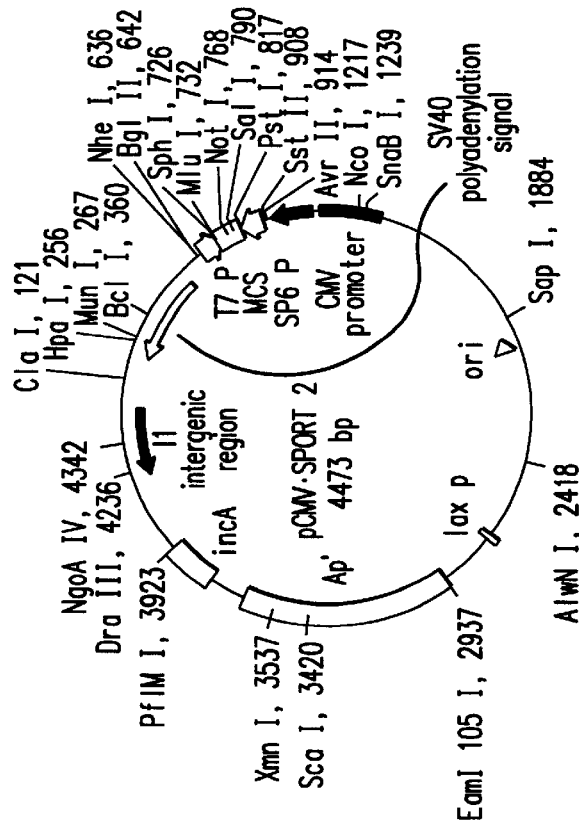
Figure 3A:
Figure 3B:
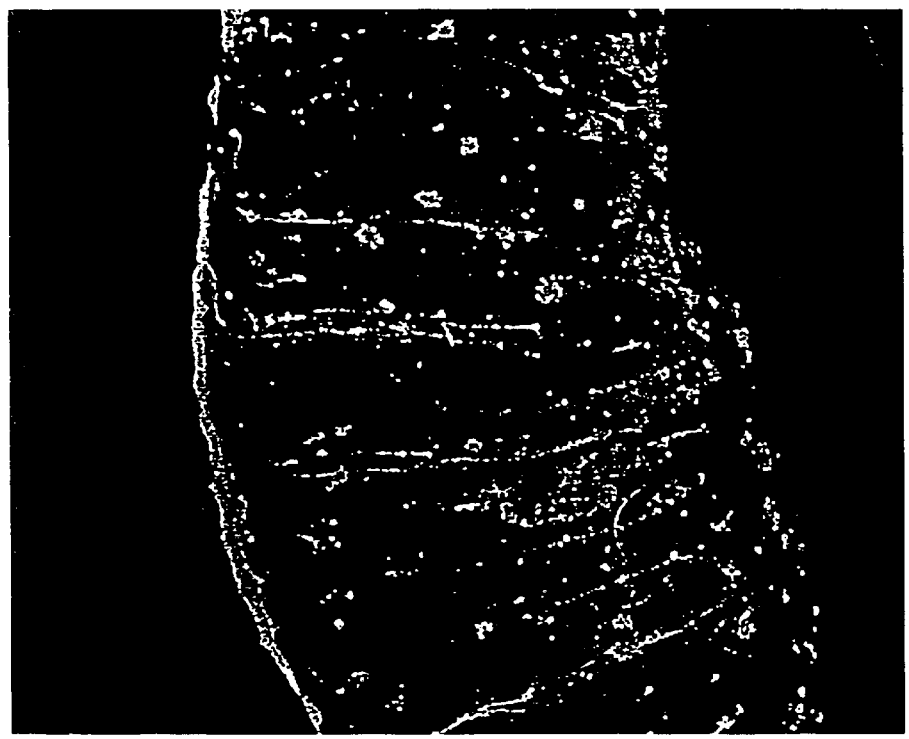
Figure 3C:
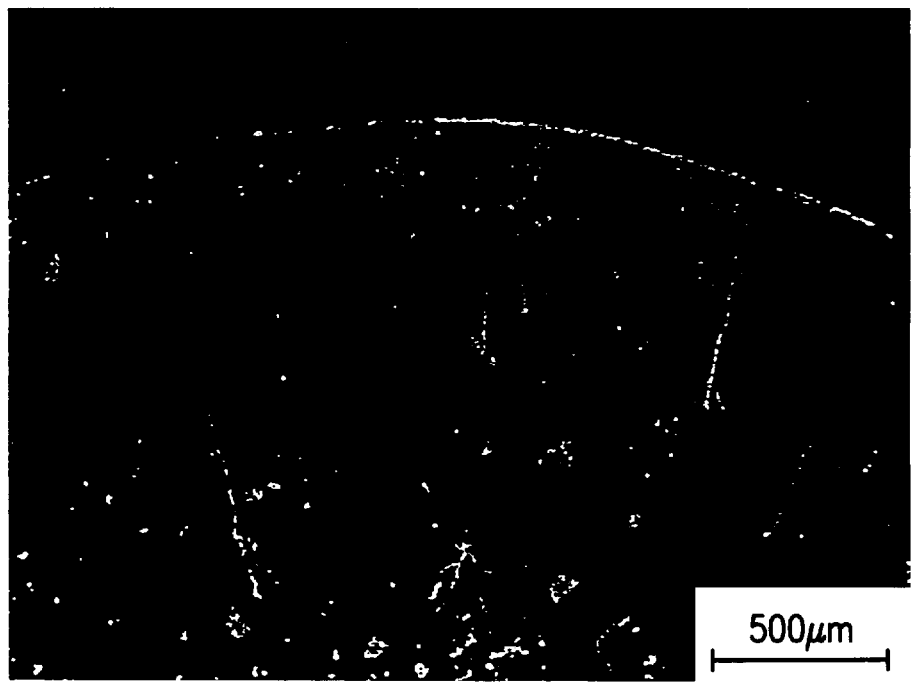
Figure 3D:
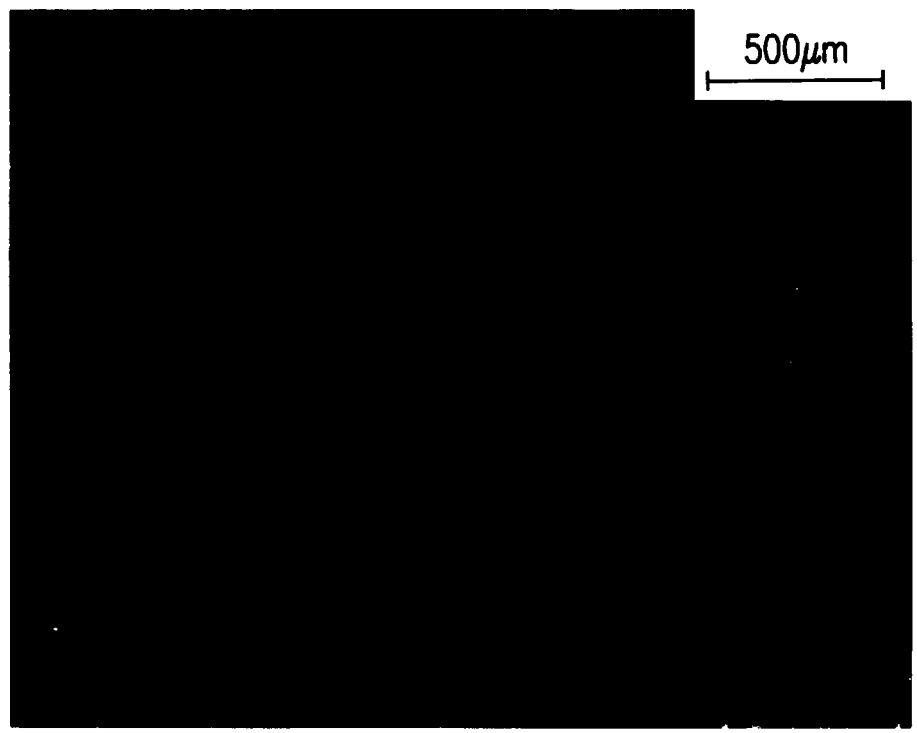
Figure 3E:
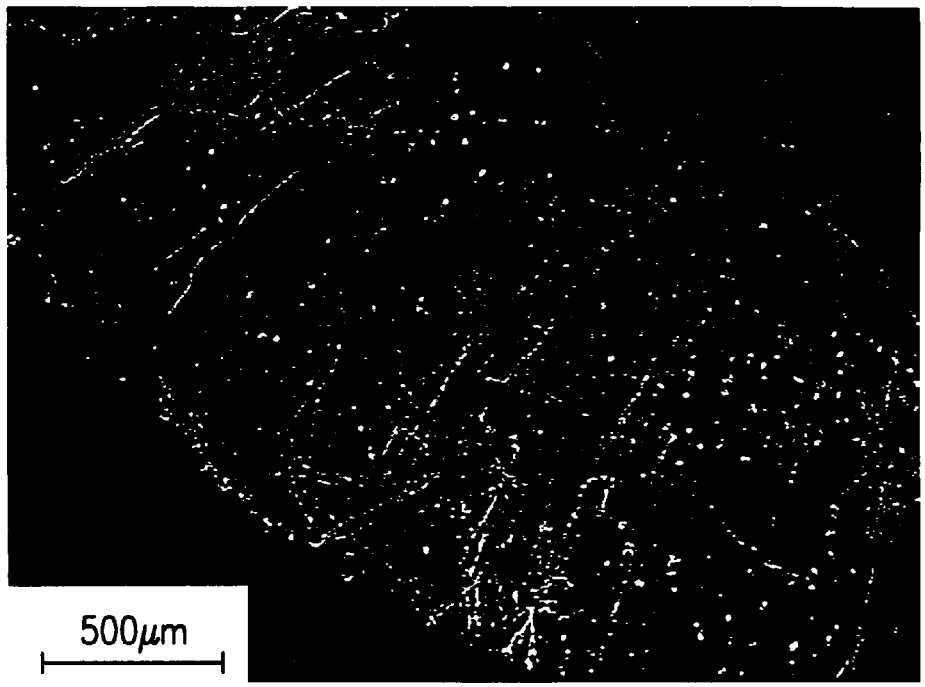
Figure 3F:
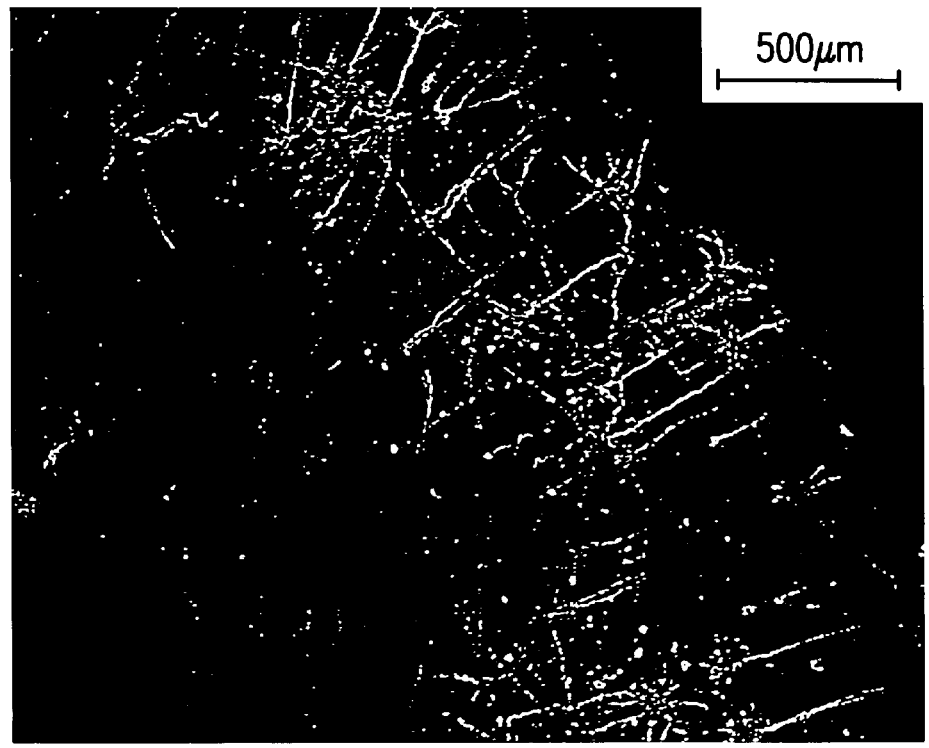
Figure 3G:
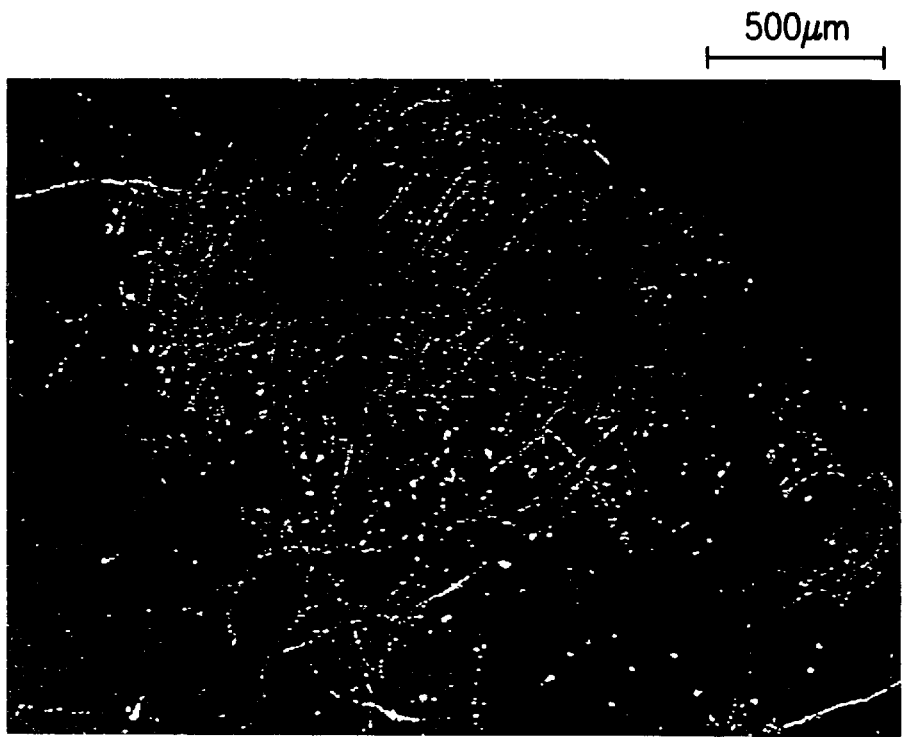
Figure 3H:
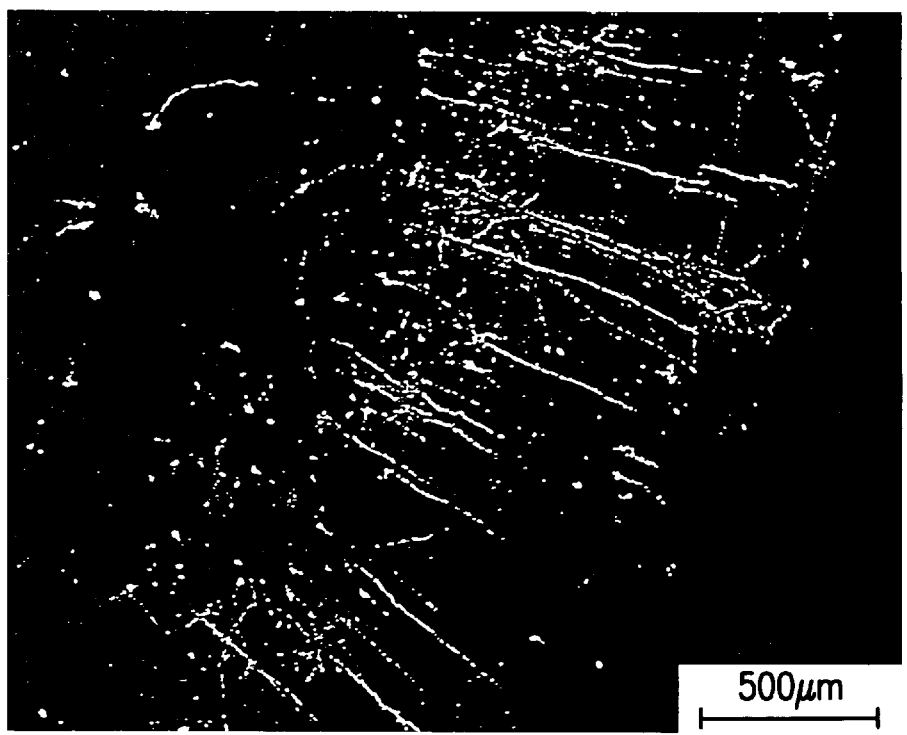
Figure 3I:
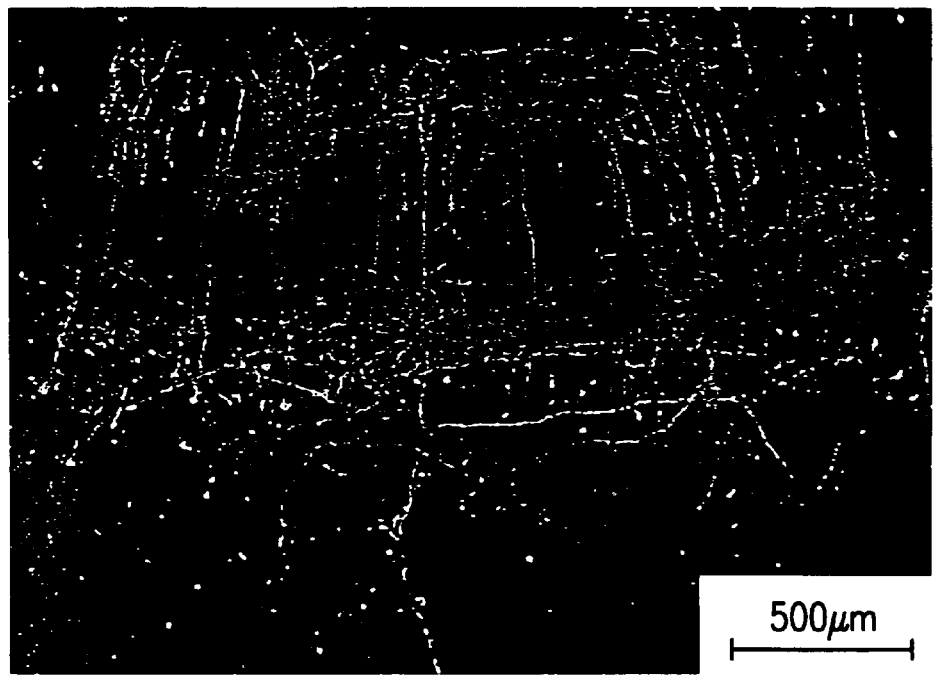
Figure 3J:
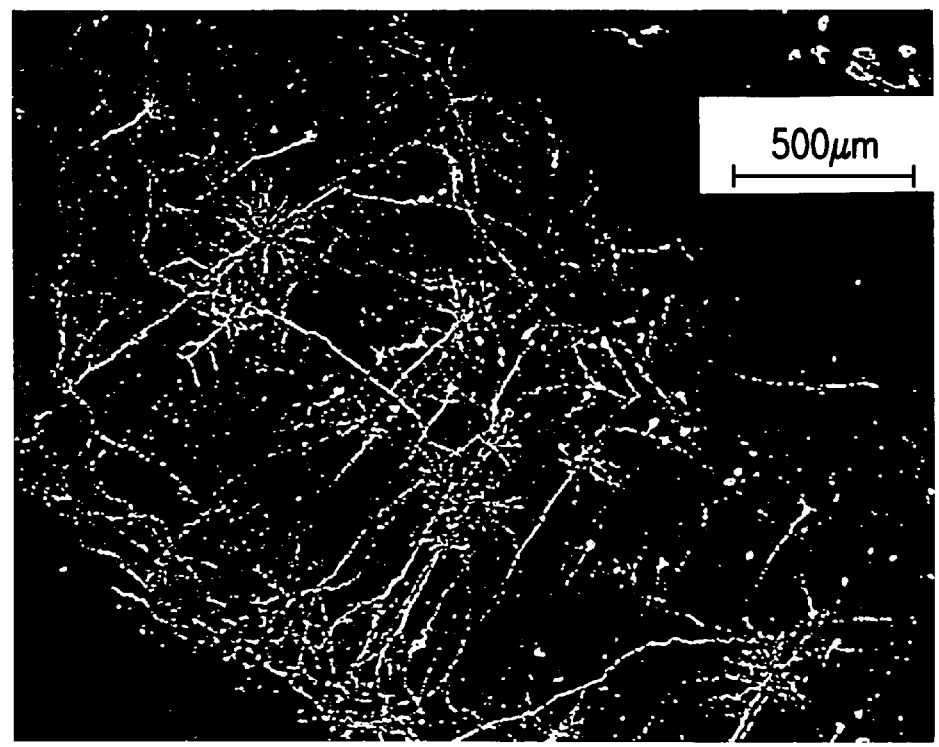
Figure 3K:
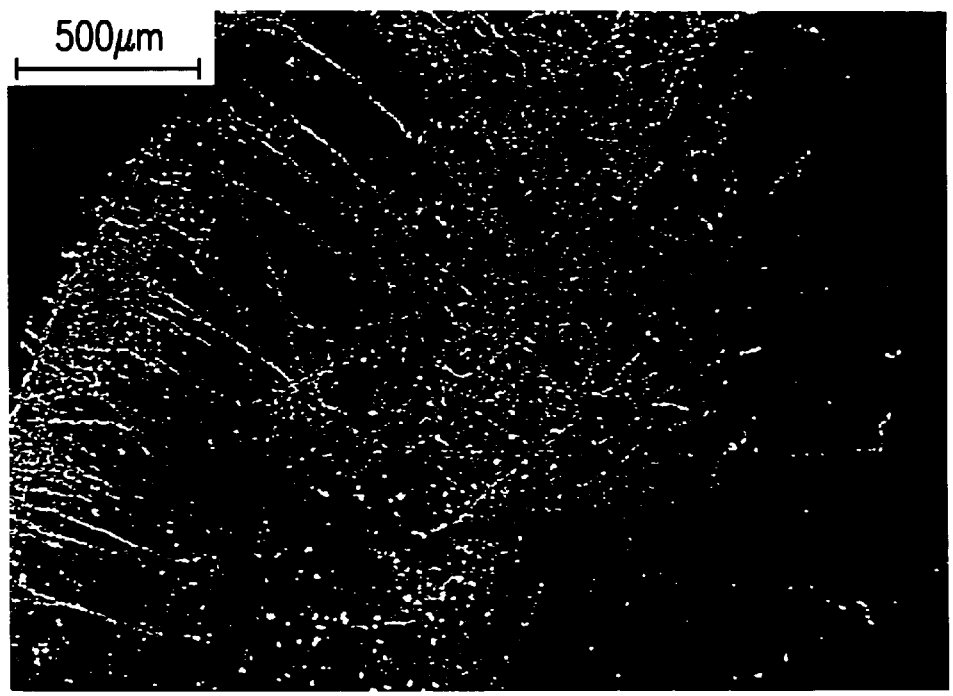
Figure 3L:
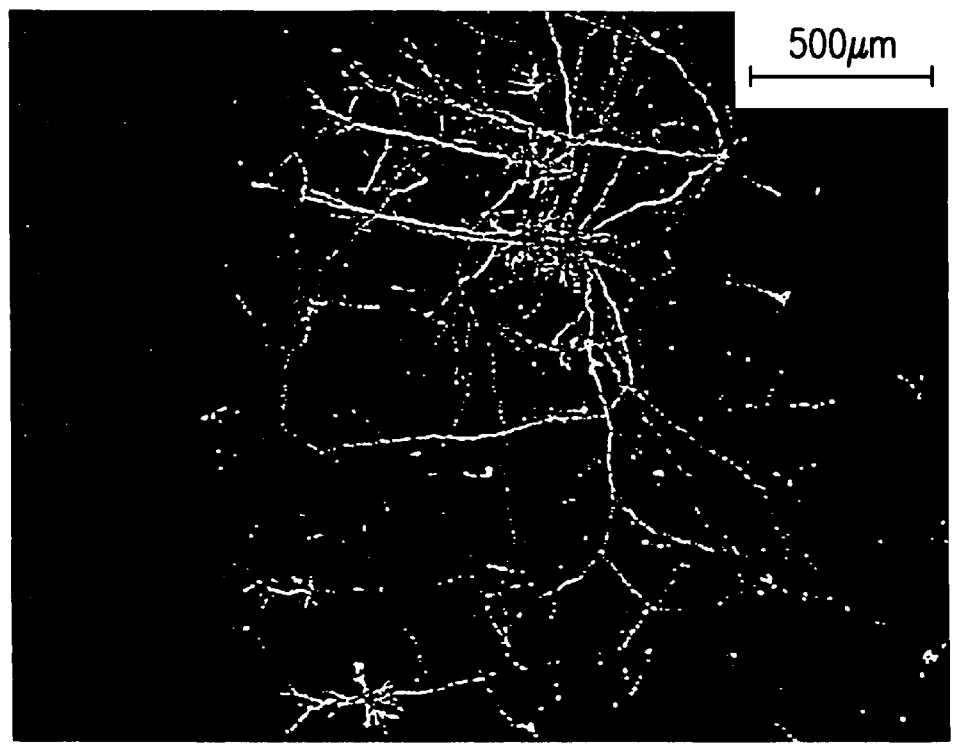
Figure 3M:
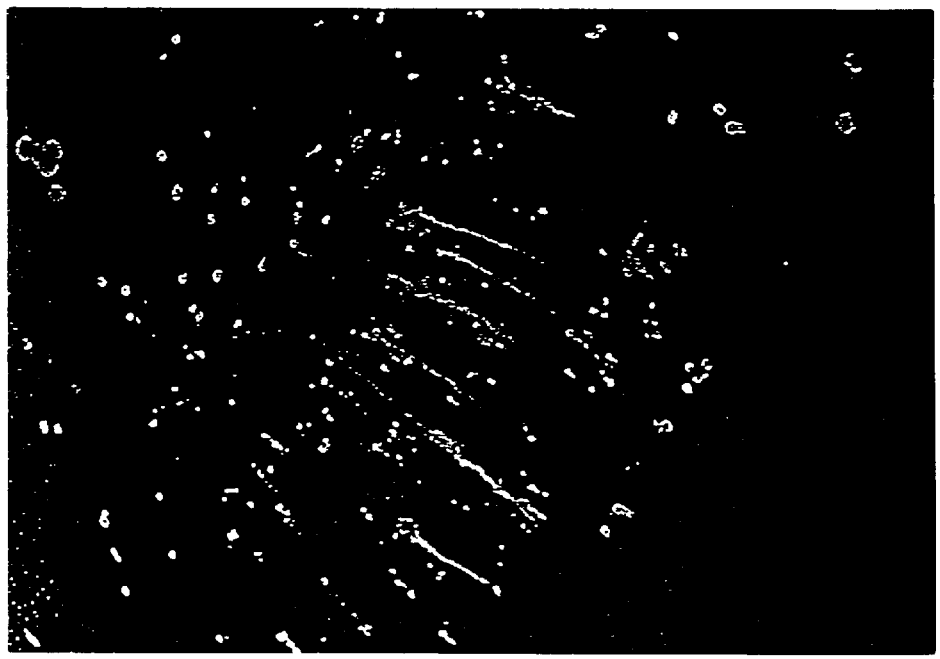
Figure 3N:
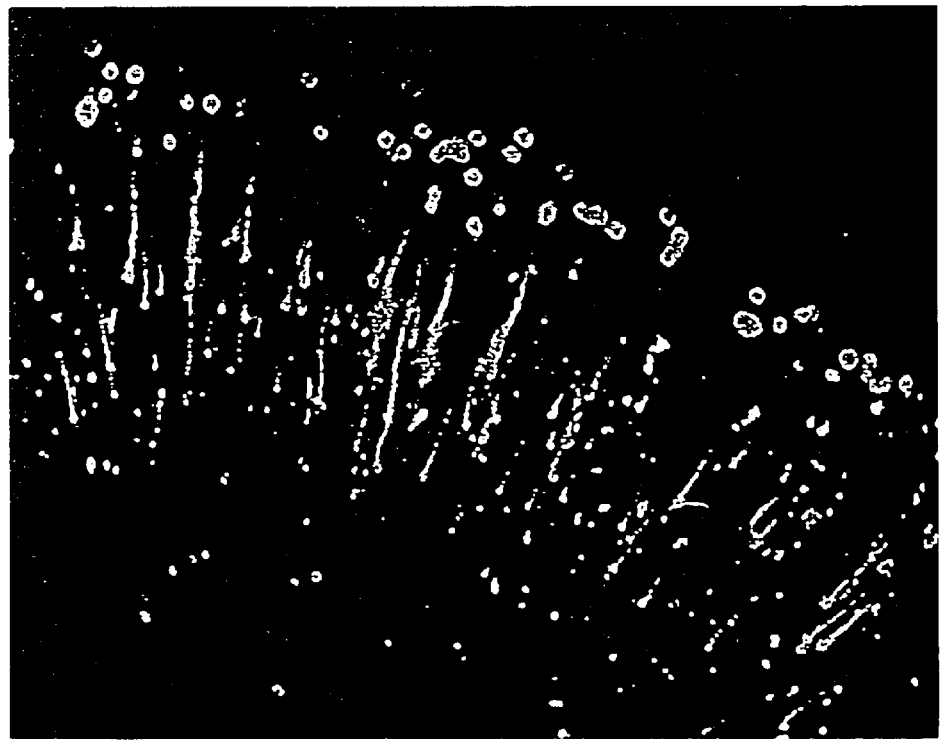

Gwag et al., 1999, "Calcium ionophores can induce either apoptosis of necrosis in cultured cortical neurons," *Neuroscience* 90(4):1339–1348.

Hannas–Djebbara et al., 1997, "Transgene expression of plasmid DNAs directed by viral or neural promoters in the rat brain," *Mol. Brain Res.* 46:91–99.

Hetts, 1998, "To Die or Not to Die: An Overview of Apoptosis and Its Role in Disease," *JAMA* 279(4):300–307.

Ibáñez and Persson, 1991, "Localization of Sequences Determining Cell Type Specificity and NGF Responsiveness in the Promoter Region of the Rat Choline Acetyltransferase Gene," *Eur. J. Neurosci* 3:1309–1315.

Krol et al., 1988, "Modulation of Eukaryotic Gene Expression by Complementary RNA or DNA Sequences," *BioTechniques* 6:958–976.

Lee et al., 1999, "The changing landscape of ischaemic brain injury mechanisms," *Nature* 399:A7–A14.

Lemaitre et al., 1987, "Specific antiviral activity of a poly (L–lysine)–conjugated oligodeoxyribonucleotide sequence complementary to vesicular stomatitis virus N protein mRNA initiation site," *Proc. Natl. Acad. Sci. U.S.A.* 84:648–652.

Letsinger et al., 1989, "Cholesteryl–conjugated oligonucleotides: Synthesis, properties, and activity as inhibitors of replication of human immunodeficiency virus in cell culture," *Proc. Natl. Acad. Sci. U.S.A.* 86:6553–6556.

Li et al., 1998, "Intact, injured, necrotic and apoptotic cells after focal cerebral ischemia in the rat," *J Neurol Sci* 156(2): 119–132.

Linnik et al., 1995, "Expression of bcl–2 From a Defective Herpes Simplex Virus–1 Vector Limits Neuronal Death in Focal Cerebral Ischemia," *Stroke* 26(9): 1670–1675.

Lönnerberg et al. 1996, "Cell Type–specific Regulation of Choline Acetyltransferase Gene Expression," *J. Biol. Chem.* 271:33358–33365.

Lönnerberg et al., 1995, "Regulatory region in choline acetyltransferase gene directs developmental and tissue–specific expression in transgenic mice," *Proc. Natl. Acad. Sci. USA* 92:4046–4050.

Martin et al., 1998, "Neurodegeneration in excitotoxicity, global cerebral ischemia, and target deprivation: A perspective on the contributions of apoptosis and necrosis," *Brain Res Bull* 46(4):281–309.

Maulik et al., 1999, "Differential Regulation of Apoptosis by Ischemia–Reperfusion and Ischemic Adaption," *Ann NY Acad Sci* 874:401–411.

Maurer et al., 1999, "Increase of Ceramide and Induction of Mixed Apoptosis/Necrosis by N–(4–Hydroxyphenyl)–retinamide in Neuroblastoma Cell Lines," *J Natl Cancer Inst* 91(13):1138–1146.

Nakashima et al., 1998, "Temporal and Spatial Profile of Apoptotic Cell Death in Transient Intracerebral Mass Lesion of the Rat," *J Neurotrauma* 16(2):143–151.

Nonaka et al., 1998, "Chronic lithium treatment robustly protects neurons in the central nervous system against excitotoxicity by inhibiting N–methyl–D–aspartate receptor–mediated calcium influx," *Proc Natl Acad Sci USA* 95(5):2642–2647.

Peel et al., 1997, "Efficient transduction of green fluorescent protein in spinal cord neurons using adeno–associated virus vectors containing cell type–specific promoters," *Gene Therapy* 4:16–24.

Pulera et al., 1998, "Apoptosis in a Neonatal Rat Model of Cerebral Hypoxia–Ischemia," *Stroke* 29(12):2622–2630.

Rink et al., 1994, "Cell death by apoptosis after lateral fluid percussion brain injury," *Soc Neurosci Abstr* 20(1): Abstract 114.7.

Steller, 1995, "Mechanisms and Genes of Cellular Suicide," *Science*, 267(5203):1445–1449.

Tarkowski et al., 1999, "Intrathecal Expression of Proteins Regulating Apoptosis in Acute Stroke," *Stroke* 30(2):321–327.

Mitchell et al., 1998, "Phencylidine and cortiscosteroids induce apoptosis of a subpopulation of striatal neurons: a neural substrate for psychosis?," *Neuroscience* 84(2):489–501.

Taylor et al., 1999, "Oxidative Metabolism, Apoptosis and Perinatal Brain Injury," *Brain Pathol* 9(1):93–117.

Twyman and Jones, 1997, "Sequences in the Proximal 5' Flanking Region of the Rat Neuron–Specific Enolase (NSE) Gene Are Sufficient for Cell Type–Specific Reporter Gene Expression," *J Mol Neurosci* 8:63–73.

Vaux, 1993, "Toward an understanding of the molecular mechanisms of physiological cell death," *Proc Natl Acad Sci USA* 90(3):786–789.

Vidal et al., 1990 "Tissue–specific control elements of the Thy–1 gene," *EMBO J* 9:833–840.

Yachida et al., 1999, "Increased BCL–2 expression in lymphocytes and its association with hepatocellular damage in patients with autoimmune hepatitis," *Clin Exp Immunol* 116(1):140–145.

Zon, 1988, "Oligonucleotide Analogues as Potential Chemotherapeutic Agents," *Pharm. Res.* 5:539–549.

```
tcgacccacg cgtccgggaa catatctcaa aataataata actatttatg acaaacccac  60
agtcaatatc atactgaatg ggcaaaagct ggaagcattc taaataccaa aggacatcat 120
tagttaacaa atgctagact aactagatac caaagcttgc tctgtgaaaa atccccacat 180
aaccattgaa gtttacaaca ccctaaaccc tgccaccttg ctcccagtat cagagagccc 240
agttaaacat aactatgtag aggtattaga ctcagtttat tctagtaggc ccaacctcca 300
agaccatcgt tgaacatcag tagactggga gctgtacgtg gatgggagca gctttgccaa 360
cccctgcaaa gtgactcttg aagaagacca caaaccctgc tccagtcaac atctggaagc 420
ttgactagtc cacgcatggc tgaagcatga ggaaactcat cacaggactc attttcctta 480
aaatttagac ttgtacagta aagacttcaa cttgaccttc ctcagactga gggctgttcc 540
cagagtatac atcaagtcac tgaggtagga caaaaggttg ctacagtcct attattttac 600
agttattata agtgtactgg aactctaaaa agaacttgtt tttataatgt tattctatac 660
aattatttat aatacaatat acaaataatg tatttagccc aggaaatgac caacctgatg 720
tgtgttatga cccatctgag cctcccatga ccacagtttt taaaataaga ttaagaactg 780
aagactggtg ggggctcata aacaatatga gtaaagtgtt agccaaaata aaacaaaaaa 840
aaaagggcgg cc                                                    852
```

FIG. 1A

```
tcgacccacg cgtccgggca tggccaggcc ggctgggctg cagagcgccg gcacgggtcc  60
acgcctcggg tgacgggctt ccaggatgtt cgggcgcggg gcggcccatc cgcatccccc 120
aacacccca cctccggcct gagcctccca gcgccggggg aaccacctcc tgtccgctgt 180
tgctggcccg catcctagca gcggcctgac gccctcccca ccctggcatg cccccttgac 240
ctgggacgat gagcatacga ctggggagcc cagtggaggc gccctcccga agcgccactg 300
cccatgctga ccacccagcc ctccggctgc tgatgtcatg agtaacacca ctgtgcccaa 360
tgcccccag gccaacagcg actccatggt gggctatgtg ttggggccct tcttcctcat 420
caccctggtc ggggtggtgg tggctgtggt aatgtatgta cagaagaaaa agcgggtgga 480
ccggctgcgc catcacctgc tccccatgta cagctatgac ccagctgagg aactgcatga 540
ggctgagcag gagctgctct ctgacatggg agacccccaag gtggtacatg gctggcagag 600
tggctaccag cacaagcgga tgccactgct ggatgtcaag acgtgacctg accccccttgc 660
cccacccttc agagcctggg gtcctggact gcctggggcc ctgccatctg cttcccctgc 720
tgtcacctgg ctccccctgc tgggtgctgg gtctccattt ctccctccac ccaccctcag 780
cagcatctgc ttcccatgcc ctcaccatca cctcactgcc cccaggcctt ctgcccttg 840
tgggtgttga gctcaccgcc cacccacagg cactcatagg aagaggcttt ccttctggga 900
tggcggcggc tggtagacac ctttgctttc tctagccctc ctgggctggg cttgggccca 960
aatccccagg caggctttgg agttgtttcc atggtgatgg ggccagatgt atagtattca 1020
gtatatattt tgtaaataaa atgttttgtg gctaaaaaaa aaaaaaaaaa aaaaaaaaaa 1080
aaaaaaaagg gcggcc                                               1096
```

FIG. 1B

```
tcgacccacg cgtccgtctt attccaaaat gttgagatac tggggagaga taccaatatc    60
atcaagccag accaacagaa gttccttcga tttgctccca cgggagttcc gtctggtgga   120
agtccatgac ccaccCctgc accaaccctc agccaacaag ccgaagcccc ccactatgct   180
ggacatcccc tcagagccat gtagtctcac catccatacg attcagttga ttcagcacaa   240
ccgacgtctt cgcaacctta ttgccacagc tcaggccag aatcagcagc agacagaagg    300
tgtaaaaact gaagagagtg aacctcttcc ctcgtgccct gggtcacctc ctctccctga   360
tgacctcctg cctttagatt gtaagaatcc caatgcacca ttccagatcc ggcacagtga   420
cccagagagt gactttatc gtgggaaagg ggaacctgtg actgaactca gctggcactc    480
ctgtcggcag ctcctctacc aggcagtggc cacaatcctg gcccacgcgg gctttgactg   540
tgctaatgag agtgtcctgg agaccctaac tgatgtggca catgagtatt gccttaagtt   600
taccaagttg ctgcgttttg ctgtggaccg ggaggcccgg ctgggacaga ctcctttcc    660
tgatgtgatg gagcaggtat tccatgaagt gggtattggc agtgtgctct ccctccagaa   720
gttctggcag caccgcatca aggactatca cagttacatg ctacagatta gtaagcaact   780
ctctgaagaa tatgaaagga ttgtcaatcc tgagaaggcc acagaggacg ctaaacctgt   840
gaagatcaag gaggaacctg tgagcgacat cactttcct gtcagtgagg agctggaggc    900
tgaccttgct tctggagacc agtcactgcc tatgggagtg cttggggctc agagcgaacg   960
cttcccatct aacctggagg ttgaagcttc accacaggct tcaagtgcag aggtaaatgc  1020
ttctcctctt tggaatctgg cccatgtgaa aatggagcct caagaaagtg aagaaggcaa  1080
tgtctctggg catggtgtgc tgggcagtga tgtcttcgag gagcctatgt caggcatgag  1140
tgaagctggg attcctcaga gccctgatga ctcagatagc agctatggtt cccactccac  1200
tgacagcctc atggggtcct ccctgtttt caaccagcgc tgcaagaaga ggatgaggaa   1260
aatataaaag gaaaagaggg agatgttttg tccagaccta ctagacccaa cagaaaaggt  1320
tagctgacta cagcagaccc tttgcagcag tagttttaac attgacttca catattcaga  1380
agtgattcta aaggactgtg gcacatagaa atgtatttg ctgagctgta caacaggatg   1440
gcacaaaatc ctgctgatag aaataagtgt aaccggccag gcacagtggc tcatgcctgt  1500
aatcccagca ttttgggagg cccaggtggg tggatcatct gaggtcagga gttcgagacc  1560
agcctgacca acatggaaaa aaccccatct ctactaaaaa tacaaaatta gccgggtgtg  1620
gtggcacatg cctgtaatcc cagctactca ggaaggctga ggcaggagaa ctgcttgaac  1680
ctgggaggtg gaggttgtgg tgagccgaga ctccagcctg gcaacaaga gtgaaactcc    1740
gtctcaaaaa taaataaata aataaagaa aaaaaaaaa aaaaaaaaa aaaaaaaaa     1800
aaaaaaaaaa aaaaaaggg cggcc                                         1825
```

FIG. 1C

```
tcgacccacg cgtccgggac aatagtgtag gttatggatg gaggtgtcgg tactaaattc    60
aataacgagt aaataatctt acttgggtag agatggcctt tgccaacaaa gtgaactgtt   120
ttggttgttt taaactcatg aagtatgggt tcagtggaaa tgtttggaac tctgaaggat   180
ttagacaagg ttttgaaaag gataatcatg ggttagaagg aagtgtttga aagtcacttt   240
gaaagttagt tttgggccag cacggtagct caccctgta atcccagcac tttgggaggc    300
tgaggtgggt agattacttg agcccaggaa ttcaagacca gcctgggcaa catggtgaaa   360
ccctgtttct ataaaaaata atctgggctt tgtagcatat gcctgtggtc ccagctactg   420
aggaggctga ggtgggagga ttgcttgagc ccaggaggca gaggttgcag tgagccaagg   480
tcacgtcact gcactctagc ctgggcaaca gagtaagaca aaaaaaaaa aaagggcgg    540
cc                                                                  542
```

FIG. 1D

```
tcgacccacg cgtccgcaaa acctaaatag aagttgttgt taccgtgtgc caatgtgtcc    60
catgtgggtt gtgccaggta gagaaacagg aagtcaatca tctgtgacag tctctattct   120
gtcgttttgc tccttggtat ttgatttgca ctatatttag ttgaagcctg ttcactgttt   180
aaaaccggag gtatcttcaa aggcatggag acctggttcc agtaaatgtc ccaccagtgg   240
ggtatagaaa gcatgctcat gaccctgccg tgtcgtctga ggtacccgtt cttatcctag   300
tggttcagga agagaaaacg cagtttgcac tttcaagaca gcttctctaa ggctggcatg   360
ttatctcctt gctttgcttt ttgccgtttt aaaatgtgta attgttccag cattccaatg   420
gtcttgtgca tagcagggga ctgtaaccaa aaataaacat gtatttgtgt aattggtttg   480
aagaagtctt gaatagctct ttactgtcct acttggggtt gataagattt gagtgtttgc   540
aatttttttac taaatgtagc tccaaagtct taaatggctt gtttgttctt aaactgttaa   600
ttgatgaaac tgtgcataag tttacaatgt actaacttat tttgcttatt atatatagtg   660
ttttattgga aattgtaacc acacacttca gcatgatgaa aataaagatt agtgtttcca   720
tttaaataaa tgttttatcc tcccataaaa aaaaaaaaaa aagggcggc c             771
```
FIG.1E

```
tcgacccacg cgtccgcagg cagtgactgc cctcggcttt ttttctgctg actaagatct    60
cctatagaga gctacaacaa tgcccaaaag aaagccaaag agaagatctg ccaggttgtc   120
tgctatgctt gtgccagtta caccagaggt gaagcctaaa agaacatcaa gttcaaggaa   180
aatgaagaca aaaagtgata tgatggaaga aaacatagat acaagtgccc aagcagttgc   240
tgaaaccaag caagaagcag ttgttgaaga agactacaat gaaaatgcta aaaatggaga   300
agccaaaatt acagaggcac cagcttctga aaagaaatt gtggaagtaa aagaagaaaa   360
tattgaagat gccacagaaa agggaggaga aaagaaagaa gcagtggcag cagaagtaaa   420
aaatgaagaa gaagatcaga aagaagatga agaagatcaa aacgaagaga aggggaagc   480
tggaaaagaa gacaaagatg aaaaagggga agaagatgga aagaggata aaaatggaaa   540
tgagaaagga gaagatgcaa aagagaaaga agatggaaaa aaaggtgaag acggaaaagg   600
aaatggagaa gatggaaaag agaaaggaga agatgaaaaa gaggaagaag acagaaaaga   660
aacaggagtt ggaaaagaga atgaggatgg aaaagagaag ggagataaaa aagaggggaa   720
agatgtaaaa gtcaaagaag atgaaaaaga gagagaagat ggaaaagaag atgaaggtgg   780
aaatgaggaa gaagctggaa aagagaaaga agatttaaaa gaagaggaag aaggaaaaga   840
ggaagatgag atcaaagaag atgatggaaa aaaagaggag ccacagagta ttgtttaaaa   900
ctgccctatg tagtttcata atttggtaac atgtaccttc atgttgtaaa gttaatagag   960
ataaatattt ttatcaaaaa ttttataaac acagcctttc tttagcattg atttaatttc  1020
agaacatctt catattgatt attagccata aagtttctaa catgaaacat ttatctataa  1080
attttgtgat tatagtagtg gaatacatag aaaaaatat gctttcaact ttgtgagtga  1140
atttcgtgtt gtgtaagtta tatgtcaaat ctttgaattt aattttact cctttatac  1200
atgtgataat tcataaagt gagggatccc aaaaaagag tttcatccca acattcttgt   1260
tctgcaggtt gctttataa agaaggtgaa ctatttcat gtaatgttaa gagttaaact   1320
tatctttccc aaatataact ttattattag cttgggaaaa atgaaattgt attcccattt  1380
ttaaaataaa tacaaatgtt tatttcagaa gggcagtttt gattatatgt gaatacacaa  1440
atttactgg atttatctta ataaaaagac tctgacgatg attgtgtttt gttatatctt  1500
caaaaatata gctagtgaaa tattgtgctt aattttttc tattgtgtta ttcatgaaaa  1560
tatttaatat tcactgacat aaaattaata taagtaaaa ttcaccattt taattataat  1620
aaaaataaag tatataattc aaaaaaaaaa aaaaaaaaa agggcggcc               1669
```
FIG.1F

```
tcgacccacg cgtccgtgat aaataactta taggtgatag tgataattcc tgattccaag    60
aatgccatct gataaaaaag aatagaaatg gaaagtggga ctgagaggga gtcagcaggc   120
atgctgcggt ggcggtcact ccctctgcca ctatccccag ggaaggaaag gctccgccat   180
ttgggaaagt ggtttctacg tcactggaca ccggttctga gcattagttt gagaactcgt   240
tcccgaatgt gctttcctcc ctctcccctg cccacctcaa gtttaataaa taaggttgta   300
cttttcttac tataaaataa atgtctgtaa ctgctgtgca ctgctgtaaa cttgttagag   360
aaaaaaataa cctgcatgtg ggctcctcag ttattgagtt tttgtgatcc tatctcagtc   420
tgggggggaa cattctcaag aggtgaaata caagaaagcc ttttttttctt ggatcttttc   480
ccgagattca aatctccgat ttcccatttg ggggcaagtt ttttcttca ccttcaatat   540
gagaattcag cgaacttgaa agaaaaatca tctgtgagtt ccttcaggtt ctcactcata   600
gtcatgatcc ttcagaggga atatgcactg gcgagtttaa agtaagggct atgatatttg   660
atggtcccaa agtacggcag ctgcaaaaag tagtggaagg aaattgtcta cgtgtcttgg   720
aaaaattagt taggaatttg gatgggtaaa aggtaccctt gccttactcc atcttatttt   780
cttagccccc tttgagtgtt ttaactggtt tcatgtccta gtaggaagtg cattctccat   840
cctcatcctc tgccctccca ggaagtcagt gattgtcttt tgggcttcc cctccaaagg   900
accttctgca gtggaagtgc cacatccagt tcttttcttt tgttgctgct gtgtttagat   960
aattgaagag atctttgtgc cacacaggat ttttttttt ttttaagaaa aacctataga  1020
tgaaaaatta ctaatgaaac tgtgtgtacg tgtctgtgcg tgcaacataa aaatacagta  1080
gcacctaagg agcttgaatc ttggttcctg taaaatttca aattgatgtg gtattaataa  1140
aaaaaaaaaa aacccaaaaa aaaaaaaaaa aaagggcgg cc                      1182
```

FIG.1G

```
tcgacccacg cgtccggagg agagagagtg aacagggagc ggggcttttg cctgttggtc    60
tccctggact gaagagaggg agaatagaag cccaagacta agattctcaa aatggtttat   120
tacccagaac tctttgtctg ggtcagtcaa gaaccatttc caaacaagga catggaggga   180
aggcttccta agggaagact tcctgtccca aaggaagtga accgcaagaa gaacgatgag   240
acaaacgctg cctccctgac tccactgggc agcagtgaac tccgctcccc aagaatcagt   300
tacctccact ttttttaatc gtaacacctc catttgtatt acatatggt  tatgggtatt   360
gatgaggtca tggtatcata tatgggattt ttttctgtgt aaatcatcaa gtataagaag   420
aaactatggg actctgagcc ttgctttaga gaatttacag tggacaaata ggtgtcatca   480
aaccagtttt taatcattct gactcaagtg aaaacgctca gaatttcaca ctgtgaatcc   540
cgtttacaac ccttacaggt gggccttcag gcctggttcg ctacaacaat gtcttccaca   600
actcaaactc ccaccgcgct cacacaaccg gtccactcct gccttttcac tcacacagct   660
cccgactgct tcttgcagag gctgagagtc cccccccac  cttttttttc atttagatgt   720
aacaaaccta gtagtttatg ttcatcaatt gtctgtatat ctctatattt tatccatgta   780
ctcttttgat gtatagaagt agtttgaaac tcattgtttc cttgtggtaa gtgaccgaga   840
tgctgccaca ggacctgaga cactgatgaa tggtgctatt ttggactttc aacatgctcc   900
ttggcgaggt agctctgatg gagttatttt ttatttccat gttctaagaa ggtgttggta   960
ctctgtttcc cttgaatgtt gttctctaga ctggattgac ttgttttcct tgtgtcttca  1020
gtgtggcttt cttcctcagt gttgtaggtt gagcgaatgc taccagagtg tgagagacca  1080
ttgtctcgtt ggctggcgct cacggacatg cagtcacggt agcgggagca atcacaaaac  1140
tgtaatttac ttaccaaatc tcttccttc  cgtagcctcg cctgcctgac ttagagaaag  1200
aaaagcaata attttacagg cattttgagg tgtctctttg ggttctttct gtttgaaagg  1260
atatttgtcg aaaaaaagag caaaaccgtt ttaaataaac tcccccctgga aaaaaaccca  1320
aaacactggc atactgagtg ggaatatgaa aatgacacct tttccaaata ttaaattgga  1380
aaacaaggtc tacaaaatca tgatactttt ttaaaaggca gagcattctt ttttcggcaa  1440
ttttgataag caaggtgtag atttacattt ttgtccttgc tcccaacgaa atggataaac  1500
aaaaataaat taccatctac tcatggaatg ttgttgtgtt agccagtctg aaagcccacc  1560
ttaattttta tataactgtc tttagctctt cttttgacag gcaggcctt  gttctgaact  1620
gtttcgcttc tgactgttaa acaccgatga cgcatgcact gcacttcttc gttttcttct  1680
tgctccccca ttggcctgag tttcttgtgc attacgcctc tccctccttc gttagaatag  1740
gtgtatcagc tgtgtaaata gagcaagaaa acagtattct gcatctgtgg catttatgta  1800
gagttgcagt tgtgtactgc tgaaaatgca ggcttttgta acagtgtgat ctttactgat  1860
gcactcatga caagtaccca atgtatttta gctattttag tagtatttgt tcaataaata  1920
cgcaagctgt aaggtaaaaa aaaaaaaaaa aaaaaaggg  cggcc             1965
```

FIG.1H

| | | | | | | |
|---|---|---|---|---|---|---|
|tcgacccacg|cgtccgggaa|cgtacgtccc|agccctcttt|agctacttag|cgcctctggg|60|
|cccgagaaca|cctgctcctt|ggctcagtct|ggcgccaccg|gcatcacgga|actgtacttc|120|
|ccagagacgt|cacaccggga|gacttccgat|tcccgctcct|gagattggac|tctcacgtgc|180|
|aggagccagt|cctcgctggg|ctctagcggg|cttctgatgg|aggagctact|cctctgggag|240|
|gacagaaatt|agcagcagcc|tctgtcacca|tccaaagatt|acaacccatg|aaaccattga|300|
|gtttgtgcct|tgtatcagaa|agcaaaggag|aatgaaaaag|cacagctaac|attgcttgag|360|
|gatctaggcg|attaattctt|tagactgtca|tcatgggtat|cccgaggact|aatgagtttt|420|
|gtgggaagat|cataagtaat|gaagttcttc|actgatttga|agttgcgggg|acacaaaaat|480|
|tgtcattgat|ggttatgctc|ttttccaccg|tctttgcttc|agtttcaaac|ttggatctcc|540|
|ggtatggagg|ggactatgat|tcttttgcag|atgttgtaca|aaaattcttt|gaatcactgt|600|
|ttgcttgtaa|tatatgccca|tatgttgtat|tagatggagg|atgtgacatt|tcagataaaa|660|
|agcttacaac|tttaaaggat|agagctagag|aggagatcca|gatggcccat|tccctttctg|720|
|ttggtgggag|tgggtatgta|tgtcccttac|tcatccggga|agtattcata|caggttttga|780|
|tcaagctgcg|ggtgtgtttt|gtccagtgct|tttcagaagc|agatcgggac|attatgacac|840|
|ttgctaacca|ttggaattgc|cctgtgttat|catcagatag|tgacttttgc|attttgacc|900|
|tgaaaactgg|gttttgccca|ttgaatagct|ttcagtggag|aaatatgaac|actattaagg|960|
|gcacacaaaa|ctatatccct|gccaaatgct|tttcccttga|tgcattctgc|catcacttca|1020|
|gcaatatgaa|taaagctcta|ctacctctct|ttgcggtgct|atgtggaaat|gaccatgtta|1080|
|atctacccat|catggagaca|ttcttaagta|aagcgcgtct|tcctcttgga|gctaccagtt|1140|
|ctaaagggag|gagacaccac|cgaatcctgg|gacttctgaa|ttggttgtct|cattttgcca|1200|
|accctaccga|agcactagat|aatgttctga|aatacctccc|aaaaaaggat|cgagaaaatg|1260|
|ttaaggaact|tctctgctgt|tccatggaag|aataccaaca|gtcccaggtg|aagctacagg|1320|
|acttcttcca|gtgtggtact|tatgtctgtc|cagatgcctt|gaatcttggt|ttaccagaat|1380|
|gggtattagt|ggctttagct|aaaggccagc|tatctccttt|catcagtgat|gctttggtcc|1440|
|taagacggac|cattcttccc|acacaggtgg|aaaacatgca|gcaaccaaat|gcccacagaa|1500|
|tatctcagcc|catcaggcaa|atcatctatg|ggcttctttt|aaatgcctca|ccacatctgg|1560|
|acaagacatc|ctggaatgca|ttgcctcctc|agcctctagc|tttcagtgaa|gtggaaagga|1620|
|ttaataaaaa|tatcagaacc|tcaatcattg|atgcagtaga|actggccaag|gatcattctg|1680|
|acttaagcag|attgactgag|ctctccttga|ggaggcggca|gatgcttctg|ttagaaaccc|1740|
|tgaaggtgaa|acagaccatt|ctggagccaa|tccctacttc|actgaagttg|cccattgctg|1800|
|tcagttgcta|ctggttgcag|cacaccgaga|ccaaagcaaa|gctacatcat|ctacaatcct|1860|
|tactgctcac|aatgctagtg|gggcccttga|ttgccataat|caacagccct|ggaaatgtgg|1920|
|accctgtacc|caggcaggct|cagtgtcttg|ctcctcgcta|gttggtaaaa|ggtaaggaag|1980|
|agctgcagga|agatggtgct|aagatgttgt|atgcagagtt|ccaaagagtg|aaggcgcaga|2040|
|cacggctggg|cacaagactg|gacttagaca|cagctcacat|cttctgtcag|tggcagtcct|2100|
|gtctccagat|ggggatgtat|ctcaaccagc|tgctgtccac|tcctctccca|gagccagacc|2160|
|taactcgact|gtacagtgga|agcctggtgc|acggactatg|ccagcaactg|ctagcatcga|2220|
|cctctgtaga|aagtgtcctg|agcatatgtc|ctgaggctaa|gcaactttat|gaatatctat|2280|
|tcaatgccca|caaggtcata|tgcccccgct|gaaatattcc|taccaaaagg|tagatcaaat|2340|
|tcaaaaaaaa|aaaggcagaa|gaaacagaat|accagctgtt|ctaagaacag|agggagaacc|2400|
|actgcacaca|ccaagtgttg|gtatgaggga|acaaccggt|ttgggttgtt|aatggttgaa|2460|
|aacttagagg|aacatagtga|ggcctccaac|attgaataaa|actcagtttg|catcaaacta|2520|
|gatgtattta|atataatcct|tacttaaaat|tcttccgtta|ccaccttga|aacaattagc|2580|
|tttttcttta|ggactgacct|gttaggggat|aaacatcaca|ataatctgaa|ttccaagtta|2640|
|ttttgtattt|tgttttaat|aaatacaacc|tgatttaaga|aaaaaaaaa|aaaagggcgg|2700|
|cc| | | | | |2702|

FIG. 1I

```
tcgacccacg cgtccgcctg ccagcggacg acgtggtcag catcatcgag gaggtggagg    60
agaagcggaa gcggaagaag aacgcccctc ccgagcccgt gccgccccc cgtgccgccc    120
ccgcccccac ccacgtccgc tccccgcagc ccccgccccc cgcccccgct cccgcacgag   180
acgagctgcc ggactggaac gaggtgctcc cgccctggga tcgggaggag gacgaggtgt   240
acccgccagg gccgtaccac ccttcccca actacatccg gccgcggaca ctgcagccgc    300
cctcggcctt gcgccgccgc cactaccacc acgccttgcc gccttcgcgc cactatcccg   360
gccgggaggc ccaggcgcgg cgcgcgcagg aggaggcgga ggcggaggag cgccggctgc   420
aggagcagga ggagctggag aattacatcg agcacgtgct gctccggcgc ccgtgactgc   480
ccttcccgta accgccccg cgcgccccg ccgcgcgcgc gcgccggcgc ccccctccgt    540
gttgcccgct ccccctcggt gtttgcatgc gccccggccc tgcccttgg ccctgccct    600
gtccccgggc tgcgtcggga cctgccagac ccccctcccg ggtcctgagc ccgaactccc   660
agagctcacc cgcgggtgac cgggggccag cccaggaggg cgggtggttt gtgcgagttc   720
ccttgccacg cggggccccg gccccatcaa gtccctctgg ggacgtcccc gtcggaaacc   780
ggaaaaagca gttccagtta attgtgtgaa gtgtgtctgt ctccagccct tcgggcctcc   840
cacgagcccc tccagcctct ccaagtcgct gtgaattgac cccttctttc ctttctctgt   900
tgtaaatacc cctcacggag gaaatagttt tgctaagaaa taaaagtgac tattttaaaa   960
aaaaaaaaaa agggcggcc                                                979
```

FIG.1J atgacaaacc cacagtcaat atcatactga                                                    30

Met Thr Asn Pro Gln Ser Ile Ser Tyr
 1               5

FIG.4A atgggcaaaa gctggaagca ttctaaatac caaaggacat cattagttaa caaatgctag    60

Met Gly Lys Ser Trp Lys His Ser Lys Tyr Gln Arg Thr Ser Leu Val
 1           5               10              15
Asn Lys Cys

FIG.4B atgctagact aa                                                                       12

Met Leu Asp
 1

FIG.4C atgggagcag ctttgccaac ccctgcaaag tga                                                33

Met Gly Ala Ala Leu Pro Thr Pro Ala Lys
 1               5               10

FIG.4D atggctgaag catga                                                                    15

Met Ala Glu Ala
 1

FIG.4E atgaggaaac tcatcacagg actcattttc cttaaaattt ag                                      42

Met Arg Lys Leu Ile Thr Gly Leu Ile Phe Leu Lys Ile
 1               5                   10

FIG.4F

```
atgttattct atacaattat ttataataca atatacaaat aa                           42
```

Met Leu Phe Tyr Thr Ile Ile Tyr Asn Thr Ile Tyr Lys
1               5                   10

FIG.4G

```
atgtatttag cccaggaaat gaccaacctg atgtgtgtta tgacccatct gagcctccca       60
tga                                                                     63
```

Met Tyr Leu Ala Gln Glu Met Thr Asn Leu Met Cys Val Met Thr His
1               5                   10                  15
Leu Ser Leu Pro 20

FIG.4H

```
atgaccaacc tgatgtgtgt tatgacccat ctgagcctcc catga                       45
```

Met Thr Asn Leu Met Cys Val Met Thr His Leu Ser Leu Pro
1               5                   10

FIG.4I

```
atgtgtgtta tgacccatct gagcctccca tga                                    33
```

Met Cys Val Met Thr His Leu Ser Leu Pro
1               5                   10

FIG.4J

```
atgacccatc tgagcctccc atga
24
```

Met Thr His Leu Ser Leu Pro
1               5

FIG.4K

```
atgaccacag tttttaaaat aagattaaga actgaagact ggtgggggct cataaacaat       60
atgagtaaag tgttagccaa aataaaacaa aaaaaaaagg gcggcc                     106
```

Met Thr Thr Val Phe Lys Ile Arg Leu Arg Thr Glu Asp Trp Trp Gly
1               5                   10                  15
Leu Ile Asn Asn Met Ser Lys Val Leu Ala Lys Ile Lys Gln Lys Lys
                20                  25                  30
Lys Gly Gly
35

FIG.4L atggccaggc cggctgggct gcagagcgcc ggcacgggtc cacgcctcgg gtga    54

Met Ala Arg Pro Ala Gly Leu Gln Ser Ala Gly Thr Gly Pro Arg Leu
 1               5                  10                  15
Gly

FIG.5A atgttcgggc gcggggcggc ccatccgcat cccccaacac ccccacctcc ggcctga    57

Met Phe Gly Arg Gly Ala Ala His Pro His Pro Thr Pro Pro Pro
 1               5                  10                  15
Pro Ala

FIG.5B atgcccccctt ga    12

Met Pro Pro
 1

FIG.5C atgagcatac gactggggag cccagtggag gcgccctccc gaagcgccac tgcccatgct    60
gaccacccag ccctccggct gctgatgtca tga                                93

Met Ser Ile Arg Leu Gly Ser Pro Val Glu Ala Pro Ser Arg Ser Ala
 1               5                  10                  15
Thr Ala His Ala Asp His Pro Ala Leu Arg Leu Leu Met Ser
                 20                  25                  30

FIG.5D atgctgacca cccagccctc cggctgctga    30

Met Leu Thr Thr Gln Pro Ser Gly Cys
 1               5

FIG.5E atgagtaaca ccactgtgcc caatgccccc caggccaaca gcgactccat ggtgggctat 60
gtgttggggc ccttcttcct catcaccctg gtcggggtgg tggtggctgt ggtaatgtat 120
gtacagaaga aaaagcgggt ggaccggctg cgccatcacc tgctccccat gtacagctat 180
gacccagctg aggaactgca tgaggctgag caggagctgc tctctgacat gggagacccc 240
aaggtggtac atggctggca gagtggctac cagcacaagc ggatgccact gctggatgtc 300
aagacgtga 309

Met Ser Asn Thr Thr Val Pro Asn Ala Pro Gln Ala Asn Ser Asp Ser
 1           5                   10                  15
Met Val Gly Tyr Val Leu Gly Pro Phe Phe Leu Ile Thr Leu Val Gly
            20                  25                  30
Val Val Val Ala Val Val Met Tyr Val Gln Lys Lys Arg Val Asp
        35                  40                  45
Arg Leu Arg His His Leu Leu Pro Met Tyr Ser Tyr Asp Pro Ala Glu
    50                  55                  60
Glu Leu His Glu Ala Glu Gln Glu Leu Leu Ser Asp Met Gly Asp Pro
65                  70                  75                  80
Lys Val Val His Gly Trp Gln Ser Gly Tyr Gln His Lys Arg Met Pro
                85                  90                  95
Leu Leu Asp Val Lys Thr
                100

FIG.5F atgccccca ggccaacagc gactccatgg tgggctatgt gttggggccc ttcttcctca 60
tcaccctggt cggggtggtg gtggctgtgg taa 93

Met Pro Pro Arg Pro Thr Ala Thr Pro Trp Trp Ala Met Cys Trp Gly
 1           5                   10                  15
Pro Ser Ser Ser Ser Pro Trp Ser Gly Trp Trp Trp Leu Trp
            20                  25                  30

FIG.5G

```
atggtgggct atgtgttggg gcccttcttc ctcatcaccc tggtcggggt ggtggtggct    60
gtggtaatgt atgtacagaa gaaaaagcgg gtggaccggc tgcgccatca cctgctcccc   120
atgtacagct atgacccagc tgaggaactg catgaggctg agcaggagct gctctctgac   180
atgggagacc ccaaggtggt acatggctgg cagagtggct accagcacaa gcggatgcca   240
ctgctggatg tcaagacgtg a                                              261
```

Met Val Gly Tyr Val Leu Gly Pro Phe Phe Leu Ile Thr Leu Val Gly
1           5                   10              15
Val Val Val Ala Val Val Met Tyr Val Gln Lys Lys Lys Arg Val Asp
              20              25              30
Arg Leu Arg His His Leu Leu Pro Met Tyr Ser Tyr Asp Pro Ala Glu
              35              40              45
Glu Leu His Glu Ala Glu Gln Glu Leu Leu Ser Asp Met Gly Asp Pro
        50              55              60
Lys Val Val His Gly Trp Gln Ser Gly Tyr Gln His Lys Arg Met Pro
65              70              75              80
Leu Leu Asp Val Lys Thr
                85

FIG.5H

```
atgtgttggg gcccttcttc ctcatcaccc tggtcggggt ggtggtggct gtggtaa      57
```

Met Cys Trp Gly Pro Ser Ser Ser Ser Pro Trp Ser Gly Trp Trp Trp
1           5                   10              15
Leu Trp

FIG.5I

```
atgtatgtac agaagaaaaa gcgggtggac cggctgcgcc atcacctgct ccccatgtac    60
agctatgacc cagctgagga actgcatgag gctgagcagg agctgctctc tgacatggga   120
gaccccaagg tggtacatgg ctggcagagt ggctaccagc acaagcggat gccactgctg   180
gatgtcaaga cgtga                                                     195
```

Met Tyr Val Gln Lys Lys Lys Arg Val Asp Arg Leu Arg His His Leu
1           5                   10              15
Leu Pro Met Tyr Ser Tyr Asp Pro Ala Glu Glu Leu His Glu Ala Glu
              20              25              30
Gln Glu Leu Leu Ser Asp Met Gly Asp Pro Lys Val Val His Gly Trp
        35              40              45
Gln Ser Gly Tyr Gln His Lys Arg Met Pro Leu Leu Asp Val Lys Thr
        50              55              60

FIG.5J

```
atgtacagaa gaaaaagcgg gtggaccggc tgcgccatca cctgctcccc atgtacagct    60
atgacccagc tgaggaactg catgaggctg agcaggagct gctctctgac atgggagacc   120
ccaaggtggt acatggctgg cagagtggct accagcacaa gcggatgcca ctgctggatg   180
tcaagacgtg acctgacccc cttgccccac ccttcagagc tggggtcct  ggactgcctg   240
gggccctgcc atctgcttcc cctgctgtca cctggctccc cctgctgggt gctgggtctc   300
catttctccc tccacccacc ctcagcagca tctgcttccc atgccctcac catcacctca   360
ctgcccccag gccttctgcc ctttgtgggt gttgagctca ccgcccaccc acaggcactc   420
ataggaagag gctttccttc tgggatggcg gcggctggta gacacctttg ctttctctag   480
```

Met Tyr Arg Arg Lys Ser Gly Trp Thr Gly Cys Ala Ile Thr Cys Ser
1               5                   10                  15
Pro Cys Thr Ala Met Thr Gln Leu Arg Asn Cys Met Arg Leu Ser Arg
                20                  25                  30
Ser Cys Ser Leu Thr Trp Glu Thr Pro Arg Trp Tyr Met Ala Gly Arg
            35                  40                  45
Val Ala Thr Ser Thr Ser Gly Cys His Cys Trp Met Ser Arg Arg Asp
        50                  55                  60
Leu Thr Pro Leu Pro His Pro Ser Glu Pro Gly Val Leu Asp Cys Leu
65                  70                  75                  80
Gly Pro Cys His Leu Leu Pro Leu Leu Ser Pro Gly Ser Pro Cys Trp
                85                  90                  95
Val Leu Gly Leu His Phe Ser Leu His Pro Pro Ser Ala Ala Ser Ala
                100                 105                 110
Ser His Ala Leu Thr Ile Thr Ser Leu Pro Pro Gly Leu Leu Pro Phe
            115                 120                 125
Val Gly Val Glu Leu Thr Ala His Pro Gln Ala Leu Ile Gly Arg Gly
        130                 135                 140
Phe Pro Ser Gly Met Ala Ala Ala Gly Arg His Leu Cys Phe Leu
145                 150                 155

FIG.5K

```
atgtacagct atgacccagc tgaggaactg catgaggctg agcaggagct gctctctgac    60
atgggagacc ccaaggtggt acatggctgg cagagtggct accagcacaa gcggatgcca   120
ctgctggatg tcaagacgtg a                                             141
```

Met Tyr Ser Tyr Asp Pro Ala Glu Glu Leu His Glu Ala Glu Gln Glu
1               5                   10                  15
Leu Leu Ser Asp Met Gly Asp Pro Lys Val Val His Gly Trp Gln Ser
                20                  25                  30
Gly Tyr Gln His Lys Arg Met Pro Leu Leu Asp Val Lys Thr
            35                  40                  45

FIG.5L

```
atgacccagc tgaggaactg catgaggctg agcaggagct gctctctgac atgggagacc    60
ccaaggtggt acatggctgg cagagtggct accagcacaa gcggatgcca ctgctggatg   120
tcaagacgtg acctgacccc cttgccccac ccttcagagc ctggggtcct ggactgcctg   180
gggccctgcc atctgcttcc cctgctgtca cctggctccc cctgctgggt gctgggtctc   240
catttctccc tccacccacc ctcagcagca tctgcttccc atgccctcac catcacctca   300
ctgcccccag gccttctgcc ctttgtgggt gttgagctca ccgcccaccc acaggcactc   360
ataggaagag gctttccttc tgggatggcg gcggctggta gacacctttg ctttctctag   420
```

| | | | | | | | | | | | | | | |
|---|---|---|---|---|---|---|---|---|---|---|---|---|---|---|
| Met | Thr | Gln | Leu | Arg | Asn | Cys | Met | Arg | Leu | Ser | Arg | Ser | Cys | Ser | Leu |
| 1 | | | | 5 | | | | | 10 | | | | | 15 | |
| Thr | Trp | Glu | Thr | Pro | Arg | Trp | Tyr | Met | Ala | Gly | Arg | Val | Ala | Thr | Ser |
| | | | 20 | | | | | 25 | | | | | 30 | | |
| Thr | Ser | Gly | Cys | His | Cys | Trp | Met | Ser | Arg | Arg | Asp | Leu | Thr | Pro | Leu |
| | | | 35 | | | | | 40 | | | | | 45 | | |
| Pro | His | Pro | Ser | Glu | Pro | Gly | Val | Leu | Asp | Cys | Leu | Gly | Pro | Cys | His |
| | | 50 | | | | | 55 | | | | | 60 | | | |
| Leu | Leu | Pro | Leu | Leu | Ser | Pro | Gly | Ser | Pro | Cys | Trp | Val | Leu | Gly | Leu |
| 65 | | | | | 70 | | | | | 75 | | | | | 80 |
| His | Phe | Ser | Leu | His | Pro | Pro | Ser | Ala | Ala | Ser | Ala | Ser | His | Ala | Leu |
| | | | | 85 | | | | | 90 | | | | | 95 | |
| Thr | Ile | Thr | Ser | Leu | Pro | Pro | Gly | Leu | Leu | Pro | Phe | Val | Gly | Val | Glu |
| | | | | 100 | | | | | 105 | | | | | 110 | |
| Leu | Thr | Ala | His | Pro | Gln | Ala | Leu | Ile | Gly | Arg | Gly | Phe | Pro | Ser | Gly |
| | | | 115 | | | | | 120 | | | | | 125 | | |
| Met | Ala | Ala | Ala | Gly | Arg | His | Leu | Cys | Phe | Leu | | | | | |
| | 130 | | | | | 135 | | | | | | | | | |

FIG.5M atgaggctga gcaggagctg ctctctgaca tgggagaccc caaggtggta catggctggc    60
agagtggcta ccagcacaag cggatgccac tgctggatgt caagacgtga cctgaccccc   120
ttgccccacc cttcagagcc tggggtcctg gactgcctgg ggccctgcca tctgcttccc   180
ctgctgtcac ctggctcccc ctgctgggtg ctgggtctcc atttctccct ccacccaccc   240
tcagcagcat ctgcttccca tgccctcacc atcacctcac tgcccccagg ccttctgccc   300
tttgtgggtg ttgagctcac cgcccaccca caggcactca taggaagagg ctttccttct   360
gggatggcgg cggctggtag acacctttgc tttctctag                          399

Met Arg Leu Ser Arg Ser Cys Ser Leu Thr Trp Glu Thr Pro Arg Trp
1               5                   10                  15
Tyr Met Ala Gly Arg Val Ala Thr Ser Thr Ser Gly Cys His Cys Trp
                20                  25                  30
Met Ser Arg Arg Asp Leu Thr Pro Leu Pro His Pro Ser Glu Pro Gly
                35                  40                  45
Val Leu Asp Cys Leu Gly Pro Cys His Leu Leu Pro Leu Leu Ser Pro
    50                  55                  60
Gly Ser Pro Cys Trp Val Leu Gly Leu His Phe Ser Leu His Pro Pro
65                  70                  75                  80
Ser Ala Ala Ser Ala Ser His Ala Leu Thr Ile Thr Ser Leu Pro Pro
                85                  90                  95
Gly Leu Leu Pro Phe Val Gly Val Glu Leu Thr Ala His Pro Gln Ala
                100                 105                 110
Leu Ile Gly Arg Gly Phe Pro Ser Gly Met Ala Ala Ala Gly Arg His
                115                 120                 125
Leu Cys Phe Leu
    130

FIG.5N atgggagacc ccaaggtggt acatggctgg cagagtggct accagcacaa gcggatgcca    60
ctgctggatg tcaagacgtg a                                              81

Met Gly Asp Pro Lys Val Val His Gly Trp Gln Ser Gly Tyr Gln His
1               5                   10                  15
Lys Arg Met Pro Leu Leu Asp Val Lys Thr
                20                  25

FIG 5O

```
atggctggca gagtggctac cagcacaagc ggatgccact gctggatgtc aagacgtgac   60
ctgaccccct tgccccaccc ttcagagcct ggggtcctgg actgcctggg gccctgccat  120
ctgcttcccc tgctgtcacc tggctccccc tgctgggtgc tgggtctcca tttctccctc  180
cacccaccct cagcagcatc tgcttcccat gccctcacca tcacctcact gccccaggc   240
cttctgccct tgtgggtgt tgagctcacc gcccacccac aggcactcat aggaagaggc   300
tttccttctg ggatggcggc ggctggtaga caccttttgct ttctctag              348
```

| | | | | | | | | | | | | | | |
|---|---|---|---|---|---|---|---|---|---|---|---|---|---|---|
Met Ala Gly Arg Val Ala Thr Ser Thr Ser Gly Cys His Cys Trp Met
 1        5              10             15
Ser Arg Arg Asp Leu Thr Pro Leu Pro His Pro Ser Glu Pro Gly Val
          20              25             30
Leu Asp Cys Leu Gly Pro Cys His Leu Leu Pro Leu Leu Ser Pro Gly
          35              40             45
Ser Pro Cys Trp Val Leu Gly Leu His Phe Ser Leu His Pro Pro Ser
 50               55              60
Ala Ala Ser Ala Ser His Ala Leu Thr Ile Thr Ser Leu Pro Pro Gly
65                70              75             80
Leu Leu Pro Phe Val Gly Val Glu Leu Thr Ala His Pro Gln Ala Leu
              85              90             95
Ile Gly Arg Gly Phe Pro Ser Gly Met Ala Ala Ala Gly Arg His Leu
          100             105            110
Cys Phe Leu
    115

FIG.5P

```
atgccactgc tggatgtcaa gacgtga
27
```

Met Pro Leu Leu Asp Val Lys Thr
 1                5

FIG.5Q

```
atgtcaagac gtgacctgac ccccttgccc cacccttcag agcctggggt cctggactgc    60
ctggggcccct gccatctgct tccc ctgctg tcacctggct ccccctgctg ggtgctgggt  120
ctccatttct ccctccaccc accctcagca gcatctgctt cccatgccct caccatcacc   180
tcactgcccc caggccttct gcccttttgtg ggtgttgagc tcaccgccca cccacaggca   240
ctcataggaa gaggctttcc ttctgggatg gcggcggctg gtagacacct ttgctttctc   300
tag                                                                 303
```

```
Met Ser Arg Arg Asp Leu Thr Pro Leu Pro His Pro Ser Glu Pro Gly
 1           5                   10                  15
Val Leu Asp Cys Leu Gly Pro Cys His Leu Leu Pro Leu Leu Ser Pro
            20                  25                  30
Gly Ser Pro Cys Trp Val Leu Gly Leu His Phe Ser Leu His Pro Pro
            35                  40                  45
Ser Ala Ala Ser Ala Ser His Ala Leu Thr Ile Thr Ser Leu Pro Pro
        50                  55                  60
Gly Leu Leu Pro Phe Val Gly Val Glu Leu Thr Ala His Pro Gln Ala
65                  70                  75                  80
Leu Ile Gly Arg Gly Phe Pro Ser Gly Met Ala Ala Ala Gly Arg His
                85                  90                  95
Leu Cys Phe Leu
            100
```

FIG.5R

```
atgccctcac catcacctca ctgcccccag gccttctgcc ctttgtgggt gttgagctca    60
ccgcccaccc acaggcactc atag                                           84
```

```
Met Pro Ser Pro Ser Pro His Cys Pro Gln Ala Phe Cys Pro Leu Trp
 1           5                   10                  15
Val Leu Ser Ser Pro Pro Thr His Arg His Ser
            20                  25
```

FIG.5S

```
atggcggcgg ctggtagaca cctttgcttt ctctag                              36
```

```
Met Ala Ala Ala Gly Arg His Leu Cys Phe Leu
 1           5                   10
```

FIG.5T

```
atggtgatgg ggccagatgt atag                                           24
```

```
Met Val Met Gly Pro Asp Val
 1           5
```

FIG.5U atggggccag atgtatag                                              18

Met Gly Pro Asp Val
 1          5

FIG.5V atgtatagta ttcagtatat attttgtaaa taa                            33

Met Tyr Ser Ile Gln Tyr Ile Phe Cys Lys
 1          5                   10

FIG.5W atgttttgtg gctaa                                                15

Met Phe Cys Gly
 1

FIG.5X

```
atgttgagat actggggaga gataccaata tcatcaagcc agaccaacag aagttccttc    60
gatttgctcc cacgggagtt ccgtctggtg gaagtccatg acccaccct gcaccaaccc    120
tcagccaaca agccgaagcc ccccactatg ctggacatcc cctcagagcc atgtagtctc    180
accatccata cgattcagtt gattcagcac aaccgacgtc ttcgcaacct tattgccaca    240
gctcaggccc agaatcagca gcagacagaa ggtgtaaaaa ctgaagagag tgaacctctt    300
ccctcgtgcc ctgggtcacc tcctctccct gatgacctcc tgcctttaga ttgtaagaat    360
cccaatgcac cattccagat ccggcacagt gacccagaga gtgactttta tcgtgggaaa    420
ggggaacctg tgactgaact cagctggcac tcctgtcggc agctcctcta ccaggcagtg    480
gccacaatcc tggcccacgc gggctttgac tgtgctaatg agagtgtcct ggagacccta    540
actgatgtgg cacatgagta ttgccttaag tttaccaagt tgctgcgttt tgctgtggac    600
cgggaggccc ggctgggaca gactcctttt cctgatgtga tggagcaggt attccatgaa    660
gtgggtattg gcagtgtgct ctccctccag aagttctggc agcaccgcat caaggactat    720
cacagttaca tgctacagat tagtaagcaa ctctctgaag aatatgaaag gattgtcaat    780
cctgagaagg ccacagagga cgctaaacct gtgaagatca aggaggaacc tgtgagcgac    840
atcacttttc ctgtcagtga ggagctggag gctgaccttg cttctggaga ccagtcactg    900
cctatgggag tgcttggggc tcagagcgaa cgcttcccat ctaacctgga ggttgaagct    960
tcaccacagg cttcaagtgc agaggtaaat gcttctcctc tttggaatct ggcccatgtg   1020
aaaatggagc tcaagaaag tgaagaaggc aatgtctctg ggcatggtgt gctgggcagt   1080
gatgtcttcg aggagcctat gtcaggcatg agtgaagctg ggattcctca gagccctgat   1140
gactcagata gcagctatgg ttcccactcc actgacagcc tcatggggtc ctcccctgtt   1200
ttcaaccagc gctgcaagaa gaggatgagg aaaatataa                          1239
```

```
Met Leu Arg Tyr Trp Gly Glu Ile Pro Ile Ser Ser Ser Gln Thr Asn
 1               5                  10                  15
Arg Ser Ser Phe Asp Leu Leu Pro Arg Glu Phe Arg Leu Val Glu Val
              20                  25                  30
His Asp Pro Pro Leu His Gln Pro Ser Ala Asn Lys Pro Lys Pro Pro
              35                  40                  45
Thr Met Leu Asp Ile Pro Ser Glu Pro Cys Ser Leu Thr Ile His Thr
 50                  55                  60
Ile Gln Leu Ile Gln His Asn Arg Arg Leu Arg Asn Leu Ile Ala Thr
65                  70                  75                  80
Ala Gln Ala Gln Asn Gln Gln Gln Thr Glu Gly Val Lys Thr Glu Glu
              85                  90                  95
Ser Glu Pro Leu Pro Ser Cys Pro Gly Ser Pro Pro Leu Pro Asp Asp
             100                 105                 110
Leu Leu Pro Leu Asp Cys Lys Asn Pro Asn Ala Pro Phe Gln Ile Arg
             115                 120                 125
```

FIG.6A

His Ser Asp Pro Glu Ser Asp Phe Tyr Arg Gly Lys Gly Glu Pro Val
    130             135                 140
Thr Glu Leu Ser Trp His Ser Cys Arg Gln Leu Leu Tyr Gln Ala Val
145             150                 155                 160
Ala Thr Ile Leu Ala His Ala Gly Phe Asp Cys Ala Asn Glu Ser Val
            165                 170                 175
Leu Glu Thr Leu Thr Asp Val Ala His Glu Tyr Cys Leu Lys Phe Thr
            180                 185                 190
Lys Leu Leu Arg Phe Ala Val Asp Arg Glu Ala Arg Leu Gly Gln Thr
        195                 200                 205
Pro Phe Pro Asp Val Met Glu Gln Val Phe His Glu Val Gly Ile Gly
    210                 215                 220
Ser Val Leu Ser Leu Gln Lys Phe Trp Gln His Arg Ile Lys Asp Tyr
225             230                 235                 240
His Ser Tyr Met Leu Gln Ile Ser Lys Gln Leu Ser Glu Glu Tyr Glu
            245                 250                 255
Arg Ile Val Asn Pro Glu Lys Ala Thr Glu Asp Ala Lys Pro Val Lys
            260                 265                 270
Ile Lys Glu Glu Pro Val Ser Asp Ile Thr Phe Pro Val Ser Glu Glu
        275                 280                 285
Leu Glu Ala Asp Leu Ala Ser Gly Asp Gln Ser Leu Pro Met Gly Val
    290                 295                 300
Leu Gly Ala Gln Ser Glu Arg Phe Pro Ser Asn Leu Glu Val Glu Ala
305             310                 315                 320
Ser Pro Gln Ala Ser Ser Ala Glu Val Asn Ala Ser Pro Leu Trp Asn
            325                 330                 335
Leu Ala His Val Lys Met Glu Pro Gln Glu Ser Glu Glu Gly Asn Val
            340                 345                 350
Ser Gly His Gly Val Leu Gly Ser Asp Val Phe Glu Glu Pro Met Ser
        355                 360                 365
Gly Met Ser Glu Ala Gly Ile Pro Gln Ser Pro Asp Asp Ser Asp Ser
    370                 375                 380
Ser Tyr Gly Ser His Ser Thr Asp Ser Leu Met Gly Ser Ser Pro Val
385                 390                 395                 400
Phe Asn Gln Arg Cys Lys Lys Arg Met Arg Lys Ile
            405                 410

FIG.6A-1 atgacccacc cctgcaccaa ccctcagcca acaagccgaa gccccccact atgctggaca   60
tccccctcaga gccatgtagt ctcaccatcc atacgattca gttga                  105

Met Thr His Pro Cys Thr Asn Pro Gln Pro Thr Ser Arg Ser Pro Pro
1               5                   10                  15
Leu Cys Trp Thr Ser Pro Gln Ser His Val Val Ser Pro Ser Ile Arg
            20                  25                  30
Phe Ser

FIG.6B

```
atgctggaca tcccctcaga gccatgtagt ctcaccatcc atacgattca gttgattcag    60
cacaaccgac gtcttcgcaa ccttattgcc acagctcagg cccagaatca gcagcagaca   120
gaaggtgtaa aaactgaaga gagtgaacct cttccctcgt gccctgggtc acctcctctc   180
cctgatgacc tcctgccttt agattgtaag aatcccaatg caccattcca gatccggcac   240
agtgacccag agagtgactt ttatcgtggg aaggggaac ctgtgactga actcagctgg    300
cactcctgtc ggcagctcct ctaccaggca gtggccacaa tcctggccca cgcgggcttt   360
gactgtgcta atgagagtgt cctggagacc ctaactgatg tggcacatga gtattgcctt   420
aagtttacca agttgctgcg ttttgctgtg gaccggggag cccggctggg acagactcct   480
tttcctgatg tgatggagca ggtattccat gaagtgggta ttggcagtgt gctctccctc   540
cagaagttct ggcagcaccg catcaaggac tatcacagtt acatgctaca gattagtaag   600
caactctctg aagaatatga aaggattgtc aatcctgaga aggccacaga ggacgctaaa   660
cctgtgaaga tcaaggagga acctgtgagc gacatcactt ttcctgtcag tgaggagctg   720
gaggctgacc ttgcttctgg agaccagtca ctgcctatgg gagtgcttgg ggctcagagc   780
gaacgcttcc catctaacct ggaggttgaa gcttcaccac aggcttcaag tgcagaggta   840
aatgcttctc ctctttggaa tctggcccat gtgaaaatgg agcctcaaga agtgaagaa    900
ggcaatgtct ctgggcatgg tgtgctgggc agtgatgtct tcgaggagcc tatgtcaggc   960
atgagtgaag ctgggattcc tcagagccct gatgactcag atagcagcta tggttcccac  1020
tccactgaca gcctcatggg gtcctcccct gttttcaacc agcgctgcaa gaagaggatg  1080
aggaaaatat aa                                                      1092
```

```
Met Leu Asp Ile Pro Ser Glu Pro Cys Ser Leu Thr Ile His Thr Ile
 1               5                  10                  15
Gln Leu Ile Gln His Asn Arg Arg Leu Arg Asn Leu Ile Ala Thr Ala
                    20                  25                  30
Gln Ala Gln Asn Gln Gln Gln Thr Glu Gly Val Lys Thr Glu Glu Ser
            35                  40                  45
Glu Pro Leu Pro Ser Cys Pro Gly Ser Pro Pro Leu Pro Asp Asp Leu
        50                  55                  60
Leu Pro Leu Asp Cys Lys Asn Pro Asn Ala Pro Phe Gln Ile Arg His
65                  70                  75                  80
Ser Asp Pro Glu Ser Asp Phe Tyr Arg Gly Lys Gly Glu Pro Val Thr
                85                  90                  95
Glu Leu Ser Trp His Ser Cys Arg Gln Leu Leu Tyr Gln Ala Val Ala
            100                 105                 110
Thr Ile Leu Ala His Ala Gly Phe Asp Cys Ala Asn Glu Ser Val Leu
        115                 120                 125
Glu Thr Leu Thr Asp Val Ala His Glu Tyr Cys Leu Lys Phe Thr Lys
    130                 135                 140
Leu Leu Arg Phe Ala Val Asp Arg Glu Ala Arg Leu Gly Gln Thr Pro
145                 150                 155                 160
Phe Pro Asp Val Met Glu Gln Val Phe His Glu Val Gly Ile Gly Ser
                165                 170                 175
Val Leu Ser Leu Gln Lys Phe Trp Gln His Arg Ile Lys Asp Tyr His
            180                 185                 190
Ser Tyr Met Leu Gln Ile Ser Lys Gln Leu Ser Glu Glu Tyr Glu Arg
        195                 200                 205
Ile Val Asn Pro Glu Lys Ala Thr Glu Asp Ala Lys Pro Val Lys Ile
    210                 215                 220
```

FIG.6C

Lys Glu Glu Pro Val Ser Asp Ile Thr Phe Pro Val Ser Glu Glu Leu
225                 230                 235                 240
Glu Ala Asp Leu Ala Ser Gly Asp Gln Ser Leu Pro Met Gly Val Leu
            245                 250                 255
Gly Ala Gln Ser Glu Arg Phe Pro Ser Asn Leu Glu Val Glu Ala Ser
            260                 265                 270
Pro Gln Ala Ser Ser Ala Glu Val Asn Ala Ser Pro Leu Trp Asn Leu
            275                 280                 285
Ala His Val Lys Met Glu Pro Gln Glu Ser Glu Glu Gly Asn Val Ser
    290                 295                 300
Gly His Gly Val Leu Gly Ser Asp Val Phe Glu Glu Pro Met Ser Gly
305                 310                 315                 320
Met Ser Glu Ala Gly Ile Pro Gln Ser Pro Asp Asp Ser Asp Ser Ser
            325                 330                 335
Tyr Gly Ser His Ser Thr Asp Ser Leu Met Gly Ser Ser Pro Val Phe
            340                 345                 350
Asn Gln Arg Cys Lys Lys Arg Met Arg Lys Ile
            355                 360

FIG.6C-1

```
atgacctcct gcctttag                                                    18
```

Met Thr Ser Cys Leu
 1           5

FIG.6D

```
atgcaccatt ccagatccgg cacagtgacc cagagagtga cttttatcgt gggaaagggg      60
aacctgtga                                                              69
```

Met His His Ser Arg Ser Gly Thr Val Thr Gln Arg Val Thr Phe Ile
 1           5                  10                  15
Val Gly Lys Gly Asn Leu
             20

FIG.6E

```
atgagagtgt cctggagacc ctaa                                             24
```

Met Arg Val Ser Trp Arg Pro
 1           5

FIG.6F

```
atgtggcaca tgagtattgc cttaagttta ccaagttgct gcgttttgct gtggaccggg      60
aggcccggct gggacagact ccttttcctg atgtga                                96
```

Met Trp His Met Ser Ile Ala Leu Ser Leu Pro Ser Cys Cys Val Leu
 1           5                  10                  15
Leu Trp Thr Gly Arg Pro Gly Trp Asp Arg Leu Leu Phe Leu Met
             20                  25                  30

FIG.6G

```
atgagtattg ccttaagttt accaagttgc tgcgttttgc tgtggaccgg gaggcccggc      60
tgggacagac tccttttcct gatgtga                                          87
```

Met Ser Ile Ala Leu Ser Leu Pro Ser Cys Cys Val Leu Leu Trp Thr
 1           5                  10                  15
Gly Arg Pro Gly Trp Asp Arg Leu Leu Phe Leu Met
             20                  25

FIG.6H

```
atggagcagg tattccatga agtgggtatt ggcagtgtgc tctccctcca gaagttctgg      60
cagcaccgca tcaaggacta tcacagttac atgctacaga ttagtaagca actctctgaa    120
gaatatgaaa ggattgtcaa tcctgagaag gccacagagg acgctaaacc tgtgaagatc    180
aaggaggaac ctgtgagcga catcactttt cctgtcagtg aggagctgga ggctgacctt    240
gcttctggag accagtcact gcctatggga gtgcttgggg ctcagagcga acgcttccca    300
tctaacctgg aggttgaagc ttcaccacag gcttcaagtg cagaggtaaa tgcttctcct    360
ctttggaatc tggcccatgt gaaaatggag cctcaagaaa gtgaagaagg caatgtctct    420
gggcatggtg tgctgggcag tgatgtcttc gaggagccta tgtcaggcat gagtgaagct    480
gggattcctc agagccctga tgactcagat agcagctatg gttcccactc cactgacagc    540
ctcatggggt cctcccctgt tttcaaccag cgctgcaaga agaggatgag gaaaatataa    600
```

Met Glu Gln Val Phe His Glu Val Gly Ile Gly Ser Val Leu Ser Leu
 1                5                      10                    15
Gln Lys Phe Trp Gln His Arg Ile Lys Asp Tyr His Ser Tyr Met Leu
                20                      25                    30
Gln Ile Ser Lys Gln Leu Ser Glu Glu Tyr Glu Arg Ile Val Asn Pro
             35                      40                    45
Glu Lys Ala Thr Glu Asp Ala Lys Pro Val Lys Ile Lys Glu Glu Pro
         50                      55                    60
Val Ser Asp Ile Thr Phe Pro Val Ser Glu Glu Leu Glu Ala Asp Leu
65                       70                    75                    80
Ala Ser Gly Asp Gln Ser Leu Pro Met Gly Val Leu Gly Ala Gln Ser
                 85                      90                    95
Glu Arg Phe Pro Ser Asn Leu Glu Val Glu Ala Ser Pro Gln Ala Ser
                100                     105                   110
Ser Ala Glu Val Asn Ala Ser Pro Leu Trp Asn Leu Ala His Val Lys
            115                     120                   125
Met Glu Pro Gln Glu Ser Glu Glu Gly Asn Val Ser Gly His Gly Val
        130                     135                   140
Leu Gly Ser Asp Val Phe Glu Glu Pro Met Ser Gly Met Ser Glu Ala
145                     150                     155                   160
Gly Ile Pro Gln Ser Pro Asp Asp Ser Asp Ser Ser Tyr Gly Ser His
                165                     170                   175
Ser Thr Asp Ser Leu Met Gly Ser Ser Pro Val Phe Asn Gln Arg Cys
            180                     185                   190
Lys Lys Arg Met Arg Lys Ile
        195

FIG 61

```
atgaagtggg tattggcagt gtgctctccc tccagaagtt ctggcagcac cgcatcaagg    60
actatcacag ttacatgcta cagattagta agcaactctc tgaagaatat gaaaggattg   120
tcaatcctga gaaggccaca gaggacgcta aacctgtga                           159
```

Met Lys Trp Val Leu Ala Val Cys Ser Pro Ser Arg Ser Ser Gly Ser
1           5               10              15
Thr Ala Ser Arg Thr Ile Thr Val Thr Cys Tyr Arg Leu Val Ser Asn
            20              25              30
Ser Leu Lys Asn Met Lys Gly Leu Ser Ile Leu Arg Arg Pro Gln Arg
        35              40              45
Thr Leu Asn Leu
        50

FIG.6J

```
atgctacaga ttagtaagca actctctgaa gaatatgaaa ggattgtcaa tcctgagaag    60
gccacagagg acgctaaacc tgtgaagatc aaggaggaac ctgtgagcga catcactttt   120
cctgtcagtg aggagctgga ggctgacctt gcttctggag accagtcact gcctatggga   180
gtgcttgggg ctcagagcga acgcttccca tctaacctgg aggttgaagc ttcaccacag   240
gcttcaagtg cagaggtaaa tgcttctcct ctttggaatc tggcccatgt gaaaatggag   300
cctcaagaaa gtgaagaagg caatgtctct gggcatggtg tgctgggcag tgatgtcttc   360
gaggagccta tgtcaggcat gagtgaagct gggattcctc agagccctga tgactcagat   420
agcagctatg gttcccactc cactgacagc ctcatggggt cctcccctgt tttcaaccag   480
cgctgcaaga agaggatgag gaaaatataa                                    510
```

Met Leu Gln Ile Ser Lys Gln Leu Ser Glu Glu Tyr Glu Arg Ile Val
1           5               10              15
Asn Pro Glu Lys Ala Thr Glu Asp Ala Lys Pro Val Lys Ile Lys Glu
            20              25              30
Glu Pro Val Ser Asp Ile Thr Phe Pro Val Ser Glu Glu Leu Glu Ala
            35              40              45
Asp Leu Ala Ser Gly Asp Gln Ser Leu Pro Met Gly Val Leu Gly Ala
        50              55              60
Gln Ser Glu Arg Phe Pro Ser Asn Leu Glu Val Glu Ala Ser Pro Gln
65              70              75              80
Ala Ser Ser Ala Glu Val Asn Ala Ser Pro Leu Trp Asn Leu Ala His
                85              90              95
Val Lys Met Glu Pro Gln Glu Ser Glu Glu Gly Asn Val Ser Gly His
            100             105             110
Gly Val Leu Gly Ser Asp Val Phe Glu Glu Pro Met Ser Gly Met Ser
        115             120             125
Glu Ala Gly Ile Pro Gln Ser Pro Asp Asp Ser Asp Ser Ser Tyr Gly
        130             135             140
Ser His Ser Thr Asp Ser Leu Met Gly Ser Ser Pro Val Phe Asn Gln
145             150             155             160
Arg Cys Lys Lys Arg Met Arg Lys Ile
                165

FIG.6K

```
atgaaaggat tgtcaatcct gagaaggcca cagaggacgc taaacctgtg a         51
```

| Met | Lys | Gly | Leu | Ser | Ile | Leu | Arg | Arg | Pro | Gln | Arg | Thr | Leu | Asn | Leu |
|---|---|---|---|---|---|---|---|---|---|---|---|---|---|---|---|
| 1 | | | | 5 | | | | | 10 | | | | | 15 | |

FIG.6L

```
atgggagtgc ttggggctca gagcgaacgc ttcccatcta acctggaggt tgaagcttca    60
ccacaggctt caagtgcaga ggtaaatgct tctcctcttt ggaatctggc catgtgaaa    120
atggagcctc aagaaagtga agaaggcaat gtctctgggc atggtgtgct gggcagtgat   180
gtcttcgagg agcctatgtc aggcatgagt gaagctggga ttcctcagag ccctgatgac   240
tcagatagca gctatggttc ccactccact gacagcctca tggggtcctc ccctgttttc   300
aaccagcgct gcaagaagag gatgaggaaa atataa                             336
```

Met Gly Val Leu Gly Ala Gln Ser Glu Arg Phe Pro Ser Asn Leu Glu
1           5                   10                  15
Val Glu Ala Ser Pro Gln Ala Ser Ser Ala Glu Val Asn Ala Ser Pro
            20                  25                  30
Leu Trp Asn Leu Ala His Val Lys Met Glu Pro Gln Glu Ser Glu Glu
            35                  40                  45
Gly Asn Val Ser Gly His Gly Val Leu Gly Ser Asp Val Phe Glu Glu
            50                  55              60
Pro Met Ser Gly Met Ser Glu Ala Gly Ile Pro Gln Ser Pro Asp Asp
65              70                  75                  80
Ser Asp Ser Ser Tyr Gly Ser His Ser Thr Asp Ser Leu Met Gly Ser
                    85                  90                  95
Ser Pro Val Phe Asn Gln Arg Cys Lys Lys Arg Met Arg Lys Ile
                100                 105                 110

FIG.6M

```
atgcttctcc tctttggaat ctggcccatg tga                              33
```

Met Leu Leu Leu Phe Gly Ile Trp Pro Met
1           5                   10

FIG.6N

```
atg gag cct caa gaa agt gaa gaa ggc aat gtc tct ggg cat ggt gtg      48
ctg ggc agt gat gtc ttc gag gag cct atg tca ggc atg agt gaa gct      96
ggg att cct cag agc cct gat gac tca gat agc agc tat ggt tcc cac     144
tcc act gac agc ctc atg ggg tcc tcc cct gtt ttc aac cag cgc tgc     192
aag aag agg atg agg aaa ata taa                                      216
```

Met Glu Pro Gln Glu Ser Glu Glu Gly Asn Val Ser Gly His Gly Val
1               5                   10                  15
Leu Gly Ser Asp Val Phe Glu Glu Pro Met Ser Gly Met Ser Glu Ala
            20                  25                  30
Gly Ile Pro Gln Ser Pro Asp Asp Ser Asp Ser Ser Tyr Gly Ser His
            35                  40                  45
Ser Thr Asp Ser Leu Met Gly Ser Ser Pro Val Phe Asn Gln Arg Cys
50                      55                  60
Lys Lys Arg Met Arg Lys Ile
65                  70

FIG. 6O

```
atgtctctgg gcatggtgtg ctgggcagtg atgtcttcga ggagcctatg tcaggcatga    60
```

Met Ser Leu Gly Met Val Cys Trp Ala Val Met Ser Ser Arg Ser Leu
1               5                   10                  15
Cys Gln Ala

FIG. 6P

```
atggtgtgct gggcagtgat gtcttcgagg agcctatgtc aggcatga               48
```

Met Val Cys Trp Ala Val Met Ser Ser Arg Ser Leu Cys Gln Ala
1               5                   10                  15

FIG 6Q

```
atgtcttcga ggagcctatg tcaggcatga                                     30
```

Met Ser Ser Arg Ser Leu Cys Gln Ala
1               5

FIG 6R

```
atgtcaggca tgagtgaagc tgggattcct cagagccctg atgactcaga tagcagctat    60
ggttcccact ccactgacag cctcatgggg tcctcccctg ttttcaacca gcgctgcaag   120
aagaggatga ggaaaatata a                                             141
```

Met Ser Gly Met Ser Glu Ala Gly Ile Pro Gln Ser Pro Asp Asp Ser
1               5                   10                  15
Asp Ser Ser Tyr Gly Ser His Ser Thr Asp Ser Leu Met Gly Ser Ser
            20                  25                  30
Pro Val Phe Asn Gln Arg Cys Lys Lys Arg Met Arg Lys Ile
            35                  40                  45

FIG 6S

```
atgagtgaag ctgggattcc tcagagccct gatgactcag atagcagcta tggttcccac   60
tccactgaca gcctcatggg gtcctcccct gttttcaacc agcgctgcaa gaagaggatg  120
aggaaaatat aa                                                      132
```

Met Ser Glu Ala Gly Ile Pro Gln Ser Pro Asp Asp Ser Asp Ser Ser
1               5                   10                  15
Tyr Gly Ser His Ser Thr Asp Ser Leu Met Gly Ser Ser Pro Val Phe
                20                  25                  30
Asn Gln Arg Cys Lys Lys Arg Met Arg Lys Ile
            35                  40

FIG.6T

```
atgactcaga tagcagctat ggttcccact ccactgacag cctcatgggg tcctcccctg   60
ttttcaacca gcgctgcaag aagaggatga                                    90
```

Met Thr Gln Ile Ala Ala Met Val Pro Thr Pro Leu Thr Ala Ser Trp
1               5                   10                  15
Gly Pro Pro Leu Phe Ser Thr Ser Ala Ala Arg Arg Gly
                20                  25

FIG.6U

```
atggttccca ctccactgac agcctcatgg ggtcctcccc tgttttcaac cagcgctgca   60
agaagaggat ga                                                       72
```

Met Val Pro Thr Pro Leu Thr Ala Ser Trp Gly Pro Pro Leu Phe Ser
1               5                   10                  15
Thr Ser Ala Ala Arg Arg Gly
                20

FIG.6V

```
atggggtcct cccctgtttt caaccagcgc tgcaagaaga ggatgaggaa aatataa      57
```

Met Gly Ser Ser Pro Val Phe Asn Gln Arg Cys Lys Lys Arg Met Arg
1               5                   10                  15
Lys Ile

FIG.6W

```
atgaggaaaa tataa                                                    15
```

Met Arg Lys Ile
1

FIG.6X

```
atgttttgtc cagacctact agacccaaca gaaaaggtta gctga                   45
```

Met Phe Cys Pro Asp Leu Leu Asp Pro Thr Glu Lys Val Ser
1               5                   10

FIG.6Y

```
atgtattttg ctgagctgta caacaggatg gcacaaaatc ctgctgatag aaataagtgt    60
aaccggccag gcacagtggc tcatgcctgt aatcccagca ttttgggagg cccaggtggg   120
tggatcatct ga                                                       132
```

Met Tyr Phe Ala Glu Leu Tyr Asn Arg Met Ala Gln Asn Pro Ala Asp
 1           5                  10                 15
Arg Asn Lys Cys Asn Arg Pro Gly Thr Val Ala His Ala Cys Asn Pro
            20                  25                 30
Ser Ile Leu Gly Gly Pro Gly Gly Trp Ile Ile
            35                  40

FIG.6Z

```
atggcacaaa atcctgctga tagaaataag tgtaaccggc caggcacagt ggctcatgcc    60
tgtaatccca gcattttggg aggcccaggt gggtggatca tctga                  105
```

Met Ala Gln Asn Pro Ala Asp Arg Asn Lys Cys Asn Arg Pro Gly Thr
 1           5                  10                 15
Val Ala His Ala Cys Asn Pro Ser Ile Leu Gly Gly Pro Gly Gly Trp
            20                  25                 30
Ile Ile

FIG.6AA

```
atgcctgtaa tcccagcatt ttgggaggcc caggtgggtg gatcatctga ggtcaggagt    60
tcgagaccag cctga                                                    75
```

Met Pro Val Ile Pro Ala Phe Trp Glu Ala Gln Val Gly Gly Ser Ser
 1           5                  10                 15
Glu Val Arg Ser Ser Arg Pro Ala
            20

FIG.6AB

```
atggaaaaaa ccccatctct actaaaaata caaaattag                           39
```

Met Glu Lys Thr Pro Ser Leu Leu Lys Ile Gln Asn
 1           5                  10

FIG.6AC

```
atgcctgtaa tcccagctac tcaggaaggc tga                                 33
```

Met Pro Val Ile Pro Ala Thr Gln Glu Gly
 1           5                  10

FIG.6AD atggatggag gtgtcggtac taaattgaat aacgagtaa                                39

Met Asp Gly Gly Val Gly Thr Lys Leu Asn Asn Glu
 1               5                      10

FIG.7A atggaggtgt cggtactaaa ttga                                                24

Met Glu Val Ser Val Leu Asn
 1               5

FIG.7B atggcctttg ccaacaaagt gaactgtttt ggttgtttta aactcatgaa gtatgggttc         60
agtggaaatg tttggaactc tgaaggattt agacaaggtt ttgaaaagga taatcatggg        120
ttagaaggaa gtgtttga                                                      138

Met Ala Phe Ala Asn Lys Val Asn Cys Phe Gly Cys Phe Lys Leu Met
 1               5                      10                      15
Lys Tyr Gly Phe Ser Gly Asn Val Trp Asn Ser Glu Gly Phe Arg Gln
                20                      25                      30
Gly Phe Glu Lys Asp Asn His Gly Leu Glu Gly Ser Val
                35                      40                      45

FIG.7C atgaagtatg gttcagtgg aaatgtttgg aactctgaag gatttagaca aggttttgaa          60
aaggataatc atgggttaga aggaagtgtt tga                                      93

Met Lys Tyr Gly Phe Ser Gly Asn Val Trp Asn Ser Glu Gly Phe Arg
 1               5                      10                      15
Gln Gly Phe Glu Lys Asp Asn His Gly Leu Glu Gly Ser Val
                20                      25                      30

FIG.7D atgggttcag tggaaatgtt tggaactctg aaggatttag acaaggtttt gaaaaggata         60
atcatgggtt ag                                                             72

Met Gly Ser Val Glu Met Phe Gly Thr Leu Lys Asp Leu Asp Lys Val
 1               5                      10                      15
Leu Lys Arg Ile Ile Met Gly
                20

FIG.7E atgtttggaa ctctgaagga tttagacaag gttttgaaaa ggataatcat gggttag          57

Met Phe Gly Thr Leu Lys Asp Leu Asp Lys Val Leu Lys Arg Ile Ile
1               5                   10                  15

FIG.7F atggtgaaac cctgtttcta taaaaaataa                                        30

Met Val Lys Pro Cys Phe Tyr Lys Lys
1               5

FIG.7G atgcctgtgg tcccagctac tgaggaggct gaggtgggag gattgcttga gcccaggagg       60
cagaggttgc agtga                                                        75

Met Pro Val Val Pro Ala Thr Glu Glu Ala Glu Val Gly Gly Leu Leu
1               5                   10                  15
Glu Pro Arg Arg Gln Arg Leu Gln
                20

FIG.7H

```
atgtgtccca tgtgggttgt gccaggtaga gaaacaggaa gtcaatcatc tgtgacagtc    60
tctattctgt cgttttgctc cttggtattt gatttgcact atatttag                108
```

Met Cys Pro Met Trp Val Val Pro Gly Arg Glu Thr Gly Ser Gln Ser
 1           5                   10                  15
Ser Val Thr Val Ser Ile Leu Ser Phe Cys Ser Leu Val Phe Asp Leu
            20                  25                  30
His Tyr Ile
       35

FIG.8A

```
atgtgggttg tgccaggtag agaaacagga agtcaatcat ctgtgacagt ctctattctg    60
tcgttttgct ccttggtatt tgatttgcac tatatttag                           99
```

Met Trp Val Val Pro Gly Arg Glu Thr Gly Ser Gln Ser Ser Val Thr
 1           5                   10                  15
Val Ser Ile Leu Ser Phe Cys Ser Leu Val Phe Asp Leu His Tyr Ile
            20                  25                  30

FIG.8B

```
atggagacct ggttcagta a                                               21
```

Met Glu Thr Trp Phe Gln
 1           5

FIG.8C

```
atgtcccacc agtggggtat agaaagcatg ctcatgaccc tgccgtgtcg tctgaggtac    60
ccgttcttat cctag                                                    75
```

Met Ser His Gln Trp Gly Ile Glu Ser Met Leu Met Thr Leu Pro Cys
 1           5                   10                  15
Arg Leu Arg Tyr Pro Phe Leu Ser
            20

FIG.8D

```
atgctcatga ccctgccgtg tcgtctgagg tacccgttct atcctag                  48
```

Met Leu Met Thr Leu Pro Cys Arg Leu Arg Tyr Pro Phe Leu Ser
 1           5                   10                  15

FIG.8E atgaccctgc cgtgtcgtct gaggtacccg ttcttatcct ag 42

Met Thr Leu Pro Cys Arg Leu Arg Tyr Pro Phe Leu Ser
1             5                      10

FIG.8F atgttatctc cttgctttgc tttttgccgt tttaaaatgt gtaattgttc cagcattcca 60
atggtcttgt gcatagcagg ggactgtaac caaaaataa 99

Met Leu Ser Pro Cys Phe Ala Phe Cys Arg Phe Lys Met Cys Asn Cys
1             5                      10                     15
Ser Ser Ile Pro Met Val Leu Cys Ile Ala Gly Asp Cys Asn Gln Lys
        20                     25                     30

FIG.8G atgtgtaatt gttccagcat tccaatggtc ttgtgcatag caggggactg taaccaaaaa 60
taa 63

Met Cys Asn Cys Ser Ser Ile Pro Met Val Leu Cys Ile Ala Gly Asp
1             5                      10                     15
Cys Asn Gln Lys
        20

FIG.8H atggtcttgt gcatagcagg ggactgtaac caaaaataa 39

Met Val Leu Cys Ile Ala Gly Asp Cys Asn Gln Lys
1             5                      10

FIG.8I atgtatttgt gtaattggtt tgaagaagtc ttgaatagct ctttactgtc ttacttgggg 60
ttgataagat ttgagtgttt gcaattttttt actaaatgta gctccaaagt cttaaatggc 120
ttgtttgttc ttaaactgtt aattgatgaa actgtgcata agtttacaat gtactaa 177

Met Tyr Leu Cys Asn Trp Phe Glu Glu Val Leu Asn Ser Ser Leu Leu
1             5                      10                     15
Ser Tyr Leu Gly Leu Ile Arg Phe Glu Cys Leu Gln Phe Phe Thr Lys
        20                     25                     30
Cys Ser Ser Lys Val Leu Asn Gly Leu Phe Val Leu Lys Leu Leu Ile
        35                     40                     45
Asp Glu Thr Val His Lys Phe Thr Met Tyr
        50                     55

FIG.8J atggcttgtt tgttcttaaa ctgttaa                                              27

Met Ala Cys Leu Phe Leu Asn Cys
 1           5

FIG.8K atgaaactgt gcataagttt acaatgtact aacttatttt gcttattata tatagtgttt         60
tattggaaat gtaa                                                            75

Met Lys Leu Cys Ile Ser Leu Gln Cys Thr Asn Leu Phe Cys Leu Leu
 1           5                   10                  15
Tyr Ile Val Phe Tyr Trp Lys Leu
                20

FIG.8L atgatgaaaa taaagattag tgtttccatt taa                                       33

Met Met Lys Ile Lys Ile Ser Val Ser Ile
 1           5                   10

FIG.8M atgaaaataa agattagtgt ttccatttaa                                           30

Met Lys Ile Lys Ile Ser Val Ser Ile
 1           5

FIG.8N atgttttatc ctcccataaa aaaaaaaaaa aaaagggcgg cc                             42

Met Phe Tyr Pro Pro Ile Lys Lys Lys Lys Lys Arg Ala Ala
 1           5                   10

FIG.8O

```
atgcccaaaa gaaagccaaa gagaagatct gccaggttgt ctgctatgct tgtgccagtt    60
acaccagagg tgaagcctaa aagaacatca agttcaagga aaatgaagac aaaaagtgat   120
atgatggaag aaaacataga tacaagtgcc caagcagttg ctgaaaccaa gcaagaagca   180
gttgttgaag aagactacaa tgaaaatgct aaaaatggag aagccaaaat tacagaggca   240
ccagcttctg aaaaagaaat tgtggaagta aaagaagaaa atattgaaga tgccacagaa   300
aagggaggag aaaagaaaga agcagtggca gcagaagtaa aaaatgaaga agaagatcag   360
aaagaagatg aagaagatca aaacgaagag aaggggaag ctggaaaaga agacaaagat    420
gaaaaagggg aagaagatgg aaaagaggat aaaaatggaa atgagaaagg agaagatgca   480
aaagagaaag aagatggaaa aaaggtgaa gacggaaaag gaaatggaga agatggaaaa    540
gagaaaggag aagatgaaaa agaggaagaa gacagaaaag aaacaggagt tggaaaagag   600
aatgaagatg gaaaagagaa gggagataaa aagaggga aagatgtaaa agtcaaagaa    660
gatgaaaaag agagagaaga tggaaaagaa gatgaaggtg gaaatgagga agaagctgga   720
aaagagaaag aagatttaaa agaagaggaa gaaggaaaag aggaagatga gatcaaagaa   780
gatgatggaa aaaagagga gccacagagt attgtttaa                          819

Met Pro Lys Arg Lys Pro Lys Arg Arg Ser Ala Arg Leu Ser Ala Met
 1               5                  10                  15
Leu Val Pro Val Thr Pro Glu Val Lys Pro Lys Arg Thr Ser Ser Ser
                20                  25                  30
Arg Lys Met Lys Thr Lys Ser Asp Met Met Glu Glu Asn Ile Asp Thr
                35                  40                  45
Ser Ala Gln Ala Val Ala Glu Thr Lys Gln Glu Ala Val Val Glu Glu
    50                  55                  60
Asp Tyr Asn Glu Asn Ala Lys Asn Gly Glu Ala Lys Ile Thr Glu Ala
65                  70                  75                  80
Pro Ala Ser Glu Lys Glu Ile Val Glu Val Lys Glu Glu Asn Ile Glu
                85                  90                  95
Asp Ala Thr Glu Lys Gly Gly Glu Lys Lys Glu Ala Val Ala Ala Glu
                100                 105                 110
Val Lys Asn Glu Glu Glu Asp Gln Lys Glu Asp Glu Glu Asp Gln Asn
            115                 120                 125
Glu Glu Lys Gly Glu Ala Gly Lys Glu Asp Lys Asp Glu Lys Gly Glu
        130                 135                 140
Glu Asp Gly Lys Glu Asp Lys Asn Gly Asn Glu Lys Gly Glu Asp Ala
145                 150                 155                 160
Lys Glu Lys Glu Asp Gly Lys Lys Gly Glu Asp Gly Lys Gly Asn Gly
                165                 170                 175
Glu Asp Gly Lys Glu Lys Gly Glu Asp Glu Lys Glu Glu Glu Asp Arg
            180                 185                 190
Lys Glu Thr Gly Val Gly Lys Glu Asn Glu Asp Gly Lys Glu Lys Gly
        195                 200                 205
```

FIG.9A

```
Asp Lys Lys Glu Gly Lys Asp Val Lys Val Lys Glu Asp Glu Lys Glu
    210              215              220
Arg Glu Asp Gly Lys Glu Asp Glu Gly Gly Asn Glu Glu Glu Ala Gly
225              230              235              240
Lys Glu Lys Glu Asp Leu Lys Glu Glu Glu Gly Lys Glu Glu Asp
                245              250              255
Glu Ile Lys Glu Asp Asp Gly Lys Lys Glu Glu Pro Gln Ser Ile Val
            260              265              270
```

FIG.9A-1

```
atgcttgtgc cagttacacc agaggtgaag cctaaaagaa catcaagttc aaggaaaatg     60
aagacaaaaa gtgatatgat ggaagaaaac atagatacaa gtgcccaagc agttgctgaa    120
accaagcaag aagcagttgt tgaagaagac tacaatgaaa atgctaaaaa tggagaagcc    180
aaaattacag aggcaccagc ttctgaaaaa gaaattgtgg aagtaaaaga agaaaatatt    240
gaagatgcca cagaaaaggg aggagaaaag aaagaagcag tggcagcaga agtaaaaaat    300
gaagaagaag atcagaaaga gatgaagaa gatcaaaacg aagagaaagg ggaagctgga    360
aaagaagaca agatgaaaaa aggggaagaa gatggaaaag aggataaaaa tggaaatgag    420
aaaggagaag atgcaaaaga gaagaagat ggaaaaaaag gtgaagacgg aaaaggaaat    480
ggagaagatg gaaagagaa aggagaagat gaaaaagagg aagaagacag aaaagaaaca    540
ggagttggaa aagagaatga agatggaaaa gagaagggag ataaaaaaga ggggaaagat    600
gtaaaagtca aagaagatga aaaagagaga gaagatggaa aagaagatga aggtggaaat    660
gaggaagaag ctggaaaaga gaaagaagat ttaaaagaag gaagaaagg aaaagaggaa    720
gatgagatca agaagatga tggaaaaaaa gaggagccac agagtattgt ttaa          774
```

```
Met Leu Val Pro Val Thr Pro Glu Val Lys Pro Lys Arg Thr Ser Ser
 1           5                  10                 15
Ser Arg Lys Met Lys Thr Lys Ser Asp Met Met Glu Glu Asn Ile Asp
             20                 25                 30
Thr Ser Ala Gln Ala Val Ala Glu Thr Lys Gln Glu Ala Val Val Glu
         35                 40                 45
Glu Asp Tyr Asn Glu Asn Ala Lys Asn Gly Glu Ala Lys Ile Thr Glu
 50                 55                 60
Ala Pro Ala Ser Glu Lys Glu Ile Val Glu Val Lys Glu Glu Asn Ile
 65                 70                 75                 80
Glu Asp Ala Thr Glu Lys Gly Gly Glu Lys Lys Glu Ala Val Ala Ala
                 85                 90                 95
Glu Val Lys Asn Glu Glu Glu Asp Gln Lys Glu Asp Glu Glu Asp Gln
                 100                105                110
Asn Glu Glu Lys Gly Glu Ala Gly Lys Glu Asp Lys Asp Glu Lys Gly
             115                120                125
Glu Glu Asp Gly Lys Glu Asp Lys Asn Gly Asn Glu Lys Gly Glu Asp
 130                135                140
Ala Lys Glu Lys Glu Asp Gly Lys Lys Gly Glu Asp Gly Lys Gly Asn
145                150                155                160
Gly Glu Asp Gly Lys Glu Lys Gly Glu Asp Glu Lys Glu Glu Glu Asp
                 165                170                175
Arg Lys Glu Thr Gly Val Gly Lys Glu Asn Glu Asp Gly Lys Glu Lys
                 180                185                190
Gly Asp Lys Lys Glu Gly Lys Asp Val Lys Val Lys Glu Asp Glu Lys
             195                200                205
Glu Arg Glu Asp Gly Lys Glu Asp Glu Gly Gly Asn Glu Glu Glu Ala
             210                215                220
Gly Lys Glu Lys Glu Asp Leu Lys Glu Glu Glu Glu Gly Lys Glu Glu
225                230                235                240
Asp Glu Ile Lys Glu Asp Asp Gly Lys Lys Glu Glu Pro Gln Ser Ile
                 245                250                255
Val
```

FIG.9B

```
atgaagacaa aaagtgatat gatggaagaa aacatagata caagtgccca agcagttgct   60
gaaaccaagc aagaagcagt tgttgaagaa gactacaatg aaaatgctaa aaatggagaa  120
gccaaaatta cagaggcacc agcttctgaa aaagaaattg tggaagtaaa agaagaaaat  180
attgaagatg ccacagaaaa gggaggagaa aagaaagaag cagtggcagc agaagtaaaa  240
aatgaagaag aagatcagaa agaagatgaa gaagatcaaa acgaagagaa aggggaagct  300
ggaaaagaag acaaagatga aaaggggaa gaagatggaa aagaggataa aaatggaaat   360
gagaaaggag aagatgcaaa agagaaagaa gatggaaaaa aaggtgaaga cggaaaagga  420
aatggagaag atggaaaaga gaaaggagaa gatgaaaaag aggaagaaga cagaaaagaa  480
acaggagttg aaaagagaa tgaagatgga aaagagaagg gagataaaaa gaggggaaa    540
gatgtaaaag tcaaagaaga tgaaaaagag agagaagatg gaaagaaga tgaaggtgga   600
aatgaggaag aagctggaaa agagaaagaa gatttaaaag aagaggaaga aggaaaagag  660
gaagatgaga tcaaagaaga tgatggaaaa aaagaggagc cacagagtat tgtttaa     717
```

```
Met Lys Thr Lys Ser Asp Met Met Glu Glu Asn Ile Asp Thr Ser Ala
 1           5               10                  15
Gln Ala Val Ala Glu Thr Lys Gln Glu Ala Val Val Glu Glu Asp Tyr
            20                  25                  30
Asn Glu Asn Ala Lys Asn Gly Glu Ala Lys Ile Thr Glu Ala Pro Ala
            35                  40                  45
Ser Glu Lys Glu Ile Val Glu Val Lys Glu Glu Asn Ile Glu Asp Ala
    50                  55                  60
Thr Glu Lys Gly Gly Glu Lys Lys Glu Ala Val Ala Ala Glu Val Lys
65                  70                  75                  80
Asn Glu Glu Glu Asp Gln Lys Glu Asp Glu Glu Asp Gln Asn Glu Glu
                85                  90                  95
Lys Gly Glu Ala Gly Lys Glu Asp Lys Asp Glu Lys Gly Glu Glu Asp
                100                 105                 110
Gly Lys Glu Asp Lys Asn Gly Asn Glu Lys Gly Glu Asp Ala Lys Glu
                115                 120                 125
Lys Glu Asp Gly Lys Lys Gly Glu Asp Gly Lys Gly Asn Gly Glu Asp
                130                 135                 140
Gly Lys Glu Lys Gly Glu Asp Glu Lys Glu Glu Glu Asp Arg Lys Glu
145                 150                 155                 160
Thr Gly Val Gly Lys Glu Asn Glu Asp Gly Lys Glu Lys Gly Asp Lys
                165                 170                 175
Lys Glu Gly Lys Asp Val Lys Val Lys Glu Asp Glu Lys Glu Arg Glu
                180                 185                 190
Asp Gly Lys Glu Asp Glu Gly Gly Asn Glu Glu Glu Ala Gly Lys Glu
                195                 200                 205
Lys Glu Asp Leu Lys Glu Glu Glu Glu Gly Lys Glu Glu Asp Glu Ile
                210                 215                 220
Lys Glu Asp Asp Gly Lys Lys Glu Glu Pro Gln Ser Ile Val
225                 230                 235
```

FIG.9C

```
atgatggaag aaaacataga tacaagtgcc caagcagttg ctgaaaccaa gcaagaagca   60
gttgttgaag aagactacaa tgaaaatgct aaaaatggag aagccaaaat tacagaggca  120
ccagcttctg aaaaagaaat tgtggaagta aaagaagaaa atattgaaga tgccacagaa  180
aagggaggag aaaagaaaga agcagtggca gcagaagtaa aaaatgaaga agaagatcag  240
aaagaagatg aagaagatca aaacgaagag aaaggggaag ctggaaaaga agacaaagat  300
gaaaaagggg aagaagatgg aaaagaggat aaaaatggaa atgagaaagg agaagatgca  360
aaagagaaag aagatggaaa aaaaggtgaa gacggaaaag gaaatggaga gatggaaaa   420
gagaaaggag aagatgaaaa agaggaagaa gacagaaaag aaacaggagt tggaaaagag  480
aatgaagatg gaaaagagaa gggagataaa aagagggga aagatgtaaa agtcaaagaa   540
gatgaaaaag agagagaaga tggaaaagaa gatgaaggtg gaaatgagga agaagctgga  600
aaagagaaag aagatttaaa agaagaggaa gaaggaaaag aggaagatga gatcaaagaa  660
gatgatggaa aaaaagagga gccacagagt attgtttaa                          699
```

```
Met Met Glu Glu Asn Ile Asp Thr Ser Ala Gln Ala Val Ala Glu Thr
 1               5                  10                  15
Lys Gln Glu Ala Val Val Glu Glu Asp Tyr Asn Glu Asn Ala Lys Asn
                20                  25                  30
Gly Glu Ala Lys Ile Thr Glu Ala Pro Ala Ser Glu Lys Glu Ile Val
                35                  40                  45
Glu Val Lys Glu Glu Asn Ile Glu Asp Ala Thr Glu Lys Gly Gly Glu
            50                  55                  60
Lys Lys Glu Ala Val Ala Ala Glu Val Lys Asn Glu Glu Glu Asp Gln
65                  70                  75                  80
Lys Glu Asp Glu Glu Asp Gln Asn Glu Glu Lys Gly Glu Ala Gly Lys
                85                  90                  95
Glu Asp Lys Asp Glu Lys Gly Glu Glu Asp Gly Lys Glu Asp Lys Asn
                100                 105                 110
Gly Asn Glu Lys Gly Glu Asp Ala Lys Glu Lys Glu Asp Gly Lys Lys
            115                 120                 125
Gly Glu Asp Gly Lys Gly Asn Gly Glu Asp Gly Lys Glu Lys Gly Glu
        130                 135                 140
Asp Glu Lys Glu Glu Glu Asp Arg Lys Glu Thr Gly Val Gly Lys Glu
145                 150                 155                 160
Asn Glu Asp Gly Lys Glu Lys Gly Asp Lys Lys Glu Gly Lys Asp Val
                165                 170                 175
Lys Val Lys Glu Asp Glu Lys Glu Arg Glu Asp Gly Lys Glu Asp Glu
                180                 185                 190
Gly Gly Asn Glu Glu Glu Ala Gly Lys Glu Lys Glu Asp Leu Lys Glu
            195                 200                 205
Glu Glu Glu Gly Lys Glu Glu Asp Glu Ile Lys Glu Asp Asp Gly Lys
        210                 215                 220
Lys Glu Glu Pro Gln Ser Ile Val
225                 230
```

FIG. 9D

```
atggaagaaa acatagatac aagtgcccaa gcagttgctg aaaccaagca agaagcagtt    60
gttgaagaag actacaatga aaatgctaaa aatggagaag ccaaaattac agaggcacca   120
gcttctgaaa aagaaattgt ggaagtaaaa gaagaaaata ttgaagatgc cacagaaaag   180
ggaggagaaa agaaagaagc agtggcagca gaagtaaaaa atgaagaaga agatcagaaa   240
gaagatgaag aagatcaaaa cgaagagaaa ggggaagctg gaaaagaaga caaagatgaa   300
aaaggggaag aagatggaaa agaggataaa aatggaaatg agaaggaga gatgcaaaa    360
gagaaagaag atggaaaaaa aggtgaagac ggaaaaggaa atggagaaga tggaaaagag   420
aaaggagaag atgaaaaaga ggaagaagac agaaaagaaa caggagttgg aaaagagaat   480
gaagatggaa aagagaaggg agataaaaaa gaggggaaag atgtaaaagt caaagaagat   540
gaaaaagaga gagaagatgg aaaagaagat gaaggtggaa atgaggaaga agctggaaaa   600
gagaaagaag atttaaaaga agaggaagaa ggaaaagagg aagatgagat caaagaagat   660
gatggaaaaa aagaggagcc acagagtatt gtttaa                            696
```

```
Met Glu Glu Asn Ile Asp Thr Ser Ala Gln Ala Val Ala Glu Thr Lys
 1               5                  10                  15
Gln Glu Ala Val Val Glu Glu Asp Tyr Asn Glu Asn Ala Lys Asn Gly
            20                  25                  30
Glu Ala Lys Ile Thr Glu Ala Pro Ala Ser Glu Lys Glu Ile Val Glu
        35                  40                  45
Val Lys Glu Glu Asn Ile Glu Asp Ala Thr Glu Lys Gly Gly Glu Lys
    50                  55                  60
Lys Glu Ala Val Ala Ala Glu Val Lys Asn Glu Glu Asp Gln Lys
65                  70                  75                  80
Glu Asp Glu Glu Asp Gln Asn Glu Glu Lys Gly Glu Ala Gly Lys Glu
                85                  90                  95
Asp Lys Asp Glu Lys Gly Glu Glu Asp Gly Lys Glu Asp Lys Asn Gly
            100                 105                 110
Asn Glu Lys Gly Glu Asp Ala Lys Glu Lys Glu Asp Gly Lys Lys Gly
        115                 120                 125
Glu Asp Gly Lys Gly Asn Gly Glu Asp Gly Lys Glu Lys Gly Glu Asp
    130                 135                 140
Glu Lys Glu Glu Glu Asp Arg Lys Glu Thr Gly Val Gly Lys Glu Asn
145                 150                 155                 160
Glu Asp Gly Lys Glu Lys Gly Asp Lys Lys Glu Gly Lys Asp Val Lys
                165                 170                 175
Val Lys Glu Asp Glu Lys Glu Arg Glu Asp Gly Lys Glu Asp Glu Gly
            180                 185                 190
Gly Asn Glu Glu Glu Ala Gly Lys Glu Lys Glu Asp Leu Lys Glu Glu
        195                 200                 205
Glu Glu Gly Lys Glu Glu Asp Glu Ile Lys Glu Asp Asp Gly Lys Lys
    210                 215                 220
Glu Glu Pro Gln Ser Ile Val
225                 230
```

FIG.9E atgaaaatgc taaaaatgga gaagccaaaa ttacagaggc accagcttct gaaaagaaa 60
ttgtggaagt aa 72

Met Lys Met Leu Lys Met Glu Lys Pro Lys Leu Gln Arg His Gln Leu
1               5                   10                  15
Leu Lys Lys Lys Leu Trp Lys
            20

FIG.9F atgctaaaaa tggagaagcc aaaattacag aggcaccagc ttctgaaaaa gaaattgtgg 60
aagtaa 66

Met Leu Lys Met Glu Lys Pro Lys Leu Gln Arg His Gln Leu Leu Lys
1               5                   10                  15
Lys Lys Leu Trp Lys
            20

FIG.9G atggagaagc caaaattaca gaggcaccag cttctgaaaa agaaattgtg gaagtaa 57

Met Glu Lys Pro Lys Leu Gln Arg His Gln Leu Leu Lys Lys Lys Leu
1               5                   10                  15
Trp Lys

FIG.9H atgccacaga aagggagga gaaaagaaag aagcagtggc agcagaagta a 51

Met Pro Gln Lys Arg Glu Glu Lys Arg Lys Lys Gln Trp Gln Gln Lys
1               5                   10                  15

FIG.9I

```
atgaagaaga agatcagaaa gaagatgaag aagatcaaaa cgaagagaaa ggggaagctg    60
gaaaagaaga caaagatgaa aaaggggaag aagatggaaa agaggataaa aatggaaatg   120
agaaaggaga agatgcaaaa gagaaagaag atggaaaaaa aggtgaagac ggaaaaggaa   180
atggagaaga tggaaaagag aaaggagaag atgaaaaaga ggaagaagac agaaaagaaa   240
caggagttgg aaaagagaat gaagatggaa aagagaaggg agataaaaaa gaggggaaag   300
atgtaa                                                              306
```

Met Lys Lys Ile Arg Lys Lys Met Lys Lys Ile Lys Thr Lys Arg
1               5                   10                  15
Lys Gly Lys Leu Glu Lys Lys Thr Lys Met Lys Lys Gly Lys Lys Met
            20                  25                  30
Glu Lys Arg Ile Lys Met Glu Met Arg Lys Glu Lys Met Gln Lys Arg
        35                  40                  45
Lys Lys Met Glu Lys Lys Val Lys Thr Glu Lys Glu Met Glu Lys Met
        50                  55                  60
Glu Lys Arg Lys Glu Lys Met Lys Lys Arg Lys Lys Thr Glu Lys Lys
65                  70                  75                  80
Gln Glu Leu Glu Lys Arg Met Lys Met Glu Lys Arg Arg Glu Ile Lys
                85                  90                  95
Lys Arg Gly Lys Met
            100

FIG.9J

```
atgaagaaga tcaaaacgaa gagaaagggg aagctggaaa agaagacaaa gatgaaaaag    60
gggaagaaga tggaaaagag gataaaaatg gaaatgagaa aggagaagat gcaaaagaga   120
aagaagatgg aaaaaaaggt gaagacggaa aaggaaatgg agaagatgga aagagaaag   180
gagaagatga aaaagaggaa gaagacagaa aagaacagg agttggaaaa gagaatgaag   240
atggaaaaga agggagat aaaaagagg ggaaagatgt aa                         282
```

Met Lys Lys Ile Lys Thr Lys Arg Lys Gly Lys Leu Glu Lys Lys Thr
1               5                   10                  15
Lys Met Lys Lys Gly Lys Lys Met Glu Lys Arg Ile Lys Met Glu Met
            20                  25                  30
Arg Lys Glu Lys Met Gln Lys Arg Lys Lys Met Glu Lys Lys Val Lys
        35                  40                  45
Thr Glu Lys Glu Met Glu Lys Met Glu Lys Arg Lys Glu Lys Met Lys
        50                  55                  60
Lys Arg Lys Lys Thr Glu Lys Lys Gln Glu Leu Glu Lys Arg Met Lys
65                  70                  75                  80
Met Glu Lys Arg Arg Glu Ile Lys Lys Arg Gly Lys Met
                85                  90

FIG.9K

```
atgaaaaagg ggaagaagat ggaaaagagg ataaaaatgg aaatgagaaa ggagaagatg        60
caaaagagaa agaagatgga aaaaaaggtg aagacggaaa aggaaatgga gaagatggaa       120
aagagaaagg agaagatgaa aaagaggaag aagacagaaa agaaacagga gttggaaaag       180
agaatgaaga tggaaaagag aagggagata aaaagaggg gaaagatgta a                 231
```

Met Lys Lys Gly Lys Lys Met Glu Lys Arg Ile Lys Met Glu Met Arg
1               5                   10                  15
Lys Glu Lys Met Gln Lys Arg Lys Lys Met Glu Lys Lys Val Lys Thr
            20                  25                  30
Glu Lys Glu Met Glu Lys Met Glu Lys Arg Lys Glu Lys Met Lys Lys
        35                  40                  45
Arg Lys Lys Thr Glu Lys Lys Gln Glu Leu Glu Lys Arg Met Lys Met
        50                  55                  60
Glu Lys Arg Arg Glu Ile Lys Lys Arg Gly Lys Met
65                  70                  75

FIG.9L

```
atggaaaaga ggataaaaat ggaaatgaga aaggagaaga tgcaaaagag aaagaagatg        60
gaaaaaaagg tgaagacgga aaaggaaatg gagaagatgg aaaagagaaa ggagaagatg       120
aaaagagga agaagacaga aaagaaacag gagttggaaa agagaatgaa gatggaaaag       180
agaagggaga taaaaagag gggaaagatg taa                                     213
```

Met Glu Lys Arg Ile Lys Met Glu Met Arg Lys Glu Lys Met Gln Lys
1               5                   10                  15
Arg Lys Lys Met Glu Lys Lys Val Lys Thr Glu Lys Glu Met Glu Lys
            20                  25                  30
Met Glu Lys Arg Lys Glu Lys Met Lys Lys Arg Lys Lys Thr Glu Lys
        35                  40                  45
Lys Gln Glu Leu Glu Lys Arg Met Lys Met Glu Lys Arg Arg Glu Ile
        50                  55                  60
Lys Lys Arg Gly Lys Met
65              70

FIG.9M

```
atggaaatga gaaaggagaa gatgcaaaag agaaagaaga tggaaaaaaa ggtgaagacg        60
gaaaggaaa tggagaagat ggaaaagaga aggagaaga tgaaaaagag gaagaagaca       120
gaaaagaaac aggagttgga aaagagaatg aagatggaaa agagaaggga gataaaaaag       180
aggggaaaga tgtaa                                                        195
```

Met Glu Met Arg Lys Glu Lys Met Gln Lys Arg Lys Lys Met Glu Lys
1               5                   10                  15
Lys Val Lys Thr Glu Lys Glu Met Glu Lys Met Glu Lys Arg Lys Glu
            20                  25                  30
Lys Met Lys Lys Arg Lys Lys Thr Glu Lys Lys Gln Glu Leu Glu Lys
        35                  40                  45
Arg Met Lys Met Glu Lys Arg Arg Glu Ile Lys Lys Arg Gly Lys Met
        50                  55                  60

FIG.9N

```
atgagaaagg agaagatgca aaagagaaag aagatggaaa aaaaggtgaa gacggaaaag      60
gaaatggaga agatggaaaa gagaaaggag aagatgaaaa agaggaagaa gacagaaaag     120
aaacaggagt tggaaaagag aatgaagatg gaaaagagaa gggagataaa aaagagggga     180
aagatgtaa                                                             189
```

Met Arg Lys Glu Lys Met Gln Lys Arg Lys Lys Met Glu Lys Lys Val
1               5                   10                  15
Lys Thr Glu Lys Glu Met Glu Lys Met Glu Lys Arg Lys Glu Lys Met
            20                  25                  30
Lys Lys Arg Lys Lys Thr Glu Lys Lys Gln Glu Leu Glu Lys Arg Met
        35                  40                  45
Lys Met Glu Lys Arg Arg Glu Ile Lys Lys Arg Gly Lys Met
50                  55                  60

FIG.9O

```
atgcaaaaga gaaagaagat ggaaaaaaag gtgaagacgg aaaaggaaat ggagaagatg      60
gaaagagaa aggagaagat gaaaagagg aagaagacag aaaagaaaca ggagttggaa      120
aagagaatga agatggaaaa gagaagggag ataaaaaaga ggggaaagat gtaa          174
```

Met Gln Lys Arg Lys Lys Met Glu Lys Lys Val Lys Thr Glu Lys Glu
1               5                   10                  15
Met Glu Lys Met Glu Lys Arg Lys Glu Lys Met Lys Lys Arg Lys Lys
            20                  25                  30
Thr Glu Lys Lys Gln Glu Leu Glu Lys Arg Met Lys Met Glu Lys Arg
        35                  40                  45
Arg Glu Ile Lys Lys Arg Gly Lys Met
50                  55

FIG.9P

```
atggaaaaaa aggtgaagac ggaaaaggaa atggagaaga tggaaaagag aaaggagaag      60
atgaaaaaga ggaagaagac agaaaagaaa caggagttgg aaaagagaat gaagatggaa     120
aagagaaggg agataaaaaa gaggggaaag atgtaa                               156
```

Met Glu Lys Lys Val Lys Thr Glu Lys Glu Met Glu Lys Met Glu Lys
1               5                   10                  15
Arg Lys Glu Lys Met Lys Lys Arg Lys Lys Thr Glu Lys Lys Gln Glu
            20                  25                  30
Leu Glu Lys Arg Met Lys Met Glu Lys Arg Arg Glu Ile Lys Lys Arg
        35                  40                  45
Gly Lys Met
50

FIG.9Q atggagaaga tggaaaagag aaaggagaag atgaaaaaga ggaagaagac agaaaagaaa    60
caggagttgg aaaagagaat gaagatggaa aagagaaggg agataaaaaa gaggggaaag   120
atgtaa                                                             126

Met Glu Lys Met Glu Lys Arg Lys Glu Lys Met Lys Lys Arg Lys Lys
1               5                   10                  15
Thr Glu Lys Lys Gln Glu Leu Glu Lys Arg Met Lys Met Glu Lys Arg
                20                  25                  30
Arg Glu Ile Lys Lys Arg Gly Lys Met
            35              40

FIG.9R atggaaaaga gaaaggagaa gatgaaaaag aggaagaaga cagaaaagaa acaggagttg    60
gaaaagagaa tgaagatgga aaagagaagg gagataaaaa agaggggaaa gatgtaa     117

Met Glu Lys Arg Lys Glu Lys Met Lys Lys Arg Lys Lys Thr Glu Lys
1               5                   10                  15
Lys Gln Glu Leu Glu Lys Arg Met Lys Met Glu Lys Arg Arg Glu Ile
                20                  25                  30
Lys Lys Arg Gly Lys Met
            35

FIG.9S atgaaaaaga ggaagaagac agaaaagaaa caggagttgg aaaagagaat gaagatggaa    60
aagagaaggg agataaaaaa gaggggaaag atgtaa                             96

Met Lys Lys Arg Lys Lys Thr Glu Lys Lys Gln Glu Leu Glu Lys Arg
1               5                   10                  15
Met Lys Met Glu Lys Arg Arg Glu Ile Lys Lys Arg Gly Lys Met
                20                  25                  30

FIG.9T atgaagatgg aaaagagaag ggagataaaa aagaggggaa agatgtaa                 48

Met Lys Met Glu Lys Arg Arg Glu Ile Lys Lys Arg Gly Lys Met
1               5                   10                  15

FIG.9U atggaaaaga gaagggagat aaaaaagagg ggaaagatgt aa                       42

Met Glu Lys Arg Arg Glu Ile Lys Lys Arg Gly Lys Met
1               5                   10

FIG.9V

```
atgaaaaaga gagagaagat ggaaaagaag atgaaggtgg aaatgaggaa gaagctggaa    60
aagagaaaga agatttaa                                                  78
```

Met Lys Lys Arg Glu Lys Met Glu Lys Lys Met Lys Val Glu Met Arg
1               5                   10                  15
Lys Lys Leu Glu Lys Arg Lys Lys Ile
            20                  25

FIG.9W

```
atggaaaaga agatgaaggt ggaaatgagg aagaagctgg aaaagagaaa gaagatttaa    60
```

Met Glu Lys Lys Met Lys Val Glu Met Arg Lys Lys Leu Glu Lys Arg
1               5                   10                  15
Lys Lys Ile

FIG.9X

```
atgaaggtgg aaatgaggaa gaagctggaa aagagaaaga agatttaa                 48
```

Met Lys Val Glu Met Arg Lys Lys Leu Glu Lys Arg Lys Lys Ile
1               5                   10                  15

FIG.9Y

```
atgaggaaga agctggaaaa gagaaagaag atttaa                              36
```

Met Arg Lys Lys Leu Glu Lys Arg Lys Lys Ile
1               5                   10

FIG.9Z

```
atgagatcaa agaagatgat ggaaaaaaag aggagccaca gagtattgtt taaaactgcc    60
ctatgtagtt tcataatttg gtaa                                           84
```

Met Arg Ser Lys Lys Met Met Glu Lys Lys Arg Ser His Arg Val Leu
1               5                   10                  15
Phe Lys Thr Ala Leu Cys Ser Phe Ile Ile Trp
            20                  25

FIG.9AA

```
atgatggaaa aaaagaggag ccacagagta ttgtttaaaa ctgccctatg tagtttcata    60
atttggtaa                                                            69
```

Met Met Glu Lys Lys Arg Ser His Arg Val Leu Phe Lys Thr Ala Leu
1               5                   10                  15
Cys Ser Phe Ile Ile Trp
            20

FIG.9AB

```
atggaaaaaa agaggagcca cagagtattg tttaaaactg ccctatgtag tttcataatt    60
tggtaa                                                                66
```

Met Glu Lys Lys Arg Ser His Arg Val Leu Phe Lys Thr Ala Leu Cys
1               5                   10                  15
Ser Phe Ile Ile Trp
                20

FIG.9AC

```
atgtaccttc atgttgtaaa gttaatagag ataaatattt ttatcaaaaa ttttataaac    60
acagcctttc tttag                                                      75
```

Met Tyr Leu His Val Val Lys Leu Ile Glu Ile Asn Ile Phe Ile Lys
1               5                   10                  15
Asn Phe Ile Asn Thr Ala Phe Leu
                20

FIG.9AD

```
atgaaacatt tatctataaa ttttgtgatt atagtagtgg aatacataga aaaaaatatg    60
ctttcaactt tgtga                                                      75
```

Met Lys His Leu Ser Ile Asn Phe Val Ile Ile Val Val Glu Tyr Ile
1               5                   10                  15
Glu Lys Asn Met Leu Ser Thr Leu
                20

FIG.9AE

```
atgctttcaa ctttgtga                                                   18
```

Met Leu Ser Thr Leu
1               5

FIG.9AF

```
atgtcaaatc tttga                                                      15
```

Met Ser Asn Leu
1

FIG.9AG

```
atgttaagag ttaaacttat ctttcccaaa tataacttta ttattagctt gggaaaaatg    60
aaattgtatt cccatttta a                                                81
```

Met Leu Arg Val Lys Leu Ile Phe Pro Lys Tyr Asn Phe Ile Ile Ser
1               5                   10                  15
Leu Gly Lys Met Lys Leu Tyr Ser His Phe
                20                  25

FIG.9AH atgaaattgt attcccattt ttaa                24

Met Lys Leu Tyr Ser His Phe
 1           5

FIG.9AI atgtttattt cagaagggca gttttga              27

Met Phe Ile Ser Glu Gly Gln Phe
 1           5

FIG.9AJ atgattgtgt tttgttatat cttcaaaaat atagctagtg aaatattgtg cttaattttt   60
ttctattgtg ttattcatga aaatatttaa                                   90

Met Ile Val Phe Cys Tyr Ile Phe Lys Asn Ile Ala Ser Glu Ile Leu
 1           5                   10                  15
Cys Leu Ile Phe Phe Tyr Cys Val Ile His Glu Asn Ile
            20                  25

FIG.9AK atgaaaatat ttaatattca ctga                24

Met Lys Ile Phe Asn Ile His
 1           5

FIG.9AL atgccatctg ataaaaaaga atag                                                        24

Met Pro Ser Asp Lys Lys Glu
 1           5

FIG.10A atggaaagtg ggactgagag ggagtcagca ggcatgctgc ggtggcggtc actccctctg    60
ccactatccc cagggaagga aaggctccgc catttgggaa agtggtttct acgtcactgg   120
acaccggttc tgagcattag tttgagaact cgttcccgaa tgtgctttcc tccctctccc   180
ctgcccacct caagtttaat aaataaggtt gtacttttct tactataa                228

Met Glu Ser Gly Thr Glu Arg Glu Ser Ala Gly Met Leu Arg Trp Arg
 1           5                   10                  15
Ser Leu Pro Leu Pro Leu Ser Pro Gly Lys Glu Arg Leu Arg His Leu
            20                  25                  30
Gly Lys Trp Phe Leu Arg His Trp Thr Pro Val Leu Ser Ile Ser Leu
            35                  40                  45
Arg Thr Arg Ser Arg Met Cys Phe Pro Pro Ser Pro Leu Pro Thr Ser
        50                  55                  60
Ser Leu Ile Asn Lys Val Val Leu Phe Leu Leu
65                  70                  75

FIG.10B atgctgcggt ggcggtcact ccctctgcca ctatccccag ggaaggaaag gctccgccat    60
ttgggaaagt ggtttctacg tcactggaca ccggttctga gcattagttt gagaactcgt   120
tcccgaatgt gctttcctcc ctctcccctg cccacctcaa gtttaataaa taaggttgta   180
cttttcttac tataa                                                    195

Met Leu Arg Trp Arg Ser Leu Pro Leu Pro Leu Ser Pro Gly Lys Glu
 1           5                   10                  15
Arg Leu Arg His Leu Gly Lys Trp Phe Leu Arg His Trp Thr Pro Val
            20                  25                  30
Leu Ser Ile Ser Leu Arg Thr Arg Ser Arg Met Cys Phe Pro Pro Ser
            35                  40                  45
Pro Leu Pro Thr Ser Ser Leu Ile Asn Lys Val Val Leu Phe Leu Leu
        50                  55                  60

FIG.10C

```
atgtgctttc ctccctctcc cctgcccacc tcaagtttaa taaataaggt tgtacttttc    60
ttactataa                                                             69
```

```
Met Cys Phe Pro Pro Ser Pro Leu Pro Thr Ser Ser Leu Ile Asn Lys
 1           5                   10                  15
Val Val Leu Phe Leu Leu
             20
```

FIG.10D

```
atgtctgtaa ctgctgtgca ctgctgtaaa cttgttagag aaaaaaataa cctgcatgtg    60
ggctcctcag ttattgagtt tttgtga                                         87
```

```
Met Ser Val Thr Ala Val His Cys Cys Lys Leu Val Arg Glu Lys Asn
 1           5                   10                  15
Asn Leu His Val Gly Ser Ser Val Ile Glu Phe Leu
             20                  25
```

FIG.10E

```
atgtgggctc ctcagttatt gagttttgt gatcctatct cagtctgggg gggaacattc     60
tcaagaggtg aaatacaaga aagcctttt ttcttggatc ttttcccgag attcaaatct    120
ccgatttccc atttggggc aagttttttt cttcaccttc aatatgagaa ttcagcgaac    180
ttgaaagaaa aatcatctgt gagttccttc aggttctcac tcatagtcat gatccttcag   240
agggaatatg cactggcgag tttaaagtaa                                     270
```

```
Met Trp Ala Pro Gln Leu Leu Ser Phe Cys Asp Pro Ile Ser Val Trp
 1           5                   10                  15
Gly Gly Thr Phe Ser Arg Gly Glu Ile Gln Glu Ser Leu Phe Phe Leu
             20                  25                  30
Asp Leu Phe Pro Arg Phe Lys Ser Pro Ile Ser His Leu Gly Ala Ser
         35                  40                  45
Phe Phe Leu His Leu Gln Tyr Glu Asn Ser Ala Asn Leu Lys Glu Lys
     50                  55                  60
Ser Ser Val Ser Ser Phe Arg Phe Ser Leu Ile Val Met Ile Leu Gln
65                   70                  75                  80
Arg Glu Tyr Ala Leu Ala Ser Leu Lys
                 85
```

FIG.10F

```
atgagaattc agcgaacttg a                                               21
```

```
Met Arg Ile Gln Arg Thr
 1           5
```

FIG.10G atgatccttc agagggaata tgcactggcg agtttaaagt aa 42

Met Ile Leu Gln Arg Glu Tyr Ala Leu Ala Ser Leu Lys
 1           5               10

FIG.10H atgcactggc gagtttaa 18

Met His Trp Arg Val
 1           5

FIG.10I atgatatttg atggtcccaa agtacggcag ctgcaaaaag tagtggaagg aaattgtcta 60
cgtgtcttgg aaaaattagt taggaatttg gatgggtaa 99

Met Ile Phe Asp Gly Pro Lys Val Arg Gln Leu Gln Lys Val Val Glu
 1           5               10              15
Gly Asn Cys Leu Arg Val Leu Glu Lys Leu Val Arg Asn Leu Asp Gly
            20              25              30

FIG.10J atggtcccaa agtacggcag ctgcaaaaag tag 33

Met Val Pro Lys Tyr Gly Ser Cys Lys Lys
 1           5               10

FIG.10K atgggtaaaa ggtacccttg ccttactcca tcttatttc ttagccccct ttga 54

Met Gly Lys Arg Tyr Pro Cys Leu Thr Pro Ser Tyr Phe Leu Ser Pro
 1           5               10              15
Leu

FIG.10L atgaaaaatt actaa 15

Met Lys Asn Tyr
 1

FIG.10M atgaaactgt gtgtacgtgt ctgtgcgtgc aacataaaaa tacagtag                48

Met Lys Leu Cys Val Arg Val Cys Ala Cys Asn Ile Lys Ile Gln
1             5                   10                  15

FIG.10N atgtggtatt aa                                                         12

Met Trp Tyr
1

FIG.10O

```
atggtttatt acccagaact ctttgtctgg gtcagtcaag aaccatttcc aaacaaggac     60
atggagggaa ggcttcctaa gggaagactt cctgtcccaa aggaagtgaa ccgcaagaag    120
aacgatgaga caaacgctgc ctccctgact ccactgggca gcagtgaact ccgctcccca   180
agaatcagtt acctccactt tttttaa                                        207
```

Met Val Tyr Tyr Pro Glu Leu Phe Val Trp Val Ser Gln Glu Pro Phe
1               5                   10                  15
Pro Asn Lys Asp Met Glu Gly Arg Leu Pro Lys Gly Arg Leu Pro Val
            20                  25                  30
Pro Lys Glu Val Asn Arg Lys Lys Asn Asp Glu Thr Asn Ala Ala Ser
        35                  40                  45
Leu Thr Pro Leu Gly Ser Ser Glu Leu Arg Ser Pro Arg Ile Ser Tyr
    50                  55                  60
Leu His Phe Phe
65

FIG.11A

```
atggagggaa ggcttcctaa gggaagactt cctgtcccaa aggaagtgaa ccgcaagaag    60
aacgatgaga caaacgctgc ctccctgact ccactgggca gcagtgaact ccgctcccca  120
agaatcagtt acctccactt tttttaa                                       147
```

Met Glu Gly Arg Leu Pro Lys Gly Arg Leu Pro Val Pro Lys Glu Val
1               5                   10                  15
Asn Arg Lys Lys Asn Asp Glu Thr Asn Ala Ala Ser Leu Thr Pro Leu
            20                  25                  30
Gly Ser Ser Glu Leu Arg Ser Pro Arg Ile Ser Tyr Leu His Phe Phe
        35                  40                  45

FIG.11B

```
atgagacaaa cgctgcctcc ctga                                           24
```

Met Arg Gln Thr Leu Pro Pro
1               5

FIG.11C

```
atggtgtatg ggtattga                                                  18
```

Met Val Tyr Gly Tyr
1               5

FIG.11D

```
atgggtattg atgaggtcat ggtatcatat atgggattttt tttctgtgta a          51
```

Met Gly Ile Asp Glu Val Met Val Ser Tyr Met Gly Phe Phe Ser Val
1               5                   10                  15

FIG.11E

```
atgaggtcat ggtatcatat atgggattttt tttctgtgta aatcatcaag tataagaaga    60
aactatggga ctctgagcct tgctttagag aatttacagt ggacaaatag gtgtcatcaa   120
accagttttt aa                                                       132
```

Met Arg Ser Trp Tyr His Ile Trp Asp Phe Phe Leu Cys Lys Ser Ser
1               5                   10                  15
Ser Ile Arg Arg Asn Tyr Gly Thr Leu Ser Leu Ala Leu Glu Asn Leu
                20                  25                  30
Gln Trp Thr Asn Arg Cys His Gln Thr Ser Phe
                35                  40

FIG.11F

```
atggtatcat atatgggatt tttttctgtg taa                                33
```

Met Val Ser Tyr Met Gly Phe Phe Ser Val
1               5                   10

FIG.11G

```
atgggattttt tttctgtgta a                                            21
```

Met Gly Phe Phe Ser Val
1               5

FIG.11H

```
atgggactct ga                                                       12
```

Met Gly Leu
1

FIG.11I

```
atgtcttcca caactcaaac tcccaccgcg ctcacacaac cggtccactc ctgccttttc    60
actcacacag ctcccgactg cttcttgcag aggctgagag tcccccccccc acctttttt   120
tcatttagat gtaacaaacc tagtagttta tgttcatcaa ttgtctgtat atctctatat   180
tttatccatg tactcttttg a                                             201
```

Met Ser Ser Thr Thr Gln Thr Pro Thr Ala Leu Thr Gln Pro Val His
1               5                   10                  15
Ser Cys Leu Phe Thr His Thr Ala Pro Asp Cys Phe Leu Gln Arg Leu
            20              25                  30
Arg Val Pro Pro Pro Pro Phe Phe Ser Phe Arg Cys Asn Lys Pro Ser
        35                  40                  45
Ser Leu Cys Ser Ser Ile Val Cys Ile Ser Leu Tyr Phe Ile His Val
    50              55                  60
Leu Phe
65

FIG.11J

```
atgttcatca attgtctgta tatctctata ttttatccat gtactctttt gatgtataga    60
agtagtttga aactcattgt ttccttgtgg taa                                 93
```

Met Phe Ile Asn Cys Leu Tyr Ile Ser Ile Phe Tyr Pro Cys Thr Leu
1               5                   10                  15
Leu Met Tyr Arg Ser Ser Leu Lys Leu Ile Val Ser Leu Trp
            20                  25                  30

FIG.11K

```
atgtactctt ttgatgtata g                                              21
```

Met Tyr Ser Phe Asp Val
1           5

FIG.11L

```
atgtatagaa gtagtttgaa actcattgtt tccttgtggt aa                       42
```

Met Tyr Arg Ser Ser Leu Lys Leu Ile Val Ser Leu Trp
1               5                   10

FIG.11M

```
atgctgccac aggacctgag acactga                                        27
```

Met Leu Pro Gln Asp Leu Arg His
1               5

FIG.11N

```
atgaatggtg ctattttgga cttttcaacat gctccttggc gaggtagctc tgatggagtt    60
attttttatt tccatgttct aagaaggtgt tggtactctg tttcccttga atgttgttct   120
ctagactgga ttgacttgtt ttccttgtgt cttcagtgtg gctttcttcc tcagtgttgt   180
aggttgagcg aatgctacca gagtgtgaga gaccattgtc tcgttggctg gcgctcacgg   240
acatgcagtc acggtagcgg gagcaatcac aaaactgtaa tttacttacc aaatctcttc   300
ctttccgtag cctcgcctgc ctga                                          324
```

Met Asn Gly Ala Ile Leu Asp Phe Gln His Ala Pro Trp Arg Gly Ser
1           5                   10                  15
Ser Asp Gly Val Ile Phe Tyr Phe His Val Leu Arg Arg Cys Trp Tyr
            20                  25                  30
Ser Val Ser Leu Glu Cys Cys Ser Leu Asp Trp Ile Asp Leu Phe Ser
        35                  40                  45
Leu Cys Leu Gln Cys Gly Phe Leu Pro Gln Cys Cys Arg Leu Ser Glu
    50                  55                  60
Cys Tyr Gln Ser Val Arg Asp His Cys Leu Val Gly Trp Arg Ser Arg
65                  70                  75                  80
Thr Cys Ser His Gly Ser Gly Ser Asn His Lys Thr Val Ile Tyr Leu
                85                  90                  95
Pro Asn Leu Phe Leu Ser Val Ala Ser Pro Ala
                100                 105

FIG.11O

```
atggtgctat tttggacttt caacatgctc cttggcgagg tagctctgat ggagttattt    60
tttatttcca tgttctaa                                                 78
```

Met Val Leu Phe Trp Thr Phe Asn Met Leu Leu Gly Glu Val Ala Leu
1           5                   10                  15
Met Glu Leu Phe Phe Ile Ser Met Phe
            20                  25

FIG.11P

```
atgctccttg gcgaggtagc tctgatggag ttatttttta tttccatgtt ctaa          54
```

Met Leu Leu Gly Glu Val Ala Leu Met Glu Leu Phe Phe Ile Ser Met
1           5                   10                  15
Phe

FIG.11Q

```
atggagttat tttttatttc catgttctaa                                    30
```

Met Glu Leu Phe Phe Ile Ser Met Phe
1           5

FIG.11R atgttgttct ctagactgga ttga     24

Met Leu Phe Ser Arg Leu Asp
1       5

FIG.11S atgctaccag agtgtgagag accattgtct cgttggctgg cgctcacgga catgcagtca     60
cggtag     66

Met Leu Pro Glu Cys Glu Arg Pro Leu Ser Arg Trp Leu Ala Leu Thr
1       5              10              15
Asp Met Gln Ser Arg
          20

FIG.11T atgcagtcac ggtag     15

Met Gln Ser Arg
1

FIG.11U atgaaaatga cacctttttcc aaatattaaa ttggaaaaca aggtctacaa aatcatgata     60
cttttttaa     69

Met Lys Met Thr Pro Phe Pro Asn Ile Lys Leu Glu Asn Lys Val Tyr
1       5              10              15
Lys Ile Met Ile Leu Phe
          20

FIG.11V atgacacctt ttccaaatat taaattggaa aacaaggtct acaaaatcat gattttttt     60
taa     63

Met Thr Pro Phe Pro Asn Ile Lys Leu Glu Asn Lys Val Tyr Lys Ile
1       5              10              15
Met Ile Leu Phe
          20

FIG.11W atgatacttt tttaa     15

Met Ile Leu Phe
1

FIG.11X atggataaac aaaaataa      18

Met Asp Lys Gln Lys
1         5

FIG.11Y atggaatgtt gttgtgttag ccagtctgaa agcccacctt aa      42

Met Glu Cys Cys Cys Val Ser Gln Ser Glu Ser Pro Pro
1         5                 10

FIG.11Z atgttgttgt gttag      15

Met Leu Leu Cys
1

FIG.11AA atgacgcatg cactgcactt cttcgttttc ttcttgctcc cccattggcc tgagtttctt      60
gtgcattact cctctccctc cttcgttaga ataggtgtat cagctgtgta a      111

Met Thr His Ala Leu His Phe Phe Val Phe Phe Leu Leu Pro His Trp
1         5                 10                15
Pro Glu Phe Leu Val His Tyr Ser Ser Pro Ser Phe Val Arg Ile Gly
            20                25               30
Val Ser Ala Val
            35

FIG.11AB atgcactgca cttcttcgtt ttcttcttgc tcccccattg gcctgagttt cttgtgcatt      60
actcctctcc ctccttcgtt agaatag      87

Met His Cys Thr Ser Ser Phe Ser Ser Cys Ser Pro Ile Gly Leu Ser
1         5                 10                15
Phe Leu Cys Ile Thr Pro Leu Pro Pro Ser Leu Glu
            20                25

FIG.11AC atgcaggctt ttgtaacagt gtga      24

Met Gln Ala Phe Val Thr Val
1         5

FIG.11AD atgcactcat ga                                                                                          12

Met His Ser
1

FIG.11AE atgacaagta cccaatgtat tttagctatt ttagtagtat tgttcaata a                                                 51

Met Thr Ser Thr Gln Cys Ile Leu Ala Ile Leu Val Val Phe Val Gln
1               5                   10                  15

FIG.11AF atgtatttta gctattttag tagtatttgt tcaataaata cgcaagctgt aaggtaa                                          57

Met Tyr Phe Ser Tyr Phe Ser Ser Ile Cys Ser Ile Asn Thr Gln Ala
1               5                   10                  15
Val Arg

FIG.11AG

```
atggaggagc tactcctctg ggaggacaga aattag                                    36
```

```
Met Glu Glu Leu Leu Leu Trp Glu Asp Arg Asn
 1           5                   10
```
FIG.12A

```
atgaaaccat tgagtttgtg ccttgtatca gaaagcaaag gagaatga                       48
```

```
Met Lys Pro Leu Ser Leu Cys Leu Val Ser Glu Ser Lys Gly Glu
 1           5                   10                  15
```
FIG.12B

```
atgaaaaagc acagctaa                                                        18
```

```
Met Lys Lys His Ser
 1           5
```
FIG.12C

```
atgggtatcc cgaggactaa tgagttttgt gggaagatca taagtaatga agttcttcac          60
tga                                                                       63
```

```
Met Gly Ile Pro Arg Thr Asn Glu Phe Cys Gly Lys Ile Ile Ser Asn
 1           5                   10                  15
Glu Val Leu His
         20
```
FIG.12D

```
atgagttttg tgggaagatc ataa                                                 24
```

```
Met Ser Phe Val Gly Arg Ser
 1           5
```
FIG.12E

```
atgaagttct tcactgattt gaagttgcgg ggacacaaaa attgtcattg a                   51
```

```
Met Lys Phe Phe Thr Asp Leu Lys Leu Arg Gly His Lys Asn Cys His
 1           5                   10                  15
```
FIG.12F atggttatgc tcttttccac cgtctttgct tcagtttcaa acttggatct ccggtatgga    60
ggggactatg attcttttgc agatgttgta caaaaattct tgaatcact gtttgcttgt   120
aatatatgcc catatgttgt attagatgga ggatgtgaca tttcagataa aaagcttaca   180
actttaaagg atagagctag agagaagatc cagatggccc attcccttc tgttggtggg   240
agtgggtatg tatgtccctt actcatccgg gaagtattca tacaggtttt gatcaagctg   300
cgggtgtgtt ttgtccagtg cttttcagaa gcagatcggg acattatgac acttgctaac   360
cattggaatt gccctgtgtt atcatcagat agtgacttt gcatttttga cctgaaaact   420
gggttttgcc cattgaatag ctttcagtgg agaaatatga acactattaa gggcacacaa   480
aactatatcc ctgccaaatg cttttccctt gatgcattct gccatcactt cagcaatatg   540
aataaagctc tactacctct ctttgcggtg ctatgtggaa atgaccatgt taatctaccc   600
atcatggaga cattcttaag taaagcgcgt cttcctcttg gagctaccag ttctaaaggg   660
aggagacacc accgaatcct gggacttctg aattggttgt ctcattttgc caaccctacc   720
gaagcactag ataatgttct gaaatacctc ccaaaaaagg atcgagaaaa tgttaaggaa   780
cttctctgct gttccatgga agaataccaa cagtcccagg tgaagctaca ggacttcttc   840
cagtgtggta cttatgtctg tccagatgcc ttgaatcttg gttaccaga atgggtatta   900
gtggctttag ctaaaggcca gctatctcct ttcatcagtg atgctttggt cctaagacgg  960
accattcttc ccacacaggt ggaaaacatg cagcaaccaa atgcccacag aatatctcag  1020
cccatcaggc aaatcatcta tgggcttctt ttaaatgcct caccacatct ggacaagaca  1080
tcctggaatg cattgcctcc tcagcctcta gctttcagtg aagtggaaag gattaataaa  1140
aatatcagaa cctcaatcat tgatgcagta gaactggcca aggatcattc tgacttaagc  1200
agattgactg agctctcctt gaggaggcgg cagatgcttc tgttagaaac cctgaaggtg  1260
aaacagacca ttctggagcc aatccctact tcactgaagt tgcccattgc tgtcagttgc  1320
tactggttgc agcacaccga gaccaaagca aagctacatc atctacaatc cttactgctc  1380
acaatgctag tgggccctt gattgccata atcaacagcc tggaaatgt ggaccctgta  1440
cccaggcagg ctcagtgtct tgctcctcgc tag                              1473

Met Val Met Leu Phe Ser Thr Val Phe Ala Ser Val Ser Asn Leu Asp
1               5                   10                  15
Leu Arg Tyr Gly Gly Asp Tyr Asp Ser Phe Ala Asp Val Val Gln Lys
            20                  25                  30
Phe Phe Glu Ser Leu Phe Ala Cys Asn Ile Cys Pro Tyr Val Val Leu
        35                  40                  45
Asp Gly Gly Cys Asp Ile Ser Asp Lys Lys Leu Thr Thr Leu Lys Asp
    50                  55                  60
Arg Ala Arg Glu Lys Ile Gln Met Ala His Ser Leu Ser Val Gly Gly
65                  70                  75                  80
Ser Gly Tyr Val Cys Pro Leu Leu Ile Arg Glu Val Phe Ile Gln Val
                85                  90                  95
Leu Ile Lys Leu Arg Val Cys Phe Val Gln Cys Phe Ser Glu Ala Asp
            100                 105                 110
Arg Asp Ile Met Thr Leu Ala Asn His Trp Asn Cys Pro Val Leu Ser
        115                 120                 125
Ser Asp Ser Asp Phe Cys Ile Phe Asp Leu Lys Thr Gly Phe Cys Pro
    130                 135                 140
Leu Asn Ser Phe Gln Trp Arg Asn Met Asn Thr Ile Lys Gly Thr Gln
145                 150                 155                 160

FIG.12G

```
Asn Tyr Ile Pro Ala Lys Cys Phe Ser Leu Asp Ala Phe Cys His His
                165                 170                 175
Phe Ser Asn Met Asn Lys Ala Leu Leu Pro Leu Phe Ala Val Leu Cys
            180                 185                 190
Gly Asn Asp His Val Asn Leu Pro Ile Met Glu Thr Phe Leu Ser Lys
        195                 200                 205
Ala Arg Leu Pro Leu Gly Ala Thr Ser Ser Lys Gly Arg Arg His His
    210                 215                 220
Arg Ile Leu Gly Leu Leu Asn Trp Leu Ser His Phe Ala Asn Pro Thr
225                 230                 235                 240
Glu Ala Leu Asp Asn Val Leu Lys Tyr Leu Pro Lys Lys Asp Arg Glu
                245                 250                 255
Asn Val Lys Glu Leu Leu Cys Cys Ser Met Glu Glu Tyr Gln Gln Ser
            260                 265                 270
Gln Val Lys Leu Gln Asp Phe Phe Gln Cys Gly Thr Tyr Val Cys Pro
        275                 280                 285
Asp Ala Leu Asn Leu Gly Leu Pro Glu Trp Val Leu Val Ala Leu Ala
    290                 295                 300
Lys Gly Gln Leu Ser Pro Phe Ile Ser Asp Ala Leu Val Leu Arg Arg
305                 310                 315                 320
Thr Ile Leu Pro Thr Gln Val Glu Asn Met Gln Gln Pro Asn Ala His
                325                 330                 335
Arg Ile Ser Gln Pro Ile Arg Gln Ile Ile Tyr Gly Leu Leu Leu Asn
            340                 345                 350
Ala Ser Pro His Leu Asp Lys Thr Ser Trp Asn Ala Leu Pro Pro Gln
        355                 360                 365
Pro Leu Ala Phe Ser Glu Val Glu Arg Ile Asn Lys Asn Ile Arg Thr
    370                 375                 380
Ser Ile Ile Asp Ala Val Glu Leu Ala Lys Asp His Ser Asp Leu Ser
385                 390                 395                 400
Arg Leu Thr Glu Leu Ser Leu Arg Arg Arg Gln Met Leu Leu Leu Glu
                405                 410                 415
Thr Leu Lys Val Lys Gln Thr Ile Leu Glu Pro Ile Pro Thr Ser Leu
            420                 425                 430
Lys Leu Pro Ile Ala Val Ser Cys Tyr Trp Leu Gln His Thr Glu Thr
        435                 440                 445
Lys Ala Lys Leu His His Leu Gln Ser Leu Leu Thr Met Leu Val
    450                 455                 460
Gly Pro Leu Ile Ala Ile Ile Asn Ser Pro Gly Asn Val Asp Pro Val
465                 470                 475                 480
Pro Arg Gln Ala Gln Cys Leu Ala Pro Arg
                485                 490
```

FIG.12G-1

<210> 374
<211> 1467
<212> DNA
<213> Homo sapiens

<400> 374
```
atgctctttt ccaccgtctt tgcttcagtt tcaaacttgg atctccggta tggaggggac    60
tatgattctt ttgcagatgt tgtacaaaaa ttctttgaat cactgtttgc ttgtaatata   120
tgcccatatg ttgtattaga tggaggatgt gacatttcag ataaaaagct tacaacttta   180
aaggatagag ctagagagaa gatccagatg gcccattccc tttctgttgg tgggagtggg   240
tatgtatgtc ccttactcat ccgggaagta ttcatacagg ttttgatcaa gctgcgggtg   300
tgttttgtcc agtgcttttc agaagcagat cgggacatta tgacacttgc taaccattgg   360
aattgccctg tgttatcatc agatagtgac ttttgcattt ttgacctgaa aactgggttt   420
tgcccattga atagctttca gtggagaaat atgaacacta ttaagggcac acaaaactat   480
atccctgcca atgcttttc ccttgatgca ttctgccatc acttcagcaa tatgaataaa   540
gctctactac ctctctttgc ggtgctatgt ggaaatgacc atgttaatct acccatcatg   600
gagacattct taagtaaagc gcgtcttcct cttggagcta ccagttctaa agggaggaga   660
caccaccgaa tcctgggact tctgaattgg ttgtctcatt ttgccaaccc taccgaagca   720
ctagataatg ttctgaaata cctcccaaaa aaggatcgag aaaatgttaa ggaacttctc   780
tgctgttcca tggaagaata ccaacagtcc caggtgaagc tacaggactt cttccagtgt   840
ggtacttatg tctgtccaga tgccttgaat cttggtttac agaatgggt attagtggct   900
ttagctaaag gccagctatc tcctttcatc agtgatgctt tggtcctaag acggaccatt   960
cttcccacac aggtggaaaa catgcagcaa ccaaatgccc acagaatatc tcagcccatc  1020
aggcaaatca tctatgggct tcttttaaat gcctcaccac atctggacaa gacatcctgg  1080
aatgcattgc ctcctcagcc tctagctttc agtgaagtgg aaaggattaa taaaaatatc  1140
agaaccctcaa tcattgatgc agtagaactg gccaaggatc attctgactt aagcagattg  1200
actgagctct ccttgaggag gcggcagatg cttctgttag aaaccctgaa ggtgaaacag  1260
accattctgg agccaatccc tacttcactg aagttgccca ttgctgtcag ttgctactgg  1320
ttgcagcaca ccgagaccaa agcaaagcta catcatctac aatccttact gctcacaatg  1380
ctagtggggc ccttgattgc cataatcaac agccctggaa atgtggaccc tgtacccagg  1440
caggctcagt gtcttgctcc tcgctag                                       1467
```

<210> 375
<211> 488
<212> PRT
<213> Homo sapiens

<400> 375
```
Met Leu Phe Ser Thr Val Phe Ala Ser Val Ser Asn Leu Asp Leu Arg
 1               5                  10                  15
Tyr Gly Gly Asp Tyr Asp Ser Phe Ala Asp Val Val Gln Lys Phe Phe
                20                  25                  30
Glu Ser Leu Phe Ala Cys Asn Ile Cys Pro Tyr Val Val Leu Asp Gly
            35                  40                  45
Gly Cys Asp Ile Ser Asp Lys Lys Leu Thr Thr Leu Lys Asp Arg Ala
        50                  55                  60
Arg Glu Lys Ile Gln Met Ala His Ser Leu Ser Val Gly Gly Ser Gly
65                  70                  75                  80
Tyr Val Cys Pro Leu Leu Ile Arg Glu Val Phe Ile Gln Val Leu Ile
                85                  90                  95
Lys Leu Arg Val Cys Phe Val Gln Cys Phe Ser Glu Ala Asp Arg Asp
               100                 105                 110
Ile Met Thr Leu Ala Asn His Trp Asn Cys Pro Val Leu Ser Ser Asp
           115                 120                 125
Ser Asp Phe Cys Ile Phe Asp Leu Lys Thr Gly Phe Cys Pro Leu Asn
       130                 135                 140
Ser Phe Gln Trp Arg Asn Met Asn Thr Ile Lys Gly Thr Gln Asn Tyr
145                 150                 155                 160
Ile Pro Ala Lys Cys Phe Ser Leu Asp Ala Phe Cys His His Phe Ser
               165                 170                 175
```

FIG.12H

```
Asn Met Asn Lys Ala Leu Leu Pro Leu Phe Ala Val Leu Cys Gly Asn
        180                 185                 190
Asp His Val Asn Leu Pro Ile Met Glu Thr Phe Leu Ser Lys Ala Arg
        195                 200                 205
Leu Pro Leu Gly Ala Thr Ser Ser Lys Gly Arg Arg His His Arg Ile
    210                 215                 220
Leu Gly Leu Leu Asn Trp Leu Ser His Phe Ala Asn Pro Thr Glu Ala
225                 230                 235                 240
Leu Asp Asn Val Leu Lys Tyr Leu Pro Lys Lys Asp Arg Glu Asn Val
                245                 250                 255
Lys Glu Leu Leu Cys Cys Ser Met Glu Glu Tyr Gln Gln Ser Gln Val
            260                 265                 270
Lys Leu Gln Asp Phe Phe Gln Cys Gly Thr Tyr Val Cys Pro Asp Ala
            275                 280                 285
Leu Asn Leu Gly Leu Pro Glu Trp Val Leu Val Ala Leu Ala Lys Gly
    290                 295                 300
Gln Leu Ser Pro Phe Ile Ser Asp Ala Leu Val Leu Arg Arg Thr Ile
305                 310                 315                 320
Leu Pro Thr Gln Val Glu Asn Met Gln Gln Pro Asn Ala His Arg Ile
                325                 330                 335
Ser Gln Pro Ile Arg Gln Ile Ile Tyr Gly Leu Leu Leu Asn Ala Ser
            340                 345                 350
Pro His Leu Asp Lys Thr Ser Trp Asn Ala Leu Pro Pro Gln Pro Leu
        355                 360                 365
Ala Phe Ser Glu Val Glu Arg Ile Asn Lys Asn Ile Arg Thr Ser Ile
        370                 375                 380
Ile Asp Ala Val Glu Leu Ala Lys Asp His Ser Asp Leu Ser Arg Leu
385                 390                 395                 400
Thr Glu Leu Ser Leu Arg Arg Arg Gln Met Leu Leu Leu Glu Thr Leu
                405                 410                 415
Lys Val Lys Gln Thr Ile Leu Glu Pro Ile Pro Thr Ser Leu Lys Leu
            420                 425                 430
Pro Ile Ala Val Ser Cys Tyr Trp Leu Gln His Thr Glu Thr Lys Ala
        435                 440                 445
Lys Leu His His Leu Gln Ser Leu Leu Leu Thr Met Leu Val Gly Pro
    450                 455                 460
Leu Ile Ala Ile Ile Asn Ser Pro Gly Asn Val Asp Pro Val Pro Arg
465                 470                 475                 480
Gln Ala Gln Cys Leu Ala Pro Arg
            485
```

FIG.12H-1

```
atggagggga ctatgattct tttgcagatg ttgtacaaaa attctttgaa tcactgtttg    60
cttgtaatat atgcccatat gttgtattag                                     90
```

Met Glu Gly Thr Met Ile Leu Leu Gln Met Leu Tyr Lys Asn Ser Leu
1               5                   10                  15
Asn His Cys Leu Leu Val Ile Tyr Ala His Met Leu Tyr
            20                  25

FIG.12I

```
atgattcttt tgcagatgtt gtacaaaaat tctttgaatc actgtttgct tgtaatatat    60
gcccatatgt tgtattag                                                  78
```

Met Ile Leu Leu Gln Met Leu Tyr Lys Asn Ser Leu Asn His Cys Leu
1               5                   10                  15
Leu Val Ile Tyr Ala His Met Leu Tyr
            20                  25

FIG.12J

```
atgttgtaca aaaattcttt gaatcactgt ttgcttgtaa tatatgccca tatgttgtat    60
tag                                                                  63
```

Met Leu Tyr Lys Asn Ser Leu Asn His Cys Leu Leu Val Ile Tyr Ala
1               5                   10                  15
His Met Leu Tyr
            20

FIG.12K

```
atgcccatat gttgtattag atggaggatg tga                                 33
```

Met Pro Ile Cys Cys Ile Arg Trp Arg Met
1               5                   10

FIG.12L

```
atgttgtatt ag                                                        12
```

Met Leu Tyr
1

FIG.12M

```
atggaggatg tgacatttca gataaaaagc ttacaacttt aa                       42
```

Met Glu Asp Val Thr Phe Gln Ile Lys Ser Leu Gln Leu
1               5                   10

FIG.12N

```
atggcccatt ccctttctgt tggtgggagt gggtatgtat gtcccttact catccgggaa    60
gtattcatac aggttttgat caagctgcgg gtgtgttttg tccagtgctt ttcagaagca   120
gatcgggaca ttatgacact tgctaaccat tggaattgcc ctgtgttatc atcagatagt   180
gacttttgca tttttgacct gaaaactggg ttttgcccat tgaatagctt tcagtggaga   240
aatatgaaca ctattaaggg cacacaaaac tatatccctg ccaaatgctt ttcccttgat   300
gcattctgcc atcacttcag caatatgaat aaagctctac tacctctctt tgcggtgcta   360
tgtggaaatg accatgttaa tctacccatc atggagacat tcttaagtaa agcgcgtctt   420
cctcttggag ctaccagttc taaagggagg agacaccacc gaatcctggg acttctgaat   480
tggttgtctc attttgccaa ccctaccgaa gcactagata atgttctgaa atacctccca   540
aaaaaggatc gagaaaatgt taaggaactt ctctgctgtt ccatggaaga ataccaacag   600
tcccaggtga agctacagga cttcttccag tgtggtactt atgtctgtcc agatgccttg   660
aatcttggtt taccagaatg ggtattagtg ctttagcta aaggccagct atctcctttc   720
atcagtgatg ctttggtcct aagacggacc attcttccca cacaggtgga aaacatgcag   780
caaccaaatg cccacagaat atctcagccc atcaggcaaa tcatctatgg gcttcttta   840
aatgcctcac acatctggac aagacatcc tggaatgcat tgcctcctca gcctctagct   900
ttcagtgaag tggaaaggat taataaaaat atcagaacct caatcattga tgcagtagaa   960
ctggccaagg atcattctga cttaagcaga ttgactgagc tctccttgag gaggcggcag  1020
atgcttctgt tagaaaccct gaaggtgaaa cagaccattc tggagccaat ccctacttca  1080
ctgaagttgc ccattgctgt cagttgctac tggttgcagc acaccgagac caaagcaaag  1140
ctacatcatc tacaatcctt actgctcaca atgctagtgg ggcccttgat tgccataatc  1200
aacagccctg gaaatgtgga ccctgtaccc aggcaggctc agtgtcttgc tcctcgctag  1260
```

```
Met Ala His Ser Leu Ser Val Gly Gly Ser Gly Tyr Val Cys Pro Leu
 1               5                  10                  15
Leu Ile Arg Glu Val Phe Ile Gln Val Leu Ile Lys Leu Arg Val Cys
                20                  25                  30
Phe Val Gln Cys Phe Ser Glu Ala Asp Arg Asp Ile Met Thr Leu Ala
                35                  40                  45
Asn His Trp Asn Cys Pro Val Leu Ser Ser Asp Ser Asp Phe Cys Ile
        50                  55                  60
Phe Asp Leu Lys Thr Gly Phe Cys Pro Leu Asn Ser Phe Gln Trp Arg
65                  70                  75                  80
Asn Met Asn Thr Ile Lys Gly Thr Gln Asn Tyr Ile Pro Ala Lys Cys
                85                  90                  95
Phe Ser Leu Asp Ala Phe Cys His His Phe Ser Asn Met Asn Lys Ala
                100                 105                 110
Leu Leu Pro Leu Phe Ala Val Leu Cys Gly Asn Asp His Val Asn Leu
                115                 120                 125
Pro Ile Met Glu Thr Phe Leu Ser Lys Ala Arg Leu Pro Leu Gly Ala
        130                 135                 140
Thr Ser Ser Lys Gly Arg Arg His His Arg Ile Leu Gly Leu Leu Asn
145                 150                 155                 160
Trp Leu Ser His Phe Ala Asn Pro Thr Glu Ala Leu Asp Asn Val Leu
                165                 170                 175
Lys Tyr Leu Pro Lys Lys Asp Arg Glu Asn Val Lys Glu Leu Leu Cys
                180                 185                 190
Cys Ser Met Glu Glu Tyr Gln Gln Ser Gln Val Lys Leu Gln Asp Phe
                195                 200                 205
```

FIG. 120

```
Phe Gln Cys Gly Thr Tyr Val Cys Pro Asp Ala Leu Asn Leu Gly Leu
    210                 215                 220
Pro Glu Trp Val Leu Val Ala Leu Ala Lys Gly Gln Leu Ser Pro Phe
225                 230                 235                 240
Ile Ser Asp Ala Leu Val Leu Arg Arg Thr Ile Leu Pro Thr Gln Val
                245                 250                 255
Glu Asn Met Gln Gln Pro Asn Ala His Arg Ile Ser Gln Pro Ile Arg
                260                 265                 270
Gln Ile Ile Tyr Gly Leu Leu Leu Asn Ala Ser Pro His Leu Asp Lys
            275                 280                 285
Thr Ser Trp Asn Ala Leu Pro Pro Gln Pro Leu Ala Phe Ser Glu Val
290                 295                 300
Glu Arg Ile Asn Lys Asn Ile Arg Thr Ser Ile Ile Asp Ala Val Glu
305                 310                 315                 320
Leu Ala Lys Asp His Ser Asp Leu Ser Arg Leu Thr Glu Leu Ser Leu
                325                 330                 335
Arg Arg Arg Gln Met Leu Leu Leu Glu Thr Leu Lys Val Lys Gln Thr
                340                 345                 350
Ile Leu Glu Pro Ile Pro Thr Ser Leu Lys Leu Pro Ile Ala Val Ser
            355                 360                 365
Cys Tyr Trp Leu Gln His Thr Glu Thr Lys Ala Lys Leu His His Leu
    370                 375                 380
Gln Ser Leu Leu Leu Thr Met Leu Val Gly Pro Leu Ile Ala Ile Ile
385                 390                 395                 400
Asn Ser Pro Gly Asn Val Asp Pro Val Pro Arg Gln Ala Gln Cys Leu
                405                 410                 415
Ala Pro Arg
```

FIG. 12O-1

```
atgtatgtcc cttactcatc cgggaagtat tcatacaggt tttga            45
```

```
Met Tyr Val Pro Tyr Ser Ser Gly Lys Tyr Ser Tyr Arg Phe
1               5                   10
```

FIG. 12P

```
atgtccctta ctcatccggg aagtattcat acaggttttg atcaagctgc gggtgtgttt    60
tgtccagtgc ttttcagaag cagatcggga cattatgaca cttgctaa             108
```

```
Met Ser Leu Thr His Pro Gly Ser Ile His Thr Gly Phe Asp Gln Ala
1               5                   10                  15
Ala Gly Val Phe Cys Pro Val Leu Phe Arg Ser Arg Ser Gly His Tyr
                20                  25                  30
Asp Thr Cys
        35
```

FIG. 12Q

```
atgacacttg ctaaccattg gaattgccct gtgttatcat cagatagtga cttttgcatt    60
tttgacctga aaactgggtt ttgcccattg aatagctttc agtggagaaa tatgaacact   120
attaagggca cacaaaacta tatccctgcc aaatgctttt cccttgatgc attctgccat   180
cacttcagca atatgaataa agctctacta cctctctttg cggtgctatg tggaaatgac   240
catgttaatc tacccatcat ggagacattc ttaagtaaag cgcgtcttcc tcttggagct   300
accagttcta aagggaggag acaccaccga atcctgggac ttctgaattg gttgtctcat   360
tttgccaacc ctaccgaagc actagataat gttctgaaat acctcccaaa aaaggatcga   420
gaaaatgtta aggaacttct ctgctgttcc atggaagaat accaacagtc ccaggtgaag   480
ctacaggact tcttccagtg tggtacttat gtctgtccag atgccttgaa tcttggttta   540
ccagaatggg tattagtggc tttagctaaa ggccagctat ctcctttcat cagtgatgct   600
ttggtcctaa gacggaccat tcttcccaca caggtggaaa acatgcagca accaaatgcc   660
cacagaatat ctcagcccat caggcaaatc atctatgggc ttcttttaaa tgcctcacca   720
catctggaca agacatcctg gaatgcattg cctcctcagc ctctagcttt cagtgaagtg   780
gaaaggatta ataaaaatat cagaacctca atcattgatg cagtagaact ggccaaggat   840
cattctgact taagcagatt gactgagctc tccttgagga ggcggcagat gcttctgtta   900
gaaaccctga aggtgaaaca gaccattctg gagccaatcc ctacttcact gaagttgccc   960
attgctgtca gttgctactg gttgcagcac accgagacca aagcaaagct acatcatcta  1020
caatccttac tgctcacaat gctagtgggg cccttgattg ccataatcaa cagccctgga  1080
aatgtggacc ctgtacccag gcaggctcag tgtcttgctc ctcgctag             1128
```

| Met | Thr | Leu | Ala | Asn | His | Trp | Asn | Cys | Pro | Val | Leu | Ser | Ser | Asp | Ser |
|---|---|---|---|---|---|---|---|---|---|---|---|---|---|---|---|
| 1 | | | | 5 | | | | 10 | | | | | 15 | | |

Asp Phe Cys Ile Phe Asp Leu Lys Thr Gly Phe Cys Pro Leu Asn Ser
                20              25              30
Phe Gln Trp Arg Asn Met Asn Thr Ile Lys Gly Thr Gln Asn Tyr Ile
            35              40              45
Pro Ala Lys Cys Phe Ser Leu Asp Ala Phe Cys His His Phe Ser Asn
        50              55              60
Met Asn Lys Ala Leu Leu Pro Leu Phe Ala Val Leu Cys Gly Asn Asp
65              70              75              80
His Val Asn Leu Pro Ile Met Glu Thr Phe Leu Ser Lys Ala Arg Leu
                85              90              95
Pro Leu Gly Ala Thr Ser Ser Lys Gly Arg Arg His His Arg Ile Leu
            100             105             110
Gly Leu Leu Asn Trp Leu Ser His Phe Ala Asn Pro Thr Glu Ala Leu
        115             120             125
Asp Asn Val Leu Lys Tyr Leu Pro Lys Lys Asp Arg Glu Asn Val Lys
130             135             140
Glu Leu Leu Cys Cys Ser Met Glu Glu Tyr Gln Gln Ser Gln Val Lys
145             150             155             160
Leu Gln Asp Phe Phe Gln Cys Gly Thr Tyr Val Cys Pro Asp Ala Leu
                165             170             175
Asn Leu Gly Leu Pro Glu Trp Val Leu Val Ala Leu Ala Lys Gly Gln
            180             185             190
Leu Ser Pro Phe Ile Ser Asp Ala Leu Val Leu Arg Arg Thr Ile Leu
        195             200             205
Pro Thr Gln Val Glu Asn Met Gln Gln Pro Asn Ala His Arg Ile Ser
210             215             220

FIG.12R

```
Gln Pro Ile Arg Gln Ile Ile Tyr Gly Leu Leu Leu Asn Ala Ser Pro
225             230             235                 240
His Leu Asp Lys Thr Ser Trp Asn Ala Leu Pro Pro Gln Pro Leu Ala
            245             250             255
Phe Ser Glu Val Glu Arg Ile Asn Lys Asn Ile Arg Thr Ser Ile Ile
            260             265             270
Asp Ala Val Glu Leu Ala Lys Asp His Ser Asp Leu Ser Arg Leu Thr
            275             280             285
Glu Leu Ser Leu Arg Arg Gln Met Leu Leu Leu Glu Thr Leu Lys
290             295             300
Val Lys Gln Thr Ile Leu Glu Pro Ile Pro Thr Ser Leu Lys Leu Pro
305             310             315             320
Ile Ala Val Ser Cys Tyr Trp Leu Gln His Thr Glu Thr Lys Ala Lys
            325             330             335
Leu His His Leu Gln Ser Leu Leu Leu Thr Met Leu Val Gly Pro Leu
            340             345             350
Ile Ala Ile Ile Asn Ser Pro Gly Asn Val Asp Pro Val Pro Arg Gln
            355             360             365
Ala Gln Cys Leu Ala Pro Arg
370             375
```

FIG.12R-1

```
atgaacacta ttaagggcac acaaaactat atccctgcca aatgctttc ccttgatgca        60
ttctgccatc acttcagcaa tatgaataaa gctctactac ctctctttgc ggtgctatgt      120
ggaaatgacc atgttaatct acccatcatg gagacattct taagtaaagc gcgtcttcct     180
cttggagcta ccagttctaa agggaggaga caccaccgaa tcctgggact tctgaattgg     240
ttgtctcatt ttgccaaccc taccgaagca ctagataatg ttctgaaata cctcccaaaa     300
aaggatcgag aaaatgttaa ggaacttctc tgctgttcca tggaagaata ccaacagtcc     360
caggtgaagc tacaggactt cttccagtgt ggtacttatg tctgtccaga tgccttgaat     420
cttggtttac cagaatgggt attagtggct ttagctaaag gccagctatc tcctttcatc     480
agtgatgctt tggtcctaag acggaccatt cttcccacac aggtggaaaa catgcagcaa     540
ccaaatgccc acagaatatc tcagcccatc aggcaaatca tctatgggct tcttttaaat    600
gcctcaccac atctggacaa gacatcctgg aatgcattgc ctcctcagcc tctagctttc    660
agtgaagtgg aaaggattaa taaaaatatc agaacctcaa tcattgatgc agtagaactg    720
gccaaggatc attctgactt aagcagattg actgagctct ccttgaggag gcggcagatg    780
cttctgttag aaaccctgaa ggtgaaacag accattctgg agccaatccc tacttcactg    840
aagttgccca ttgctgtcag ttgctactgg ttgcagcaca ccgagaccaa agcaaagcta    900
catcatctac aatccttact gctcacaatg ctagtggggc ccttgattgc cataatcaac    960
agccctggaa atgtggaccc tgtacccagg caggctcagt gtcttgctcc tcgctag      1017
```

FIG.12S

Met Asn Thr Ile Lys Gly Thr Gln Asn Tyr Ile Pro Ala Lys Cys Phe
1               5                   10                  15
Ser Leu Asp Ala Phe Cys His His Phe Ser Asn Met Asn Lys Ala Leu
            20                  25                  30
Leu Pro Leu Phe Ala Val Leu Cys Gly Asn Asp His Val Asn Leu Pro
            35                  40                  45
Ile Met Glu Thr Phe Leu Ser Lys Ala Arg Leu Pro Leu Gly Ala Thr
50                      55                  60
Ser Ser Lys Gly Arg Arg His His Arg Ile Leu Gly Leu Leu Asn Trp
65                  70                      75                  80
Leu Ser His Phe Ala Asn Pro Thr Glu Ala Leu Asp Asn Val Leu Lys
                85                  90                  95
Tyr Leu Pro Lys Lys Asp Arg Glu Asn Val Lys Glu Leu Leu Cys Cys
            100                 105                 110
Ser Met Glu Glu Tyr Gln Gln Ser Gln Val Lys Leu Gln Asp Phe Phe
            115                 120                 125
Gln Cys Gly Thr Tyr Val Cys Pro Asp Ala Leu Asn Leu Gly Leu Pro
    130                 135                 140
Glu Trp Val Leu Val Ala Leu Ala Lys Gly Gln Leu Ser Pro Phe Ile
145                 150                 155                 160
Ser Asp Ala Leu Val Leu Arg Arg Thr Ile Leu Pro Thr Gln Val Glu
                165                 170                 175
Asn Met Gln Gln Pro Asn Ala His Arg Ile Ser Gln Pro Ile Arg Gln
            180                 185                 190
Ile Ile Tyr Gly Leu Leu Leu Asn Ala Ser Pro His Leu Asp Lys Thr
        195                 200                 205
Ser Trp Asn Ala Leu Pro Pro Gln Pro Leu Ala Phe Ser Glu Val Glu
    210                 215                 220
Arg Ile Asn Lys Asn Ile Arg Thr Ser Ile Ile Asp Ala Val Glu Leu
225                 230                 235                 240
Ala Lys Asp His Ser Asp Leu Ser Arg Leu Thr Glu Leu Ser Leu Arg
            245                 250                 255
Arg Arg Gln Met Leu Leu Leu Glu Thr Leu Lys Val Lys Gln Thr Ile
            260                 265                 270
Leu Glu Pro Ile Pro Thr Ser Leu Lys Leu Pro Ile Ala Val Ser Cys
            275                 280                 285
Tyr Trp Leu Gln His Thr Glu Thr Lys Ala Lys Leu His His Leu Gln
        290                 295                 300
Ser Leu Leu Leu Thr Met Leu Val Gly Pro Leu Ile Ala Ile Ile Asn
305                 310                 315                 320
Ser Pro Gly Asn Val Asp Pro Val Pro Arg Gln Ala Gln Cys Leu Ala
                325                 330                 335
Pro Arg

FIG.12S-1 atgcttttcc cttga                                                            15

Met Leu Phe Pro
 1

FIG.12T atgcattctg ccatcacttc agcaatatga                                            30

Met His Ser Ala Ile Thr Ser Ala Ile
 1            5

FIG.12U

| | | | | | |
|---|---|---|---|---|---|
| atgaataaag | ctctactacc | tctctttgcg | gtgctatgtg | gaaatgacca | tgttaatcta | 60
| cccatcatgg | agacattctt | aagtaaagcg | cgtcttcctc | ttggagctac | cagttctaaa | 120
| gggaggagac | accaccgaat | cctgggactt | ctgaattggt | tgtctcattt | tgccaaccct | 180
| accgaagcac | tagataatgt | tctgaaatac | ctcccaaaaa | aggatcgaga | aaatgttaag | 240
| gaacttctct | gctgttccat | ggaagaatac | caacagtccc | aggtgaagct | acaggacttc | 300
| ttccagtgtg | gtacttatgt | ctgtccagat | gccttgaatc | ttggtttacc | agaatgggta | 360
| ttagtggctt | tagctaaagg | ccagctatct | cctttcatca | gtgatgcttt | ggtcctaaga | 420
| cggaccattc | ttcccacaca | ggtggaaaac | atgcagcaac | caaatgccca | cagaatatct | 480
| cagcccatca | ggcaaatcat | ctatgggctt | cttttaaatg | cctcaccaca | tctggacaag | 540
| acatcctgga | atgcattgcc | tcctcagcct | ctagctttca | gtgaagtgga | aaggattaat | 600
| aaaaatatca | gaacctcaat | cattgatgca | gtagaactgg | ccaaggatca | ttctgactta | 660
| agcagattga | ctgagctctc | cttgaggagg | cggcagatgc | ttctgttaga | aaccctgaag | 720
| gtgaaacaga | ccattctgga | gccaatccct | acttcactga | agttgcccat | tgctgtcagt | 780
| tgctactggt | tgcagcacac | cgagaccaaa | gcaaagctac | atcatctaca | atccttactg | 840
| ctcacaatgc | tagtggggcc | cttgattgcc | ataatcaaca | gccctggaaa | tgtggaccct | 900
| gtacccaggc | aggctcagtg | tcttgctcct | cgctag | | | 936

FIG.12V

```
Met Asn Lys Ala Leu Leu Pro Leu Phe Ala Val Leu Cys Gly Asn Asp
 1           5                   10                  15
His Val Asn Leu Pro Ile Met Glu Thr Phe Leu Ser Lys Ala Arg Leu
            20                  25                  30
Pro Leu Gly Ala Thr Ser Ser Lys Gly Arg Arg His His Arg Ile Leu
            35                  40                  45
Gly Leu Leu Asn Trp Leu Ser His Phe Ala Asn Pro Thr Glu Ala Leu
 50                      55                  60
Asp Asn Val Leu Lys Tyr Leu Pro Lys Lys Asp Arg Glu Asn Val Lys
65                  70                      75                  80
Glu Leu Leu Cys Cys Ser Met Glu Glu Tyr Gln Gln Ser Gln Val Lys
                85                  90                  95
Leu Gln Asp Phe Phe Gln Cys Gly Thr Tyr Val Cys Pro Asp Ala Leu
                100                 105                 110
Asn Leu Gly Leu Pro Glu Trp Val Leu Val Ala Leu Ala Lys Gly Gln
            115                 120                 125
Leu Ser Pro Phe Ile Ser Asp Ala Leu Val Leu Arg Arg Thr Ile Leu
            130                 135                 140
Pro Thr Gln Val Glu Asn Met Gln Gln Pro Asn Ala His Arg Ile Ser
145                 150                 155                 160
Gln Pro Ile Arg Gln Ile Ile Tyr Gly Leu Leu Leu Asn Ala Ser Pro
                165                 170                 175
His Leu Asp Lys Thr Ser Trp Asn Ala Leu Pro Pro Gln Pro Leu Ala
            180                 185                 190
Phe Ser Glu Val Glu Arg Ile Asn Lys Asn Ile Arg Thr Ser Ile Ile
            195                 200                 205
Asp Ala Val Glu Leu Ala Lys Asp His Ser Asp Leu Ser Arg Leu Thr
210                 215                 220
Glu Leu Ser Leu Arg Arg Arg Gln Met Leu Leu Leu Glu Thr Leu Lys
225                 230                 235                 240
Val Lys Gln Thr Ile Leu Glu Pro Ile Pro Thr Ser Leu Lys Leu Pro
                245                 250                 255
Ile Ala Val Ser Cys Tyr Trp Leu Gln His Thr Glu Thr Lys Ala Lys
                260                 265                 270
Leu His His Leu Gln Ser Leu Leu Thr Met Leu Val Gly Pro Leu
            275                 280                 285
Ile Ala Ile Ile Asn Ser Pro Gly Asn Val Asp Pro Val Pro Arg Gln
            290                 295                 300
Ala Gln Cys Leu Ala Pro Arg
305                 310
```

FIG.12V-1 atgtggaaat ga　　　　　　　　　　　　　　　　　　　　　　　　　　12

Met Trp Lys
1

FIG.12W atgaccatgt taatctaccc atcatggaga cattcttaa　　　　　　　　39

Met Thr Met Leu Ile Tyr Pro Ser Trp Arg His Ser
1　　　　　　5　　　　　　　　　　10

FIG.12X atgttaatct acccatcatg gagacattct taa　　　　　　　　　　33

Met Leu Ile Tyr Pro Ser Trp Arg His Ser
1　　　　　5　　　　　　　　　10

FIG.12Y

```
atggagacat tcttaagtaa agcgcgtctt cctcttggag ctaccagttc taaagggagg    60
agacaccacc gaatcctggg acttctgaat tggttgtctc attttgccaa ccctaccgaa   120
gcactagata atgttctgaa ataccctcca aaaaggatc  gagaaaatgt taaggaactt   180
ctctgctgtt ccatggaaga ataccaacag tcccaggtga agctacagga cttcttccag   240
tgtggtactt atgtctgtcc agatgccttg aatcttggtt taccagaatg ggtattagtg   300
gctttagcta aaggccagct atctcctttc atcagtgatg ctttggtcct aagacggacc   360
attcttccca cacaggtgga aaacatgcag caaccaaatg cccacagaat atctcagccc   420
atcaggcaaa tcatctatgg gcttctttta aatgcctcac cacatctgga caagacatcc   480
tggaatgcat tgcctcctca gcctctagct ttcagtgaag tggaaaggat taataaaaat   540
atcagaacct caatcattga tgcagtagaa ctggccaagg atcattctga cttaagcaga   600
ttgactgagc tctccttgag gaggcggcag atgcttctgt tagaaaccct gaaggtgaaa   660
cagaccattc tggagccaat ccctacttca ctgaagttgc ccattgctgt cagttgctac   720
tggttgcagc acaccgagac caaagcaaag ctacatcatc tacaatcctt actgctcaca   780
atgctagtgg ggcccttgat tgccataatc aacagccctg gaaatgtgga ccctgtaccc   840
aggcaggctc agtgtcttgc tcctcgctag                                    870
```

FIG.12Z

Met Glu Thr Phe Leu Ser Lys Ala Arg Leu Pro Leu Gly Ala Thr Ser
1               5                   10                  15
Ser Lys Gly Arg Arg His His Arg Ile Leu Gly Leu Leu Asn Trp Leu
            20                  25                  30
Ser His Phe Ala Asn Pro Thr Glu Ala Leu Asp Asn Val Leu Lys Tyr
            35                  40                  45
Leu Pro Lys Lys Asp Arg Glu Asn Val Lys Glu Leu Leu Cys Cys Ser
        50                  55                  60
Met Glu Glu Tyr Gln Gln Ser Gln Val Lys Leu Gln Asp Phe Phe Gln
65                  70                  75                  80
Cys Gly Thr Tyr Val Cys Pro Asp Ala Leu Asn Leu Gly Leu Pro Glu
                85                  90                  95
Trp Val Leu Val Ala Leu Ala Lys Gly Gln Leu Ser Pro Phe Ile Ser
                100                 105                 110
Asp Ala Leu Val Leu Arg Arg Thr Ile Leu Pro Thr Gln Val Glu Asn
            115                 120                 125
Met Gln Gln Pro Asn Ala His Arg Ile Ser Gln Pro Ile Arg Gln Ile
            130                 135                 140
Ile Tyr Gly Leu Leu Leu Asn Ala Ser Pro His Leu Asp Lys Thr Ser
145                 150                 155                 160
Trp Asn Ala Leu Pro Pro Gln Pro Leu Ala Phe Ser Glu Val Glu Arg
                165                 170                 175
Ile Asn Lys Asn Ile Arg Thr Ser Ile Ile Asp Ala Val Glu Leu Ala
            180                 185                 190
Lys Asp His Ser Asp Leu Ser Arg Leu Thr Glu Leu Ser Leu Arg Arg
            195                 200                 205
Arg Gln Met Leu Leu Leu Glu Thr Leu Lys Val Lys Gln Thr Ile Leu
        210                 215                 220
Glu Pro Ile Pro Thr Ser Leu Lys Leu Pro Ile Ala Val Ser Cys Tyr
225                 230                 235                 240
Trp Leu Gln His Thr Glu Thr Lys Ala Lys Leu His His Leu Gln Ser
                245                 250                 255
Leu Leu Leu Thr Met Leu Val Gly Pro Leu Ile Ala Ile Ile Asn Ser
            260                 265                 270
Pro Gly Asn Val Asp Pro Val Pro Arg Gln Ala Gln Cys Leu Ala Pro
        275                 280                 285
Arg

FIG.12Z-1 atgttaagga acttctctgc tgttccatgg aagaatacca acagtcccag gtga    54

Met Leu Arg Asn Phe Ser Ala Val Pro Trp Lys Asn Thr Asn Ser Pro
1               5                   10                  15
Arg

FIG.12AA

```
atggaagaat accaacagtc ccaggtgaag ctacaggact tcttccagtg tggtacttat      60
gtctgtccag atgccttgaa tcttggttta ccagaatggg tattagtggc tttagctaaa     120
ggccagctat ctcctttcat cagtgatgct ttggtcctaa gacggaccat tcttcccaca     180
caggtggaaa acatgcagca accaaatgcc cacagaatat ctcagcccat caggcaaatc     240
atctatgggc ttctttaaa tgcctcacca catctggaca agacatcctg gaatgcattg      300
cctcctcagc ctctagcttt cagtgaagtg gaaaggatta ataaaaatat cagaacctca     360
atcattgatg cagtagaact ggccaaggat cattctgact taagcagatt gactgagctc     420
tccttgagga ggcggcagat gcttctgtta gaaaccctga aggtgaaaca gaccattctg     480
gagccaatcc ctacttcact gaagttgccc attgctgtca gttgctactg gttgcagcac     540
accgagacca aagcaaagct acatcatcta caatccttac tgctcacaat gctagtgggg     600
cccttgattg ccataatcaa cagccctgga aatgtggacc ctgtacccag gcaggctcag     660
tgtcttgctc ctcgctag                                                   678
```

| | | | | | | | | | | | | | |
|---|---|---|---|---|---|---|---|---|---|---|---|---|---|
|Met|Glu|Glu|Tyr|Gln|Gln|Ser|Gln|Val|Lys|Leu|Gln|Asp|Phe|Phe|Gln|
|1| | | |5| | | | |10| | | | |15|
|Cys|Gly|Thr|Tyr|Val|Cys|Pro|Asp|Ala|Leu|Asn|Leu|Gly|Leu|Pro|Glu|
| | | |20| | | | |25| | | | |30| | |
|Trp|Val|Leu|Val|Ala|Leu|Ala|Lys|Gly|Gln|Leu|Ser|Pro|Phe|Ile|Ser|
| | |35| | | | |40| | | | |45| | | |
|Asp|Ala|Leu|Val|Leu|Arg|Arg|Thr|Ile|Leu|Pro|Thr|Gln|Val|Glu|Asn|
| |50| | | | |55| | | | |60| | | | |
|Met|Gln|Gln|Pro|Asn|Ala|His|Arg|Ile|Ser|Gln|Pro|Ile|Arg|Gln|Ile|
|65| | | | |70| | | | |75| | | | |80|
|Ile|Tyr|Gly|Leu|Leu|Leu|Asn|Ala|Ser|Pro|His|Leu|Asp|Lys|Thr|Ser|
| | | | |85| | | | |90| | | | |95| |
|Trp|Asn|Ala|Leu|Pro|Pro|Gln|Pro|Leu|Ala|Phe|Ser|Glu|Val|Glu|Arg|
| | | |100| | | | |105| | | | |110| | |
|Ile|Asn|Lys|Asn|Ile|Arg|Thr|Ser|Ile|Ile|Asp|Ala|Val|Glu|Leu|Ala|
| | |115| | | | |120| | | | |125| | | |
|Lys|Asp|His|Ser|Asp|Leu|Ser|Arg|Leu|Thr|Glu|Leu|Ser|Leu|Arg|Arg|
| |130| | | | |135| | | | |140| | | | |
|Arg|Gln|Met|Leu|Leu|Leu|Glu|Thr|Leu|Lys|Val|Lys|Gln|Thr|Ile|Leu|
|145| | | | |150| | | | |155| | | | |160|
|Glu|Pro|Ile|Pro|Thr|Ser|Leu|Lys|Leu|Pro|Ile|Ala|Val|Ser|Cys|Tyr|
| | | | |165| | | | |170| | | | |175| |
|Trp|Leu|Gln|His|Thr|Glu|Thr|Lys|Ala|Lys|Leu|His|His|Leu|Gln|Ser|
| | | |180| | | | |185| | | | |190| | |
|Leu|Leu|Leu|Thr|Met|Leu|Val|Gly|Pro|Leu|Ile|Ala|Ile|Ile|Asn|Ser|
| | |195| | | | |200| | | | |205| | | |
|Pro|Gly|Asn|Val|Asp|Pro|Val|Pro|Arg|Gln|Ala|Gln|Cys|Leu|Ala|Pro|
| |210| | | | |215| | | | |220| | | | |
|Arg| | | | | | | | | | | | | | | |
|225| | | | | | | | | | | | | | | |

FIG.12AB atgtctgtcc agatgccttg a            21

Met Ser Val Gln Met Pro
1              5

FIG.12AC atgggtatta gtggctttag ctaa          24

Met Gly Ile Ser Gly Phe Ser
1              5

FIG.12AD atgctttggt cctaa                    15
Met Leu Trp Ser
1

FIG.12AE

```
atgcagcaac caaatgccca cagaatatct cagcccatca ggcaaatcat ctatgggctt    60
cttttaaatg cctcaccaca tctggacaag acatcctgga atgcattgcc tcctcagcct   120
ctagctttca gtgaagtgga aaggattaat aaaaatatca gaacctcaat cattgatgca   180
gtagaactgg ccaaggatca ttctgactta agcagattga ctgagctctc cttgaggagg   240
cggcagatgc ttctgttaga aaccctgaag gtgaaacaga ccattctgga gccaatccct   300
acttcactga agttgcccat tgctgtcagt tgctactggt tgcagcacac cgagaccaaa   360
gcaaagctac atcatctaca atccttactg ctcacaatgc tagtggggcc cttgattgcc   420
ataatcaaca gccctggaaa tgtggaccct gtacccaggc aggctcagtg tcttgctcct   480
cgctag                                                              486
```

```
Met Gln Gln Pro Asn Ala His Arg Ile Ser Gln Pro Ile Arg Gln Ile
 1               5                  10                  15
Ile Tyr Gly Leu Leu Leu Asn Ala Ser Pro His Leu Asp Lys Thr Ser
                20                  25                  30
Trp Asn Ala Leu Pro Pro Gln Pro Leu Ala Phe Ser Glu Val Glu Arg
            35                  40                  45
Ile Asn Lys Asn Ile Arg Thr Ser Ile Ile Asp Ala Val Glu Leu Ala
        50                  55                  60
Lys Asp His Ser Asp Leu Ser Arg Leu Thr Glu Leu Ser Leu Arg Arg
65                  70                  75                  80
Arg Gln Met Leu Leu Leu Glu Thr Leu Lys Val Lys Gln Thr Ile Leu
                85                  90                  95
Glu Pro Ile Pro Thr Ser Leu Lys Leu Pro Ile Ala Val Ser Cys Tyr
            100                 105                 110
Trp Leu Gln His Thr Glu Thr Lys Ala Lys Leu His His Leu Gln Ser
        115                 120                 125
Leu Leu Leu Thr Met Leu Val Gly Pro Leu Ile Ala Ile Ile Asn Ser
    130                 135                 140
Pro Gly Asn Val Asp Pro Val Pro Arg Gln Ala Gln Cys Leu Ala Pro
145                 150                 155                 160
Arg
```

FIG. 12AF

```
atgcccacag aatatctcag cccatcaggc aaatcatcta tgggcttctt ttaa           54
```

```
Met Pro Thr Glu Tyr Leu Ser Pro Ser Gly Lys Ser Ser Met Gly Phe
 1               5                  10                  15
Phe
```

FIG. 12AG

```
atgggcttct tttaa                                                     15
```

```
Met Gly Phe Phe
 1
```

FIG. 12AH atgcctcacc acatctggac aagacatcct ggaatgcatt gcctcctcag cctctag    57

Met Pro His His Ile Trp Thr Arg His Pro Gly Met His Cys Leu Leu
 1               5                   10                  15
Ser Leu

FIG.12AI atgcattgcc tcctcagcct ctag    24

Met His Cys Leu Leu Ser Leu
 1               5

FIG.12AJ atgcttctgt tagaaaccct gaaggtgaaa cagaccattc tggagccaat ccctacttca    60
ctgaagttgc ccattgctgt cagttgctac tggttgcagc acaccgagac caaagcaaag   120
ctacatcatc tacaatcctt actgctcaca atgctagtgg ggcccttgat tgccataatc   180
aacagccctg gaaatgtgga ccctgtaccc aggcaggctc agtgtcttgc tcctcgctag   240

Met Leu Leu Leu Glu Thr Leu Lys Val Lys Gln Thr Ile Leu Glu Pro
 1               5                   10                  15
Ile Pro Thr Ser Leu Lys Leu Pro Ile Ala Val Ser Cys Tyr Trp Leu
               20                   25                  30
Gln His Thr Glu Thr Lys Ala Lys Leu His His Leu Gln Ser Leu Leu
               35                   40                  45
Leu Thr Met Leu Val Gly Pro Leu Ile Ala Ile Ile Asn Ser Pro Gly
    50                   55                  60
Asn Val Asp Pro Val Pro Arg Gln Ala Gln Cys Leu Ala Pro Arg
 65                  70                  75

FIG.12AK atgctagtgg ggcccttgat tgccataatc aacagccctg gaaatgtgga ccctgtaccc    60
aggcaggctc agtgtcttgc tcctcgctag    90

Met Leu Val Gly Pro Leu Ile Ala Ile Ile Asn Ser Pro Gly Asn Val
 1               5                   10                  15
Asp Pro Val Pro Arg Gln Ala Gln Cys Leu Ala Pro Arg
               20                  25

FIG.12AL atgtggaccc tgtacccagg caggctcagt gtcttgctcc tcgctagttg gtaa    54

Met Trp Thr Leu Tyr Pro Gly Arg Leu Ser Val Leu Leu Leu Ala Ser
 1               5                   10                  15
Trp

FIG.12AM

```
atggtgctaa gatgttgtat gcagagttcc aaagagtga
   39
```

Met Val Leu Arg Cys Cys Met Gln Ser Ser Lys Glu
 1           5                    10

FIG.12AN

```
atgttgtatg cagagttcca aagagtgaag gcgcagacac ggctgggcac aagactggac    60
ttagacacag ctcacatctt ctgtcagtgg cagtcctgtc tccagatggg gatgtatctc   120
aaccagctgc tgtccactcc tctcccagag ccagacctaa ctcgactgta cagtggaagc   180
ctggtgcacg gactatgcca gcaactgcta gcatcgacct ctgtagaaag tctcctgagc   240
atatgtcctg aggctaagca actttatgaa tatctattca atgcccacaa ggtcatatgc   300
ccccgctga                                                           309
```

Met Leu Tyr Ala Glu Phe Gln Arg Val Lys Ala Gln Thr Arg Leu Gly
 1           5                    10                   15
Thr Arg Leu Asp Leu Asp Thr Ala His Ile Phe Cys Gln Trp Gln Ser
             20                  25                   30
Cys Leu Gln Met Gly Met Tyr Leu Asn Gln Leu Leu Ser Thr Pro Leu
             35                  40                   45
Pro Glu Pro Asp Leu Thr Arg Leu Tyr Ser Gly Ser Leu Val His Gly
             50                  55                   60
Leu Cys Gln Gln Leu Leu Ala Ser Thr Ser Val Glu Ser Leu Leu Ser
65                   70                   75                   80
Ile Cys Pro Glu Ala Lys Gln Leu Tyr Glu Tyr Leu Phe Asn Ala His
                     85                  90                   95
Lys Val Ile Cys Pro Arg
                     100

FIG.12AO

```
atgcagagtt ccaaagagtg a                                              21
```

Met Gln Ser Ser Lys Glu
 1           5

FIG.12AP

```
atggggatgt atctcaacca gctgctgtcc actcctctcc cagagccaga cctaactcga    60
ctgtacagtg gaagcctggt gcacggacta tgccagcaac tgctagcatc gacctctgta   120
gaaagtctcc tgagcatatg tcctgaggct aagcaacttt atgaatatct attcaatgcc   180
cacaaggtca tatgcccccg ctga                                          204
```

Met Gly Met Tyr Leu Asn Gln Leu Leu Ser Thr Pro Leu Pro Glu Pro
1               5                   10                  15
Asp Leu Thr Arg Leu Tyr Ser Gly Ser Leu Val His Gly Leu Cys Gln
            20                  25                  30
Gln Leu Leu Ala Ser Thr Ser Val Glu Ser Leu Leu Ser Ile Cys Pro
        35                  40                  45
Glu Ala Lys Gln Leu Tyr Glu Tyr Leu Phe Asn Ala His Lys Val Ile
    50                  55                  60
Cys Pro Arg
65

FIG.12AQ

```
atgtatctca accagctgct gtccactcct ctcccagagc cagacctaac tcgactgtac    60
agtggaagcc tggtgcacgg actatgccag caactgctag catcgacctc tgtagaaagt   120
ctcctgagca tatgtcctga ggctaagcaa ctttatgaat atctattcaa tgcccacaag   180
gtcatatgcc ccgctga                                                  198
```

Met Tyr Leu Asn Gln Leu Leu Ser Thr Pro Leu Pro Glu Pro Asp Leu
1               5                   10                  15
Thr Arg Leu Tyr Ser Gly Ser Leu Val His Gly Leu Cys Gln Gln Leu
            20                  25                  30
Leu Ala Ser Thr Ser Val Glu Ser Leu Leu Ser Ile Cys Pro Glu Ala
        35                  40                  45
Lys Gln Leu Tyr Glu Tyr Leu Phe Asn Ala His Lys Val Ile Cys Pro
    50                  55                  60
Arg
65

FIG.12AR

```
atgccagcaa ctgctagcat cgacctctgt agaaagtctc ctgagcatat gtcctga       57
```

Met Pro Ala Thr Ala Ser Ile Asp Leu Cys Arg Lys Ser Pro Glu His
1               5                   10                  15
Met Ser

FIG.12AS

```
atgaatatct attcaatgcc cacaaggtca tatgcccccg ctgaaatatt cctaccaaaa     60
ggtagatcaa attcaaaaaa aaaaaggcag aagaaacaga ataccagctg ttctaagaac   120
agagggagaa ccactgcaca caccaagtgt tggtatgagg gaaacaaccg gtttgggttg   180
ttaatggttg aaaacttaga ggaacatagt gaggcctcca acattgaata a            231
```

```
Met Asn Ile Tyr Ser Met Pro Thr Arg Ser Tyr Ala Pro Ala Glu Ile
 1               5                  10                  15
Phe Leu Pro Lys Gly Arg Ser Asn Ser Lys Lys Arg Gln Lys Lys
           20                  25                  30
Gln Asn Thr Ser Cys Ser Lys Asn Arg Gly Arg Thr Thr Ala His Thr
       35                      40                      45
Lys Cys Trp Tyr Glu Gly Asn Asn Arg Phe Gly Leu Leu Met Val Glu
   50                      55                      60
Asn Leu Glu Glu His Ser Glu Ala Ser Asn Ile Glu
65                  70                  75
```

FIG.12AT

```
atgcccacaa ggtcatatgc ccccgctgaa atattcctac caaaaggtag atcaaattca     60
aaaaaaaaaa ggcagaagaa acagaatacc agctgttcta agaacagagg gagaaccact   120
gcacacacca agtgttggta tgagggaaac aaccggtttg ggttgttaat ggttgaaaac   180
ttagaggaac atagtgaggc ctccaacatt gaataa                             216
```

```
Met Pro Thr Arg Ser Tyr Ala Pro Ala Glu Ile Phe Leu Pro Lys Gly
 1               5                  10                  15
Arg Ser Asn Ser Lys Lys Lys Arg Gln Lys Lys Gln Asn Thr Ser Cys
           20                  25                  30
Ser Lys Asn Arg Gly Arg Thr Thr Ala His Thr Lys Cys Trp Tyr Glu
       35                      40                      45
Gly Asn Asn Arg Phe Gly Leu Leu Met Val Glu Asn Leu Glu Glu His
   50                      55                      60
Ser Glu Ala Ser Asn Ile Glu
65                  70
```

FIG.12AU

```
atgcccccgc tgaaatattc ctaccaaaag gtagatcaaa ttcaaaaaaa aaaaggcaga     60
agaaacagaa taccagctgt tctaagaaca gagggagaac cactgcacac accaagtgtt   120
ggtatgaggg aaacaaccgg tttgggttgt taa                                153
```

```
Met Pro Pro Leu Lys Tyr Ser Tyr Gln Lys Val Asp Gln Ile Gln Lys
 1               5                  10                  15
Lys Lys Gly Arg Arg Asn Arg Ile Pro Ala Val Leu Arg Thr Glu Gly
           20                  25                  30
Glu Pro Leu His Thr Pro Ser Val Gly Met Arg Glu Thr Thr Gly Leu
       35                      40                      45
Gly Cys
   50
```

FIG 12AV atgagggaaa caaccggttt gggttgttaa　　　　　　　　　　　　　　　　30

Met Arg Glu Thr Thr Gly Leu Gly Cys
 1               5

FIG.12AW atggttgaaa acttagagga acatagtgag gcctccaaca ttgaataa　　　　48

Met Val Glu Asn Leu Glu Glu His Ser Glu Ala Ser Asn Ile Glu
 1               5                  10                  15

FIG.12AX atgtatttaa tataa　　　　　　　　　　　　　　　　　　　　　15

Met Tyr Leu Ile
 1

FIG.12AY

```
atgcgccccg gccctgcccc ttggccctgc ccctgtcccc gggctgcgtc gggacctgcc    60
agaccccct cccgggtcct gagcccgaac tcccagagct cacccgcggg tgaccggggg    120
ccagcccagg agggcgggtg gtttgtgcga gttcccttgc cacgcggggc cccggcccca   180
tcaagtccct ctggggacgt ccccgtcgga aaccggaaaa agcagttcca gttaattgtg   240
tga                                                                 243
```

```
Met Arg Pro Gly Pro Ala Pro Trp Pro Cys Pro Cys Pro Arg Ala Ala
 1               5                  10                  15
Ser Gly Pro Ala Arg Pro Pro Ser Arg Val Leu Ser Pro Asn Ser Gln
                20                  25                  30
Ser Ser Pro Ala Gly Asp Arg Gly Pro Ala Gln Glu Gly Gly Trp Phe
            35                  40                  45
Val Arg Val Pro Leu Pro Arg Gly Ala Pro Ala Pro Ser Ser Pro Ser
        50                  55                  60
Gly Asp Val Pro Val Gly Asn Arg Lys Lys Gln Phe Gln Leu Ile Val
65                  70                  75                  80
```

FIG.13

COMPOSITIONS AND METHODS FOR DIAGNOSING AND TREATING CONDITIONS, DISORDERS, OR DISEASES INVOLVING CELL DEATH

TABLE OF CONTENTS

1 INTRODUCTION
2 BACKGROUND OF THE INVENTION
  2.1 Mechanisms which Lead to Cell Death
  2.2 Selected Factors and Conditions which Inhibit Cell Death Mechanisms
3 SUMMARY OF THE INVENTION
  3.1 Definitions
4 BRIEF DESCRIPTION OF THE FIGURES
5 DETAILED DESCRIPTION OF THE INVENTION
  5.1 The Protective Sequences
  5.2 Protein Products of the Protective Sequences
  5.3 Antibodies to the Protective Sequence Products
  5.4 Uses of the Protective Sequences, Protective Sequence Products and Antibodies
    5.4.1 Composition and Methods for the Treatment of Conditions, Disorders, or Diseases Involving Cell Death
      5.4.1.1 Examples of Conditions, Disorders, or Diseases Involving Cell Death
      5.4.1.2 Modulatory Antisense, Ribozyme and Triple Helix Approaches
      5.4.1.3 Gene Replacement Therapy
      5.4.1.4 Detection of Protective Nucleic Acid Molecules
      5.4.1.5 Detection of Protective Sequence Products
    5.4.2 Screening Assays for Compounds which Interact with Protective Sequence Products or Modulate Protective Sequence Activity
      5.4.2.1 In Vitro Screening Assays for Compounds which Bind to Protective Sequence Products
      5.4.2.2 Assays for Proteins which Interact with Protective Sequence Products
      5.4.2.3 Assays for Compounds which Interfere with or Potentiate Protective Sequence Products Macromolecule Interaction
      5.4.2.4 Assays for the Identification of Compounds which Modulate Conditions, Disorders, or Diseases Involving Cell Death
    5.4.3 Additional Uses for the Protective Sequences, Protective Sequence Products, or Their Regulatory Elements
  5.5 Pharmaceutical Preparations and Methods of Administration
    5.5.1 Effective Dose
    5.5.2 Formulations and Use
6 EXAMPLE: SEQUENCE AND CHARACTERIZATION OF PROTECTIVE SEQUENCES
  6.1 Materials and Methods
    6.1.1 Preparation of DNA
    6.1.2 Sequence Characterization of the DNA
    6.1.3 Sequence Comparison
    6.1.4 Immuno-Cytochemistry Protocol for the Characterization of Protected Cells
  6.2 Results
    6.2.1 Protective sequence CNI-0071
    6.2.2 Protective sequence CNI-00712
    6.2.3 Protective sequence CNI-00714
    6.2.4 Protective sequence CNI-00715
    6.2.5 Protective sequence CNI-00716
    6.2.6 Protective sequence CNI-00717
    6.2.7 Protective sequence CNI-00720
    6.2.8 Protective sequence CNI-00721
    6.2.9 Protective sequence CNI-00723
    6.2.10 Protective sequence CNI-00724
7 DEPOSIT OF MICROORGANISMS
8 REFERENCES CITED

1 INTRODUCTION

The present invention relates to compositions and methods for the treatment and diagnosis of conditions, disorders, or diseases involving cell death, including, but not limited to, neurological disorders such as stroke. Nucleic acids are described herein which, when introduced into a cell either predisposed to undergo cell death or in the process of undergoing cell death, prevent, delay, or rescue the cell from death relative to a corresponding cell into which no exogenous nucleic acids have been introduced Such nucleic acids are referred to as "protective sequences". Protective sequences or their products are identified by their ability to prevent, delay, or rescue a cell, cells, tissues, organs, or organisms from dying. Protective sequences or their products are also identified via their ability to interact with other genes or gene products involved in conditions or disorders involving cell death.

The invention further includes recombinant DNA molecules and cloning vectors comprising protective sequences, and host cells and host organisms engineered to contain such DNA molecules and cloning vectors. The present invention further relates to protective sequence products and to antibodies directed against such protective sequence products.

The protective sequences identified, their products, or antibodies may be used diagnostically, prophylactically, therapeutically or as targets for therapeutic intervention. In this regard, the present invention provides methods for the identification and prophylactic or therapeutic use of compounds in the treatment and diagnosis of conditions, disorders, or diseases involving cell death. Additionally, methods are provided for the diagnostic monitoring of patients undergoing clinical evaluation for the treatment of conditions or disorders involving cell death, for monitoring the efficacy of compounds in clinical trials and for identifying subjects who may be predisposed to such conditions, disorders, or diseases involving cell death.

2 BACKGROUND OF THE INVENTION

2.1 Mechanisms which Lead to Cell Death

It is widely recognized that at least two distinct cell death mechanisms exist for mammalian cells. These two mechanisms are necrosis and apoptosis, and are significant components of numerous conditions, disorders and disease states.

Necrosis plays an important physiologic role in signaling the presence of certain conditions. When cells die as a result of necrosis, the dying cells release substances that activate the body's immune response in a local, and in some cases widespread, reaction to the necrosis-inducing condition. This response is important in, for example, bacterial infection.

Experimental evidence in a wide variety of cells throughout the body has revealed that every cell can initiate a program of self-destruction, called apoptosis. This program can be initiated by a wide variety of natural and unnatural events. There are at least four distinct pathways for executing this program of cell death, and it is virtually certain that dozens, if not hundreds, of different intracellular biochemical cascades interact with each pathway. It is equally likely that certain cell types, such as cells in the heart or neurons, will utilize specialized signaling pathways that are not generally represented elsewhere in the body. However, since cell death is neither always necessary nor desired, it would be desirable to manipulate the manner in which cells start their death process. In some circumstances, preventing, delaying, or rescuing cells from death would either alleviate the disease or allow more time for definitive treatment to be administered to the patient. An example of this situation is brain cell death caused by ischemic stroke: preventing, delaying, or rescuing cells from death until the blood supply to the brain could be restored would greatly reduce, if not eliminate, the possibility of a person's death and/or long-term disability from stroke (Lee J M, et al. Nature 1999, 399(supp): A7–A14; Tarkowski E, et al. Stroke 1999, 30(2): 321–7; Pulera M R, et al. Stroke 1998, 29(12): 2622–30). In still other circumstances, the failure of cells to die may itself lead to disease such as cancer (Hetts S W. JAMA 1998, 297(4): 300–7).

Cell death plays an important role in the normal function of mammalian organisms. While it may seem counterintuitive for cells to have death as a normal part of their life cycle, controlled and physiologically appropriate cell death is important in regulating both the absolute and relative numbers of cells of a specific type. (Hetts S W. JAMA 1998, 297(4): 300–7; Garcia I, et al. Science 1992, 258(5080): 302–4). When the mechanism of apoptosis does not function properly and normal cell death does not occur, the resulting disease is characterized by unregulated cellular proliferation, as occurs in a neoplastic disease or an autoimmune disease (Hetts S W. JAMA 1998, 297(4): 300–7; Yachida M, et al. Clin Exp Immunol 1999, 116(1): 140–5).

One method for regulating cell death involves manipulating the threshold at which the process of cell death begins. This threshold varies significantly by cell type, tissue type, the type of injury or insult suffered by the cell, cellular maturity, and the physiologic conditions in the cell's environment (Steller H., Science 1995, 267(5203): 1445–9). Although it is probable that certain cellular injuries or insults irrevocably induce death, lesser injuries or insults may begin the dying process without inducing irreversible cell death. What constitutes a lesser injury or insult may vary tremendously with changes in the factors influencing that cell's death threshold. The ability to alter a cell's threshold for responding to an injury or insult, that is, to either promote or discourage cell death, would be a desirable goal for the treatment of conditions involving cell death. The ability to better control cell death, by either discouraging or promoting the mechanisms of cell death, would be an important invention for ameliorating disease (U.S. Pat. Nos. 5,925,640; 5,786,173; 5,858,715; 5,856,171).

Recent evidence suggests that the mechanisms of cellular death may be more complex than the two discrete pathways of apoptosis and necrosis. Examples of this evidence may be found in the central nervous system (CNS). In the complex CNS cellular environment, both necrosis and apoptosis are observed with commonly studied conditions, disorders, or diseases such as focal ischemia, global ischemia, toxic insults, prolonged seizures, excitotoxicity, and traumatic brain injury. In some reports, both apoptosis and necrosis have been described (Choi W S, et al. J Neurosci Res 1999, 57(1): 86–94; Li Y, et al. J Neurol Sci 1998, 156(2): 119–32; Lee J-M, et al. Nature 1999, 399(supp): A8–A14; Baumgartner W A, et al. Ann Thorac Surg 1999, 67(6): 1871–3; Fujikawa D G, et al. Eur J Neurosci 1999, 11(5): 1605–14; Gwag B J, et al Neuroscience 1999, 90(4): 1339–48; Mitchell I J, et al. 1998, 84(2): 489–501; Nakashima K, et al. J Neurotrauma 1999, 16(2): 143–51; Ginsburg, Md. Cerebrovascular Disease: Pathophysiology, Diagnosis, and Management 1998 Ch 42; Rink A D, et al. Soc Neurosci Abstr 1994, 20:250(Abstract)). Similar observations also occurred with brain tumor cells. (Maurer B J, et al. J Natl Cancer Inst 1999, 91(13): 1138–46) Other investigators found that neurons die by either apoptosis or necrosis under different environmental conditions (Taylor D L, et al. Brain Pathol 1999, 9(1): 93–117). There also are reports of a unique type of neuronal cell death following stroke. This new type of cell death has features common to both necrosis and apoptosis (Fukuda T, et al. Neurosci Res 1999, 33(1): 49–55). Other investigators believe that neuronal cell death is best represented by a continuum between apoptosis and necrosis, possibly mediated by calcium levels (Lee J-M, et al. 1999, 399(supp): A7–A14), or a combination of direct ischemic damage followed by indirect damage from excitotoxicity and loss of interneuronal connections (Martin L J, et al. Brian Res Bull 1998, 46(4): 281–309). Further complicating the picture of neuronal cell death is the observation that the death of one or more neurons in one region of the brain can induce the death of neurons in other brain regions. This phenomenon has been observed with stroke as described above (Martin L J, et al. Brain Res Bull 1998, 46(4): 281–309) as well as neuronal cell death induced by the withdrawal of growth factors (Ryu B R, et al. J Neurobiol 1999, 39(4): 536–46). Given the complex nature of actions and interactions among the many physiologic and molecular forces in brain tissue, and the different abilities of many substances acting either alone or in combination to induce cellular injury or death, it is difficult to determine with any degree of certainty if a nerve cell death process is due to apoptosis or necrosis (Graham D I, Greenfield's Neuropathology Ch 3 1997).

Despite the challenges in classifying the mechanism of cellular death, there is broad agreement that most, if not all, cells share common features in their death mechanisms (see, e.g., Lee J. M., et al., Nature 1999, 399 (supp): A7–A14).

2.2 Selected Factors and Conditions which Inhibit Cell Death Mechanisms

Several factors have been reported to inhibit the cell death pathway. One of the best-known factors is the gene product bcl-2 (Adams J M, et al. Science 1998, 281(5381): 1322–6; Vaux D L, et al. Proc Natl Acad Sci 1993, 90(3): 786–9; U.S. Pat. No. 5,856,171 and references cited therein). Expression of bcl-2 is believed to regulate apoptotic death in neurons, kidney, heart, liver, blood and skin cells under experimental conditions. In addition to regulating death by apoptosis, bcl-2 is believed to regulate death caused by non-apoptotic mechanisms. Factors related to bcl-2 have been shown to be over-expressed in cancer and autoimmune conditions, disorders, or diseases (U.S. Pat. No. 5,856,171 and references cited therein). Other related factors acting on the same pathway as bcl-2 also delay or prevent cell death.

In the brain, several factors have been shown to influence the cell death pathway. In excitotoxic injury to neurons, it was shown that lithium or bcl-2 each individually protected neurons against cell death (Nonaka S, et al. Proc Natl Acad Sci 1998, 95(5): 2642–7; Behl C, et al. Biochem Biophys Res Commun 1993, 197(2): 949–56). During ischemic injury to neurons, it was shown that nerve growth factor (NGF) and bcl-2 individually offered protection against neuronal death (Guegan C, et al. Neurobiol Dis 1999, 6(3): 180–9; Linnik M D, et al. Stroke 1995, 26(9): 1670–4).

Factors acting to prevent cell death do not act solely in the brain. In the heart, increased tolerance to non-lethal ischemic injury was associated with an increased expression of the bcl-2 gene, suggesting that bcl-2 was involved in protecting the cardiac muscle cells against ischemic injury (Maulik N, et al. *Ann NY Acad Sci* 1999, 874:401–11). This same study demonstrated that lower levels of bcl-2 expression were associated with higher rates of cardiac cell death. A similar result was found for mechanical injury to heart papillary muscle cells.

Recently, it has been demonstrated that bcl-2 prevented cell death in a brain ischemia model (Guegan C, et al. *Neurobiol Dis* 1999, 6(3): 180–9; Linnik M D, et al. *Stroke* 1995, 26(9): 1670–4). It was shown that the activity of bcl-2 to prevent neuronal death was consistently demonstrated across several different physiologic insults. It also has been demonstrated that the distinction between apoptotic death and necrotic death is open to question, so the possibility exists that bcl-2 can prevent or delay the necrotic cell death pathway, the apoptotic cell death pathway or perhaps an as yet undemonstrated cell death pathway.

Preventing cell death is an important medical goal. Several types of mammalian cells, most notably neurons and cardiac muscle cells, have limited if any capacity to regenerate. Preventing the death of these cells from conditions such as heart attack, stroke, shock, infection, cancer, Alzheimer's disease or traumatic injury, to name a few, would be an important medical advance as the heart and brain cannot grow sufficient cells to replace those cells lost to disease or infection.

In addition to preventing cell death, delaying and/or rescuing cells from programmed cell death is also an important medical goal. In many pathological conditions where there is an expectation that the disease will be successfully treated, such as many types of infection, hypoxia, ischemia or metabolic disturbances, delaying cell death would allow the pathological condition to be treated without permanent damage to the cells. In other words, the cells may be put into a suspended state from which they could successfully be rescued and emerge with their normal function intact.

3 SUMMARY OF THE INVENTION

The present invention relates to the discovery, identification and characterization of protective sequences and to compositions and methods for the treatment and diagnosis of conditions, disorders, or diseases involving cell death. Protective sequences refer to nucleic acid molecules comprising nucleic acid sequences which, when introduced into a cell either predisposed to undergo cell death or in the process of undergoing cell death, prevent, delay, or rescue the cell from death relative to a corresponding cell into which no exogenous nucleic acids have been introduced. For example, protective sequences may act to prevent, delay, ameliorate, inhibit, reduce, or rescue neuronal cell death (e.g. apoptosis, necrosis and related cellular events). The invention further relates to the discovery, identification and characterization of gene products encoded by such nucleic acid molecules, or by degenerate, e.g., allelic or homologous, variants thereof. Protective sequences also can be regulatory nucleic acids. Protective sequences further can be both coding sequences and regulatory sequences.

The invention further relates to target sequences. Target sequences include, but are not limited to, upstream and downstream regulatory sequences, upstream and downstream complete or partial gene or gene product sequences, antibodies, antisense molecules or sequences, ribozyme molecules, and other inhibitors or modulators directed against such protective sequences and protective sequence products.

Protective sequences and protective sequence products can be utilized prophylactically and/or therapeutically to prevent, delay ameliorate, inhibit, reduce, or rescue conditions of cell death or symptoms of conditions, disorders, or diseases involving cell death. The modulation of the expression of protective sequences, e.g., endogenous protective sequences, and/or the activity of the protective sequence products, e.g., endogenous protective sequence products, can also be utilized prophylactically or therapeutically to prevent, delay, ameliorate, inhibit, reduce, or rescue conditions of cell death or symptoms of conditions, disorders, or diseases involving cell death. Further, protective sequences and protective sequence products can be used to diagnose individuals exhibiting or predisposed to such conditions, disorders, or diseases involving cell death.

The compositions of the present invention include, in particular, nucleic acid molecules which comprise the following sequences: (a) nucleic acids of protective sequences, as well as allelic variants, homologs, mutants and fragments thereof; (b) nucleic acids which encode protective sequence products; (c) nucleic acids which encode protective sequence regulatory elements; (d) nucleic acids which encode fusion proteins comprising protective sequence products or one or more protective sequence product domains fused to a heterologous polypeptide; (e) nucleic acids which encode fusion proteins comprising protective sequence regulatory elements fused to a heterologous polypeptide; (f) nucleic acids which hybridize to the above described sequences under highly stringent or moderately stringent conditions, including, but not limited to, human homologs; and (g) complementary (e.g., antisense) nucleic acids of the sequences described in (a) through (f), above. The nucleic acid molecules of the invention include, but are not limited to, cDNA, genomic DNA and RNA sequences.

The present invention also encompasses expression gene products of the protective sequences listed above; i.e., proteins and/or polypeptides that are encoded by the above protective sequences.

Mimics, agonists and antagonists of the protective sequences, protective sequence products, genes, gene products, or their regulatory elements are also included in the present invention. Such mimics, agonists and antagonists will include, for example, small molecules, large molecules (e.g., protective sequence product fragments or protective sequence product ligands) and antibodies directed against a protective sequence product. Mimics, agonists and antagonists of the invention also include nucleic acids, such as antisense and ribozyme molecules, and gene or regulatory sequence replacement constructs, which can be used to modulate, inhibit or enhance expression of a protective sequence.

The present invention further encompasses cloning and expression vectors, which may include, but are not limited to, bacterial, fungal, insect, plant, and mammalian vectors, which contain the protective nucleic acid sequences of the invention, which can be used as probes or to express those protective nucleic acid sequences, protective sequence products, genes and/or gene products in host cells or organisms. The present invention also relates to cells that have been transformed, transfected, or infected with such vectors, and to cells engineered to contain or express the protective nucleic acid sequences, protective sequence products, genes, gene products, and/or regulatory elements of the invention.

Further, non-human host organisms which have been transformed, transfected, or infected with these protective nucleic acid sequences, or their regulatory elements, are also encompassed in the present invention. Host organisms of the invention include organisms transformed, transfected, or infected with the cloning vectors described above, including, but not limited to, non-human transgenic animals, and particularly transgenic non-human mammals which have been engineered to express a protective sequence, protective sequence product, gene, gene product, or regulatory element of the invention, or "knock-outs" which have been engineered to not express the protective sequence, protective sequence product, gene, gene product, or regulatory element of the invention.

The transgenic animals of the invention include animals which express a mutant variant or polymorphism of a protective sequence, protective sequence product, gene, gene product, or regulatory element, particularly a mutant variant or polymorphism of a protective sequence, protective sequence product, gene, gene product, or regulatory element which is associated with a condition, disorder, or disease involving cell death. The transgenic animals of the invention further include those that express a protective sequence transgene at higher or lower levels than normal. The transgenic animals of the invention further include those which express the protective sequence, protective sequence product, gene, gene product, or regulatory element in all their cells, "mosaic" animals which express the protective sequence, protective sequence product, gene, gene product, or regulatory element in only some of their cells, and those in which the protective sequence, protective sequence product, gene, gene product, or regulatory element is selectively introduced into and expressed in a specific cell type(s). The transgenic animals of the invention also include "knock-out" animals. Knock-out animals comprise animals that have been engineered to no longer express the protective sequence, protective sequence product, gene, gene product, or regulatory element.

The present invention also relates to methods and compositions for the diagnosis of conditions, disorders, or diseases involving cell death, as well as for the identification of subjects susceptible to such conditions, disorders, or diseases. Such methods comprise, for example, measuring expression of the protective sequence, protective sequence product, gene, gene product, or regulatory element in a patient sample, or detecting a mutation in the protective sequence, protective sequence product, gene, gene product, or regulatory element in the genome of a mammal, including a human, suspected of exhibiting such a condition, disorder, or disease. The protective nucleic acid molecules of the invention can be used also as diagnostic hybridization probes, or as primers for diagnostic PCR analysis to identify protective sequences, protective sequence products, genes, gene products, or regulatory element mutations, allelic variations or regulatory defects, such as defects in the expression of the protective sequence, protective sequence product, gene, gene product, or regulatory element. Such diagnostic PCR analyses can be used to diagnose individuals with a condition, disorder, or disease involving cell death associated with a particular protective sequence, protective sequence product, gene, gene product, or regulatory element mutation, allelic variation or regulatory defect. Such diagnostic PCR analyses can be used also to identify individuals susceptible to such conditions, disorders, or diseases involving cell death.

Methods and compositions, including pharmaceutical compositions, for the treatment of conditions, disorders, or diseases involving cell death also are included in the invention. Such methods and compositions can increase, decrease or otherwise modulate the level of protective sequences, protective sequence products, genes, gene products, or their regulatory elements in a patient in need of such treatment. Such methods and compositions can also modulate the level of protective sequence expression (e.g., endogenous protective sequence expression) and/or the level of activity of a protective sequence product, (e.g., endogenous protective sequence product). Further, since the protective sequence or protective sequence product need not normally be involved in such conditions, disorders, or diseases, such methods include, for example, modulating the expression of the protective sequence and/or the activity of the protective sequence product for the treatment of conditions, disorders, or diseases involving cell death which are normally mediated by some other gene.

In one embodiment, such methods and compositions are utilized for the treatment of the types of conditions, disorders, or diseases, which can be prevented, delayed or rescued from cell death and include, but are not limited to, those associated with the central nervous system including neurological and psychiatric conditions, disorders, or diseases; those of the peripheral nervous system; conditions, disorders, or diseases caused by physical injury; conditions, disorders, or diseases of the blood vessels or heart; conditions, disorders, or diseases of the respiratory system; neoplastic conditions, disorders, or diseases; conditions, disorders, or diseases of blood cells; conditions, disorders, or diseases of the gastrointestinal tract; conditions, disorders, or diseases of the liver; conditions, disorders, or diseases of the pancreas; conditions, disorders, or diseases of the kidney; conditions, disorders, or diseases of the ureters, urethra or bladder; conditions, disorders, or diseases of the male genital system; conditions, disorders, or diseases of the female genital tract; conditions, disorders, or diseases of the breast; conditions, disorders, or diseases of the endocrine system; conditions, disorders, or diseases of the thymus or pineal gland; conditions, disorders, or diseases of the skin or mucosa; conditions, disorders, or diseases of the musculoskeletal system; conditions, disorders, or diseases causing a fluid or hemodynamic derangement; inherited conditions, disorders, or diseases; conditions, disorders, or diseases of the immune system or spleen; conditions, disorders, or diseases caused by a nutritional disease; and conditions, disorders, or diseases typically occurring in infancy or childhood, as described in Section 5.4.1.1. below.

In yet another embodiment, the methods and compositions of the invention are utilized for the prevention, or delay, of cell death in the event of one or more infections which may be caused by bacteria; viruses; members of the family rickettsiae or chlamydia; fungi, yeast, hyphae or pseudohyphae; prions; protozoans; or metazoans.

In a further embodiment, the compounds and methods of the invention can be used to treat infections or conditions, disorders, or diseases which cause cell death in organ systems including, but not limited to, blood vessels, heart, red blood cells, white blood cells, lymph nodes, spleen, respiratory system, oral cavity, gastrointestinal tract, liver and biliary tract, pancreas, kidney, lower urinary tract, upper urinary tract and bladder, male sexual organs and genitalia, female sexual organs and genitalia, breast, thyroid gland, adrenal gland, parathyroid gland, skin, musculoskeletal system, bone marrow or bones.

In another embodiment, the compounds and methods of the invention can be used to treat further physiological impacts on organs caused by the infections which induce cell death including, but not limited to, fever equal to or greater than 101.5 degrees Fahrenheit, a decrease or increase in pulse rate by more than 20 beats per minute, a decrease or increase in supine systolic blood pressure by more than 30 millimeters of mercury, an increase or decrease in respiratory rate by more than 8 breaths per minute, an increase or decrease in blood pH by more than 0.10 pH units, an increase or decrease in one or more serum electrolytes outside of the clinical laboratory's usual reference range, an increase or decrease in the partial pressure of arterial oxygen or carbon dioxide outside of the clinical laboratory's usual reference range, an increase or decrease in white or red blood cells outside of the laboratory's usual reference range, an acute confusional state such as delirium where delirium is defined by the American Psychiatric Association's DSM-IV Manual or a diminished level of consciousness or attention.

In another embodiment, the compounds and methods of the invention can be used to promote cell death. These compounds could be useful for treating and/or ameliorating conditions caused by, for example, cancer and autoimmune diseases, both of which are manifested by an uncontrolled growth of cells.

The invention still further relates to methods for identifying compounds which modulate the expression of a protective sequence and/or the synthesis or activity of a protective sequence product. Such compounds include therapeutic compounds which can be used as pharmaceutical compositions to reduce or eliminate the symptoms of conditions, disorders, or diseases involving cell death. Cellular and non-cellular assays are described which can be used to identify compounds which interact with a protective sequence, protective sequence product, gene, gene product, and/or regulatory element, e.g., modulate the activity of a protective sequence and/or bind to a protective sequence product. Such cell-based assays of the invention utilize cells, cell lines, or engineered cells or cell lines that express the protective sequence, protective sequence product, gene, gene product, and/or regulatory element.

In one embodiment, such methods comprise contacting a compound to a cell which expresses a protective sequence, protective sequence product, gene, gene product, and/or regulatory element, measuring the level of protective sequence expression, gene product expression or gene product activity, and comparing this level to the level of protective sequence expression, gene product expression or gene product activity produced by the cell in the absence of the compound, such that if the level obtained in the presence of the compound differs from that obtained in its absence, a compound which modulates the expression of the protective sequence and/or the synthesis or activity of protective sequence products has been identified.

In an alternative embodiment, such methods comprise administering a compound to a host, e.g., a transgenic animal which expresses a protective sequence transgene or a mutant protective sequence transgene, and measuring the level of protective sequence expression, gene product expression or gene product activity. The measured level is compared to the level of protective sequence expression, gene product expression or gene product activity in a host which is not exposed to the compound, such that if the level obtained when the host is exposed to the compound differs from that obtained when the host is not exposed to the compound, a compound which modulates the expression of the protective sequence and/or the synthesis or activity of protective sequence products, and/or the symptoms of conditions, disorders, or diseases involving cell death, has been identified.

3.1 Definitions

"Protective sequence", as used herein, refers to nucleic acid molecules comprising nucleic acid sequences which, when introduced into a cell predisposed to either undergo cell death or in the process of undergoing cell death, prevent, delay, or rescue the cell from death relative to a corresponding cell into which no exogenous protective nucleic acids have been introduced. In one embodiment, a protective sequence encodes a protective sequence product. In another embodiment, protective sequences are any transcriptional products of the sequences disclosed herein. In another embodiment, protective sequences comprise regulatory elements of the sequences disclosed herein which modulate the expression of a nucleic acid within a cell. For example, protective sequences, their products, or their regulatory elements may act to prevent, delay, or rescue a cell, cells, tissues, organs, or organisms from dying. Compounds which modulate protective sequence expression or activity of the protective sequence product can be used in the treatment of conditions, disorders or diseases associated with cell death processes. It is to be understood that the protective sequences described above can act to ameliorate or delay symptoms related to cell death. Although the protective sequences may be involved directly in such cell death related conditions or disorders, in certain cases, the protective sequences will not normally be involved in such conditions or disorders, but will be effective for the treatment and/or prevention of such disorders. In these cases, modulation of the expression of the protective sequence and/or the activity of the protective sequence product will be useful for the treatment of conditions, disorders, or diseases involving cell death which are normally mediated by some other gene.

"Cell death", as used herein, refers to any mechanism and/or pathway whereby a cell undergoes a series of events which ultimately would lead to the death of the cell. For example, cell death may be caused by various processes including, but not limited to, apoptosis or programmed cell death, necrosis, or an as yet unidentified cell death pathway. Cell death may be induced in individual cells as a consequence of numerous internal and external stimuli including, but not limited to, genetic predisposition, toxic chemicals or processes, heat, cold, rapid environmental changes, radiation, viruses, prions, bacteria, disruption of nutrient balance, or exposure to bi-products and signaling from other cells undergoing cell death. The protective sequences disclosed herein, when introduced into a cell (e.g. a neuronal cell) which has undergone an event that would ultimately lead to cell death (e.g. ischemia), are capable of rescuing the cell from cell death. Moreover, when a protective sequence, in combination with a reporter gene (e.g. green fluorescent protein), is introduced into a cell which has undergone an event that would ultimately lead to cell death, expression of the reporter gene is an indication that the protective sequence is capable of rescuing the cell from cell death.

4 BRIEF DESCRIPTION OF THE FIGURES

FIGS. 1(A–J). Protective nucleic acids. See Table 1 for the identity, the sequence identifier number, the length in base pairs and the Accession Number for each of the sequences shown in these figures.

FIG. 2. Restriction map and diagram of plasmid pCMV•SPORT2. This plasmid was used as the cloning vector for the protective sequences. Each clone was ligated into the SalI-NotI restriction sites of the plasmid.

FIGS. 3(A–N). Protected Cortical Neurons Visualized by Detection of EGFP Expressing Cells. FIGS. 3A and 3B represent non-stroked, positive control samples. FIG. 3C represents a positive control, stroked sample using Bcl-2. FIG. 3D represents a stroked, negative control sample. FIG. 3E represents a stroked sample protected by CNI-00711. FIG. 3F represents a stroked sample protected by CNI-00712. FIG. 3G represents a stroked sample protected by CNI-00714. FIG. 3H represents a stroked sample protected by CNI-00715. FIG. 3I represents a stroked sample protected by CNI-00716. FIG. 3J represents a stroked sample protected by CNI-00717. FIG. 3K represents a stroked sample protected by CNI-00720. FIG. 3L represents a stroked sample protected by CNI-00721. FIG. 3M represents a stroked sample protected by CNI-00723. FIG. 3N represents a stroked sample protected by CNI-00724.

FIGS. 4(A–L). Open Reading Frames for CNI-007 11. This Figure depicts the twelve (12) potential ORFs for CNI-0071 1. Also shown are the nucleotide sequences which encode the ORFs.

FIGS. 5(A–X). Open Reading Frames for CNI-00712. This Figure depicts the 24 potential ORFs for CNI-00712. Also shown are the nucleotide sequences which encode the ORFs.

FIGS. 6(A–AD). Open Reading Frames for CNI-00714. This Figure depicts the 30 potential ORFs for CNI-00714. Also shown are the nucleotide sequences which encode the ORFs.

FIGS. 7(A–H). Open Reading Frames for CNI-00715. This Figure depicts the eight (8) potential ORFs for CNI-00715. Also shown are the nucleotide sequences which encode the ORFs.

FIGS. 8(A–O). Open Reading Frames for CNI-00716. This Figure depicts the fifteen (15) potential ORFs for CNI-00716. Also shown are the nucleotide sequences which encode the ORFs.

FIGS. 9(A–AL). Open Reading Frames for CNI-00717. This Figure depicts the 38 potential ORFs for CNI-00717. Also shown are the nucleotide sequences which encode the ORFs.

FIGS. 10(A–O). Open Reading Frames for CNI-00720. This Figure depicts the fifteen (15) potential ORFs for CNI-00720. Also shown are the nucleotide sequences which encode the ORFs.

FIGS. 11(A–AG). Open Reading Frames for CNI-0072 1. This Figure depicts the 33 potential ORFs for CNI-00721. Also shown are the nucleotide sequences which encode the ORFs.

FIGS. 12(A–AY). Open Reading Frames for CNI-00723. This Figure depicts the 51 potential ORFs for CNI-00723. Also shown are the nucleotide sequences which encode the ORFs.

FIGS. 13. Open Reading Frame for CNI-00724. This Figure depicts the single potential ORF for CNI-00724. Also shown is the nucleotide sequence which encodes the ORF.

5 DETAILED DESCRIPTION OF THE INVENTION

Protective sequences of the invention are described herein. Also described are recombinant, cloned and degenerate variants, homologs, orthologs, mutants and fragments thereof. The compositions of the invention further include protective sequence products (e.g. proteins or RNA) which are encoded or produced by the nucleic acid molecules of the invention, and the modulation of protective sequence expression and/or gene product activity in the treatment of conditions, disorders, or diseases involving cell death. Further, antibodies directed against the protective sequence products, or conserved variants or fragments thereof, and viral-, cell-, plant-, and animal-based models by which the protective sequences may be further characterized and utilized are also discussed in this section.

5.1 The Protective Sequences

The protective sequences of the invention are described in this section. Specifically, these protective sequences have been shown to prevent, delay, or rescue cell death in a cell predisposed for undergoing cell death, whether the pathway that leads to the cell death involves apoptosis, necrosis or an as yet undefined pathway. The protective sequences, their SEQ ID NOS and additional information related to the protective sequences are listed below, in Table 1.

The protective sequences listed in Table 1 may be obtained using cloning methods well known to those skilled in the art, including but not limited to the use of appropriate probes to detect the protective sequences within an appropriate cDNA or gDNA (genomic DNA) library. (See, for example, Sambrook et al., 1989, Molecular Cloning: A Laboratory Manual, Cold Spring Harbor Laboratories, which is incorporated by reference herein in its entirety). Probes for the novel sequences reported herein may be obtained directly from CNI-NPP1-CP10, which represents a composite deposit containing the isolated clones, which was deposited with the NRRL as Accession No. B-30231. Alternatively, oligonucleotide probes for the novel protective sequences may be synthesized based on the DNA sequences disclosed herein.

TABLE 1

PROTECTIVE SEQUENCES

| Protective sequence | SEQ ID NO: | Figure No. | Length (bp) (NotI-SalI fragment |
|---|---|---|---|
| CNI-00711 | 1 | 1A | 852 |
| CNI-00712 | 26 | 1B | 1096 |
| CNI-00714 | 75 | 1C | 1825 |
| CNI-00715 | 136 | 1D | 542 |
| CNI-00716 | 153 | 1E | 771 |
| CNI-00717 | 184 | 1F | 1669 |
| CNI-00720 | 261 | 1G | 1182 |
| CNI-00721 | 292 | 1H | 1965 |
| CNI-00723 | 359 | 1I | 2702 |
| CNI-00724 | 462 | 1J | 979 |

The isolated protective nucleic acid molecules of the invention include, in particular, nucleic acid molecules which comprise the following sequences: (a) nucleic acids of protective sequences, as well as allelic variants, homologs, mutants and fragments thereof; (b) nucleic acids which encode protective sequence products and/or their regulatory elements, or fragments thereof; (c) nucleic acids which encode fusion proteins comprising protective sequence products and/or their regulatory elements, or one or more protective sequence product domains and/or their regulatory elements fused to a heterologous polypeptide; (d) nucleic acids which hybridize to the above described sequences under highly stringent or moderately stringent conditions, including, but not limited to human homologs; and (e) complementary (e.g., antisense) nucleic acids of the sequences described in (a) through (d), above. The nucleic acid molecules of the invention include, but are not limited to, cDNA, genomic DNA and RNA sequences.

The nucleic acids of the invention also include nucleic acids which have at least 65%, 70%, 75%, 80%, 85%, 90%, 95%, 98% or more nucleic acid identity to the protective nucleic acids of (a)–(d) above. The nucleic acids of the invention further include nucleic acids which encode polypeptides having at least 65%, 70%, 75%, 80%, 85%, 90%, 95%, 98% or higher amino acid sequence identity to the polypeptides encoded by the protective nucleic acids of (a)–(d).

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical overlapping positions/total # of positions×100). In one embodiment, the two sequences are the same length.

The determination of percent identity between two sequences also can be accomplished using a mathematical algorithm. A preferred, non-limiting example of a mathematical algorithm utilized for the comparison of two sequences is the algorithm of Karlin and Altschul (1990) *Proc. Natl. Acad. Sci. USA* 87:2264–2268, modified as in Karlin and Altschul (1993) *Proc. Natl. Acad. Sci. USA* 90:5873–5877. Such an algorithm is incorporated into the NBLAST and XBLAST programs of Altschul, et al. (1990) *J Mol. Biol.* 215:403–410. BLAST nucleotide searches can be performed with the NBLAST program, score=100, wordlength=12 to obtain nucleic acids homologous to a nucleic acid molecules of the invention. BLAST protein searches can be performed with the XBLAST program, score=50, wordlength=3 to obtain amino acid sequences homologous to a protein molecules of the invention. To obtain gapped alignments for comparison purposes, Gapped BLAST can be utilized as described in Altschul et al. (1997) *Nucleic Acids Res.* 25:3389–3402. Alternatively, PSI-Blast can be used to perform an iterated search that detects distant relationships between molecules (Id.). When utilizing BLAST, Gapped BLAST and PSI-Blast programs, the default parameters of the respective programs (e.g., XBLAST and NBLAST) can be used (see http://www.ncbi.nlm.nih.gov). Another preferred, non-limiting example of a mathematical algorithm utilized for the comparison of sequences is the algorithm of Myers and Miller, (1988) *CABIOS* 4:11–17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12 and a gap penalty of 4 can be used.

The percent identity between two sequences can be determined using techniques similar to those described above, with or without allowing gaps. In calculating percent identity, typically only exact matches are counted.

The nucleic acids of the invention further include: (a) any nucleic acid which hybridizes to a nucleic acid molecule of the invention under moderately stringent conditions, e.g., hybridization to filter-bound DNA in 6× sodium chloride/sodium citrate (SSC) at about 45° C. followed by one or more washes in 0.2×SSC/0.1% SDS at about 50–65° C., or (b) under highly stringent conditions, e.g., hybridization to filter-bound nucleic acid in 6×SSC at about 45° C. followed by one or more washes in 0.1×SSC/0.2% SDS at about 68° C., or under other hybridization conditions which are apparent to those of skill in the art (see, for example, Ausubel F.M. et al., eds., 1989, Current Protocols in Molecular Biology, Vol. I, Green Publishing Associates, Inc., and John Wiley & sons, Inc., New York, at pp. 6.3.1–6.3.6 and 2.10.3). Preferably the nucleic acid molecule that hybridizes to the nucleic acid of (a) and (b), above, is one which comprises the complement of a nucleic acid molecule which encodes a protective sequence product. In a preferred embodiment, nucleic acid molecules comprising the nucleic acids of (a) and (b), above, encode protective sequence products.

Functionally equivalent protective sequence products include naturally occurring protective sequence products present in the same or different species. Functionally equivalent protective sequence products also include gene products which retain at least one of the biological activities of the protective sequence products, and/or which are recognized by and bind to antibodies (polyclonal or monoclonal) directed against the protective sequence products.

Among the nucleic acid molecules of the invention are deoxyoligonucleotides ("oligos") which hybridize under highly stringent or moderately stringent conditions to the nucleic acid molecules described above. In general, for probes between 14 and 70 nucleotides in length the melting temperature (TM) is calculated using the formula: Tm (° C.)=81.5+16.6(log[monovalent cations (molar)])+0.41 (% G+C)−(500/N) where N is the length of the probe. If the hybridization is carried out in a solution containing formamide, the melting temperature is calculated using the equation Tm (° C.)=81.5+16.6(log[monovalent cations (molar)])+0.41(% G+C)−(0.61% formamide)−(500/N) where N is the length of the probe. In general, hybridization is carried out at about 20–25 degrees below Tm (for DNA–DNA hybrids) or 10–15 degrees below Tm (for RNA–DNA hybrids).

Exemplary highly stringent conditions may refer, e.g., to washing in 6×SSC/0.05% sodium pyrophosphate at 37° C. (for about 14-base oligos), 48° C. (for about 17-base oligos), 55° C. (for about 20-base oligos) and 60° C. (for about 23-base oligos).

Fragments of the nucleic acid molecules can be at least 10 nucleotides in length. Fragments of the nucleic acid molecules can refer also to exons or introns, and, further, can refer to portions of coding regions that encode domains of protective sequence products.

The invention also encompasses (a) DNA vectors which contain any of the foregoing coding sequences and/or their complements (i.e., antisense); (b) DNA expression vectors which contain any of the foregoing coding sequences operatively associated with a regulatory element which directs the expression of the coding sequences; and (c) genetically engineered host cells which contain such vectors or have been engineered to contain and/or express a nucleic acid sequence of the invention, e.g., any of the foregoing coding sequences operatively associated with a regulatory element which directs the expression of the coding sequences in the host cell. As used herein, regulatory elements include but are not limited to inducible and non-inducible promoters, enhancers, operators and other elements known to those skilled in the art which drive and regulate expression. The invention further includes fragments of any of the DNA sequences disclosed herein.

The nucleic acid molecules may encode or act as antisense molecules, useful, for example, in protective sequence regulation, and/or as hybridization probes and/or as primers in amplification reactions of protective nucleic acid sequences. Further, such sequences may be used as part of ribozyme and/or triple helix sequences, also useful for protective sequence regulation. Still further, such molecules may be used as components of diagnostic methods whereby, for example, the presence of a particular allele involved in a condition, disorder, or disease involving cell death may be detected.

The protective nucleic acids of the invention can be readily obtained, for example, by standard sequencing and the sequences provided herein.

As will be appreciated by those skilled in the art, DNA sequence polymorphisms of a protective sequence will exist within a population of individual organisms (e.g., within a human population). Such polymorphisms may exist, for example, among individuals within a population due to natural allelic variation. Such polymorphisms include ones that lead to changes in amino acid sequence. An allele is one of a group of alternative forms of a gene that occur at a given genetic locus.

As used herein, the phrase "allelic variant" refers to a nucleic acid that occurs at a given locus or to a gene product encoded by that nucleic acid. Such natural allelic variations can typically result in 1–5% variance in the nucleic acid of a given gene. Sequencing the gene of interest in a number of different individuals can identify alternative alleles. Using hybridization probes to identify the same genetic locus in a variety of individuals can readily carry this out.

As used herein, the terms "gene" and "recombinant gene" refer to nucleic acid molecules comprising any of up to six open reading frames which may or may not encode a polypeptide of the invention. For example, the terms "gene" and "recombinant gene" refer to nucleic acid molecules encoding any of the open reading frames shown in FIGS. 4–13, and described in Tables 2–11, respectively. The term can further include nucleic acid molecules comprising upstream and/or exon/intron sequences and structures.

TABLE 2

OPEN READING FRAMES FOR CNI-00711

| OPEN READING FRAME NUMBER | LENGTH | LOCATION | SEQUENCE ID. NO. |
|---|---|---|---|
| 1 | 30 Nucleotide | 48–77 of Seq. Id. No. 1 | 2 |
|   | 9 Amino Acid |   | 3 |
| 2 | 60 Nucleotide | 78–137 of Seq. Id. No. 1 | 4 |
|   | 19 Amino Acid |   | 5 |
| 3 | 12 Nucleotide | 131–142 of Seq. Id. No. 1 | 6 |
|   | 3 Amino Acids |   | 7 |
| 4 | 33 Nucleotide | 342–374 of Seq. Id. No. 1 | 8 |
|   | 10 Amino Acids |   | 9 |
| 5 | 15 Nucleotide | 436–450 of Seq. Id. No. 1 | 10 |
|   | 4 Amino Acids |   | 11 |
| 6 | 42 Nucleotide | 447–488 of Seq. Id. No. 1 | 12 |
|   | 13 Amino Acids |   | 13 |
| 7 | 42 Nucleotide | 647–688 of Seq. Id. No. 1 | 14 |
|   | 13 Amino Acids |   | 15 |
| 8 | 63 Nucleotide | 688–750 of Seq. Id. No. 1 | 16 |
|   | 20 Amino Acids |   | 17 |
| 9 | 45 Nucleotide | 706–750 of Seq. Id. No. 1 | 18 |
|   | 14 Amino Acids |   | 19 |
| 10 | 33 Nucleotide | 718–750 of Seq. Id. No. 1 | 20 |
|   | 10 Amino Acids |   | 21 |
| 11 | 24 Nucleotide | 727–750 of Seq. Id. No. 1 | 22 |
|   | 7 Amino Acids |   | 23 |

TABLE 2-continued

OPEN READING FRAMES FOR CNI-00711

| OPEN READING FRAME NUMBER | LENGTH | LOCATION | SEQUENCE ID. NO. |
|---|---|---|---|
| 12 | 106 Nucleotide | 747–842 of Seq. Id. No. 1 | 24 |
|   | 35 Amino Acids |   | 25 |

TABLE 3

OPEN READING FRAMES FOR CNI-00712

| OPEN READING FRAME NUMBER | LENGTH | LOCATION | SEQUENCE ID. NO. |
|---|---|---|---|
| 1 | 54 Nucleotide | 20–73 of Seq. Id. No. 26 | 27 |
|   | 17 Amino Acid |   | 28 |
| 2 | 57 Nucleotide | 86–142 of Seq. Id. No. 26 | 29 |
|   | 18 Amino Acid |   | 30 |
| 3 | 12 Nucleotide | 228–239 of Seq. Id. No. 26 | 31 |
|   | 3 Amino Acids |   | 32 |
| 4 | 93 Nucleotide | 249–341 of Seq. Id. No. 26 | 33 |
|   | 30 Amino Acids |   | 34 |
| 5 | 30 Nucleotide | 304–333 of Seq. Id. No. 26 | 35 |
|   | 9 Amino Acids |   | 36 |
| 6 | 309 Nucleotide | 338–646 of Seq. Id. No. 26 | 37 |
|   | 102 Amino Acids |   | 38 |
| 7 | 93 Nucleotide | 360–452 of Seq. Id. No. 26 | 39 |
|   | 30 Amino Acids |   | 40 |
| 8 | 261 Nucleotide | 386–646 of Seq. Id. No. 26 | 41 |
|   | 86 Amino Acids |   | 42 |
| 9 | 57 Nucleotide | 396–452 of Seq. Id. No. 26 | 43 |
|   | 18 Amino Acids |   | 44 |
| 10 | 195 Nucleotide | 452–646 of Seq. Id. No. 26 | 45 |
|   | 64 Amino Acids |   | 46 |
| 11 | 480 Nucleotide | 456–935 of Seq. Id. No. 26 | 47 |
|   | 159 Amino Acids |   | 48 |
| 12 | 141 Nucleotide | 506–646 of Seq. Id. No. 26 | 49 |
|   | 46 Amino Acids |   | 50 |
| 13 | 420 Nucleotide | 516–935 of Seq. Id. No. 26 | 51 |
|   | 139 Amino Acids |   | 52 |
| 14 | 399 Nucleotide | 537–935 of Seq. Id. No.26 | 53 |
|   | 132 Amino Acids |   | 54 |
| 15 | 81 Nucleotide | 566–646 of Seq. Id. No. 26 | 55 |
|   | 26 Amino Acids |   | 56 |
| 16 | 348 Nucleotide | 588–935 of Seq. Id. No. 26 | 57 |
|   | 115 Amino Acids |   | 58 |
| 17 | 27 Nucleotide | 620–646 of Seq. Id. No. 26 | 59 |
|   | 8 Amino Acids |   | 60 |
| 18 | 303 Nucleotide | 633–935 of Seq. Id. No. 26 | 61 |
|   | 100 Amino Acids |   | 62 |

TABLE 4

OPEN READING FRAMES FOR CNI-00714

| OPEN READING FRAME NUMBER | LENGTH | LOCATION | SEQUENCE ID. NO. |
|---|---|---|---|
| 1 | 1239 Nucleotide | 29–1267 of Seq. Id. No. 75 | 76 |
|   | 412 Amino Acid |   | 77 |
| 2 | 105 Nucleotide | 126–230 of Seq. Id. No. 75 | 78 |
|   | 34 Amino Acid |   | 79 |
| 3 | 1092 Nucleotide | 76–1267 of Seq. Id. No. 75 | 80 |
|   | 363 Amino Acids |   | 81 |
| 4 | 18 Nucleotide | 360–377 of Seq. Id. No. 75 | 82 |
|   | 5 Amino Acids |   | 83 |
| 5 | 69 Nucleotide | 393–461 of Seq. Id. No. 75 | 84 |
|   | 22 Amino Acids |   | 85 |

TABLE 4-continued

OPEN READING FRAMES FOR CNI-00714

| OPEN READING FRAME NUMBER | LENGTH | LOCATION | SEQUENCE ID. NO. |
|---|---|---|---|
| 6 | 24 Nucleotide | 546–569 of Seq. Id. No. 75 | 86 |
|   | 7 Amino Acids |   | 87 |
| 7 | 96 Nucleotide | 573–668 of Seq. Id. No. 75 | 88 |
|   | 31 Amino Acids |   | 89 |
| 8 | 87 Nucleotide | 582–668 of Seq. Id. No. 75 | 90 |
|   | 28 Amino Acids |   | 91 |
| 9 | 600 Nucleotide | 668–1267 of Seq. Id. No. 75 | 92 |
|   | 199 Amino Acids |   | 93 |
| 10 | 159 Nucleotide | 684–842 of Seq. Id. No. 75 | 94 |
|   | 52 Amino Acids |   | 95 |
| 11 | 510 Nucleotide | 758–1267 of Seq. Id. No. 75 | 96 |
|   | 169 Amino Acids |   | 97 |
| 12 | 51 Nucleotide | 792–842 of Seq. Id. No. 75 | 98 |
|   | 16 Amino Acids |   | 99 |
| 13 | 336 Nucleotide | 932–1267 of Seq. Id. No. 75 | 100 |
|   | 111 Amino Acids |   | 101 |
| 14 | 33 Nucleotide | 1017–1049 of Seq. Id. No. 75 | 102 |
|   | 10 Amino Acids |   | 103 |
| 15 | 216 Nucleotide | 1052–1267 of Seq. Id. No. 75 | 104 |
|   | 71 Amino Acids |   | 105 |
| 16 | 60 Nucleotide | 1080–1139 of Seq. Id. No. 75 | 106 |
|   | 19 Amino Acids |   | 107 |
| 17 | 48 Nucleotide | 1092–1139 of Seq. Id. No. 75 | 108 |
|   | 15 Amino Acids |   | 109 |
| 18 | 30 Nucleotide | 1110–1139 of Seq. Id. No. 75 | 110 |
|   | 9 Amino Acids |   | 111 |
| 19 | 41 Nucleotide | 1127–1267 of Seq. Id. No. 75 | 112 |
|   | 46 Amino Acids |   | 113 |
| 20 | 132 Nucleotide | 1136–1267 of Seq. Id. No. 75 | 114 |
|   | 43 Amino Acids |   | 115 |
| 21 | 90 Nucleotide | 1167–1256 of Seq. Id. No. 75 | 116 |
|   | 29 Amino Acids |   | 117 |
| 22 | 72 Nucleotide | 1185–1256 of Seq. Id. No. 75 | 118 |
|   | 23 Amino Acids |   | 119 |
| 23 | 57 Nucleotide | 1211–1267 of Seq. Id. No. 75 | 120 |
|   | 18 Amino Acids |   | 121 |
| 24 | 15 Nucleotide | 1253–1267 of Seq. Id. No. 75 | 122 |
|   | 4 Amino Acids |   | 123 |
| 25 | 45 Nucleotide | 1283–1327 of Seq. Id. No. 75 | 124 |
|   | 14 Amino Acids |   | 125 |
| 26 | 132 Nucleotide | 1411–1542 of Seq. Id. No. 75 | 126 |
|   | 43 Amino Acids |   | 127 |
| 27 | 105 Nucleotide | 1438–1542 of Seq. Id. No. 75 | 128 |
|   | 34 Amino Acids |   | 129 |
| 28 | 75 Nucleotide | 1493–1567 of Seq. Id. No. 75 | 130 |
|   | 24 Amino Acids |   | 131 |
| 29 | 39 Nucleotide | 1573–1611 of Seq. Id. No. 75 | 132 |
|   | 12 Amino Acids |   | 133 |
| 30 | 33 Nucleotide | 1528–1660 of Seq. Id. No. 75 | 134 |
|   | 10 Amino Acids |   | 135 |

TABLE 5

OPEN READING FRAMES FOR CNI-00715

| OPEN READING FRAME NUMBER | LENGTH | LOCATION | SEQUENCE ID. NO. |
|---|---|---|---|
| 1 | 39 Nucleotide | 34–72 of Seq. Id. No. 136 | 137 |
|   | 12 Amino Acid |   | 138 |
| 2 | 24 Nucleotide | 38–61 of Seq. Id. No. 136 | 139 |
|   | 7 Amino Acid |   | 140 |
| 3 | 138 Nucleotide | 93–230 of Seq. Id. No. 136 | 141 |
|   | 45 Amino Acids |   | 142 |
| 4 | 93 Nucleotide | 138–230 of Seq. Id. No. 136 | 143 |
|   | 30 Amino Acids |   | 144 |

TABLE 5-continued

OPEN READING FRAMES FOR CNI-00715

| OPEN READING FRAME NUMBER | LENGTH | LOCATION | SEQUENCE ID. NO. |
|---|---|---|---|
| 5 | 72 Nucleotide | 145–216 of Seq. Id. No. 136 | 145 |
|   | 23 Amino Acids |   | 146 |
| 6 | 57 Nucleotide | 160–216 of Seq. Id. No. 136 | 147 |
|   | 18 Amino Acids |   | 148 |
| 7 | 30 Nucleotide | 352–381 of Seq. Id. No. 136 | 149 |
|   | 9 Amino Acids |   | 150 |
| 8 | 75 Nucleotide | 399–473 of Seq. Id. No. 136 | 151 |
|   | 24 Amino Acids |   | 152 |

TABLE 6

OPEN READING FRAMES FOR CNI-00716

| OPEN READING FRAME NUMBER | LENGTH | LOCATION | SEQUENCE ID. NO. |
|---|---|---|---|
| 1 | 108 Nucleotide | 53–160 of Seq. Id. No. 153 | 154 |
|   | 35 Amino Acid |   | 155 |
| 2 | 99 Nucleotide | 62–160 of Seq. Id. No. 153 | 156 |
|   | 32 Amino Acid |   | 157 |
| 3 | 21 Nucleotide | 205–225 of Seq. Id. No. 153 | 158 |
|   | 6 Amino Acids |   | 159 |
| 4 | 75 Nucleotide | 226–300 of Seq. Id. No. 153 | 160 |
|   | 24 Amino Acids |   | 161 |
| 5 | 48 Nucleotide | 253–300 of Seq. Id. No. 153 | 162 |
|   | 15 Amino Acids |   | 163 |
| 6 | 42 Nucleotide | 259–300 of Seq. Id. No. 153 | 164 |
|   | 13 Amino Acids |   | 165 |
| 7 | 99 Nucleotide | 358–456 of Seq. Id. No. 153 | 166 |
|   | 32 Amino Acids |   | 167 |
| 8 | 63 Nucleotide | 394–456 of Seq. Id. No. 153 | 168 |
|   | 20 Amino Acids |   | 169 |
| 9 | 39 Nucleotide | 418–456 of Seq. Id. No. 153 | 170 |
|   | 12 Amino Acids |   | 171 |
| 10 | 177 Nucleotide | 459–635 of Seq. Id. No. 153 | 172 |
|   | 58 Amino Acids |   | 173 |
| 11 | 27 Nucleotide | 574–600 of Seq. Id. No. 153 | 174 |
|   | 8 Amino Acids |   | 175 |
| 12 | 75 Nucleotide | 604–678 of Seq. Id. No. 153 | 176 |
|   | 24 Amino Acids |   | 177 |
| 13 | 33 Nucleotide | 693–725 of Seq. Id. No. 153 | 178 |
|   | 10 Amino Acids |   | 179 |
| 14 | 30 Nucleotide | 696–725 of Seq. Id. No. 153 | 180 |
|   | 9 Amino Acids |   | 181 |
| 15 | 42 Nucleotide | 730–771 of Seq. Id. No. 153 | 182 |
|   | 14 Amino Acids |   | 183 |

TABLE 7

OPEN READING FRAMES FOR CNI-00717

| OPEN READING FRAME NUMBER | LENGTH | LOCATION | SEQUENCE ID. NO. |
|---|---|---|---|
| 1 | 819 Nucleotide | 80–898 of Seq. Id. No. 184 | 185 |
|   | 272 Amino Acid |   | 186 |
| 2 | 774 Nucleotide | 125–898 of Seq. Id. No. 184 | 187 |
|   | 257 Amino Acid |   | 188 |
| 3 | 717 Nucleotide | 182–898 of Seq. Id. No. 184 | 189 |
|   | 238 Amino Acids |   | 190 |
| 4 | 699 Nucleotide | 200–898 of Seq. Id. No. 184 | 191 |
|   | 232 Amino Acids |   | 192 |
| 5 | 696 Nucleotide | 203–898 of Seq. Id. No. 184 | 193 |
|   | 231 Amino Acids |   | 194 |

TABLE 7-continued

OPEN READING FRAMES FOR CNI-00717

| OPEN READING FRAME NUMBER | LENGTH | LOCATION | SEQUENCE ID. NO. |
|---|---|---|---|
| 6 | 72 Nucleotide | 279–350 of Seq. Id. No. 184 | 195 |
|   | 23 Amino Acids |  | 196 |
| 7 | 66 Nucleotide | 285–350 of Seq. Id. No. 184 | 197 |
|   | 21 Amino Acids |  | 198 |
| 8 | 57 Nucleotide | 294–350 of Seq. Id. No. 184 | 199 |
|   | 18 Amino Acids |  | 200 |
| 9 | 51 Nucleotide | 369–419 of Seq. Id. No. 184 | 201 |
|   | 16 Amino Acids |  | 202 |
| 10 | 306 Nucleotide | 423–728 of Seq. Id. No. 184 | 203 |
|    | 101 Amino Acids |  | 204 |
| 11 | 282 Nucleotide | 447–728 of Seq. Id. No. 184 | 205 |
|    | 93 Amino Acids |  | 206 |
| 12 | 231 Nucleotide | 498–728 of Seq. Id. No. 184 | 207 |
|    | 76 Amino Acids |  | 208 |
| 13 | 213 Nucleotide | 516–728 of Seq. Id. No. 184 | 209 |
|    | 70 Amino Acids |  | 210 |
| 14 | 195 Nucleotide | 534–728 of Seq. Id. No. 184 | 211 |
|    | 64 Amino Acids |  | 212 |
| 15 | 189 Nucleotide | 540–728 of Seq. Id. No. 184 | 213 |
|    | 62 Amino Acids |  | 214 |
| 16 | 174 Nucleotide | 555–728 of Seq. Id. No. 184 | 215 |
|    | 57 Amino Acids |  | 216 |
| 17 | 156 Nucleotide | 573–728 of Seq. Id. No. 184 | 217 |
|    | 51 Amino Acids |  | 218 |
| 18 | 126 Nucleotide | 603–728 of Seq. Id. No. 184 | 219 |
|    | 41 Amino Acids |  | 220 |
| 19 | 117 Nucleotide | 612–728 of Seq. Id. No. 184 | 221 |
|    | 38 Amino Acids |  | 222 |
| 20 | 96 Nucleotide | 633–728 of Seq. Id. No. 184 | 223 |
|    | 31 Amino Acids |  | 224 |
| 21 | 48 Nucleotide | 681–728 of Seq. Id. No. 184 | 225 |
|    | 15 Amino Acids |  | 226 |
| 22 | 42 Nucleotide | 687–728 of Seq. Id. No. 184 | 227 |
|    | 13 Amino Acids |  | 228 |
| 23 | 78 Nucleotide | 741–818 of Seq. Id. No. 184 | 229 |
|    | 25 Amino Acids |  | 230 |
| 24 | 60 Nucleotide | 759–818 of Seq. Id. No. 184 | 231 |
|    | 19 Amino Acids |  | 232 |
| 25 | 48 Nucleotide | 771–818 of Seq. Id. No. 184 | 233 |
|    | 15 Amino Acids |  | 234 |
| 26 | 36 Nucleotide | 783–818 of Seq. Id. No. 184 | 235 |
|    | 11 Amino Acids |  | 236 |
| 27 | 84 Nucleotide | 846–929 of Seq. Id. No. 184 | 237 |
|    | 27 Amino Acids |  | 238 |
| 28 | 69 Nucleotide | 861–929 of Seq. Id. No. 184 | 239 |
|    | 22 Amino Acids |  | 240 |
| 29 | 66 Nucleotide | 864–929 of Seq. Id. No. 184 | 241 |
|    | 21 Amino Acids |  | 242 |
| 30 | 75 Nucleotide | 931–1005 of Seq. Id. No. 184 | 243 |
|    | 24 Amino Acids |  | 244 |
| 31 | 75 Nucleotide | 1062–1136 of Seq. Id. No. 184 | 245 |
|    | 24 Amino Acids |  | 246 |
| 32 | 18 Nucleotide | 1119–1136 of Seq. Id. No. 184 | 247 |
|    | 5 Amino Acids |  | 248 |
| 33 | 15 Nucleotide | 1162–1176 of Seq. Id. No. 184 | 249 |
|    | 4 Amino Acids |  | 250 |
| 34 | 81 Nucleotide | 1304–1384 of Seq. Id. No. 184 | 251 |
|    | 26 Amino Acids |  | 252 |
| 35 | 24 Nucleotide | 1361–1384 of Seq. Id. No. 184 | 253 |
|    | 7 Amino Acids |  | 254 |
| 36 | 27 Nucleotide | 1396–1422 of Seq. Id. No. 184 | 255 |
|    | 8 Amino Acids |  | 256 |
| 37 | 90 Nucleotide | 1478–1567 of Seq. Id. No. 184 | 257 |
|    | 29 Amino Acids |  | 258 |
| 38 | 24 Nucleotide | 1554–1577 of Seq. Id. No. 184 | 259 |
|    | 7 Amino Acids |  | 260 |

TABLE 8

OPEN READING FRAMES FOR CNI-00720

| OPEN READING FRAME NUMBER | LENGTH | LOCATION | SEQUENCE ID. NO. |
|---|---|---|---|
| 1 | 24 Nucleotide | 62–85 of Seq. Id. No. 261 | 262 |
|   | 7 Amino Acid |  | 263 |
| 2 | 228 Nucleotide | 88–315 of Seq. Id. No. 261 | 264 |
|   | 75 Amino Acid |  | 265 |
| 3 | 195 Nucleotide | 121–315 of Seq. Id. No. 261 | 266 |
|   | 64 Amino Acids |  | 267 |
| 4 | 69 Nucleotide | 247–315 of Seq. Id. No. 261 | 268 |
|   | 22 Amino Acids |  | 269 |
| 5 | 87 Nucleotide | 321–407 of Seq. Id. No. 261 | 270 |
|   | 28 Amino Acids |  | 271 |
| 6 | 270 Nucleotide | 376–645 of Seq. Id. No. 261 | 272 |
|   | 89 Amino Acids |  | 273 |
| 7 | 21 Nucleotide | 593–559 of Seq. Id. No. 261 | 274 |
|   | 6 Amino Acids |  | 275 |
| 8 | 42 Nucleotide | 604–645 of Seq. Id. No. 261 | 276 |
|   | 13 Amino Acids |  | 277 |
| 9 | 18 Nucleotide | 623–640 of Seq. Id. No. 261 | 278 |
|   | 5 Amino Acids |  | 279 |
| 10 | 99 Nucleotide | 651–749 of Seq. Id. No. 261 | 280 |
|    | 32 Amino Acids |  | 281 |
| 11 | 33 Nucleotide | 661–693 of Seq. Id. No. 261 | 282 |
|    | 10 Amino Acids |  | 283 |
| 12 | 54 Nucleotide | 742–795 of Seq. Id. No. 261 | 284 |
|    | 17 Amino Acids |  | 285 |
| 13 | 15 Nucleotide | 1020–1034 of Seq. Id. No. 261 | 286 |
|    | 4 Amino Acids |  | 287 |
| 14 | 48 Nucleotide | 1034–1081 of Seq. Id. No. 261 | 288 |
|    | 15 Amino Acids |  | 289 |
| 15 | 12 Nucleotide | 1126–1137 of Seq. Id. No. 261 | 290 |
|    | 3 Amino Acids |  | 291 |

TABLE 9

OPEN READING FRAMES FOR CNI-00721

| OPEN READING FRAME NUMBER | LENGTH | LOCATION | SEQUENCE ID. NO. |
|---|---|---|---|
| 1 | 207 Nucleotide | 112–318 of Seq. Id. No. 292 | 293 |
|   | 68 Amino Acids |  | 294 |
| 2 | 147 Nucleotide | 172–318 of Seq. Id. No. 292 | 295 |
|   | 48 Amino Acids |  | 296 |
| 3 | 24 Nucleotide | 236–259 of Seq. Id. No. 292 | 297 |
|   | 7 Amino Acids |  | 298 |
| 4 | 18 Nucleotide | 345–362 of Seq. Id. No. 292 | 299 |
|   | 5 Amino Acids |  | 300 |
| 5 | 51 Nucleotide | 352–402 of Seq. Id. No. 292 | 301 |
|   | 16 Amino Acids |  | 302 |
| 6 | 132 Nucleotide | 362–493 of Seq. Id. No. 292 | 303 |
|   | 43 Amino Acids |  | 304 |
| 7 | 33 Nucleotide | 370–402 of Seq. Id. No. 292 | 305 |
|   | 10 Amino Acids |  | 306 |
| 8 | 21 Nucleotide | 382–402 of Seq. Id. No. 292 | 307 |
|   | 6 Amino Acids |  | 308 |
| 9 | 12 Nucleotide | 426–437 of Seq. Id. No. 292 | 309 |
|   | 3 Amino Acids |  | 310 |
| 10 | 201 Nucleotide | 589–789 of Seq. Id. No. 292 | 311 |
|    | 66 Amino Acids |  | 312 |
| 11 | 93 Nucleotide | 738–830 of Seq. Id. No. 292 | 313 |
|    | 30 Amino Acids |  | 314 |
| 12 | 21 Nucleotide | 776–796 of Seq. Id. No. 292 | 315 |
|    | 6 Amino Acids |  | 316 |
| 13 | 42 Nucleotide | 789–830 of Seq. Id. No. 292 | 317 |
|    | 13 Amino Acids |  | 318 |
| 14 | 27 Nucleotide | 840–866 of Seq. Id. No. 292 | 319 |
|    | 8 Amino Acids |  | 320 |

TABLE 9-continued

OPEN READING FRAMES FOR CNI-00721

| OPEN READING FRAME NUMBER | LENGTH | LOCATION | SEQUENCE ID. NO. |
|---|---|---|---|
| 15 | 324 Nucleotide | 866–1189 of Seq. Id. No. | 321 |
| | 107 Amino Acids | 292 | 322 |
| 16 | 78 Nucleotide | 870–947 of Seq. Id. No. | 323 |
| | 25 Amino Acids | 292 | 324 |
| 17 | 54 Nucleotide | 894–947 of Seq. Id. No. | 325 |
| | 17 Amino Acids | 292 | 326 |
| 18 | 30 Nucleotide | 918–947 of Seq. Id. No. | 327 |
| | 9 Amino Acids | 292 | 328 |
| 19 | 24 Nucleotide | 976–999 of Seq. Id. No. | 329 |
| | 7 Amino Acids | 292 | 330 |
| 20 | 66 Nucleotide | 1057–1122 of Seq. Id. No. | 331 |
| | 21 Amino Acids | 292 | 332 |
| 21 | 15 Nucleotide | 1108–1122 of Seq. Id. No. | 333 |
| | 4 Amino Acids | 292 | 334 |
| 22 | 69 Nucleotide | 1346–1414 of Seq. Id. No. | 335 |
| | 22 Amino Acids | 292 | 336 |
| 23 | 63 Nucleotide | 1352–1414 of Seq. Id. No. | 337 |
| | 20 Amino Acids | 292 | 338 |
| 24 | 15 Nucleotide | 1400–1414 of Seq. Id. No. | 339 |
| | 4 Amino Acids | 292 | 340 |
| 25 | 18 Nucleotide | 1491–1508 of Seq. Id. No. | 341 |
| | 5 Amino Acids | 292 | 342 |
| 26 | 42 Nucleotide | 1523–1564 of Seq. Id. No. | 343 |
| | 13 Amino Acids | 292 | 344 |
| 27 | 15 Nucleotide | 1528–1542 of Seq. Id. No. | 345 |
| | 4 Amino Acids | 292 | 346 |
| 28 | 111 Nucleotide | 1647–1757 of Seq. Id. No. | 347 |
| | 36 Amino Acids | 292 | 348 |
| 29 | 87 Nucleotide | 1654–1740 of Seq. Id. No. | 349 |
| | 28 Amino Acids | 292 | 350 |
| 30 | 24 Nucleotide | 1826–1849 of Seq. Id. No. | 351 |
| | 7 Amino Acids | 292 | 352 |
| 31 | 12 Nucleotide | 1859–1870 of Seq. Id. No. | 353 |
| | 3 Amino Acids | 292 | 354 |
| 32 | 51 Nucleotide | 1867–1917 of Seq. Id. No. | 355 |
| | 16 Amino Acids | 292 | 356 |
| 33 | 57 Nucleotide | 1881–1937 of Seq. Id. No. | 357 |
| | 18 Amino Acids | 292 | 358 |

TABLE 10

OPEN READING FRAMES FOR CNI-00723

| OPEN READING FRAME NUMBER | LENGTH | LOCATION | SEQUENCE ID. NO. |
|---|---|---|---|
| 1 | 36 Nucleotide | 217–252 of Seq. Id. No. | 360 |
| | 11 Amino Acids | 359 | 361 |
| 2 | 48 Nucleotide | 288–335 of Seq. Id. No. | 362 |
| | 15 Amino Acids | 359 | 363 |
| 3 | 18 Nucleotide | 332–349 of Seq. Id. No. | 364 |
| | 5 Amino Acids | 359 | 365 |
| 4 | 63 Nucleotide | 393–455 of Seq. Id. No. | 366 |
| | 20 Amino Acids | 359 | 367 |
| 5 | 24 Nucleotide | 412–435 of Seq. Id. No. | 368 |
| | 7 Amino Acids | 359 | 369 |
| 6 | 51 Nucleotide | 439–489 of Seq. Id. No. | 370 |
| | 16 Amino Acids | 359 | 371 |
| 7 | 1473 Nucleotide | 489–1961 of Seq. Id. No. | 372 |
| | 490 Amino Acids | 359 | 373 |
| 8 | 1467 Nucleotide | 495–1961 of Seq. Id. No. | 374 |
| | 488 Amino Acids | 359 | 375 |
| 9 | 90 Nucleotide | 544–633 of Seq. Id. No. | 376 |
| | 29 Amino Acids | 359 | 377 |
| 10 | 78 Nucleotide | 556–633 of Seq. Id. No. | 378 |
| | 25 Amino Acids | 359 | 379 |
| 11 | 63 Nucleotide | 571–633 of Seq. Id. No. | 380 |
| | 20 Amino Acids | 359 | 381 |
| 12 | 33 Nucleotide | 614–646 of Seq. Id. No. | 382 |
| | 10 Amino Acids | 359 | 383 |
| 13 | 12 Nucleotide | 622–633 of Seq. Id. No. | 384 |
| | 3 Amino Acids | 359 | 385 |
| 14 | 42 Nucleotide | 634–675 of Seq. Id. No. | 386 |
| | 13 Amino Acids | 359 | 387 |
| 15 | 1260 Nucleotide | 702–1961 of Seq. Id. No. | 388 |
| | 419 Amino Acids | 359 | 389 |
| 16 | 45 Nucleotide | 736–780 of Seq. Id. No. | 390 |
| | 14 Amino Acids | 359 | 391 |
| 17 | 108 Nucleotide | 740–847 of Seq. Id. No. | 392 |
| | 35 Amino Acids | 359 | 393 |
| 18 | 1128 Nucleotide | 834–1961 of Seq. Id. No. | 394 |
| | 375 Amino Acids | 359 | 395 |
| 19 | 1017 Nucleotide | 945–1961 of Seq. Id. No. | 396 |
| | 338 Amino Acids | 359 | 397 |
| 20 | 15 Nucleotide | 986–1000 of Seq. Id. No. | 398 |
| | 4 Amino Acids | 359 | 399 |
| 21 | 30 Nucleotide | 1000–1029 of Seq. Id. No. | 400 |
| | 9 Amino Acids | 359 | 401 |
| 22 | 936 Nucleotide | 1026–1961 of Seq. Id. No. | 402 |
| | 311 Amino Acids | 359 | 403 |
| 23 | 12 Nucleotide | 1061–1072 of Seq. Id. No. | 404 |
| | 3 Amino Acids | 359 | 405 |
| 24 | 39 Nucleotide | 1069–1107 of Seq. Id. No. | 406 |
| | 12 Amino Acids | 359 | 407 |
| 25 | 33 Nucleotide | 1075–1107 of Seq. Id. No. | 408 |
| | 10 Amino Acids | 359 | 409 |
| 26 | 870 Nucleotide | 1092–1961 of Seq. Id. No. | 410 |
| | 289 Amino Acids | 359 | 411 |
| 27 | 54 Nucleotide | 1258–1311 of Seq. Id. No. | 412 |
| | 17 Amino Acids | 359 | 413 |
| 28 | 678 Nucleotide | 1284–1961 of Seq. Id. No. | 414 |
| | 225 Amino Acids | 359 | 415 |
| 29 | 21 Nucleotide | 1342–1362 of Seq. Id. No. | 416 |
| | 6 Amino Acids | 359 | 417 |
| 30 | 24 Nucleotide | 1379–1402 of Seq. Id. No. | 418 |
| | 7 Amino Acids | 359 | 419 |
| 31 | 15 Nucleotide | 1429–1443 of Seq. Id. No. | 420 |
| | 4 Amino Acids | 359 | 421 |
| 32 | 486 Nucleotide | 1476–1961 of Seq. Id. No. | 422 |
| | 161 Amino Acids | 359 | 423 |
| 33 | 54 Nucleotide | 1489–1542 of Seq. Id. No. | 424 |
| | 17 Amino Acids | 359 | 425 |
| 34 | 15 Nucleotide | 1528–1542 of Seq. Id. No. | 426 |
| | 4 Amino Acids | 359 | 427 |
| 35 | 57 Nucleotide | 1543–1599 of Seq. Id. No. | 428 |
| | 18 Amino Acids | 359 | 429 |
| 36 | 24 Nucleotide | 1576–1599 of Seq. Id. No. | 430 |
| | 7 Amino Acids | 359 | 431 |
| 37 | 240 Nucleotide | 1722–1961 of Seq. Id. No. | 432 |
| | 79 Amino Acids | 359 | 433 |
| 38 | 90 Nucleotide | 1872–1961 of Seq. Id. No. | 434 |
| | 29 Amino Acids | 359 | 435 |
| 39 | 54 Nucleotide | 1915–1968 of Seq. Id. No. | 436 |
| | 17 Amino Acids | 359 | 437 |
| 40 | 39 Nucleotide | 1993–2031 of Seq. Id. No. | 438 |
| | 12 Amino Acids | 359 | 439 |
| 41 | 309 Nucleotide | 2004–2312 of Seq. Id. No. | 440 |
| | 102 Amino Acids | 359 | 441 |
| 42 | 21 Nucleotide | 2011–2031 of Seq. Id. No. | 442 |
| | 6 Amino Acids | 359 | 443 |
| 43 | 204 Nucleotide | 2109–2312 of Seq. Id. No. | 444 |
| | 67 Amino Acids | 359 | 445 |
| 44 | 198 Nucleotide | 2115–2312 of Seq. Id. No. | 446 |
| | 65 Amino Acids | 359 | 447 |
| 45 | 57 Nucleotide | 2198–2254 of Seq. Id. No. | 448 |
| | 18 Amino Acids | 359 | 449 |
| 46 | 231 Nucleotide | 2269–2499 of Seq. Id. No. | 450 |
| | 76 Amino Acids | 359 | 451 |

TABLE 10-continued

OPEN READING FRAMES FOR CNI-00723

| OPEN READING FRAME NUMBER | LENGTH | LOCATION | SEQUENCE ID. NO. |
|---|---|---|---|
| 47 | 216 Nucleotide | 2284–2499 of Seq. Id. No. 359 | 452 |
|  | 71 Amino Acids |  | 453 |
| 48 | 153 Nucleotide | 2300–2454 of Seq. Id. No. 359 | 454 |
|  | 50 Amino Acids |  | 455 |
| 49 | 30 Nucleotide | 2423–2452 of Seq. Id. No. 359 | 456 |
|  | 4 Amino Acids |  | 457 |
| 50 | 48 Nucleotide | 2452–2499 of Seq. Id. No. 359 | 458 |
|  | 15 Amino Acids |  | 459 |
| 51 | 15 Nucleotide | 2522–2536 of Seq. Id. No. 359 | 460 |
|  | 4 Amino Acids |  | 461 |

TABLE 11

OPEN READING FRAME FOR CNI-00724

| OPEN READING FRAME NUMBER | LENGTH | LOCATION | SEQUENCE ID. NO. |
|---|---|---|---|
| 1 | 243 Nucleotide | 567–809 of Seq. Id. No. 462 | 463 |
|  | 80 Amino Acids |  | 464 |

In a specific embodiment, the nucleic acid molecules comprise nucleic acids that encode an open reading frame of at least 3 contiguous amino acid residues from a full-length protein. In alternate embodiments, the nucleic acid molecules comprise an open reading frame which encodes at least about 5, 8, 10, 20, 30, 40, 50, 60, 70, 80, 90, 100, 150, 200, 250, 300, 350, 400, 450 or more contiguous amino acid residues of a protein.

The sequence obtained from clones containing partial coding sequences or non-coding sequences can be used to obtain the entire coding region by using the RACE method, for example (Chenchik, et al., 1995, CLONTECHniques (X) 1:5–8; Barnes, 1994, Proc. Natl. Acad. Sci. USA 91:2216–2220; and Cheng et al., Proc. Natl. Acad. Sci. USA 91: 5695–5699). Oligonucleotides can be designed based on the sequence obtained from the partial clone that can amplify a reverse transcribed mRNA encoding the entire coding sequence. Alternatively, probes can be used to screen cDNA libraries prepared from an appropriate cell or cell line in which the protective sequence is transcribed.

With respect to allelic variants of protective sequences associated with a condition, disorder, or disease involving cell death, any and all such nucleotide variations and resulting amino acid polymorphisms or variations which are the result of natural allelic variation of the protective sequence are intended to be within the scope of the present invention. Such allelic variants include, but are not limited to, ones that do not alter the functional activity of the protective sequence product.

With respect to the cloning of additional allelic variants of the isolated protective sequence and homologues and orthologs from other species (e.g., guinea pig, cow, mouse), the isolated protective sequences disclosed herein may be labeled and used to screen a CDNA library constructed from mRNA obtained from appropriate cells or tissues (e.g., brain) derived from the organism (e.g., guinea pig, cow and mouse) of interest. The hybridization conditions used generally should be of a lower stringency when the cDNA library is derived from an organism different from the type of organism from which the labeled sequence was derived, and can routinely be determined based on, e.g., relative relatedness of the target and reference organisms.

Alternatively, the labeled fragment may be used to screen a genomic library derived from the organism of interest, again, using appropriately stringent conditions. Appropriate stringency conditions are well known to those of skill in the art as discussed above, and will vary predictably depending on the specific organisms from which the library and the labeled sequences are derived. For guidance regarding such conditions, see, for example, Sambrook, et al., 1989, Molecular Cloning, A Laboratory Manual, Second Edition, Cold Spring Harbor Press, N.Y.; and Ausubel, et al., 1989–1999, Current Protocols in Molecular Biology, Green Publishing Associates and Wiley Interscience, N.Y., both of which are incorporated herein by reference in their entirety.

Additionally, the cloning of homologs and orthologs of the isolated protective sequence from other species (e.g. mouse) could also occur using the knowledge of syntenic regions and/or genes. Syntenic genes are genes which are believed to be located on the same chromosome because they are lost along with a marker gene which is known to be located on that chromosome. There are well-established genetic maps of specific chromosome regions that show syntenic regions between chromosomes of humans and other species that can be utilized, by one skilled in the art, for this purpose.

Further, a protective sequence allelic variant may be isolated from, for example, human nucleic acid, by performing PCR using two degenerate oligonucleotide primer pools designed on the basis of amino acid sequences within the protective sequence product of interest. The template for the reaction may be cDNA obtained by reverse transcription of mRNA prepared from, for example, human or non-human cell lines or tissue known or suspected to express a wild type or mutant protective sequence allele. In one embodiment, the allelic variant is isolated from an individual who has a condition, disorder, or disease involving cell death. Such variants are described in the examples below.

The PCR product may be subcloned and sequenced to ensure that the amplified sequences represent the sequences of a protective nucleic acid sequence. The PCR fragment may then be used to isolate a full-length cDNA clone by a variety of methods. For example, the amplified fragment may be labeled and used to screen a bacteriophage cDNA library. Alternatively, the labeled fragment may be used to isolate genomic clones via the screening of a genomic library.

PCR technology also may be utilized to isolate full-length CDNA sequences. For example, RNA may be isolated, following standard procedures, from an appropriate cellular or tissue source. A reverse transcription reaction may be performed on the RNA using an oligonucleotide primer specific for the most 5' end of the amplified fragment for the priming of first strand synthesis. The resulting RNA/DNA hybrid may then be "tailed" with guanines using a standard terminal transferase reaction. The hybrid may be digested with RNAase H and second strand synthesis may then be primed with a poly-C primer. Thus, cDNA sequences upstream of the amplified fragment may easily be isolated. For a review of cloning strategies which may be used, see e.g., Sambrook et al., 1989, supra, or Ausubel et al, supra.

In cases where the isolated protective sequence is the normal, or wild type gene, this gene may be used to isolate mutant alleles of the protective sequence. Such an isolation is preferable in processes and disorders that are known or suspected to have a genetic basis. Mutant alleles may be isolated from individuals either known or suspected to have a genotype which contributes to symptoms of conditions, disorders, or diseases involving cell death. Mutant alleles and mutant allele products may then be utilized in the therapeutic and diagnostic assay systems described below.

A cDNA of the mutant protective sequence may be isolated, for example, by using PCR, a technique well known to those of skill in the art. In this case, the first CDNA strand may be synthesized by hybridizing an oligo-dT oligonucleotide to mRNA isolated from tissue known or suspected to be expressed in an individual putatively carrying the mutant allele, and by extending the new strand with reverse transcriptase. The second strand of the cDNA is then synthesized using an oligonucleotide that hybridizes specifically to the 5' end of the normal protective sequence. Using these two primers, the product is then amplified via PCR, cloned into a suitable vector and subjected to DNA sequence analysis through methods well known to those of skill in the art. By comparing the DNA sequence of the mutant protective sequence to that of the normal protective sequence, the mutation(s) responsible for the loss or alteration of function of the mutant gene product can be ascertained.

Alternatively, a genomic or CDNA library can be constructed and screened using DNA or RNA, respectively, from a tissue known to or suspected of expressing the protective sequence of interest in an individual suspected of or known to carry the mutant allele. The normal protective sequence or any suitable fragment thereof may then be labeled and used as a probed to identify the corresponding mutant allele in the library. The clone containing this protective sequence may then be purified through methods routinely practiced in the art, and subjected to sequence analysis as described above in this Section.

Additionally, an expression library can be constructed utilizing DNA isolated from or CDNA synthesized from a tissue known to or suspected of expressing the protective sequence of interest in an individual suspected of or known to carry the mutant allele. In this manner, protective sequence products made by the tissue containing the putative mutant alleles may be expressed and screened using standard antibody screening techniques in conjunction with antibodies raised against the normal protective sequence product, as described, below, in Section 5.3 (For screening techniques, see, for example, Harlow, E. and Lane, eds., 1988, "Antibodies: A Laboratory Manual", Cold Spring Harbor Press, Cold Spring Harbor.) In cases where the mutation results in an expressed protective sequence product with altered function (e.g., as a result of a missense mutation), a polyclonal set of antibodies are likely to cross-react with the mutant protective sequence product. Library clones detected via their reaction with such labeled antibodies can be purified and subjected to sequence analysis as described in this Section, above.

The invention also includes nucleic acid molecules, preferably DNA molecules that are the complements of the nucleic acids of the preceding paragraphs.

In certain embodiments, the protective nucleic acid molecules of the invention are present as part of protective nucleic acid molecules comprising nucleic acid sequences which do not contain heterologous (e.g., cloning vector or expression vector) sequences. In other embodiments, the protective nucleic acid molecules of the invention further comprise vector sequences, e.g., cloning vectors or expression vectors.

5.2 Protein Products of the Protective Sequences

Protective sequence products or fragments thereof of the invention can be prepared for a variety of uses, including but not limited to, prophylactic or therapeutic modulators of protective sequence product function, for the generation of antibodies, diagnostic assays, or for the identification of other cellular or extracellular protective sequence products involved in the regulation of conditions, disorders, or diseases involving cell death.

The protective sequence products of the invention include, but are not limited to, human protective sequence products and non-human protective sequence products, e.g., mammalian (such as bovine or guinea pig), protective sequence products.

Protective sequence products of the invention, sometimes referred to herein as a "protective sequence protein" or "protective sequence polypeptide," includes those gene products encoded by any of up to six translational reading frames of the protective sequence sequences depicted in Table 1, as well as gene products encoded by other human allelic variants and non-human variants of protective sequence products which can be identified by the methods herein described. Among such protective sequence product variants are protective sequence products comprising amino acid residues encoded by polymorphisms of such protective sequence products.

In addition, protective sequence products of the invention may include proteins that represent functionally equivalent gene products. Functionally equivalent protective sequence products may include, for example, protective sequence products encoded by one of the nucleic acid molecules described in Section 5.1, above. In preferred embodiments, such functionally equivalent protective sequence products are naturally occurring gene products. Functionally equivalent protective sequence products also include gene products which retain at least one of the biological activities of the protective sequence products described above, and/or which are recognized by and bind to antibodies (polyclonal or monoclonal) directed against protective sequence products of the invention.

Equivalent protective sequence products may contain deletions, including internal deletions, additions, including additions yielding fusion proteins, or substitutions of amino acid residues within and/or adjacent to the amino acid sequence encoded by the protective sequence sequences described, above, in Section 5.1. Generally, deletions will be deletions of single amino acid residues, or deletions of no more than about 2, 3, 4, 5, 10 or 20 amino acid residues, either contiguous or non-contiguous. Generally, additions or substitutions, other than additions which yield fusion proteins, will be additions or substitutions of single amino acid residues, or additions or substitutions of no more than about 2, 3, 4, 5, 10 or 20 amino acid residues, either contiguous or non-contiguous. Preferably, these modifications result in a "silent" change, in that the change produces a protective sequence product with the same activity as the original protective sequence product. However, nucleic acid changes resulting in amino acid additions or substitutions may also be made for the purpose of modifying the protective sequence product in order to generally enhance their use as therapeutic agents or components for assays, such modifications to include, but not be limited to, stabilizing the product against degradation, enhancing pharmacokinetic properties, modifying site tropisms at the level of cells, tissues, organs, or organisms.

Amino acid substitutions may be made on the basis of similarity in polarity, charge, solubility, hydrophobicity, hydrophilicity and/or the amphipathic nature of the residues involved. For example, nonpolar (hydrophobic) amino acids include alanine, leucine, isoleucine, valine, proline, phenylalanine, tryptophan and methionine; polar neutral amino acids include glycine, serine, threonine, cysteine, tyrosine, asparagine and glutamine; positively charged (basic) amino acids include arginine, lysine and histidine; and negatively charged (acidic) amino acids include aspartic acid and glutamic acid. Additionally, non-natural amino acids, including, but not limited to, D-amino acids may be used.

Alternatively, where alteration of function is desired, addition(s), deletion(s) or non-conservative alterations can produce altered, including reduced-activity, protective sequence products. Such alterations can, for example, alter one or more of the biological functions of the protective sequence product. Further, such alterations can be selected so as to generate protective sequence products which include, but are not limited to, products which are better suited for expression, scale up, etc. in the host cells chosen. For example, cysteine residues can be deleted or substituted with another amino acid residue in order to eliminate disulfide bridges.

Protein fragments and/or peptides of the invention may comprise at least as many contiguous amino acid residues as necessary to represent an epitope fragment (that is to be recognized by an antibody directed to the protein). Examples of such protein fragments and/or peptides of the invention are shown by the open reading frames of the protective sequences shown in FIGS. 4–13, and described in Tables 2–11, respectively. In one nonlimiting embodiment of the invention, such protein fragments or peptides comprise at least about 3 contiguous amino acid residues from a full-length protein. In alternate embodiments, the protein fragments and peptides of the invention can comprise about 5, 8, 10, 20, 30, 40, 50, 60, 70, 80, 90, 100, 150, 200, 250, 300, 350, 400, 450 or more contiguous amino acid residues of a protein.

Peptides and/or proteins corresponding to one or more domains of the protein as well as fusion proteins in which a protein, or a portion of a protein such as a truncated protein or peptide or a protein domain, is fused to an unrelated protein are also within the scope of this invention. Such proteins and peptides can be designed on the basis of the nucleic acids disclosed in Section 5.1, above. Fusion proteins include, but are not limited to, IgFc fusions which stabilize the protein or peptide and prolong half-life in vivo; or fusions to any amino acid sequence which allows the fusion protein to be anchored to the cell membrane; or fusions to an enzyme, fluorescent protein, luminescent protein or a epitope tagged protein or peptide which provides a marker function.

The protein sequences described above can include a domain, which comprises a protein transduction domain which targets the protective sequence product for delivery to various tissues and more particularly across the brain blood barrier, using, for example, the protein transduction domain of human immunodeficiency virus TAT protein (Schwarze el al., 1999, Science 285:1569–72).

The protein sequences described above can include a domain, which comprises a signal sequence that targets the gene product for secretion. As used herein, a signal sequence includes a peptide of at least about 15 or 20 amino acid residues in length which occurs at the N-terminus of secretory and membrane-bound proteins and which contains at least about 70% hydrophobic amino acid residues such as alanine, leucine, isoleucine, phenylalanine, proline, tyrosine, tryptophan or valine. In a preferred embodiment, a signal sequence contains at least about 10 to 40 amino acid residues, preferably about 19–34 amino acid residues and has at least about 60–80%, more preferably 65–75% and more preferably at least about 70% hydrophobic residues. A signal sequence serves to direct a protein containing such a sequence to a lipid bilayer.

A signal sequence of a polypeptide of the invention can be used to facilitate secretion and isolation of the secreted protein or other proteins of interest. Signal sequences are typically characterized by a core of hydrophobic amino acids, which are generally cleaved from the mature protein during secretion in one or more cleavage events. Such signal peptides contain processing sites that allow cleavage of the signal sequence from the mature proteins as they pass through the secretory pathway. Thus, the invention pertains to the described polypeptides having a signal sequence (that is, "immature" polypeptides), as well as to the signal sequences themselves and to the polypeptides in the absence of a signal sequence (i.e., the "mature" cleavage products). It is to be understood that polypeptides of the invention can further comprise polypeptides comprising any signal sequence having characteristics as described above and a mature polypeptide sequence.

In one embodiment, a nucleic acid sequence encoding a signal sequence of the invention can be operably linked in an expression vector to a protein of interest, such as a protein which is ordinarily not secreted or is otherwise difficult to isolate. The signal sequence directs secretion of the protein, such as from a eukaryotic host into which the expression vector is transformed, and the signal sequence is subsequently or concurrently cleaved. The protein can then be readily purified from the extracellular medium by art recognized methods. Alternatively, the signal sequence can be linked to the protein of interest using a sequence which facilitates purification, such as with a GST domain.

Finally, the proteins of the invention also include protein sequences wherein domains encoded by any transcriptional or post-transcriptional, and/or translational or post-translational modifications, or fragments thereof, have been deleted. The polypeptides of the invention can further comprise posttranslational modifications, including, but not limited to glycosylations, acetylations and myrisalations.

The protective sequence products, peptide fragments thereof and fusion proteins thereof may be produced by recombinant DNA technology using techniques well known in the art. Thus, methods for preparing the protective sequence products, polypeptides, peptides, fusion peptide and fusion polypeptides of the invention by expressing nucleic acid containing protective sequence sequences are described herein. Methods that are well known to those skilled in the art can be used to construct expression vectors containing protective sequence product coding sequences and appropriate transcriptional and translational control signals. These methods include, for example, in vitro recombinant DNA techniques, synthetic techniques and in vivo genetic recombination. See, for example, the techniques described in Sambrook, et al., 1989, supra, and Ausubel, et al., 1989, supra. Alternatively, RNA capable of encoding protective sequence product sequences may be chemically synthesized using, for example, synthesizers. See, for example, the techniques described in "Oligonucleotide Synthesis", 1984, Gait, ed., IRL Press, Oxford.

A variety of host-expression vector systems may be utilized to express the protective sequence product coding sequences of the invention. Such host-expression systems represent vehicles by which the coding sequences of interest may be produced and subsequently purified, but also represent cells which may, when transformed or transfected with the appropriate nucleotide coding sequences, exhibit the protective sequence product of the invention in situ. These include, but are not limited to, microorganisms such as bacteria (e.g., E. coli, B. subtilis) transformed with recombinant bacteriophage DNA, plasmid DNA or cosmid DNA expression vectors containing protective sequence product coding sequences; yeast (e.g., Saccharomyces, Pichia) transformed with recombinant yeast expression vectors containing the protective sequence product coding sequences; insect cell systems infected with recombinant virus expression vectors (e.g., baculovirus) containing the protective sequence product coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing protective sequence product coding sequences; or mammalian cell systems (e.g., COS, CHO, BHK, 293, 3T3) harboring recombinant expression constructs containing promoters derived from the genome of mammalian cells (e.g., metallothionine promoter) or from mammalian viruses (e.g., the adenovirus late promoter; the vaccinia virus 7.5K promoter).

In bacterial systems, a number of expression vectors may be advantageously selected depending upon the use intended for the protective sequence product being expressed. For example, when a large quantity of such a protein is to be produced, for the generation of pharmaceutical compositions of protective sequence product or for raising antibodies to protective sequence product, for example, vectors which direct the expression of high levels of fusion protein products which are readily purified may be desirable. Such vectors include, but are not limited to, the E. coli expression vector pUR278 (Ruther et al., 1983, EMBO J. 2:1791), in which the protective sequence product coding sequence may be ligated individually into the vector in frame with the lacZ coding region so that a fusion protein is produced; pIN vectors (Inouye and Inouye, 1985, Nucleic Acids Res. 13:3101–3109; Van Heeke and Schuster, 1989, J. Biol. Chem. 264:5503–5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned protective sequence product can be released from the GST moiety.

In an insect system, Autographa californica, nuclear polyhidrosis virus (AcNPV) is used as a vector to express foreign genes. The virus grows in Spodoptera frugiperda cells. The protective sequence product coding sequence may be cloned individually into non-essential regions (for example the polyhedrin gene) of the virus and placed under control of an AcNPV promoter (for example the polyhedrin promoter). Successful insertion of protective sequence product coding sequence will result in inactivation of the polyhedrin gene and production of non-occluded recombinant virus (i.e., virus lacking the proteinaceous coat coded for by the polyhedrin gene). These recombinant viruses are then used to infect Spodoptera frugiperda cells in which the inserted gene is expressed. (e.g., see Smith, et al., 1983, J. Virol. 46:584; Smith, U.S. Pat. No. 4,215,051).

In mammalian host cells, a number of viral-based expression systems may be utilized. In cases where an adenovirus is used as an expression vector, the protective sequence product coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing protective sequence products in infected hosts. (See, e.g., Logan and Shenk, 1984, Proc. Natl. Acad. Sci. USA 81:3655–3659). Specific initiation signals may also be required for efficient translation of inserted protective sequence product coding sequences. These signals include the ATG initiation codon and adjacent sequences. In cases where an entire protective sequence, including its own initiation codon and adjacent sequences, is inserted into the appropriate expression vector, no additional translational control signals may be needed. However, in cases where only a portion of the protective sequence coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner, et al., 1987, Methods in Enzymol. 153:516–544).

In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation and phosphorylation of the gene product may be used. Such mammalian host cells include, but are not limited to, CHO, VERO, BHK, HeLa, COS, MDCK, 293, 3T3 and WI38.

For long-term, high-yield production of recombinant proteins, stable expression is preferred. For example, cell lines that stably express the protective sequence product may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines that express the protective sequence product. Such engineered cell lines may be particularly useful in screening and evaluation of compounds that affect the endogenous activity of the protective sequence product.

A number of selection systems may be used, including, but not limited to, the herpes simplex virus thymidine kinase (Wigler, et al, 1977, *Cell* 11:223), hypoxanthine-guanine phosphoribosyltransferase (Szybalska and Szybalski, 1962, *Proc. Natl. Acad. Sci. USA* 48:2026), and adenine phosphoribosyltransferase (Lowy, et al., 1980, *Cell* 22:817) genes can be employed in tk⁻, hgprt⁻ or aprt⁻ cells, respectively. Also, antimetabolite resistance can be used as the basis of selection for the following genes: dhfr, which confers resistance to methotrexate (Wigler, et al., 1980, *Proc. Natl. Acad. Sci. USA* 77:3567; O'Hare, et al., 1981, *Proc. Natl. Acad. Sci. USA* 78:1527); gpt, which confers resistance to mycophenolic acid (Mulligan and Berg, 1981, *Proc. Natl. Acad. Sci. USA* 78:2072); neo, which confers resistance to the aminoglycoside G-418 (Colberre-Garapin, et al., 1981, *J. Mol. Biol.* 150:1); and hygro, which confers resistance to hygromycin (Santerre, et al., 1984, *Gene* 30:147).

Alternatively, the expression characteristics of an endogenous protective sequence within a cell line or microorganism may be modified by inserting a heterologous DNA regulatory element into the genome of a stable cell line or cloned microorganism such that the inserted regulatory element is operatively linked with the endogenous protective sequence. For example, an endogenous protective sequence which is normally "transcriptionally silent", i.e., a protective sequence which is normally not expressed, or is expressed only at very low levels in a cell line or microorganism, may be activated by inserting a regulatory element which is capable of promoting the expression of a normally expressed protective sequence product in that cell line or microorganism. Alternatively, a transcriptionally silent, endogenous protective sequence may be activated by insertion of a promiscuous regulatory element which works across cell types.

Methods, which are well known to those skilled in the art, can be used to construct vectors containing the protective sequence operatively associated with appropriate transcriptional/translational control signals. These methods include in vitro recombinant DNA techniques, and synthetic techniques. See, for example, the techniques described in Sambrook, et al., 1992, Molecular Cloning, A Laboratory Manual, Cold Spring Harbor Laboratory, N.Y. and Ausubel et al., 1989, Current Protocols in Molecular Biology, Greene Publishing Associates & Wiley Interscience, N.Y.

The protective sequences may be associated operatively with a variety of different promoter/enhancer elements. The expression elements of these vectors may vary in their strength and specificities. Depending on the host/vector system utilized, any one of a number of suitable transcription and translation elements may be used. The promoter may be in the form of the promoter that is associated naturally with the gene of interest. Alternatively, the DNA may be positioned under the control of a recombinant or heterologous promoter, i.e., a promoter that is not associated normally with that gene. For example, tissue specific promoter/enhancer elements may be used to regulate the expression of the transferred DNA in specific cell types. Examples of transcriptional control regions which exhibit tissue specificity which have been described and could be used, include, but are not limited to: choline acetyltransferase (ChAT) gene control region which is active in cholinergic cells in the brain (Lonnerberg et al., 1996, JBC 271:33358–65; Lonnerberg et al., 1995, PNAS 92:4046–50; Ibenez and Perrson, 1991 Eur. J. Neurosci. 3:1309–15), mouse Thy-1.2 gene control region which is active in adult neurons including hippocampus, thalamus, cerebellum, cortex, RGC, DRG, and MN in the brain (Caroni, 1997, J Neurosci. Meth. 71:3–9; Vidal et al., 1990, EMBO J 9:833–40), neuron specific enolase (NSE) gene control region which is active in pan-neuronal, neuron specific, deep layers of cerebral and neocortex (not in white matter) areas of the brain (Hannas-Djebbara et al., 1997, Brain Res. Mol. Brain Res. 46:91–9; Peel et al., 1997, Gene Therapy 4:16–24; Twyman et al., 1997, J Mol Neurosci 8:63–73; Forss-Petter et al., 1990, Neuron 5:187–97), elastase I gene control region which is active in pancreatic acinar cells (Swift et al., 1984, Cell 38:639–646; Ornitz et al., 1986, Cold Spring Harbor Symp. Quant. Biol. 50:399–409; MacDonald, 1987, Hepatology 7:42S–51S); insulin gene control region which is active in pancreatic beta cells (Hanahan, 1985, Nature 315:115–122); immunoglobulin gene control region which is active in lymphoid cells (Grosschedl et al., 1984, Cell 38:647–658; Adams et al., 1985, Nature 318:533–538; Alexander et al., 1987, Mol. Cell. Biol. 7:1436–1444); albumin gene control region which is active in liver (Pinkert et al., 1987, Genes and Devel. 1:268–276); alpha-fetoprotein gene control region which is active in liver (Krumlauf et al., 1985, Mol. Cell. Biol. 5:1639–1648; Hammer et al., 1987, Science 235:53–58); alpha-1-antitrypsin gene control region which is active in liver (Kelsey et al., 1987, Genes and Devel. 1:161–171); beta-globin gene control region which is active in myeloid cells (Magram et al., 1985, Nature 315:338–340; Kollias et al., 1986, Cell 46:89–94); myelin basic protein gene control region which is active in oligodendrocyte cells in the brain (Readhead et al., 1987, Cell 48:703–712); myosin light chain-2 gene control region which is active in skeletal muscle (Shani, 1985, Nature 314:283–286) and gonadotropic releasing hormone gene control region which is active in the hypothalamus (Mason et al., 1986, Science 234:1372–1378). Promoters isolated from the genome of viruses which grow in mammalian cells (e.g., CMV, RSV, vaccinia virus 7.5K, SV40, HSV, adenoviruses MLP, and MMTV LTR promoters) may be used, as well as promoters produced by recombinant DNA or synthetic techniques. Further, promoters specifically activated within bone, i.e., the osteocalcin promoter, which is specifically activated within cells of osteoblastic lineage, may be used to target expression of nucleic acids within bone cells.

A heterologous regulatory element may be inserted into a stable cell line or cloned microorganism, such that it is operatively linked with an endogenous protective sequence, using techniques, such as targeted homologous recombination, which are well known to those of skill in the art, and described e.g., in Chappel, U.S. Pat. No. 5,272,071; PCT publication No. WO 91/06667, published May 16, 1991.

Alternatively, utilizing an antibody specific for the fusion protein being expressed may readily purify any fusion protein. For example, a system described by Janknecht, et al. allows for the ready purification of non-denatured fusion proteins expressed in human cell lines (Janknecht, et al., 1991, Proc. Natl. Acad. Sci. USA 88:8972–8976). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$-nitriloacetic acid-agarose columns and histidine-tagged proteins are selectively eluted with imidazole-containing buffers. The protective sequence products can also be expressed in transgenic animals. Animals of any species, including, but not limited to, mice, rats, rabbits, guinea pigs, pigs, micro-pigs, goats, sheep, cows and non-human primates, e.g., baboons, monkeys and chimpanzees may be used to generate transgenic animals. The term "transgenic," as used herein, refers to animals expressing protective sequences from a different species (e.g., mice expressing human protective sequences), as well as animals which have been genetically engineered to overexpress endogenous (i.e., same species) sequences or animals which have been genetically engineered to no longer express endogenous protective sequences (i.e., "knock-out" animals), and their progeny.

Any technique known in the art may be used to introduce a protective sequence transgene into animals to produce the founder lines of transgenic animals. Such techniques include, but are not limited to, pronuclear microinjection (Hoppe and Wagner, 1989, U.S. Pat. No. 4,873,191); retrovirus mediated gene transfer into germ lines (Van der Putten, et al., 1985, *Proc. Natl. Acad. Sci., USA* 82:6148–6152); gene targeting in embryonic stem cells (Thompson, et al., 1989, *Cell* 56:313–321); electroporation of embryos (Lo, 1983, *Mol Cell. Biol.* 3:1803–1814); and sperm-mediated gene transfer (Lavitrano et al., 1989, *Cell* 57:717–723) (For a review of such techniques, see Gordon, 1989, Transgenic Animals, Intl. Rev. Cytol. 115, 171–229).

Any technique known in the art may be used to produce transgenic animal clones containing a protective sequence transgene, for example, nuclear transfer into enucleated oocytes of nuclei from cultured embryonic, fetal or adult cells induced to quiescence (Campbell, et al., 1996, *Nature* 380:64–66; Wilmut, et al., *Nature* 385:810–813).

The present invention provides for transgenic animals which carry a protective sequence transgene in all their cells, as well as animals which carry the transgene in some, but not all their cells, i.e., mosaic animals. The transgene may be integrated as a single transgene or in concatamers, e.g., head-to-head tandems or head-to-tail tandems. The transgene also may be selectively introduced into and activated in a particular cell type by following, for example, the teaching of Lasko et al. (Lasko, et al., 1992, *Proc. Natl. Acad. Sci. USA* 89:6232–6236). The regulatory sequences required for such a cell-type specific activation will depend on the particular cell type of interest, and will be apparent to those of skill in the art. When it is desired that the cerebral transgene be integrated into the chromosomal site of the endogenous protective sequence, gene targeting is preferred. Briefly, when such a technique is to be utilized, vectors containing some nucleic acids homologous to the endogenous protective sequence are designed for the purpose of integrating, via homologous recombination with chromosomal sequences, into and disrupting the function of the nucleic acid of the endogenous protective sequence. The transgene also may be selectively introduced into a particular cell type, thus inactivating the endogenous protective sequence in only that cell type, by following, for example, the teaching of Gu, et aL (Gu, et al., 1994, *Science* 265, 103–106). The regulatory sequences required for such a cell-type specific inactivation will depend on the particular cell type of interest, and will be apparent to those of skill in the art.

Once transgenic animals have been generated, the expression of the recombinant protective sequence may be assayed utilizing standard techniques. Initial screening may be accomplished by Southern blot analysis or PCR techniques to analyze animal tissues to assay whether integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis and RT-PCR (reverse transcriptase PCR). Samples of protective sequence-expressing tissue also may be evaluated immunocytochemically using antibodies specific for the transgene product.

Protective proteins can be used, e.g., to treat cell death-related conditions, disorders, or diseases. Such protective sequence products include, but are not limited to, soluble derivatives such as peptides or polypeptides corresponding to one or more domains of the protective sequence product which are modified such that they are deleted for one or more hydrophobic domains. Alternatively, antibodies to the protein or anti-idiotypic antibodies which mimic the protective sequence product (including Fab fragments), modulators, antagonists or agonists can be used to treat cell death-related conditions, disorders, or diseases involving the protective sequence product. In yet another approach, nucleotide constructs encoding such protective sequence products can be used to genetically engineer host cells to express such protective sequence products in vivo; these genetically engineered cells can function as "bioreactors" in the body delivering a continuous supply of protective sequence product, peptides and soluble polypeptides.

5.3 Antibodies to the Protective Sequence Products

Described herein are methods for the production of antibodies capable of specifically recognizing one or more protective sequence product epitopes or epitopes of conserved variants or peptide fragments of the protective sequence products of the invention. Further, antibodies that specifically recognize mutant forms of the protective sequence products of the invention are encompassed by the invention. The terms "specifically bind" and "specifically recognize" refer to antibodies which bind to protective sequence product epitopes involved in conditions, disorders, or diseases involving cell death at a higher affinity than they bind to protective sequence product epitopes not involved in such conditions, disorders, or diseases (e.g., random epitopes).

Such antibodies may include, but are not limited to, polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies and epitope-binding fragments of any of the above. Such antibodies may be used, for example, in the detection of a protective sequence product in a biological sample and may, therefore, be utilized as part of a diagnostic or prognostic technique whereby patients may be tested for abnormal levels of protective sequence products, and/or for the presence of abnormal forms of such protective sequence products. Such antibodies also may be utilized in conjunction with, for example, compound screening schemes, as described, below, in Section 5.4.2, for the evaluation of the effect of test compounds on protective sequence product levels and/or activity. Additionally, such antibodies can be used in conjunction with the gene therapy techniques described below, in Section 5.4.1.3., to evaluate, for example, the normal and/or engineered cells prior to their introduction into the patient.

Antibodies derived from the protective sequence or protective sequence product, including, but not limited to, antibodies and anti-idiotypic antibodies that mimic activity or function additionally may be used in methods for inhibiting abnormal protective sequence product activity. Thus, such antibodies may, therefore, be utilized as part of treatment methods for protective sequence product-mediated conditions, disorders, or diseases.

For the production of antibodies against a protective sequence, various host animals may be immunized with a protective sequence or protective sequence product, or a portion thereof. Such host animals may include, but are not limited to, rabbits, mice and rats, to name but a few. Various adjuvants may be used to increase the immunological response, depending on the host species, including, but not limited to, Freund's (complete and incomplete), mineral gels such as aluminum hydroxide, surface active substances such as lysolecithin, pluronic polyols, polyanions, peptides, oil emulsions, keyhole limpet hemocyanin, dinitrophenol and potentially useful human adjuvants such as BCG (bacille Calmette-Guerin) and *Corynebacterium parvum.*

Polyclonal antibodies are heterogeneous populations of antibody molecules derived from the sera of animals immunized with an antigen, such as protective sequence product, or an antigenic functional derivative thereof. For the production of polyclonal antibodies, host animals such as those described above, may be immunized with protective sequence product supplemented with adjuvants as also described above.

Monoclonal antibodies, which are homogeneous populations of antibodies to a particular antigen, may be obtained by any technique that provides for the production of antibody molecules by continuous cell lines in culture. These include, but are not limited to, the hybridoma technique of Kohler and Milstein, (1975, *Nature* 256:495–497; and U.S. Pat. No. 4,376,110), the human B-cell hybridoma technique (Kosbor et al., 1983, *Immunology Today* 4:72; Cole et al., 1983, *Proc. Natl. Acad. Sci. USA* 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison, et al., 1984, *Proc. Natl. Acad. Sci.,* 81:6851–6855; Neuberger, et al., 1984, *Nature* 312:604–608; Takeda, et al., 1985, *Nature,* 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region. (See, e.g., Cabilly et al., U.S. Pat. No. 4,816,567; and Boss et al., U.S. Pat. No. 4,816,397, which are incorporated herein by reference in their entirety.)

In addition, techniques have been developed for the production of humanized antibodies. (See, e.g., Queen, U.S. Pat. No. 5,585,089, which is incorporated herein by reference in its entirety.) An immunoglobulin light or heavy chain variable region consists of a "framework" region interrupted by three hypervariable regions, referred to as complementarily determining regions (CDRs). The extent of the framework region and CDRs have been precisely defined (see, "Sequences of Proteins of Immunological Interest", Kabat, E. et al., U.S. Department of Health and Human Services (1983)). Briefly, humanized antibodies are antibody molecules from non-human species having one or more CDRs from the non-human species and a framework region from a human immunoglobulin molecule.

Alternatively, techniques described for the production of single chain antibodies (U.S. Pat. No. 4,946,778; Bird, 1988, *Science* 242:423–426; Huston, et al., 1988, *Proc. Natl. Acad. Sci. USA* 85:5879–5883; and Ward, et al., 1989, *Nature* 334:544–546) can be adapted to produce single chain antibodies against protective sequence products. Single chain antibodies are formed by linking the heavy and light chain fragments of the Fv region via an amino acid bridge, resulting in a single chain polypeptide.

Antibody fragments that recognize specific epitopes may be generated by known techniques. For example, such fragments include, but are not limited to: the $F(ab')_2$ fragments, which can be produced by pepsin digestion of the antibody molecule and the Fab fragments, which can be generated by reducing the disulfide bridges of the $F(ab')_2$ fragments. Alternatively, Fab expression libraries may be constructed (Huse, et al., 1989, *Science* 246:1275–1281) to allow rapid and easy identification of monoclonal Fab fragments with the desired specificity.

5.4 Uses of the Protective Sequences, Protective Sequence Products and Antibodies Described herein are various uses and applications of protective sequences, protective sequence products, including peptide fragments and fusion proteins thereof and of antibodies and anti-idiotypic antibodies derived from the protective sequence products and peptide fragments thereof. The application relates to compositions and methods for the treatment of conditions, disorders, or diseases involving cell death. Such applications include, but are not limited to, the prophylactic or therapeutic use of protective sequences which, when introduced into a cell predisposed to undergo cell death or in the process of dying, to prevent, delay, or rescue a cell, cells, tissue, organs, or organisms from dying, as described below in Section 5.4.1

Additionally, such applications include methods for the treatment of conditions, disorders, or diseases involving cell death, including, but not limited to, those associated with the central nervous system including neurological and psychiatric conditions, disorders, or diseases, and others as described below, in Section 5.4.1.1, and for the identification of compounds which modulate the expression of the protective sequence and/or the synthesis or activity of the protective sequence product, as described below, in Section 5.4.1. Such compounds can include, for example, other cellular products that are involved in such processes as the regulation of cell death. These compounds can be used, for example, in the amelioration of conditions, disorders, or diseases involving cell death.

One example of the type of injury that can cause cell death in neuronal cells is stroke, which often is the result of ischemic injury. A relatively broad time window (8 hours to perhaps several days or longer) exists between the onset of ischemic injury (i.e. cessation or marked reduction in blood flow) before most neural cells actually die. There are many complex pathways and perhaps hundreds of different signaling molecules which are likely to be involved, leaving many different intervention points each with the potential to prevent, delay, arrest and reverse the cell death program. These delayed biochemical intervention points represent ideal clinical intervention points as they correspond to the time period during which most stroke patients present for medical treatment.

Many current medications for the treatment of stroke affect the physical and biochemical events that are acutely related to the initial onset of stroke, and, thus, must be administered soon after the biochemical cascades begin. These approaches all suffer from the necessity of administering the drugs within a very brief time window following a stroke. However, many stroke patients do not even realize that they have suffered from a stroke until a time point at which many of the current treatments are ineffective. This is because many stroke patients often do not present at the emergency room prior to the passing of at least 13 hours from the onset of the stroke. The methods and compounds of the present invention, however, can be administered during the broader time window between stroke and the onset of the pathways leading to cell death.

In addition to stroke, a variety of other conditions, disorders, and diseases lead to the activation of the same biochemical cascades which lead to neuronal cell death in stroke. There is growing evidence that numerous other disease states that induce cell death programs are related to those induced by stroke. Cell death programs have been increasingly implicated in Alzheimer's disease, a well-known neurodegenerative condition which leads to substantial loss of specific neuronal populations in the neocortex and hippocampus. Vascular dementia (multi-infarct dementia) is another disorder in which stroke-like cell death pathways are active. In vascular dementia, a repetitive process of small blood vessel diseases induces regional brain cell death, leading to a progressive loss of cognitive abilities. A partial list of other brain diseases which activate brain cell death pathways similar to those observed in stroke include, but are not limited to, Parkinson's disease, traumatic injury, Down's syndrome, Huntington's disease, HIV infection and intracranial infections.

One notable example from the preceding list is physical trauma to the nervous system. Although such trauma can be caused by a multitude of different physical insults to the head, neck, spine and other parts of the nervous system, all result in focal damage to, and death of, neural tissue and its component cells. Focally damaged areas behave similarly to stroke-induced infarcts in that a wider area of neural damage and death, a penumbra, is induced via biochemical and cellular mechanisms which are similar or identical to those occurring in stroke.

While, for clarity, the uses described in this section are primarily uses related to conditions, disorders, or diseases involving cell death, it is to be noted that each of the diagnostic and therapeutic treatments described herein can be additionally utilized in connection with other defects associated with the protective sequences of the invention.

Additionally, described herein are various applications of protective sequences, protective sequence products, genes, gene products, and/or their regulatory elements, including, but not limited to, prognostic and diagnostic evaluation of conditions, disorders, or diseases as described below in Section 5.4.1.1.

A variety of methods can be employed for the diagnostic and prognostic evaluation of conditions, disorders, or diseases involving cell death and for the identification of subjects having a predisposition to such conditions, disorders, or diseases.

Since protective sequences or protective sequence products need not normally be involved in all conditions, disorders, or diseases involving cell death, methods of the invention include, for example, modulating the expression of the protective sequence and/or the activity of the protective sequence product for the treatment of conditions, disorders, or diseases involving cell death which are normally mediated by some other gene.

For cell death related conditions, disorders, or diseases in which the protective sequences or protective sequence products are involved normally, such diagnostic and prognostic methods may, for example, utilize reagents such as the protective nucleic acids described in Section 5.1, and antibodies directed against protective sequence products, including peptide fragments thereof, as described, above, in Section 5.3.

Specifically, such reagents may be used, for example, for:

(1) the detection of the presence of protective sequence mutations, or the detection of either over- or under-expression of the protective sequence relative to wild-type levels of expression;

(2) the detection of over- or under-abundance of protective sequence products relative to wild-type abundance of the protective sequence product; and (3) the detection of an aberrant level of protective sequence product activity relative to wild-type protective sequence product activity levels.

Protective nucleic acids can, for example, be used to diagnose a condition, disorder, or disease involving cell death using, for example, the techniques for mutation/polymorphism detection described above in Section 5.1.

Mutations at a number of different genetic loci may lead to phenotypes related to conditions, disorders, or diseases involving cell death. Ideally, the treatment of patients suffering from such conditions, disorders, or diseases will be designed to target the particular genetic loci containing the mutation mediating the condition, disorder, or disease. Genetic polymorphisms have been linked to differences in drug effectiveness. Thus, identification of alterations in protective sequence, protein or gene flanking regions can be utilized in pharmacogenetic methods to optimize therapeutic drug treatments.

In one embodiment of the present invention, therefore, alterations, i.e., polymorphisms, in the protective sequence or protein encoded by genes comprising such polymorphisms, are associated with a drug or drugs' efficacy, tolerance or toxicity, and may be used in pharmacogenomic methods to optimize therapeutic drug treatments, including therapeutic drug treatments for one of the conditions, disorders, or diseases described herein contained in Section 5.4.1.1, e.g., central nervous system conditions, disorders, or diseases. Such polymorphisms can be used, for example, to refine the design of drugs by decreasing the incidence of adverse events in drug tolerance studies, e.g., by identifying patient subpopulations of individuals who respond or do not respond to a particular drug therapy in efficacy studies, wherein the subpopulations have a polymorphism associated with drug responsiveness or unresponsiveness. The pharmacogenomic methods of the present invention also can provide tools to identify new drug targets for designing drugs and to optimize the use of already existing drugs, e.g., to increase the response rate to a drug and/or to identify and exclude non-responders from certain drug treatments (e.g., individuals having a particular polymorphism associated with unresponsiveness or inferior responsiveness to the drug treatment) or to decrease the undesirable side effects of certain drug treatments and/or to identify and exclude individuals with marked susceptibility to such side effects (e.g., individuals having a particular polymorphism associated with an undesirable side effect to the drug treatment).

In an embodiment of the present invention, polymorphisms in the protective sequence or flanking this sequence, or variations in protective sequence expression, or activity, e.g., variations due to altered methylation, differential splicing or post-translational modification of the protective sequence product, may be utilized to identify an individual having a disease or condition resulting from a disorder involving cell death and thus define the most effective and safest drug treatment. Assays such as those described herein may be used to identify such polymorphisms or variations in protective sequence expression or activity. Once a polymorphism in the protective sequence or in a flanking sequence in linkage disequilibrium with a disorder-causing allelle, or a variation in protective sequence expression has been identified in an individual, an appropriate drug treatment can be prescribed to the individual.

For the detection of protective sequence mutations or polymorphisms, any nucleated cell can be used as a starting source for genomic nucleic acid. For the detection of protective sequence expression or protective sequence products, any cell type or tissue in which the protective sequence is expressed may be utilized.

Nucleic acid-based detection techniques are described, below, in Section 5.4.1.4. Peptide detection techniques are described, below, in Section 5.4.1.5.

The methods described herein may be performed, for example, by utilizing pre-packaged diagnostic kits. The invention therefore also encompasses kits for detecting the presence of a polypeptide or nucleic acid of the invention in a biological sample (i.e., a test sample). Such kits can be used, e.g., to determine if a subject is suffering from or is at increased risk of developing a condition, disorder, or disease associated with a disorder-causing allele, or aberrant expression or activity of a polypeptide of the invention. For example, the kit can comprise a labeled compound or agent capable of detecting the polypeptide or MRNA or DNA or protective sequence sequences, e.g., encoding the polypeptide in a biological sample. The kit can comprise further a means for determining the amount of the polypeptide or MRNA in the sample (e.g., an antibody that binds the polypeptide or an oligonucleotide probe that binds to DNA or MRNA encoding the polypeptide). Kits can also include instructions for observing that the tested subject is suffering from, or is at risk of developing, a condition, disorder, or disease associated with aberrant expression of the polypeptide if the amount of the polypeptide or mRNA encoding the polypeptide is above or below a normal level, or if the DNA correlates with presence of an allele which causes a condition, disorder, or disease.

For antibody-based kits, the kit can comprise, for example: (1) a first antibody (e.g., attached to a solid support) which binds to a polypeptide of the invention; and, optionally, (2) a second, different antibody which binds to either the polypeptide or to the first antibody and is conjugated to a detectable agent.

For oligonucleotide-based kits, the kit can comprise, for example: (1) an oligonucleotide (e.g., a detectably labeled oligonucleotide) which hybridizes to a nucleic acid sequence encoding a polypeptide of the invention, or (2) a pair of primers useful for amplifying a nucleic acid molecule encoding a polypeptide of the invention.

The kit also can comprise, for example, one or more buffering agents, preservatives or protein stabilizing agents. The kit also can comprise components necessary for detecting the detectable agent (e.g., an enzyme or a substrate). The kit can contain also a control sample or a series of control samples that can be assayed and compared to the test sample. Each component of the kit usually is enclosed within an individual container and all of the various containers are within a single package along with instructions for observing whether the tested subject is suffering from or is at risk of developing a condition, disorder, or disease associated with polymorphisms which correlate with alleles which cause conditions, disorders, or diseases involving cell death, and/or aberrant levels of mRNA, polypeptides or activity.

Additionally, the application relates to the compositions and methods for the development of screening assays for the identification of compounds, described in Section 5.4.2 below, which interact with or modulate protective sequences, protective sequence products, genes, gene products, and/or their regulatory elements.

5.4.1 Composition and Methods for the Treatment of Conditions, Disorders, or Diseases Involving Cell Death This application relates to compositions and methods for the treatment of conditions, disorders, or diseases involving cell death. Such applications include, but are not limited to, the prophylactic or therapeutic use of protective sequences, protective sequence products, genes, gene products, or the regulatory elements, target sequences, or variants of any of the aforementioned sequences or products, which, when introduced into a cell predisposed to undergo cell death or in the process of dying, prevent, delay, or rescue a cell, cells, tissue, organs, or organisms from dying. The application further relates to the methods and compositions whereby a condition, disorder, or disease involving cell death, including but not limited to, the conditions, disorders, or diseases mentioned in Section 5.4.1.1, may be treated wherein such methods can comprise administering antibodies, antisense molecules or sequences, ribozyme molecules, or other inhibitors or modulators directed against such protective sequences, protective sequence products, genes, gene products, or the regulatory elements, target sequences, or variants of any of the aforementioned sequences or products.

The application relates to compositions and methods for those instances whereby the condition, disorder, or disease involving cell death results from protective sequence mutations, such methods can comprise supplying the subject with a nucleic acid molecule encoding an unimpaired protective sequence product such that an unimpaired protective sequence product is expressed and the cell, cells, tissue, organ, organism displaying symptoms of the condition, disorder, or disease is prevented, delayed, or rescued from death.

In another embodiment of methods for the treatment of conditions, disorders, or diseases involving cell death resulting from protective sequence mutations, such methods can comprise supplying the subject with a cell comprising a nucleic acid molecule which encodes an unimpaired protective sequence product such that the cell expresses the unimpaired protective sequence product and the cell, cells, tissue, organ, or organism displaying symptoms of the condition, disorder, or disease is prevented, delayed, or rescued from death.

In cases in which a loss of normal protective sequence product function results in the development of a condition, disorder, or disease involving cell death, an increase in protective sequence product activity would facilitate progress towards an asymptomatic state in individuals exhibiting a deficient level of protective sequence expression and/or gene product activity. Methods for enhancing the expression or synthesis of protective sequence product can include, for example, methods such as those described below, in Section 5.4.1.3.

Alternatively, symptoms of a condition, disorder, or disease involving cell death may be prevented, delayed, or rescued by administering a compound which decreases the level of protective sequence expression and/or gene product activity. Methods for inhibiting or reducing the level of protective sequence product synthesis or expression can include, for example, methods such as those described in Section 5.4.1.2.

In cases where the development of a condition, disorder, or disease involving cell death is due to a sequence or gene other than a protective sequence, modulating, including but not limited to, mimicking, agonizing, or antagonizing the expression of a protective sequence and/or the activity of a protective sequence product, or their regulatory elements, can be used for the treatment of the condition, disorder, or disease involving cell death. This is because protective sequences are nucleic acid molecules comprising nucleic acid sequences which, when introduced into a cell predisposed to undergo cell death, prevent, delay, or rescue such cell death relative to a corresponding cell into which no exogenous protective sequence has been introduced.

The proteins and peptides which may be used in the methods of the invention include synthetic (e.g., recombinant or chemically synthesized) proteins and peptides, as well as naturally occurring proteins and peptides. The proteins and peptides may have both naturally occurring and non-naturally occurring amino acid residues (e.g., D-amino acid residues) and/or one or more non-peptide bonds (e.g., imino, ester, hydrazide, semicarbazide, and azo bonds). The proteins or peptides may also contain additional chemical groups (i.e., functional groups) present at the amino and/or carboxy termini, such that, for example, the stability, bioavailability, and/or inhibitory activity of the peptide is enhanced. Exemplary functional groups include hydrophobic groups (e.g. carbobenzoxyl, dansyl, and t-butyloxycarbonyl, groups), an acetyl group, a 9-fluorenylmethoxy-carbonyl group and macromolecular carrier groups (e.g., lipid-fatty acid conjugates, polyethylene glycol, or carbohydrates) including peptide groups. Additional proteins and peptides which may be used in the methods of the invention include those described in WO 99/59615, which is herein incorporated by reference in its entirety.

5.4.1.1 Examples of Conditions, Disorders, or Diseases Involving Cell Death

The types of conditions, disorders, or diseases which can be prevented, delayed, or rescued by the compounds and methods of the present invention include, but are not limited to, those associated with the central nervous system including neurological and psychiatric conditions, disorders, or diseases; those of the peripheral nervous system; conditions, disorders, or diseases caused by physical injury; conditions, disorders, or diseases of the blood vessels or heart; conditions, disorders, or diseases of the respiratory system; neoplastic conditions, disorders, or diseases; conditions, disorders, or diseases of blood cells; conditions, disorders, or diseases of the gastrointestinal tract; conditions, disorders, or diseases of the liver; conditions, disorders, or diseases of the pancreas; conditions, disorders, or diseases of the kidney; conditions, disorders, or diseases of the ureters, urethra or bladder; conditions, disorders, or diseases of the male genital system; conditions, disorders, or diseases of the female genital tract; conditions, disorders, or diseases of the breast; conditions, disorders, or diseases of the endocrine system; conditions, disorders, or diseases of the thymus or pineal gland; conditions, disorders, or diseases of the skin or mucosa; conditions, disorders, or diseases of the musculoskeletal system; conditions, disorders, or diseases causing a fluid or hemodynamic derangement; inherited conditions, disorders, or diseases; conditions, disorders, or diseases of the immune system or spleen; conditions, disorders, or diseases caused by a nutritional disease; and conditions, disorders, or diseases typically occurring in infancy or childhood.

Conditions, disorders, or diseases involving the central nervous system include, but are not limited to, common pathophysiologic complications such as increased intracraneal pressure and cerebral herniation, septic embolism, cerebral edema, suppurative endovasculitis and hydrocephalus; infections such as meningitis, acute meningitis, acute lymphocytic meningitis, chronic meningitis, purulent meningitis, syphilitic gumma, encephalitis, cerebral abscess, epidural abscess, subdural abscess, brain abscess, viral encephalitis, acute viral encephalitis, encephalomeningitis, aseptic meningitis, post-infectious encephalitis, subacute encephalitis, chronic encephalitis, chronic meningitis, chronic encephalomeningitis, slow virus diseases and unconventional agent encephalopathies; protozoal infections such as malaria, toxoplasmosis, amebiasis and trypanosomiasis; rickettsial infections such as typhus and Rocky Mountain spotted fever; metazoal infections such as echinococcosis and cysticercosis; vascular diseases such as ischemic encephalopathy, cerebral infarction, intracranial hemorrhage, intraparenchymal hemorrhage, subarachnoid hemorrhage, mixed intraparenchymal and subarachnoid hemorrhage; conditions involving the eye such as macular degeneration, glaucoma, retinopathy of prematurity, retinitis pigmentosa, diabetic retinopathy, or other traumatic injuries to the retina or optic nerve; trauma such as epidural hematoma, subdural hematoma, parenchymal injuries; tumors such as primary intrachranial tumors, astrocytoma, oligodendroglioma, ependymoma, medulloblastoma and meningioma; degenerative diseases such as Altzheimer's disease, Huntington's disease, Parkinsonism, idiopathic Parkinson's disease and motor neuron disease; demyelinating diseases such as multiple sclerosis; nutritional, environmental and metabolic conditions, disorders, or diseases.

Conditions, disorders, or diseases of the peripheral nervous system include, but are not limited to, peripheral neuropathy, acute idiopathic polyneuropathy, diabetic neuropathy and peripheral nerve tumors.

Conditions, disorders, or diseases caused by physical injury include, but are not limited to, the direct, indirect, immediate, or delayed effects of: changes in temperature such as frostbite and thermal burns; an increase in atmospheric pressure such as air blast or immersion blast caused by an explosion; a decrease in atmospheric pressure such as caisson disease or high-altitude hypoxia; mechanical violence from penetrating or non-penetrating traumatic injury; electromechanical energy such as radiation injury from either charged particles or electromagnetic waves; electrocution or non-ionizing radiation such as radio waves, microwaves, laser light or ultrasound.

Conditions, disorders, or diseases of the blood vessels or heart include, but are not limited to, hypertension (high blood pressure), heart failure; ischemic or atherosclerotic heart disease; myocardial infarction; cardiac arrest; hypertensive heart disease; cor pulmonale; valvular heart disease such as that caused by rheumatic fever, aortic valve stenosis, mitral annulus calcification, carcinoid heart disease, nonbacterial thrombotic endocarditis, or nonbacterial verrucous endocarditis; infectious endocarditis caused by organisms including, but not limited to, Streptococcus species, Staphylococcus species, enterococci, pneumococci, gram-negative rods, Candida species, Aspergillus species, or culture-negative endocarditis; congenital heart disease such as atrial septal defect, ventricular septal defect, patent ductus arteriosis, coarctation of the aorta, Tetralogy of Fallot, tricuspid atresia, pulmonary stenosis or atresia, aortic stenosis or atresia, bicuspid aortic valve, or hypoplastic left heart syndrome; cardiomyopathy; pericarditis; pericardial effusion; rheumatoid heart disease; congenital anomalies of the blood vessels; arteriosclerosis including, but not limited to atherosclerosis, Monckeberg's medial calcific stenosis, hyaline arteriosclerosis, or hyperplastic arteriosclerosis; one or more of the vasculidities including, but not limited to, polyarteritis nodosa, hypersensitivity angiitis, Wegener's granulomatosis, giant cell (temporal) arteritis, Takayasu's arteritis, Kawasaki's disease, thromboangiitis obliterans, infectious vasculitis, Raynaud's disease; arteriosclerotic aortic aneurysm; syphilitic aortic aneurysm; dissecting aortic aneurysm; varicose veins; thrombophlebitis; lymphangitis; lymphedema; telangiectases; or arteriovenous malformations (AVM).

Conditions, disorders, or diseases of the respiratory system include, but are not limited to, pulmonary congestion; heart failure; embolism; infarction; pulmonary hypertension; adult respiratory distress syndrome (ARDS); obstructive lung disease; restrictive lung disease; chronic obstructive pulmonary disease; asthma; sarcoidosis; diffuse interstitial or infiltrative lung diseases including, but not limited to, idiopathic pulmonary fibrosis, pneumoconiosis, hypersensitivity pneumonitis, Goodpasture's syndrome, idiopathic pulmonary hemosiderosis, collagen-vascular diseases, or pulmonary eosinophilia; serofibrinous pleuritis; suppurative pleuritis; hemorrhagic pleuritis; pleural effusions; pneumothorax; hemothorax or pneumohemothorax.

Neoplastic conditions, disorders, or diseases include, but are not limited to, benign tumors composed of one parenchymal cell type such as fibromas, myxomas, lipomas, hemangiomas, meningiomas, leiomyomas, adenomas, nevi, moles, or papillomas; benign mixed tumors derived from one germ layer such as a mixed tumor of salivary gland origin; benign mixed tumors derived from more than one germ layer such as a teratoma; primary malignant tumors or metastases of malignant tumors composed of one parenchymal cell type such as sarcomas, Ewing's tumor, leukemia, myeloma, histiocytosis X, Hodgkin's disease, lymphomas, carcinomas, melanomas, bronchial adenoma, small cell lung cancer, or seminoma; primary malignant tumors or metastases of mixed malignant tumors derived from one germ layer such as Wilms' tumor or malignant mixed salivary gland tumor; primary malignant tumor or metastases of mixed malignant tumors derived from one germ layer such as malignant teratoma or teratocarcinoma; undifferentiated benign tumor or undifferentiated malignant tumor.

Conditions, disorders, or diseases of blood cells include, but are not limited to, anemia due to one or more of the following conditions: acute blood loss, chronic blood loss, hemolytic anemia, sickle cell disease, thalassemia syndromes, autoimmune hemolytic anemia, traumatic anemia, or diminished erythropoesis from megaloblastic anemia, iron deficiency, aplastic anemia, idiopathic bone marrow failure; polycythemia; hemorrhagic diatheses related to increased vascular fragility; hemorrhagic diatheses related to a reduction in platelets; idiopathic or thrombotic thrombocytopenic purpura; hemorrhagic diatheses related to defective platelet function; hemorrhagic diatheses related to abnormalities in clotting factor(s); disseminated intravascular coagulation (DIC); neutropenia; agranulocytosis; leukocytosis; plasma cell dyscrasias such as myeloma, Waldenstrom's macroglobulinemia, or heavy-chain disease; or histiocytosis.

Conditions, disorders, or diseases of the gastrointestinal tract include, but are not limited to, congenital anomalies such as atresia, fistulas, or stenosis; periodontal disease; periapical disease; xerostomia; necrotizing sialometaplasia; esophageal rings or webs; hernia; Mallory-Weiss syndrome; esophagitis; diverticulosis; diverticulitis; scleroderma; esophageal varices; acute or chronic gastritis; peptic ulcer; gastric erosion or ulceration; ischemic bowel disease; infarction; embolism; Crohn's disease; obstruction from foreign bodies, hernia, adhesion, intussusception, or volvulus; ileus; megacolon; angoidysplasia; ulcerative colitis; psuedomembranous colitis; or polyps.

Conditions, disorders, or diseases of the liver include, but are not limited to, acute hepatic failure due to one of more of metabolic, circulatory, toxic, microbial, or neoplastic causes; chronic hepatic failure due to one or more of metabolic, circulatory, toxic, microbial, or neoplastic causes; hereditary hyperbilirubinemias; infarct; embolism; hepatic circulation thrombosis or obstruction; fulminant hepatic necrosis; portal hypertension; alcoholic liver disease; post-necrotic cirrhosis; biliary cirrhosis; cirrhosis associated with alpha-1-antitrypsin deficiency; Wilson's disease; or Reye's syndrome.

Conditions, disorders, or diseases of the pancreas include, but are not limited to, congenital aberrant pancreas, congenital anomalies of pancreatic ducts, stromal fatty infiltration, pancreatic atrophy, acute hemorrhagic pancreatitis, chronic pancreatitis, chronic calcifying pancreatitis, chronic obstructive pancreatitis, pancreatic psuedocyst, diabetes mellitus, or gestational diabetes.

Conditions, disorders, or diseases of the kidney include, but are not limited to, congenital anomalies; polycystic renal disease; dialysis-associated cystic disease; glomerular disease, including, but not limited to, acute glomerulonephritis, acute proliferative glomerulonephritis, rapidly progressive glomerulonephritis, postinfectious rapidly progressive glomerulonephritis, Goodpasture's syndrome, idiopathic rapidly progressive glomerulonephritis, nephrotic syndrome, membranous glomerulonephritis, lipoid nephrosis, focal segmental glomerulosclerosis, membranoproliferative glomerulonephritis, focal proliferative glomerulonephritis, chronic glomerulonephritis, or hereditary nephritis; acute tubular necrosis; acute renal failure; tubulointerstitial diseases including, but not limited to, pyelonephritis, drug-induced interstitial nephritis, analgesic nephritis, urate nephropathy, hypercalcemia and nephrocalcinosis, hypokalemic nephropathy, myeloma-induced tubulointerstitial disease, radiation nephritis, immunologically medicated tubulointerstitial disease; hypertension; malignant hypertension; renal artery stenosis; renal diseases secondary to microangiopathic hemolytic anemia; atheroembolic renal disease; sickle cell disease nephropathy; diffuse cortical necrosis; renal infarcts; obstructive uropathy; or urolithiasis.

Conditions, disorders, or diseases of the ureters, urethra or bladder include, but are not limited to, congenital anomalies; inflammatory diseases; physical obstruction by causes including, but not limited to calculi, strictures, neoplasia, blood clot, or pregnancy; sclerosing retroperitonitis; acute cystitis; chronic cystitis; interstitial cystitis; emphysematous cystitis; eosinophilic cystitis; encrusted cystitis; fistula; or neurogenic bladder.

Conditions, disorders, or diseases of the male genital system include, but are not limited to, congenital anomalies;

balanoposthitis; condyloma; phimosis; paraphimosis; dysplastic epithelial lesions; nonspecific epididymitis or orchitis; granulomatous orchitis; torsion of the testis or its vascular supply; granulomatous prostatitis; acute or chronic prostatitis; or benign prostatic hyperplasia.

Conditions, disorders, or diseases of the female genital tract include, but are not limited to, congenital anomalies, lichen scleroses, acute cervicitis, chronic cervicitis, cervical polyps; acute endometritis; chronic endometritis; endometriosis; dysfunctional uterine bleeding; endometrial hyperplasia; senile cystic endometrial atrophy; salpingitis; polycystic ovary disease; pre-eclampsia or eclampsia (toxemia of pregnancy); placentitis; threatened abortion; or ectopic pregnancy.

Conditions, disorders, or diseases of the breast include, but are not limited to, congenital anomalies, acute mastitis, chronic mastitis, galactocele, granulomas, traumatic fat necrosis, mammary duct ectasia, fibrocystic disease, sclerosing adenitis, epithelial hyperplasia, hypertrophy, or gynecomastia.

Conditions, disorders, or diseases of the endocrine system include, but are not limited to, congenital anomalies; Sheehan's pituitary necrosis; empty sella syndrome; hyperthyroidism (thyrotoxicosis) from causes including, but not limited to, Graves' disease, toxic multinodular goiter, toxic adenoma, acute or subacute thyroiditis, TSH-secreting tumor, neonatal thyrotoxicosis, iatrogenic thyrotoxicosis; Hashimoto's thyroiditis; hypothyroidism (cretinism or myxedema) from causes including, but not limited to, surgical or radioactive ablation, primary idiopathic myxedema, iodine deficiency, goitrogenic agents, hypopituitarism, hypothalamic lesions, TSH resistance, subacute thyroiditis, or chronic thyroiditis; diffuse nontoxic simple or multinodular goiter; multiple endocrine neoplasia syndromes; primary or secondary hyperparathyroidism; chief cell hyperplasia; clear cell hyperplasia; hypoparathyroidism; pseudo- and pseudopseudohypoparathyrodism; Addison's disease; Waterhouse-Friderichsen syndrome; secondary adrenocortical insufficiency; Cushing's syndrome; Conn's syndrome; or congenital adrenal hyperplasia.

Conditions, disorders, or diseases of the skin or mucosa include, but are not limited to, melanocytic proliferative disorders; inflammatory dermatoses including, but not limited to, eczematous dermatitis, urticaria, erythema multiforme, cutaneous necrotizing vasculitis, cutaneous lupus erythematosus, graft-versus-host disease, panniculitis, acne vulgaris, rosacea, lichen planus, lichen sclerosus et atrophicus, pityriasis, psoriasis, or parapsoriasis; blistering diseases including, but not limited to, pemphigus, bullous pemphigoid, dermatitis herpetiformis, or porphyria.

Conditions, disorders, or diseases of the musculoskeletal system include, but are not limited to, muscular atrophy; segmental necrosis; myositis; muscular dystrophy, including, but not limited to, Duchenne type, Becker type, Fascioscapulohumeral, Limb-Girdle, myotonic dystrophy, or ocular myopathy; congenital myopathies; myasthenia gravis; traumatic myositis ossificans; nodular fasciitis; desmoid tumors; palmar fibromatosis; congenital bone disorders including, but not limited to, osteogenesis imperfecta, achondroplasia, osteopetrosis, osteochondromatosis, endochondromatosis; osteomyelitis; fractures; osteoporosis; osteomalacia; bony changes secondary to hyperparathyroidism; Paget's disease; hypertrophic osteoarthropathy; fibrous dysplasia; or nonossifying fibroma.

Conditions, disorders, or diseases causing a fluid or hemodynamic derangement include, but are not limited to, systemic edema; anasarca; edema from increased hydrostatic pressure including, but not limited to congestive heart failure, cirrhosis of the liver, constrictive pericarditis, venous obstruction; edema from reduced oncotic pressure including, but not limited to, cirrhosis of the liver, malnutrition, protein-losing renal disease, protein-losing gastroenteropathy, protein loss through increased vascular permeability; edema from lymphatic obstruction including, but not limited to, cancer, inflammatory injury, surgical injury, traumatic injury, or radiation injury; edema from increased osmotic tension in the interstitial fluid including, but not limited to, sodium retention from excessive salt intake or increased renal sodium retention, reduced renal perfusion, acute or chronic renal failure, acute or chronic renal insufficiency; edema from increased endothelial permeability including, but not limited to, inflammation, shock, burns, trauma, allergic reaction, immunologic reaction, or adult respiratory distress syndrome; ascites; pericardial effusion; hydrothorax; hyperemia; hemorrhage; mural thrombus or occlusive thrombus diminishing or obstructing vascular flow; phlebothrombosis; blood clot; embolism; thromboembolism; disseminated intravascular coagulation (DIC); amniotic fluid infusion; amniotic fluid embolism; systemic embolism disease; septic embolism; fat embolism; pulmonary embolism; air gas embolism (caisson disease or decompression sickness); anemic (white) infarction; hemorrhagic (red) infarction; cerebral infarction; septic infarction; ischemia; cardiogenic shock from conditions including, but not limited to, myocardial infarction, cardiac arrest, cardiac rupture, cardiac tamponade, pulmonary embolism, cardiac valvular obstruction, or cardiac arrhythmias; hypovolemic shock from conditions including, but not limited to, hemorrhage, vomiting, diarrhea, diaphoresis, extensive injury to bone or soft tissues, burns, or accumulation of intraperitoneal fluid; shock due to peripheral blood pooling from conditions including, but not limited to, spinal cord injury, general anesthesia, regional anesthesia, local anesthesia, drug-induced ganglionic or adrenergic blockade, gram-negative septicemia, or gram-positive septicemia; anaphylaxis, or disseminated intravascular coagulation (DIC).

Inherited conditions, disorders, or diseases include, but are not limited to, Down's syndrome, Edwards' syndrome, Patau's syndrome, other trisomies, Cri du Chat syndrome, Klinefelter's syndrome, XYY syndrome, Turner's syndrome, Multi-X female syndrome, hermaphrodism or pseudohermaphrodism, Marfan's syndrome, neurofibromatosis, vonHippel-Lindau disease, familial hypercholesterolemia, albinism, alkaptonuria, Fabry's disease, Fragile-X syndrome, Ehlers-Danlos syndromes, inherited neoplastic syndromes, inherited autosomal dominant conditions, Huntington's disease, Alport's disease, sickle-cell disease, thalessemia, tuberous sclerosis, vonWillebrand's disease, polycystic kidney disease, Pompe's disease, GM1-gangliosidosis; Tay-Sachs disease, Sandhoff-Jatzkewitz disease, metachromatic leukodystrophy, multiple sufatase deficiency, Krabbe's disease, Gaucher's disease, Niemann-Pick disease, all types of mucopolysaccharidoses, I-cell disease, Hurler's polydystrophy, fucosidosis, mannosidosis, aspartylglycosaminuria, Wolman's disease, or acid phosphatase deficiency, inherited autosomal recessive conditions, inherited sex-linked conditions.

Conditions, disorders, or diseases of the immune system or spleen include, but are not limited to, Type I hypersensitivity conditions (anaphylaxis and other basophil or mast cell mediated conditions), Type II hypersensitivity conditions (cytotoxic conditions involving phagocytosis or lysis of target cell), Type III hypersensitivity conditions (immune complex conditions involving antigen-antibody complexes), Type IV hypersensitivity conditions (cell-mediated conditions), transplant rejection, systemic lupus erythematosus, Sjogren's syndrome, CREST, scleroderma, polymyositis-dermatomyositis, mixed connective tissue disease, polyarteritis nodosa, amyloidosis, X-linked agammaglobulinemia, comrnmon variable immunodeficiency, isolated IgA deficiency, DiGeorge's syndrome, severe combined immunodeficiency, Wiscott-Aldrich syndrome, infection with HIV virus, acquired immune deficiency syndrome (AIDS), congenital anomalies of the immune system, hypersplenism, splenomegaly, congenital anomalies of the spleen, congestive splenomegaly, infarcts, or splenic rupture.

Conditions, disorders, or diseases caused by a nutritional disease include, but are not limited to, marasmus, kwashiorkor, fat-soluble vitamin deficiency or toxicity (Vitamins A, D, E, or K), water-soluble vitamin deficiency or toxicity (thiamine, riboflavin, niacin, pyridoxine, folate, cobalamin, Vitamin C), mineral deficiency or toxicity (iron, calcium, magnesium, sodium, potassium, chloride, zinc, copper, iodine, cobalt, chromium, selenium, nickel, vanadium, manganese, molybdenum, rickets, osteomalacia, beriberi, hypoprothrombinemia, pellagra, megaloblastic anemia, scurvy, pernicious anemia, lack of gastric intrinsic factor, removal or pathophysiological functioning in the terminal ileum, microcytic anemia, or obesity.

Conditions, disorders, or diseases typically occurring in infancy or childhood include, but are not limited to, preterm birth, congenital malformations from genetic causes, congenital malformations from infectious causes, congenital malformations from toxic or teratogenic causes, congenital malformations from radiation, congenital malformations from idiopathic causes, small for gestational age infants, perinatal trauma, perinatal asphyxia, perinatal ischemia or hypoxia, birth injury, intracranial hemorrhage, deformations, respiratory distress syndrome of the newborn, atelectasis, hemolytic disease of the newborn, kernicterus, hydrops fetalis, congenital anemia of the newborn, icterus gravis, phenylketonuria, galactosemia, cystic fibrosis, hamartoma, or choristoma.

In another embodiment, the compounds and methods of the invention can be used to treat infections that cause cell death. The infections may be caused by bacteria; viruses; members of the family rickettsiae or chlamydia; fungi, yeast, hyphae or pseudohyphae; prions; protozoas; or metazoas.

Examples of aerobic or anaerobic bacteria which may cause such infections include, but are not limited to, gram-positive cocci, gram-positive bacilli (gram-positive rods), gram-negative cocci, gram-negative bacilli (gram-negative rods), Mycoplasma species, Ureaplasma species, Treponema species, Leptospira species, Borrelia species, Vibrio species, Mycobacteria species, members of Actinomycetes or L-forms (cell-wall deficient forms).

Examples of DNA, RNA or both DNA and RNA viruses which may cause such infections include, but are not limited to, members of the families adenoviridae, parvoviridae, papovaviridae, herpesviridae, poxviridae, picornaviridae, orthomyxoviridae, paramyxoviridae, rhabdoviridae, bunyaviridae, arenaviridae, coronaviridae, retroviridae, reoviridae, togaviridae and caliciviridae.

Examples of members of the families rickettsiae or chlamydiae which may cause such infections include, but are not limited to, Rickettsia species, Rochalimaea species, Coxiella species or Chlamydia species.

Examples of fungi, yeast, hyphae or pseudohyphae which may cause such infections include, but are not limited to, members of Ascomycota, Basidiomycota, Zygomycota, or Deutoeromycota (Fungi Imperfecti); Candida species, Cryptococcus species, Torulopsis species, Rhodotorula species, Sporothrix species, Phialophora species, Cladosporium species, Xylohypha species, Blastomyces species, Histoplasma species, Coccidioides species, Paracoccidioides species, Geotrichum species, Aspergillus species, Rhizopus species, Mucor species, Pseudoallescheria species or Absidia species.

Examples of prions which may cause such infections include, but are not limited to, the causative agent of Creutzfeldt-Jakob Disease, the causative agent of Gerstmann-Straussler-Scheinker Disease, the causative agent of fatal familial insomnia, the causative agent of kuru, and the causative agent of bovine spongiform encephalopathy.

Examples of protozoa at any point in their life cycle which may cause such infections include, but are not limited to, Entamoeba species, Naegleria species, Acanthamoeba species, Pneumocystis species, Balantidium species, members of order Leptomyxida, Plasmodium species, Toxoplasma species, Leishmania species and Trypanosoma species.

Examples of metazoa at any point in their life cycle which may cause such infections include, but are not limited to, members of Platyhelminthes such as the organisms in Cestoda (tapeworms) or Trematoda (flukes); or members of Aschelminthes such as the organisms in Acanthocephala, Chaetognatha, Cycliophora, Gastrotricha, Nematoda or Rotifera.

In a further embodiment, the compounds and methods of the invention can be used to treat infections or disorders which cause cell death in organ systems including, but not limited to, blood vessels, heart, red blood cells, white blood cells, lymph nodes, spleen, respiratory system, oral cavity, gastrointestinal tract, liver and biliary tract, pancreas, kidney, lower urinary tract, upper urinary tract and bladder, male sexual organs and genitalia, female sexual organs and genitalia, breast, thyroid gland, adrenal gland, parathyroid gland, skin, musculoskeletal system, bone marrow or bones.

In a further embodiment, the compounds and methods of the invention can be used to treat further physiological impacts on organs caused by the infections which induce cell death including, but not limited to, fever equal to or greater than 101.5 degrees Fahrenheit, a decrease or increase in pulse rate by more than 20 beats per minute, a decrease or increase in supine systolic blood pressure by more than 30 millimeters of mercury, an increase or decrease in respiratory rate by more than 8 breaths per minute, an increase or decrease in blood pH by more than 0.10 pH units, an increase or decrease in one or more serum electrolytes outside of the clinical laboratory's usual reference range, an increase or decrease in the partial pressure of arterial oxygen or carbon dioxide outside of the clinical laboratory's usual reference range, an increase or decrease in white or red blood cells outside of the laboratory's usual reference range, an acute confusional state such as delirium where delirium is defined by the American Psychiatric Association's DSM-IV Manual or a diminished level of consciousness or attention.

5.4.1.2 Modulatory Antisense, Ribozyme and Triple Helix Approaches

In another embodiment, the types of conditions, disorders, or diseases involving cell death which may be prevented, delayed, or rescued by modulating protective sequence expression, protective sequence product activity, or their regulatory elements by using protective sequences in conjunction with well-known antisense, gene "knock-out," ribozyme and/or triple helix methods, are described. Among the compounds which may exhibit the ability to modulate the activity, expression or synthesis of the protective sequence, the protective sequence product, or its regulatory elements, including the ability to prevent, delay, or rescue a cell, cells, tissue, organ, or organism from the symptoms of a condition, disorder, or disease involving cell death are antisense, ribozyme and triple helix molecules. Such molecules may be designed to modulate, reduce or inhibit either unimpaired, or if appropriate, mutant protective sequence activity. Techniques for the production and use of such molecules are well known to those of skill in the art.

Antisense RNA and DNA molecules act to directly block the translation of mRNA by hybridizing to targeted mRNA and preventing protein translation. Antisense approaches involve the design of oligonucleotides which are complementary to a protective sequence mRNA. The antisense oligonucleotides will bind to the complementary protective sequence mRNA transcripts and prevent translation. Absolute complementarity, although preferred, is not required.

A sequence "complementary" to a portion of an RNA, as referred to herein, means a sequence having sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

In one embodiment, oligonucleotides complementary to non-coding regions of the protective sequence of interest could be used in an antisense approach to inhibit translation of endogenous mRNA. Antisense nucleic acids should be at least six nucleotides in length, and are preferably oligonucleotides ranging from 6 to about 50 nucleotides in length. In specific aspects, the oligonucleotide is at least 10 nucleotides, at least 17 nucleotides, at least 25 nucleotides or at least 50 nucleotides.

Regardless of the choice of target sequence, it is preferred that in vitro studies are first performed to quantitate the ability of the antisense oligonucleotide to inhibit protective sequence expression. It is preferred that these studies utilize controls that distinguish between antisense gene inhibition and nonspecific biological effects of oligonucleotides. It is also preferred that these studies compare levels of the cerebral RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleic acid of the oligonucleotide differs from the antisense sequence no more than is necessary to prevent specific hybridization to the target sequence.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger, et al., 1989, *Proc. Natl. Acad. Sci. U.S.A.* 86:6553–6556; Lemaitre, et al., 1987, *Proc. Natl. Acad. Sci. U.S.A.* 84:648–652; PCT Publication No. WO 88/09810, published Dec. 15, 1988) or the blood-brain barrier (see, e.g., PCT Publication No. WO 89/10134, published Apr. 25, 1988), hybridization-triggered cleavage agents (see, e.g., Krol et al., 1988, *BioTechniques* 6:958–976) or intercalating agents (see, e.g., Zon, 1988, *Pharm. Res.* 5:539–549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide may also comprise at least one modified sugar moiety selected from the group including but not limited to arabinose, 2-fluoroarabinose, xylulose, and hexose.

In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomenc oligonucleotide. An α-anomeric oligonucleotide forms specific double-stranded hybrids with complementary RNA in which, contrary to the usual β-units, the strands run parallel to each other (Gautier, et al., 1987, *Nucl. Acids Res.* 15:6625–6641). The oligonucleotide is a 2'-0-methylribonucleotide (Inoue, et al., 1987, *Nucl. Acids Res.* 15:6131–6148), or a chimeric RNA-DNA analogue (Inoue, et al., 1987, *FEBS Lett.* 215:327–330).

Oligonucleotides of the invention may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein, et al. (1988, *Nucl. Acids Res.* 16:3209), methylphosphonate oligonucleotides can be prepared by use of controlled pore glass polymer supports (Sarin, et al., 1988, *Proc. Natl. Acad. Sci. U.S.A.* 85:7448–7451), etc.

While antisense nucleotides complementary to the protective sequence coding region sequence could be used, those complementary to the transcribed, untranslated region are most preferred.

Antisense molecules should be delivered to cells that express the protective sequence in vivo. A number of methods have been developed for delivering antisense DNA or RNA to cells; e.g., antisense molecules can be injected directly into the tissue site, or modified antisense molecules, designed to target the desired cells (e.g., antisense linked to peptides or antibodies which specifically bind receptors or antigens expressed on the target cell surface) can be administered systemically.

A preferred approach to achieve intracellular concentrations of the antisense sufficient to suppress translation of endogenous mRNAs utilizes a recombinant DNA construct in which the antisense oligonucleotide is placed under the control of a strong pol III or pol II promoter. The use of such a construct to transfect target cells in the patient will result in the transcription of sufficient amounts of single stranded RNAs which will form complementary base pairs with the endogenous protective sequence transcripts and thereby prevent translation of the protective sequence mRNA. For example, a vector can be introduced e.g., such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bemoist and Chambon, 1981, *Nature* 290:304–310), the promoter contained in the 3'-long terminal repeat of Rous sarcoma virus (Yamamoto, et al., 1980, *Cell* 22:787–797), the herpes thymidine kinase promoter (Wagner, et al., 1981, *Proc. Natl. Acad. Sci. U.S.A.* 78:1441–1445), the regulatory sequences of the metallothionein gene (Brinster, et al., 1982, *Nature* 296:39–42), etc. Any type of plasmid, cosmid, YAC or viral vector can be used to prepare the recombinant DNA construct that can be introduced directly into the tissue site. Alternatively, viral vectors can be used that selectively infect the desired tissue, in which case administration may be accomplished by another route (e.g., systemically).

Ribozyme molecules designed to catalytically cleave target gene mRNA transcripts can also be used to prevent translation of target gene mRNA and, therefore, expression of target gene product. (See, e.g., PCT International Publication WO 90/11364, published Oct. 4, 1990; Sarver, et al., 1990, *Science* 247, 1222–1225).

Ribozymes are enzymatic RNA molecules capable of catalyzing the specific cleavage of RNA. (For a review, see Rossi, 1994, *Current Biology* 4:469–471). The mechanism of ribozyme action involves sequence specific hybridization of the ribozyme molecule to complementary target RNA, followed by an endonucleolytic cleavage event. The composition of ribozyme molecules must include one or more sequences complementary to the target gene mRNA, and must include the well known catalytic sequence responsible for mRNA cleavage. For this sequence, see, e.g., U.S. Pat. No. 5,093,246, which is incorporated herein by reference in its entirety.

While ribozymes that cleave mRNA at site specific recognition sequences can be used to destroy target gene mRNAs, the use of hammerhead ribozymes is preferred. Hammerhead ribozymes cleave mRNAs at locations dictated by flanking regions which form complementary base pairs with the target MRNA. The sole requirement is that the target mRNA have the following sequence of two bases: 5'-UG-3'. The construction and production of hammerhead ribozymes is well known in the art and is described more fully in Myers, 1995, *Molecular Biology and Biotechnology: A Comprehensive Desk Reference,* VCH Publishers, New York, (see especially FIG. 4, page 833) and in Haseloff and Gerlach, 1988, *Nature,* 334:585–591, which is incorporated herein by reference in its entirety.

Preferably the ribozyme is engineered so that the cleavage recognition site is located near the 5' end of the target gene MRNA, i.e., to increase efficiency and minimize the intracellular accumulation of non-functional mRNA transcripts.

The ribozymes of the present invention also include RNA endoribonucleases (hereinafter "Cech-type ribozymes") such as the one which occurs naturally in *Tetrahymena thermophila* (known as the IVS, or L-19 IVS RNA) and which has been extensively described by Thomas Cech and collaborators (Zaug, et al., 1984, *Science,* 224:574–578; Zaug and Cech, 1986, *Science,* 231:470–475; Zaug, et al., 1986, *Nature,* 324:429–433; published International patent application No. WO 88/04300 by University Patents Inc.; Been and Cech, 1986, *Cell,* 47:207–216). The Cech-type ribozymes have an eight base pair active site that hybridizes to a target RNA sequence whereafter cleavage of the target RNA takes place. The invention encompasses those Cech-type ribozynes that target eight base-pair active site sequences that are present in the target gene.

As in the antisense approach, the ribozymes can be composed of modified oligonucleotides (e.g., for improved stability, targeting, etc.) and should be delivered to cells that express the target gene in vivo. A preferred method of delivery involves using a DNA construct "encoding" the ribozyme under the control of a strong constitutive pol III or pol II promoter, so that transfected cells will produce sufficient quantities of the ribozyme to destroy endogenous target gene messages and inhibit translation. Because ribozymes, unlike antisense molecules, are catalytic, a lower intracellular concentration is required for efficiency.

Endogenous target gene expression can also be reduced by inactivating or "knocking out" the target gene or its promoter using targeted homologous recombination (e.g., see Smithies, et al, 1985, *Nature* 317:230–234; Thomas and Capecchi, 1987, *Cell* 51:503–512; Thompson, et al., 1989, *Cell* 5:313–321; each of which is incorporated by reference herein in its entirety). For example, a mutant, non-functional target gene (or a completely unrelated DNA sequence) flanked by DNA homologous to the endogenous target gene (either the coding regions or regulatory regions of the target gene) can be used, with or without a selectable marker and/or a negative selectable marker, to transfect cells which express the target gene in vivo. Insertion of the DNA construct, via targeted homologous recombination, results in inactivation of the target gene. Such approaches are particularly suited in the agricultural field where modifications to ES (embryonic stem) cells can be used to generate animal offspring with an inactive target gene (e.g., see Thomas and Capecchi, 1987 and Thompson, 1989, supra). However this approach can be adapted for use in humans provided the recombinant DNA constructs are directly administered or targeted to the required site in vivo using appropriate viral vectors.

Alternatively, endogenous target gene expression can be reduced by targeting deoxyribonucleotide sequences complementary to the regulatory region of the target gene (i.e., the target gene promoter and/or enhancers) to form triple helical structures which prevent transcription of the target gene in target cells in the body. (See generally, Helene, 1991, *Anticancer Drug Des.,* 6(6):569–584; Helene, et al., 1992, *Ann. N.Y. Acad. Sci.,* 660:27–36; and Maher, 1992, *Bioassays* 14(12):807–815).

Nucleic acid molecules to be used in triple helix formation for the inhibition of transcription should be single stranded and composed of deoxynucleotides. The base composition of these oligonucleotides must be designed to promote triple helix formation via Hoogsteen base pairing rules, which generally require sizable stretches of either purines or pyrimidines to be present on one strand of a duplex. Nucleic acids may be pyrimidine-based, which will result in TAT and CGC$^+$ triplets across the three associated strands of the resulting triple helix. The pyrimidine-rich molecules provide base complementarity to a purine-rich region of a single strand of the duplex in a parallel orientation to that strand. In addition, nucleic acid molecules may be chosen which are purine-rich, for example, contain a stretch of G residues. These molecules will form a triple helix with a DNA duplex that is rich in GC pairs, in which the majority of the purine residues are located on a single strand of the targeted duplex, resulting in GGC triplets across the three strands in the triplex.

Alternatively, the potential sequences that can be targeted for triple helix formation may be increased by creating a so-called "switchback" nucleic acid molecule. Switchback molecules are synthesized in an alternating 5'-3', 3'-5' manner, such that they base pair with first one strand of a duplex and then the other, eliminating the necessity for a sizable stretch of either purines or pyrimidines to be present on one strand of a duplex.

In instances wherein the antisense, ribozyme, and/or triple helix molecules described herein are utilized to inhibit mutant gene expression, it is possible that the technique may so efficiently reduce or inhibit the transcription (triple helix) and/or translation (antisense, ribozyme) of mRNA produced by normal target gene alleles which the possibility may arise wherein the concentration of normal target gene product present may be lower than is necessary for a normal phenotype. In such cases, to ensure that substantially normal levels of target gene activity are maintained, therefore, nucleic acid molecules which encode and express target gene polypeptides exhibiting normal target gene activity may, be introduced into cells via gene therapy methods such as those described, below, in Section 5.4.1.3 which do not contain sequences susceptible to whatever antisense, ribozyme, or triple helix treatments are being utilized. Alternatively, in instances whereby the target gene encodes an extracellular protein, it may be preferable to co-administer normal target gene protein in order to maintain the requisite level of target gene activity.

Anti-sense RNA and DNA, ribozyme, and triple helix molecules of the invention may be prepared by any method known in the art for the synthesis of DNA and RNA molecules, as discussed above. These include techniques for chemically synthesizing oligodeoxyribonucleotides and oligoribonucleotides well known in the art such as for example solid-phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

5.4.1.3 Gene Replacement Therapy

Protective nucleic acid sequences, described above in Section 5.1, can be utilized for transferring recombinant protective nucleic acid sequences to cells and expressing said sequences in recipient cells. Such techniques can be used, for example, in marking cells or for the treatment of a condition, disorder, or disease involving cell death. Such treatment can be in the form of gene replacement therapy. Specifically, one or more copies of a normal protective sequence or a portion of the protective sequence which directs the production of a protective sequence product exhibiting normal protective sequence function, may be inserted into the appropriate cells within a patient, using vectors which include, but are not limited to adenovirus, adeno-associated virus and retrovirus vectors, in addition to other particles which introduce DNA into cells, such as liposomes.

Because the protective sequence of the invention may be expressed in the brain, such gene replacement therapy techniques should be capable of delivering protective sequences to these cell types within patients. Thus, in one embodiment, techniques which are well known to those of skill in the art (see, e.g., PCT Publication No. WO 89/10134, published Apr. 25, 1988) can be used to enable protective sequences to cross the blood-brain barrier readily and to deliver the sequences to cells in the brain. With respect to delivery which is capable of crossing the blood-brain barrier, viral vectors such as, for example, those described above, are preferable.

In another embodiment, techniques for delivery involve direct administration, e.g., by stereotactic delivery of such protective sequences to the site of the cells in which the protective sequences are to be expressed.

Methods for introducing genes for expression in mammalian cells are well known in the field. Generally, for such gene therapy methods, the nucleic acid is directly administered in vivo into a target cell or a transgenic mouse that expresses SP-10 promoter operably linked to a reporter gene. This can be accomplished by any methods known in the art, e.g., by constructing it as part of an appropriate nucleic acid expression vector and administering it so that it becomes intracellular, e.g., by infection using a defective or attenuated retroviral or other viral vector (see U.S. Pat. No. 4,980,286), by direct injection of naked DNA, by use of microparticle bombardment (e.g., a gene gun; Biolistic, Dupont), by coating with lipids or cell-surface receptors or transfecting agents, by encapsulation in liposomes, microparticles, or microcapsules, by administering it in linkage to a peptide which is known to enter the nucleus, or by administering it in linkage to a ligand subject to receptor-mediated endocytosis (see e.g., Wu and Wu, 1987, J. Biol. Chem. 262:4429–4432), which can be used to target cell types specifically expressing the receptors. In another embodiment, a nucleic acid-ligand complex can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180 dated Apr. 16, 1992; WO 92/22635 dated Dec. 23, 1992; WO 92/20316 dated Nov. 26, 1992; WO 93/14188 dated Jul. 22, 1993; WO 93/20221 dated Oct. 14, 1993).

Additional methods which may be utilized to increase the overall level of protective sequence expression and/or gene product activity include using targeted homologous recombination methods, discussed in Section 5.2, above, to modify the expression characteristics of an endogenous protective sequence in a cell or microorganism by inserting a heterologous DNA regulatory element such that the inserted regulatory element is operatively linked with the endogenous protective sequence in question. Targeted homologous recombination can thus be used to activate transcription of an endogenous protective sequence which is "transcriptionally silent", i.e., is not normally expressed or is normally expressed at very low levels, or to enhance the expression of an endogenous protective sequence which is normally expressed.

Further, the overall level of protective sequence expression and/or gene product activity may be increased by the introduction of appropriate protective sequence-expressing cells, preferably autologous cells, into a patient at positions and in numbers which are sufficient to ameliorate the symptoms of a condition, disorder, or disease involving cell death. Such cells may be either recombinant or non-recombinant.

Among the cells that can be administered to increase the overall level of protective sequence expression in a patient are normal cells, preferably brain cells, which express the protective sequence. Alternatively, cells, preferably autologous cells, can be engineered to express protective sequences, and may then be introduced into a patient in positions appropriate for the amelioration of the symptoms of a condition, disorder, or disease involving cell death. Alternately, cells which express an unimpaired protective sequence and which are from a MHC matched individual can be utilized, and may include, for example, brain cells. The expression of the protective sequences is controlled by the appropriate gene regulatory sequences to allow such expression in the necessary cell types. Such gene regulatory sequences are well known to the skilled artisan. Such cell-based gene therapy techniques are well known to those skilled in the art, see, e.g., Anderson, U.S. Pat. No. 5,399,349.

When the cells to be administered are non-autologous cells, they can be administered using well-known techniques that prevent a host immune response against the introduced cells from developing. For example, the cells may be introduced in an encapsulated form that, while allowing for an exchange of components with the immediate extracellular environment, does not allow the introduced cells to be recognized by the host immune system.

Additionally, compounds, such as those identified via techniques such as those described, in Section 5.4.2, which are capable of modulating protective sequences, protective sequence product activity, or their regulatory sequences can be administered using standard techniques which are well known to those of skill in the art. In instances in which the compounds to be administered are to involve an interaction with brain cells, the administration techniques should include well known methods that allow for a crossing of the blood-brain barrier.

5.4.1.4 Detection of Protective Nucleic Acid Molecules

A variety of methods can be employed to screen for the presence of protective sequence-specific mutations or polymorphisms (including polymorphisms flanking protective sequences) and to detect and/or assay levels of protective nucleic acid sequences.

Mutations or polymorphisms within or flanking the protective sequences can be detected by utilizing a number of techniques. Nucleic acid from any nucleated cell can be used as the starting point for such assay techniques, and may be isolated according to standard nucleic acid preparation procedures that are well known to those of skill in the art.

Protective nucleic acid sequences may be used in hybridization or amplification assays of biological samples to detect abnormalities involving protective sequence structure, including point mutations, insertions, deletions, inversions, translocations and chromosomal rearrangements. Such assays may include, but are not limited to, Southern analyses, single-stranded conformational polymorphism analyses (SSCP) and PCR analyses.

Diagnostic methods for the detection of protective sequence-specific mutations or polymorphisms can involve for example, contacting and incubating nucleic acids obtained from a sample, e.g., derived from a patient sample or other appropriate cellular source with one or more labeled nucleic acid reagents including recombinant DNA molecules, cloned genes or degenerate variants thereof, such as described in Section 5.1, above, under conditions favorable for the specific annealing of these reagents to their complementary sequences within or flanking the protective sequence. The diagnostic methods of the present invention further encompass contacting and incubating nucleic acids for the detection of single nucleotide mutations or polymorphisms of the protective sequence. Preferably, these nucleic acid reagent sequences within the protective sequence are 15 to 30 nucleotides in length.

After incubation, all non-annealed nucleic acids are removed from the reaction. The presence of nucleic acids that have hybridized, if any such molecules exist, is then detected. Using such a detection scheme, the nucleic acid from the cell type or tissue of interest can be immobilized, for example, to a solid support such as a membrane, or a plastic surface such as that on a microtiter plate or polystyrene beads. In this case, after incubation, non-annealed, labeled nucleic acid reagents of the type described in Section 5.1 are easily removed. Detection of the remaining, annealed, labeled nucleic acid reagents is accomplished using standard techniques well known to those skilled in the art. The protective sequences of the invention to which the nucleic acid reagents have annealed can be compared to the annealing pattern expected from a normal protective sequence of the invention in order to determine whether a protective sequence mutation is present.

In a preferred embodiment, protective sequence mutations or polymorphisms can be detected by using a microassay of nucleic acid sequences of the invention immobilized to a substrate or "gene chip" (see, e.g. Cronin, et al., 1996, Human Mutation 7:244–255). Alternative diagnostic methods for the detection of protective sequence-specific nucleic acid molecules (or flanking sequences), in patient samples or other appropriate cell sources, may involve their amplification, e.g., by PCR (the experimental embodiment set forth in Mullis, 1987, U.S. Pat. No. 4,683,202), followed by the analysis of the amplified molecules using techniques well known to those of skill in the art, such as, for example, those listed above. The resulting amplified sequences can be compared to those which would be expected if the nucleic acid being amplified contained only normal copies of the protective sequence in order to determine whether a protective sequence mutation or polymorphism in linkage disequilibrium with a disease-causing allele exists.

Among those nucleic acid sequences that are preferred for such amplification-related diagnostic screening analyses are oligonucleotide primers that amplify exon sequences. The sequences of such oligonucleotide primers are, therefore, preferably derived from cerebral intron sequences so that the entire exon, or coding region, can be analyzed as discussed below. Primer pairs useful for amplification of cerebral exons are preferably derived from adjacent introns. Appropriate primer pairs can be chosen such that each of the cerebral exons present within the gene will be amplified. Primers for the amplification of exons can be routinely designed by one of ordinary skill.

Additional nucleic acid sequences which are preferred for such amplification-related analyses are those which will detect the presence of a polymorphism which differs from the sequence depicted in the Figures. Such polymorphisms include ones that represent mutations associated with a condition, disorder, or disease involving cell death.

Amplification techniques are well known to those of skill in the art and can routinely be utilized in connection with primers such as those described above. In general, hybridization conditions can be as follows: In general, for probes between 14 and 70 nucleotides in length, the melting temperature TM is calculated using the formula: $Tm(° C.) = 81.5 + 16.6(\log[\text{monovalent cations}]) + 0.41(\% \ G+C) - (500/N)$ where N is the length of the probe. If the hybridization is carried out in a solution containing formamide, the melting temperature is calculated using the equation $Tm(° C.) = 81.5 + 16.6(\log[\text{monovalent cations}]) + 0.41(\% \ G+C) - (0.61\% \ \text{formamide}) - (500/N)$ where N is the length of the probe. Additionally, well-known genotyping techniques can be performed to identify individuals carrying protective sequence mutations. Such techniques include, for example, the use of restriction fragment length polymorphisms (RFLPs), which involve sequence variations in one of the recognition sites for the specific restriction enzyme used.

Further, improved methods for analyzing DNA polymorphisms, which can be utilized for the identification of protective sequence-specific mutations, have been described which capitalize on the presence of variable numbers of short, tandemly repeated DNA sequences between the restriction enzyme sites. For example, Weber (U.S. Pat. No. 5,075,217) describes a DNA marker based on length polymorphisms in blocks of (dC-dA)n-(dG-dT)n short tandem repeats. The average separation of (dC-dA)n-(dG-dT)n blocks is estimated to be 30,000–60,000 bp. Markers which are so closely spaced exhibit a high frequency of co-inheritance, and are extremely useful in the identification of genetic mutations, such as, for example, mutations within the protective sequence of the invention, and the diagnosis of diseases and disorders related to mutations of the protective sequences of the invention.

Also, Caskey et al. (U.S. Pat. No. 5,364,759) describe a DNA profiling assay for detecting short tri- and tetra nucleotide repeat sequences. The process includes extracting the DNA of interest, amplifying the extracted DNA and labeling the repeat sequences to form a genotypic map of the individual's DNA.

Other methods well known in the art may be used to identify single nucleotide polymorphisms (SNPs), including biallelic SNPs or biallelic markers which have two alleles, both of which are present at a fairly high frequency in a population. Conventional techniques for detecting SNPs include, e.g., conventional dot blot analysis, single stranded conformational polymorphism (SSCP) analysis (see, e.g., Orita et al., 1989, *Proc. Natl. Acad. Sci. USA* 86:2766–2770), denaturing gradient gel electrophoresis (DGGE), heteroduplex analysis, mismatch cleavage detection and other routine techniques well known in the art (see, e.g., Sheffield et al., 1989, *Proc. Natl. Acad. Sci.* 86:5855–5892; Grompe, 1993, *Nature Genetics* 5:111–117). Alternative, preferred methods of detecting and mapping SNPs involve microsequencing techniques wherein an SNP site in a target DNA is detecting by a single nucleotide primer extension reaction (see, e.g., Goelet et al., PCT Publication No. WO 92/15712; Mundy, U.S. Pat. No. 4,656,127; Vary and Diamond, U.S. Pat. No. 4,851,331; Cohen et al., PCT Publication No. WO 91/02087; Chee et al., PCT Publication No. WO 95/11995; Landegren et al., 1988, *Science* 241:1077–1080; Nicerson et al., 1990, *Proc. Natl. Acad. Sci. U.S.A.* 87:8923–8927; Pastinen et al.,1997, *Genome Res.* 7:606–614; Pastinen et al., 1996, *Clin. Chem.* 42:1391–1397; Jalanko et al., 1992, *Clin. Chem.* 38:39–43; Shumaker et al., 1996, *Hum. Mutation* 7:346–354; Caskey et al., PCT Publication No. WO 95/00669).

The level of protective sequence expression also can be assayed. For example, RNA from a cell type or tissue known, or suspected, to express the protective sequence, such as brain, may be isolated and tested utilizing hybridization or PCR techniques such as are described, above. The isolated cells can be derived from cell culture or from a patient. The analysis of cells taken from culture may be a necessary step in the assessment of cells to be used as part of a cell-based gene therapy technique or, alternatively, to test the effect of compounds on the expression of the protective sequence. Such analyses may reveal both quantitative and qualitative aspects of the expression pattern of the protective sequence, including activation or inactivation of protective sequence expression.

In one embodiment of such a detection scheme, a cDNA molecule is synthesized from an RNA molecule of interest (e.g., by reverse transcription of the RNA molecule into cDNA). A sequence within the cDNA is then used as the template for a nucleic acid amplification reaction, such as a PCR amplification reaction, or the like. The nucleic acid reagents used as synthesis initiation reagents (e.g., primers) in the reverse transcription and nucleic acid amplification steps of this method are chosen from among the protective sequence nucleic acid reagents described in Section 5.1. The preferred lengths of such nucleic acid reagents are at least 9–30 nucleotides. For detection of the amplified product, the nucleic acid amplification may be performed using radioactively or non-radioactively labeled nucleotides. Alternatively, enough amplified product may be made such that the product may be visualized by standard ethidium bromide staining or by utilizing any other suitable nucleic acid staining method.

Additionally, it is possible to perform such protective sequence expression assays "in situ", i.e., directly upon tissue sections (fixed and/or frozen) of patient tissue obtained from biopsies or resections, such that no nucleic acid purification is necessary. Nucleic acid reagents such as those described in Section 5.1 may be used as probes and/or primers for such in situ procedures (see, for example, Nuovo, G. J., 1992, "PCR In Situ Hybridization: Protocols And Applications", Raven Press, NY).

Alternatively, if a sufficient quantity of the appropriate cells can be obtained, standard Northern blot analysis can be performed to determine the level of mRNA expression of the protective sequence.

5.4.1.5 Detection of Protective Sequence Products

Protective sequence products of the invention, including both wild-type and mutant protective sequence products, conserved variants and polypeptide fragments thereof, which are discussed, above, in Section 5.2, may be detected using antibodies which are directed against such gene products. Such antibodies, which are discussed in Section 5.3, above, may thereby be used as diagnostics and prognostics for a condition, disorder, or disease involving cell death. Such methods may be used to detect abnormalities in the level of protective sequence expression or of protective sequence product synthesis, or abnormalities in the structure, temporal expression and/or physical location of protective sequence product. The antibodies and immunoassay methods described herein have, for example, important in vitro applications in assessing the efficacy of treatments for conditions, disorders, or diseases involving cell death. Antibodies, or fragments of antibodies, such as those described below, may be used to screen potentially therapeutic compounds in vitro to determine their effects on protective sequence expression and protective sequence product production. The compounds which have beneficial effects on conditions, disorders, or diseases involving cell death can thereby be identified, and a therapeutically effective dose determined.

In vitro immunoassays may also be used, for example, to assess the efficacy of cell-based gene therapy for a condition, disorder, or disease involving cell death. Antibodies directed against protective sequence products may be used in vitro to determine, for example, the level of protective sequence expression achieved in cells genetically engineered to produce the protective sequence product. In the case of intracellular protective sequence products, such an assessment is done, preferably, using cell lysates or extracts. Such analysis will allow for a determination of the number of transformed cells necessary to achieve therapeutic efficacy in vivo, as well as optimization of the gene replacement protocol.

The tissue or cell type to be analyzed generally will include those that are known, or suspected, to express the protective sequence. The protein isolation methods employed herein may, for example, be such as those described in Harlow and Lane (1988, "Antibodies: A Laboratory Manual", Cold Spring Harbor Laboratory Press, Cold Spring Harbor, N.Y.). The isolated cells can be derived from cell culture or from a patient. The analysis of cells taken from culture may be a necessary step in the assessment of cells to be used as part of a cell-based gene therapy technique or, alternatively, to test the effect of compounds on the expression of the protective sequence.

Preferred diagnostic methods for the detection of protective sequence products, conserved variants or peptide fragments thereof, may involve, for example, immunoassays wherein the protective sequence products or conserved variants or peptide fragments are detected by their interaction with an anti-protective sequence product-specific antibody.

For example, antibodies, or fragments of antibodies, such as those described, above, in Section 5.3, may be used to, quantitatively or qualitatively, detect the presence of protective sequence products or conserved variants or peptide fragments thereof. This can be accomplished, for example, by immunofluorescence techniques employing a fluorescently labeled antibody (see below, this Section) coupled with light microscopic, flow cytometric or fluorimetric detection. Such techniques are especially preferred for protective sequence products that are expressed on the cell surface.

The antibodies (or fragments thereof) useful in the present invention may, additionally, be employed histologically, as in immunofluorescence or immunoelectron microscopy, for in situ detection of protective sequence products, conserved variants or peptide fragments thereof. In situ detection may be accomplished by removing a histological specimen from a patient, and applying thereto a labeled antibody which binds to a protective sequence polypeptide. The antibody (or fragment) is preferably applied by overlaying the labeled antibody (or fragment) onto a biological sample. Through the use of such a procedure, it is possible to determine not only the presence of the protective sequence product, conserved variants or peptide fragments, but also its distribution in the examined tissue. Using the present invention, those of ordinary skill will readily recognize that any of a wide variety of histological methods (such as staining procedures) can be modified in order to achieve in situ detection of a protective sequence product.

Immunoassays for protective sequence products, conserved variants or peptide fragments thereof will typically comprise incubating a sample, such as a biological fluid, a tissue extract, freshly harvested cells or lysates of cells in the presence of a detectably labeled antibody capable of identifying the protective sequence product, conserved variants or peptide fragments thereof, and detecting the bound antibody by any of a number of techniques well-known in the art.

The biological sample may be brought in contact with and immobilized onto a solid phase support or carrier, such as nitrocellulose, which is capable of immobilizing cells, cell particles or soluble proteins. The support may then be washed with suitable buffers followed by treatment with the detectably labeled protective sequence product specific antibody. The solid phase support may then be washed with the buffer a second time to remove unbound antibody. The amount of bound label on the solid support may then be detected by conventional means.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

One of the ways in which the protective sequence product-specific antibody can be detectably labeled is by linking the same to an enzyme, such as for use in an enzyme immunoassay (EIA) (Voller, A., "The Enzyme Linked Immunosorbent Assay (ELISA)", 1978, Diagnostic Horizons 2:1–7, Microbiological Associates Quarterly Publication, Walkersville, Md.); Voller, A. et al., 1978, J Clin. Pathol. 31:507–520; Butler, J. E., 1981, Meth. Enzymol. 73:482–523; Maggio, E. (ed.), 1980, Enzyme Immunoassay, CRC Press, Boca Raton, Fla.,; Ishikawa, E. et al., (eds.), 1981, Enzyme Immunoassay, Kgaku Shoin, Tokyo). The enzyme that is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, α-glycerophosphate, dehydrogenase, triose phosphate isomerase, horseradish peroxidase, alkaline phosphatase, asparaginase, glucose oxidase, β-galactosidase, ribonuclease, urease, catalase, glucose-6-phosphate dehydrogenase, glucoamylase and acetylcholinesterase. The detection can be accomplished by colorimetric methods that employ a chromogenic substrate for the enzyme. Detection also may be accomplished by visual comparison of the extent of enzymatic reaction of a substrate in comparison with similarly prepared standards.

Detection may be accomplished also using any of a variety of other immunoassays. For example, by radioactively labeling the antibodies or antibody fragments, it is possible to detect protective sequence products through the use of a radioimmunoassay (RIA) (see, for example, Weintraub, B., Principles of Radioimmunoassays, Seventh Training Course on Radioligand Assay Techniques, The Endocrine Society, March, 1986). The radioactive isotope can be detected by such means as the use of a gamma counter or a scintillation counter or by autoradiography.

It is also possible to label the antibody with a fluorescent compound. When the fluorescently labeled antibody is exposed to light of the proper wavelength, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

5.4.2 Screening Assays for Compounds which Interact with Protective Sequence Products or Modulate Protective Sequence Activity The following assays are designed to identify compounds which bind to a protective sequence product, compounds which bind to proteins, or portions of proteins which interact with a protective sequence product, compounds which modulate, e.g., interfere with, the interaction of a protective sequence product with proteins and compounds which modulate the activity of the protective sequence (i.e., modulate the level of protective sequence expression and/or modulate the level of protective sequence product activity). Assays may additionally be utilized which identify compounds which bind to protective sequence regulatory sequences (e.g., promoter sequences; see e.g., Platt, 1994, J. Biol. Chem. 269, 28558–28562), and which can modulate the level of protective sequence expression. Such compounds may include, but are not limited to, small organic molecules, such as ones which are able to cross the blood-brain barrier, gain to and/or entry into an appropriate cell and affect expression of the protective sequence or some other gene involved in a protective sequence regulatory pathway.

Methods for the identification of such proteins are described, below, in Section 5.4.2.2. Such proteins may be involved in the control and/or regulation of functions related to cell death. Further, among these compounds are compounds which affect the level of protective sequence expression and/or protective sequence product activity and which can be used in the therapeutic treatment of conditions, disorders, or diseases involving cell death as described, below, in Section 5.4.2.3.

Compounds may include, but are not limited to, peptides such as, for example, soluble peptides, including but not limited to, Ig-tailed fusion peptides, and members of random peptide libraries; (see, e.g., Lam, et al., 1991, *Nature* 354:82–84; Houghten, et al., 1991, *Nature* 354:84–86), and combinatorial chemistry-derived molecular library made of D- and/or L- configuration amino acids, phosphopeptides (including, but not limited to members of random or partially degenerate, directed phosphopeptide libraries; see, e.g., Songyang, et al., 1993, *Cell* 72:767–778), antibodies (including, but not limited to, polyclonal, monoclonal, humanized, anti-idiotypic, chimeric or single chain antibodies, and FAb, F(ab')$_2$ and FAb expression library fragments, and epitope-binding fragments thereof), and small organic or inorganic molecules.

Such compounds may further comprise compounds, in particular drugs or members of classes or families of drugs, known to ameliorate the symptoms of a condition, disorder, or disease involving cell death.

Such compounds include families of antidepressants such as lithium salts, carbamazepine, valproic acid, lysergic acid diethylamide (LSD), p-chlorophenylalanine, p-propyldopacetamide dithiocarbamate derivatives e.g., FLA 63; anti-anxiety drugs, e.g., diazepam; monoamine oxidase (MAO) inhibitors, e.g., iproniazid, clorgyline, phenelzine and isocarboxazid; biogenic amine uptake blockers, e.g., tricyclic antidepressants such as desipramine, imipramine and amitriptyline; serotonin reuptake inhibitors e.g., fluoxetine; antipsychotic drugs such as phenothiazine derivatives (e.g., chlorpromazine (thorazine) and trifluopromazine)), butyrophenones (e.g., haloperidol (Haldol)), thioxanthene derivatives (e.g., chlorprothixene), and dibenzodiazepines (e.g., clozapine); benzodiazepines; dopaminergic agonists and antagonists e.g., L-DOPA, cocaine, amphetamine, α-methyl-tyrosine, reserpine, tetrabenazine, benzotropine, pargyline; noradrenergic agonists and antagonists e.g., clonidine, phenoxybenzamine, phentolamine, tropolone.

Compounds identified via assays such as those described herein may be useful, for example, in elaborating the biological function of protective sequence products and for ameliorating conditions, disorders, or diseases involving cell death. Assays for testing the effectiveness of compounds identified by, for example, techniques such as those described in Sections 5.4.2.1–5.4.2.3, are discussed, below, in Section 5.4.2.4.

5.4.2.1 In Vitro Screening Assays for Compounds which Bind to Protective Sequence Products In vitro systems may be designed to identify compounds capable of binding the protective sequence products of the invention. Compounds identified may be useful, for example, in modulating the activity of unimpaired and/or mutant protective sequence products, may be useful in elaborating the biological function of the protective sequence product, may be utilized in screens for identifying compounds which disrupt normal protective sequence product interactions or may in themselves disrupt such interactions.

The principle of the assays used to identify compounds which bind to the protective sequence product involves preparing a reaction mixture of the protective sequence product and the test compound under conditions and for a time sufficient to allow the two components to interact and bind, thus forming a complex which can be removed and/or detected in the reaction mixture. These assays can be conducted in a variety of ways. For example, one method to conduct such an assay involves anchoring a protective sequence product or a test substance onto a solid support and detecting protective sequence product/test compound complexes formed on the solid support at the end of the reaction. In one embodiment of such a method, the protective sequence product may be anchored onto a solid support, and the test compound, which is not anchored, may be labeled, either directly or indirectly.

In practice, microtiter plates are conveniently utilized as the solid support. The anchored component may be immobilized by non-covalent or covalent attachments. Non-covalent attachment may be accomplished by simply coating the solid surface with a solution of the protein and drying. Alternatively, an immobilized antibody, preferably a monoclonal antibody, specific for the protein to be immobilized may be used to anchor the protein to the solid surface. The surfaces may be prepared in advance and stored.

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the previously non-immobilized component (the antibody, in turn, may be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for the protective sequence product or the test compound to anchor any complexes formed in solution, and a labeled antibody specific for the other component of the possible complex to detect anchored complexes.

5.4.2.2 Assays for Proteins which Interact with Protective Sequence Products Any method suitable for detecting protein-protein interactions may be employed for identifying protective sequence product-protein interactions.

Among the traditional methods that may be employed are co-immunoprecipitation, cross-linking and co-purification through gradients or chromatographic columns. Utilizing procedures such as these allows for the identification of proteins, including intracellular proteins, which interact with protective sequence products. Once isolated, such a protein can be identified and can be used in conjunction with standard techniques, to identify proteins it interacts with. For example, at least a portion of the amino acid sequence of a protein which interacts with the protective sequence product can be ascertained using techniques well known to those of skill in the art, such as via the Edman degradation technique (see, e.g., Creighton, 1983, "Proteins: Structures and Molecular Principles," W. H. Freeman & Co., N.Y., pp.34–49). The amino acid sequence obtained may be used as a guide for the generation of oligonucleotide mixtures that can be used to screen for gene sequences encoding such proteins. Screening may be accomplished, for example, by standard hybridization or PCR techniques. Techniques for the generation of oligonucleotide mixtures and the screening are well known. (See, e.g., Ausubel, supra, and 1990, "PCR Protocols: A Guide to Methods and Applications," Innis, et al., eds. Academic Press, Inc., New York).

Additionally, methods may be employed which result in the simultaneous identification of genes that encode a protein that interacts with a protective sequence product. These methods include, for example, probing expression libraries with labeled protective sequence product, using the protective sequence product in a manner similar to the well-known technique of antibody probing of $\lambda$gt11 libraries.

One method that detects protein interactions in vivo, the two-hybrid system, is described in detail for illustration only and not by way of limitation. One version of this system has been described (Chien, et al., 1991, *Proc. Natl Acad. Sci. USA*, 88:9578–9582) and is commercially available from Clontech (Palo Alto, Calif.).

Briefly, utilizing such a system, plasmids are constructed which encode two hybrid proteins: one consists of the DNA-binding domain of a transcription activator protein fused to the protective sequence product and the other consists of the transcription activator protein's activation domain fused to an unknown protein which is encoded by a cDNA which has been recombined into this plasmid as part of a cDNA library. The DNA-binding domain fusion plasmid and the cDNA library are transformed into a strain of the yeast Saccharomyces cerevisiae that contains a reporter gene (e.g., HBS or lacZ) whose regulatory region contains the transcription activator's binding site. Either hybrid protein alone cannot activate transcription of the reporter gene: the DNA-binding domain hybrid cannot because it does not provide activation function and the activation domain hybrid cannot because it cannot localize to the activator's binding sites. Interaction of the two hybrid proteins reconstitutes the functional activator protein and results in expression of the reporter gene, which is detected by an assay for the reporter gene product.

The two-hybrid system or related methodologies may be used to screen activation domain libraries for proteins that interact with the "bait" gene product. By way of example, and not by way of limitation, protective sequence products of the invention may be used as the bait gene product. Total genomic or cDNA sequences are fused to the DNA encoding an activation domain. This library and a plasmid encoding a hybrid of a bait protective sequence product fused to the DNA-binding domain are co-transformed into a yeast reporter strain, and the resulting transformants are screened for those which express the reporter gene. For example, a bait protective sequence, such as the open reading frame of the gene, can be cloned into a vector such that it is translationally fused to the DNA encoding the DNA-binding domain of the GAL4 protein. These colonies are purified and the library plasmids responsible for reporter gene expression are isolated. DNA sequencing is then used to identify the proteins encoded by the library plasmids.

A cDNA library of the cell line, from which proteins which interact with bait protective sequence products are to be detected, can be made using methods routinely practiced in the art. According to the particular system described herein, for example, the cDNA fragments can be inserted into a vector such that they are translationally fused to the transcriptional activation domain of GAL4. Such a library can be co-transformed along with the bait protective sequence-GAL4 fusion plasmid into a yeast strain that contains a lacZ gene driven by a promoter that contains GAL4 activation sequence. A cDNA encoded protein, fused to a GAL4 transcriptional activation domain that interacts with bait protective sequence product will reconstitute an active GAL4 protein and thereby drive expression of the HIS3 gene. Colonies that express HIS3 can be detected by their growth on petri dishes containing semi-solid agar based media lacking histidine. The CDNA can then be purified from these strains, and used to produce and isolate the bait protective sequence product-interacting protein using techniques routinely practiced in the art.

5.4.2.3 Assays for Compounds which Interfere with or Potentiate Protective Sequence Products Macromolecule Interaction The protective sequence products may, in vivo, interact with one or more macromolecules, including intracellular macromolecules, such as proteins. Such macromolecules may include, but are not limited to, nucleic acid molecules and those proteins identified via methods such as those described, above, in Sections 5.4.2.1–5.4.2.2. For purposes of this discussion, the macromolecules are referred to herein as "binding partners". Compounds that disrupt protective sequence product binding to a binding partner may be useful in regulating the activity of the protective sequence product, especially mutant protective sequence products. Such compounds may include, but are not limited to molecules such as peptides, and the like, as described, for example, in Section 5.4.2.1 above.

The basic principle of an assay system used to identify compounds which interfere with or potentiate the interaction between the protective sequence product and a binding partner or partners involves preparing a reaction mixture containing the protective sequence product and the binding partner under conditions and for a time sufficient to allow the two to interact and bind, thus forming a complex. In order to test a compound for inhibitory activity, the reaction mixture is prepared in the presence and absence of the test compound. The test compound may be initially included in the reaction mixture, or may be added at a time subsequent to the addition of protective sequence product and its binding partner. Control reaction mixtures are incubated without the test compound or with a compound that is known not to block complex formation. The formation of any complexes between the protective sequence product and the binding partner is then detected. The formation of a complex in the control reaction, but not in the reaction mixture containing the test compound, indicates that the compound interferes with the interaction of the protective sequence product and the binding partner. Additionally, complex formation within reaction mixtures containing the test compound and normal protective sequence product also may be compared to complex formation within reaction mixtures containing the test compound and a mutant protective sequence product. This comparison may be important in those cases wherein it is desirable to identify compounds that disrupt interactions of mutant but not normal protective sequence product.

In order to test a compound for potentiating activity, the reaction mixture is prepared in the presence and absence of the test compound. The test compound may be initially included in the reaction mixture, or may be added at a time subsequent to the addition of protective sequence product and its binding partner. Control reaction mixtures are incubated without the test compound or with a compound that is known not to block complex formation. The formation of any complexes between the protective sequence product and the binding partner is then detected. Increased formation of a complex in the reaction mixture containing the test compound, but not in the control reaction, indicates that the compound enhances and therefore potentiates the interaction of the protective sequence product and the binding partner. Additionally, complex formation within reaction mixtures containing the test compound and normal protective sequence product may also be compared to complex formation within reaction mixtures containing the test compound and a mutant protective sequence product. This comparison may be important in those cases wherein it is desirable to identify compounds that enhance interactions of mutant but not normal protective sequence product.

In alternative embodiments, the above assays may be performed using a reaction mixture containing the protective sequence product, a binding partner and a third compound which disrupts or enhances protective sequence product binding to the binding partner. The reaction mixture is prepared and incubated in the presence and absence of the test compound, as described above, and the formation of any complexes between the protective sequence product and the binding partner is detected. In this embodiment, the formation of a complex in the reaction mixture containing the test compound, but not in the control reaction, indicates that the test compound interferes with the ability of the second compound to disrupt protective sequence product binding to its binding partner.

The assays for compounds that interfere with or potentiate the interaction of the protective sequence products and binding partners can be conducted in a heterogeneous or homogeneous format. Heterogeneous assays involve anchoring either the protective sequence product or the binding partner onto a solid support and detecting complexes formed on the solid support at the end of the reaction. In homogeneous assays, the entire reaction is carried out in a liquid phase. In either approach, the order of addition of reactants can be varied to obtain different information about the compounds being tested. For example, test compounds which interfere with or potentiate the interaction between the protective sequence products and the binding partners, e.g., by competition, can be identified by conducting the reaction in the presence of the test substance; i.e., by adding the test substance to the reaction mixture prior to or simultaneously with the protective sequence product and interactive intracellular binding partner. Alternatively, test compounds which disrupt preformed complexes, e.g., compounds with higher binding constants which displace one of the components from the complex, can be tested by adding the test compound to the reaction mixture after complexes have been formed. The various formats are described briefly below.

In a heterogeneous assay system, either the protective sequence product or the interactive binding partner, is anchored onto a solid surface, while the non-anchored species is labeled, either directly or indirectly. In practice, microtiter plates are conveniently utilized. The anchored species may be immobilized by non-covalent or covalent attachments. Non-covalent attachment may be accomplished simply by coating the solid surface with a solution of the protective sequence product or binding partner and drying. Alternatively, an immobilized antibody specific for the species to be anchored may be used to anchor the species to the solid surface. The surfaces may be prepared in advance and stored.

In order to conduct the assay, the partner of the immobilized species is exposed to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, may be directly labeled or indirectly labeled with a labeled anti-Ig antibody). Depending upon the order of addition of reaction components, test compounds which inhibit complex formation or which disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds which inhibit complex formation or which disrupt preformed complexes can be identified.

In an alternate embodiment of the invention, a homogeneous assay can be used. In this approach, a preformed complex of the protective sequence product and the interactive binding partner is prepared in which either the protective sequence product or its binding partners is labeled, but the signal generated by the label is quenched due to complex formation (see, e.g., U.S. Pat. No. 4,109,496 by Rubenstein which utilizes this approach for immunoassays). The addition of a test substance that competes with and displaces one of the species from the preformed complex will result in the generation of a signal above background. In this way, test substances that disrupt protective sequence product/binding partner interaction can be identified.

In another embodiment of the invention, these same techniques can be employed using peptide fragments which correspond to the binding domains of the protective sequence product and/or the binding partner (in cases where the binding partner is a protein), in place of one or both of the full length proteins. Any number of methods routinely practiced in the art can be used to identify and isolate the binding sites. These methods include, but are not limited to, mutagenesis of the gene encoding one of the proteins and screening for disruption of binding in a co-immunoprecipitation assay. Compensating mutations in the gene encoding the second species in the complex can then be selected. Sequence analysis of the genes encoding the respective proteins will reveal the mutations that correspond to the region of the protein involved in interactive binding. Alternatively, one protein can be anchored to a solid surface using methods described in this Section above, and allowed to interact with and bind to its labeled binding partner, which has been treated with a proteolytic enzyme, such as trypsin. After washing, a short, labeled peptide comprising the binding domain may remain associated with the solid material, which can be isolated and identified by amino acid sequencing. Also, once the gene coding for the segments is engineered to express peptide fragments of the protein, it can then be tested for binding activity and purified or synthesized.

For example, and not by way of limitation, a protective sequence product can be anchored to a solid material as described, above, in this Section by making a GST-1 fusion protein and allowing it to bind to glutathione agarose beads. The binding partner can be labeled with a radioactive isotope, such as $^{35}S$, and cleaved with a proteolytic enzyme such as trypsin. Cleavage products can then be added to the anchored GST-1 fusion protein and allowed to bind. After washing away unbound peptides, labeled bound material, representing the binding partner binding domain, can be eluted, purified and analyzed for amino acid sequence by well-known methods. Peptides so identified can be produced synthetically or produced using recombinant DNA technology.

5.4.2.4 Assays for the Identification of Compounds which Modulate Conditions, Disorders, or Diseases Involving Cell Death Compounds, including, but not limited to, binding compounds identified via assay techniques such as those described, above, in Sections 5.4.2.1–5.4.2.3, can be tested for the ability to ameliorate symptoms of a condition, disorder, or disease involving cell death.

It should be noted that the assays described herein can be used to identify compounds which affect activity by either affecting protective sequence expression or by affecting the level of protective sequence product activity. For example, compounds may be identified which are involved in another step in the pathway in which the protective sequence and/or protective sequence product is involved, such as, for example, a step which is either "upstream" or "downstream" of the step in the pathway mediated by the protective sequence. Such compounds may, by affecting this same pathway, modulate the effect on the development of conditions, disorders, or diseases involving cell death. Such compounds can be used as part of a therapeutic method for the treatment of the condition, disorder, or disease.

Described below are cell-based and animal model-based assays for the identification of compounds exhibiting such an ability to ameliorate symptoms of a condition, disorder, or disease involving cell death.

First, cell-based systems can be used to identify compounds which may act to ameliorate symptoms of a condition, disorder, or disease, including, but not limited to, those described in Section 5.4.1.1. Such cell systems can include, for example, recombinant or non-recombinant cell, such as cell lines, which express the protective sequence of interest.

In utilizing such cell systems, cells which express the protective sequence of interest may be exposed to a compound suspected of exhibiting an ability to ameliorate symptoms of a condition, disorder, or disease involving cell death at a sufficient concentration and for a sufficient time to elicit such an amelioration of such symptoms in the exposed cells. After exposure, the cells can be assayed to measure alterations in the expression of the protective sequence, e.g., by assaying cell lysates for cerebral mRNA transcripts (e.g., by Northern analysis) or for protective sequence products expressed by the cell; compounds which modulate expression of the protective sequence are good candidates as therapeutics.

In addition, animal-based systems or models for a condition, disorder, or disease involving cell death, for example, transgenic mice containing a human or altered form of a protective sequence, may be used to identify compounds capable of ameliorating symptoms of the condition, disorder, or disease. Such animal models may be used as test substrates for the identification of drugs, pharmaceuticals, therapies and interventions. For example, animal models may be exposed to a compound suspected of exhibiting an ability to ameliorate symptoms, at a sufficient concentration and for a sufficient time to elicit such an amelioration of symptoms of a condition, disorder, or disease involving cell death. The response of the animals to the exposure may be monitored by assessing the reversal of the symptoms of the condition, disorder, or disease.

With regard to intervention, any treatments that reverse any aspect of symptoms of a condition, disorder, or disease involving cell death, should be considered as candidates for human therapeutic intervention in such conditions, disorders, or diseases. Dosages of test agents may be determined by deriving dose-response curves, as discussed in Section 5.5.1, below.

5.4.3 Additional Uses for the Protective Sequences, Protective Sequence Products, or Their Regulatory Elements In addition to the uses described above, the polynucleotides of the present invention can be used for various other purposes. For example, they can be used to express recombinant protein for analysis, characterization or therapeutic use; as molecular weight markers on gels; as chromosome markers or tags (when labeled) to identify chromosomes or to map related gene positions; to compare with endogenous DNA sequences in patients to identify potential genetic conditions, disorders, or diseases; as probes to hybridize and thus discover novel, related DNA sequences; as a source of information to derive PCR primers for genetic fingerprinting; as a probe to "subtract-out" known sequences in the process of discovering other novel polynucleotides; to raise anti-protein antibodies using DNA immunization techniques; and as an antigen to raise anti-DNA antibodies or elicit another immune response.

The proteins provided by the present invention can similarly be used to raise antibodies or to elicit another immune response; as a reagent (including the labeled reagent) in assays designed to quantitatively determine levels of the protein (or its receptor) in biological fluids; as markers for tissues in which the corresponding protein is preferentially expressed (either constitutively or at a particular stage of tissue differentiation or development or in a disease state); and, of course, to isolate correlative receptors or ligands. Where the protein binds or potentially binds to another protein (such as, for example, in a receptor-ligand interaction), the protein can be used to identify the other protein with which binding occurs or to identify inhibitors of the binding interaction. Proteins involved in these binding interactions can also be used to screen for peptide or small molecule inhibitors or agonists of the binding interaction.

Methods for performing the uses listed above are well known to those skilled in the art. References disclosing such methods include without limitation "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

5.5 Pharmaceutical Preparations and Methods of Administration

The compounds which are determined to affect protective sequence expression or gene product activity can be administered to a patient at therapeutically effective doses to treat or ameliorate a condition, disorder, or disease involving cell death or modulate a cell death-related process described herein. A therapeutically effective dose refers to that amount of the compound sufficient to result in amelioration of symptoms of such a condition, disorder, or disease.

5.5.1 Effective Dose

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. While compounds which exhibit toxic side effects may be used, care should be taken to design a delivery system which targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range which includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of antibody, protein, or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight.

The skilled artisan will appreciate that certain factors may influence the dosage required to effectively treat a subject, including but not limited to the severity of the disease or condition, disorder, or disease, previous treatments, the general health and/or age of the subject, and other diseases present. Moreover, treatment of a subject with a therapeutically effective amount of a protein, polypeptide, or antibody can include a single treatment or, preferably, can include a series of treatments. In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

5.5.2 Formulations and Use

Pharmaceutical compositions for use in accordance with the present invention may be formulated in conventional manner using one or more physiologically acceptable carriers or excipients.

Thus, the compounds and their physiologically acceptable salts and solvates may be formulated for administration by inhalation or insufflation (either through the mouth or the nose) or oral, buccal, parenteral rectal or topical administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In certain embodiments, it may be desirable to administer the pharmaceutical compositions of the invention locally to the area in need of treatment. This may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of a malignant tumor or neoplastic or pre-neoplastic tissue.

For topical application, the compounds may be combined with a carrier so that an effective dosage is delivered, based on the desired activity.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device that may contain one or more unit dosage forms containing the active ingredient. The pack may for example comprise metal or plastic foil, such as a blister pack. The pack or dispenser device may be accompanied by instructions for administration.

6 EXAMPLE: SEQUENCE AND CHARACTERIZATION OF PROTECTIVE SEQUENCES

In the example presented herein, the sequence and characterization of the protective sequences are provided.

6.1 Materials and Methods

6.1.1 Preparation of DNA

A human fetal brain cDNA library (Gibco), in which individual clones were inserted into the NotI-SalI site of the pCMV•SPORT2 vector, was diluted 200,000 fold in LB broth (DIFCO Laboratories) containing 0.2 mg/ml ampicillin (Sigma). The diluted library (100–140 µl) was then plated and grown on LB agar (DIFCO Laboratories) bioassay plates with 0.2 mg/ml ampicillin. Plates were incubated at 37° C. for 24 hours. Single colonies were then used to inoculate deep-well blocks containing 1.5 ml LB broth containing 0.2 mg/ml ampicillin. Inoculated cultures were incubated at 37° C. with agitation at 150–200 rpm for 18–24 hours. Replicate plates were created from the cultures by adding 20 µl of culture to 80 µl of LB broth containing 18% glycerol and 0.2 mg/ml ampicillin and stored at −80° C. Remaining bacterial cells were centrifuged at 1000×g for 6 minutes to collect the cells at the bottom. Following centrifugation, the broth was decanted off of the bacterial pellet and the pellet resuspended and then stored in 100 μl of Cell Resuspension Solution (Promega) at 4° C. for up to one week.

Plasmid DNA was extracted using Promega MagneSil kits with a modified protocol. The pelleted bacteria were re-suspended and 50 μl was transferred into a round bottom plate that rests on a magnet. Cell Lysis Solution (50 μl) was added and the plate was incubated at room temperature without agitation for 30 seconds. Following lysis, 70 μl of a Neutralization Solution/MagneSil Paramagnetic Particles mixture (pre-mixed at a ratio of 6:1) was added. The reaction was mixed by pipetting and incubated at room temperature without agitation for 5 minutes to allow the magnetic particles to be drawn to the magnet. The supernatant containing plasmid DNA was then transferred to a new plate and stored at −20° C.

Individual clones were chosen for their ability to delay or prevent cell death when introduced into a cell predisposed to undergoing cell death, relative to a corresponding cell into which no exogenous protective sequence had been introduced.

6.1.2 Sequence Characterization of the DNA

The cDNA inserts of the clonally pure plasmids which are selected for their ability to protect cells from cell death when introduced into cells predisposed to undergo cell death are sequenced using the ABI Big Dye terminator Cycle Sequencing Ready Reaction Kit and subsequently analyzed on the AB13 10 capillary sequencing machine (PE Biosystems, Foster City, Calif.).

Briefly, 0.5 μg of plasmid DNA is mixed with 3.2 pmole of either the M13 forward (5'-TGTAAAACGACGGCCAGT-3'; SEQ ID NO:465) or the M13 reverse (5'-CAGGAAACAGCTATGACC-3'; SEQ ID NO:466) sequencing primer and 8 μl of the terminator ready reaction mix in a total volume of 20 μl. The cycle sequencing reaction is carried out in a thernocycler (PCR machine) using standard methods known by those skilled in the art. The extension products from the sequencing reaction are purified by precipitation using isopropanol. 80 μl of 75% isopropanol is added to the sample and after thorough mixing, the sample is incubated at room temperature (25° C.) for 20 minutes. The sample is then centrifuged at 12,000×g for 20 minutes at room temperature. The supernatant is removed and the pellet is rinsed once by addition of 250 μl of 75% isopropanol followed by centrifugation as above for 5 minutes. The supernatant is removed and the sample air-dried for 10 minutes. The sample is then resuspended in 20 μl of TSR (template suppression reagent) and denatured by heating at 94° C. for 2 minutes and rapidly cooling on ice. The subsequent electrophoresis and analysis is carried out on the ABI310 sequencer according to the manufacturer's protocol. The entire cDNA clone is similarly sequenced by the use of sequence specific internal primers as required.

6.1.3 Sequence Comparison

The sequence data for the protective cDNA clones is compared using the BLAST 2.0 algorithm (Altschul, S F et al., 1997, Nuc. Acids Res. 25:3389) against known sequences in the GeneBank sequence database maintained by NCBI (National Center for Biotechnology Information). This program uses the two-hit method to find homology within the database. The BLAST nucleotide searches are performed with the "BLAST N" program (wordlength=11) to obtain nucleic acids homologous to nucleic acid molecules of the invention. BLAST protein searches of potential ORFs are performed with the "BLAST P" program (wordlength=3) to obtain amino acid sequences homologous to the ORFs of the invention.

6.1.4 Immuno-Cytochemistry Protocol for the Characterization of Protected Cells Transfected tissue is immersed in freshly prepared 2.5% paraformaldehyde (PFA) in phosphate buffered saline (PBS) for two hours to fix the tissue. PFA is removed by aspiration and the fixed tissue washed consecutively four times in PBS for 15 minutes, changing the PBS solution between each wash. Upon removal of the final PBS wash, the tissue is immersed in a blocking solution consisting of 10% goat serum, 2% bovine serum albumin (BSA), and 0.25% Triton X-100 for a duration of two hours.

After removal of the blocking solution, the tissue is immersed in a primary antibody solution, freshly prepared by adding rabbit anti-GFP polyclonal (1:2000 μl) into blocking solution, for an incubation period of twelve hours at 4° C.

After removal of the primary antibody solution, the tissue is washed consecutively four times in PBS for 10 minutes, changing the PBS solution between each wash. An anti-rabbit, flourescently conjugated secondary antibody, diluted in PBS at a concentration of 1:500, is then added to the tissue and allowed to incubate at room temperature for four hours. The secondary antibody solution is removed by aspiration and the tissue washed consecutively four times in PBS for 15 minutes, changing the PBS solution between each wash. After the final wash is removed, the tissue is mounted on glass slides and dried at 37° C. for thirty minutes. A three-minute xylene incubation is performed before the addition of coverslips to preserve the slices.

6.2 Results

The following protective sequences, which were obtained using the methods described in Section 6.1, were chosen based on their ability to prevent, delay, or rescue cells predisposed to undergo cell death, relative to a corresponding cell into which no exogenous protective sequence had been introduced.

6.2.1 Protective sequence CNI-00711

Protective sequence CNI-00711 (SEQ ID NO:1) comprises 852 nucleotides. Twelve (12) potential open reading frames ("ORFs") have been identified within the protective sequence and are depicted in Table 2. BLAST sequence comparison analysis of CNI-00711 against known sequences in the GenBank sequence database reveals 89% homology, at the nucleotide level, with the UV exon, containing part of the envelope region of a human endogenous retrovirus (HERV) type C (ACC. No. AF058907). The homologous clone was initially described as a germ-line insertion of HERV into the human pleiotrophin gene. The insertion occurred between the 5' untranslated region (UTR) and the coding region. The homology between CNI-00711 and HERV exists for 366 base pairs out of the 412 bases found within the UV1 exon of the HERV insertion.

6.2.2 Protective sequence CNI-00712

Protective sequence CNI-00712 (SEQ.ID NO:26) is a completely novel sequence which comprises 1096 nucleotides. Twenty-four (24) potential ORFs have been identified within the protective sequence and are depicted in Table 3. The longest ORF of the clone is 160 amino acids. BLAST sequence comparison analysis of CI-00712 against known nucleotide and protein sequences in the GenBank database reveals no significant homology at either the nucleotide or amino acid level.

6.2.3 Protective sequence CNI-00714

Protective sequence CNI-00714 (SEQ. ID NO:75) comprises 1825 nucleotides. Thirty (30) potential ORFs have been identified within the protective sequence and are depicted in Table 4. The longest ORF of the CDNA encodes 412 amino acids. BLAST sequence comparison analysis of CNI-00714 against known nucleic acids in the GenBank database reveals homology with the sequence encoding the human KIAA0764 gene (ACC. No. AB018307). At the nucleotide level, the overall percent homology between CNI-00714 and KIAA0764 is 76%. At the amino acid level, the CNI-00714 and KLAA0764 proteins are identical except for a 2 amino acid deletion near the N-terminus. KLAA0764 is an unidentified brain cDNA that shows high level expression in lung and brain.

6.2.4 Protective sequence CNI-00715

Protective sequence CNI-00715 (SEQ. ID NO:136) comprises 542 nucleotides. Eight (8) potential ORFs have been identified within the protective sequence and are depicted in Table 5. BLAST sequence comparison analysis of CNI-00715 against known nucleic acids in the GenBank database reveals a 97% identity (503/520 bases) with a human DNA sequence, clone 425C14, which is from chromosome 6Q22. This clone contains the heat shock factor 2 gene (HSF2) and an unknown gene which is similar to the gene which encodes the placental protein, DIFF33 (ACC. No. HS425C14). Additionally, a relatively high homology—74% identity (64/87 bases)—is also observed with a short region within the coding region of the bestrophin gene. Bestrophin is the gene responsible for Best macular dystrophy (ACC.No. AF057170).

6.2.5 Protective sequence CNI-00716

Protective sequence CNI-00716 (SEQ. ID NO:153) is a completely novel sequence which comprises 771 nucleotides. Fifteen (15) potential ORFs have been identified within the protective sequence and are depicted in Table 6. The longest ORF is 58 amino acids. BLAST sequence comparison analysis of CNI-00716 against known nucleotide and protein sequences in the GenBank database reveals no significant homology at either the nucleotide or the amino acid level.

6.2.6 Protective sequence CNI-00717

Protective sequence CNI-00717 (SEQ ID NO:184) comprises 1669 nucleotides. Thirty eight (38) potential ORFs have been identified within the protective sequence and are depicted in Table 7. BLAST sequence comparison analysis of CNI-00717 against known nucleic acids in the GenBank database reveals 61% (573/935 bases) identity within the coding region ofthe mouse GARP34 mRNA (ACC No. AB018374). The ORF of CNI-00717 in this region of homology is 272 amino acids in length. When this amino acid sequence is compared to the amino acid sequence of GARP34, there is 50% identity (132/265 amino acids).

6.2.7 Protective sequence CNI-00720

Protective sequence CNI-00720 (SEQ. ID NO:261) comprises 1182 nucleotides. Fifteen (15) potential ORFs have been identified within the protective sequence and are depicted in Table 8. Two relatively long ORFs of 75 and 89 amino acids were documented. Neither ORF was homologous to any known sequences in the Genbank database. BLAST sequence comparison analysis of CNI-00720 against known nucleic acids in the GenBank database reveals homology with the 3' UTR of two human genes—neuroendocrine-specific protein-like protein 1 (NSPL1) (ACC.No. 119297) and reticulon 3 (RTN3) (ACC. No. RTN3). NSPL1 and RTN3 are identical neuron-specific genes that belong to the reticulon gene family. There is 99% identity between the nucleic acid of CNI-00720 and the 3' UTRs of NSPL1 and RTN3. Additionally, there is 97% identity within the 5' UTR of the human protein tyrosine kinase, t-Ror-1(Ror1) mRNA (ACC. No.HSU38894).

6.2.8 Protective sequence CNI-00721

Protective sequence CNI-00721 (SEQ. ID NO:292) comprises 1965 nucleotides. Thirty-three (33) potential ORFs have been identified within the protective sequence and are depicted in Table 9. BLAST sequence comparison analysis of CNI-00721 against known nucleic acids in the GenBank database revealed strong homology with the human p311 mRNA (ACC. No.HSU36189). There is 99% identity (465/470 bases) between the CNI-00721 cDNA and the p311 mRNA. The homology is 100% within the coding sequence region.

6.2.9 Protective sequence CNI-00723

Protective sequence CNI-00723 (SEQ. ID NO:359) comprises 2702 nucleotides. Fifty-one (51) potential ORFs have been identified within the protective sequence and are depicted in Table 10. BLAST sequence comparison analysis of CNI-00723 against known nucleic acids in the GenBank database reveals a short stretch of homology with the Drosophila asteroid mRNA (ACC.No AF047010). The CNI-00723 cDNA is 35% identical (73/209 bases) to the asteroid mRNA with the homology occurring within the coding region of the mRNA. The longest ORF of CNI-00723 is 490 amino acids. This ORF is 37% identical (55/144 amino acids) to the Drosophila asteroid protein.

6.2.10 Protective sequence CNI-00724

Protective sequence CNI-00724 (SEQ. ID NO:462) is a completely novel sequence which comprises 979 nucleotides. Only a single potential ORF has been identified within the protective sequence and it is depicted in Table 11. This ORF, which is 80 amino acids in length, revealed no homology with any known amino acid sequence in the GenBank database. BLAST sequence comparison analysis of CNI-00724 against known nucleic acids in the GenBank database reveals that homology exists with a human VGF nerve growth factor inducible mRNA (ACC. No. NM_003378). There is 94% identity (821/872 bases) between the CNI-00724 insert and the VGF nerve growth factory inducible MRNA. This homology is observed in the 3' portion of the coding sequence and in the 3' UTR of the VGF nerve growth factory inducible mRNA.

7 DEPOSIT OF MICROORGANISMS

The following microorganisms were deposited with the Agricultural Research Service (NRRL), U. S. Department of Agriculture, 1815 N. University Street, Peoria, Ill., 61604, under the provisions of the Budapest Treaty on the International Recognition of the Deposit of Microorganisms for the Purposes of Patent Procedure, and comply with the criteria set forth in 37 C.F.R. § 1.801–1.809 regarding availability and permanency of deposits. The deposits were made on the date indicated and assigned the indicated accession number:

| Microorganism Deposit | NRRL Deposit No. | Date of Deposit |
|---|---|---|
| *Escherichia coli* CNI-NPP1-CP10 | B-30231 | November 3, 1999 |

CNI-NPP1-CP10 represents a composite deposit of a mixture of ten (10) strains. To distinguish and isolate each of the individual strains, an aliquot of the mixture can be streaked out to single colonies on nutrient media (e.g., LB plates) supplemented with 100 μg/ml ampicillin, single colonies grown and then DNA can be extracted using standard procedures.

Next, a sample of the DNA preparation can be digested with Not I and Sal I, and the resulting products can be separated by standard gel electrophoresis techniques using a 1% agarose gel in TAE buffer. Liberated inserts are of the following approximate sizes:

1: CNI-00711 852 bp
2: CNI-00712 1096 bp
3: CNI-00714 1825 bp
4: CNI-00715 542 bp
5: CNI-00716 771 bp
6: CNI-00717 1669 bp
7: CNI-00720 1182 bp
8: CNI-00721 1965 bp
9: CNI-00723 2702 bp
10: CNI-00724 979 bp

8 REFERENCES CITED

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings.

All publications, patents, and patent applications mentioned in this specification are herein incorporated by reference to the same extent as if each individual publication or patent application was specifically and individually indicated to be incorporated by reference.

SEQUENCE LISTING

<160> NUMBER OF SEQ ID NOS: 466

<210> SEQ ID NO 1
<211> LENGTH: 852
<212> TYPE: DNA
<213> ORGANISM: Homo sapiens

<400> SEQUENCE: 1

```
tcgacccacg cgtccgggaa catatctcaa aataataata actatttatg acaaacccac      60
agtcaatatc atactgaatg ggcaaaagct ggaagcattc taaataccaa aggacatcat     120
tagttaacaa atgctagact aactagatac caaagcttgc tctgtgaaaa atccccacat     180
aaccattgaa gtttacaaca ccctaaaccc tgccaccttg ctcccagtat cagagagccc     240
agttaaacat aactatgtag aggtattaga ctcagtttat tctagtaggc caacctcca     300
agaccatcgt tgaacatcag tagactggga gctgtacgtg gatgggagca gctttgccaa     360
cccctgcaaa gtgactcttg aagaagacca caaaccctgc tccagtcaac atctggaagc     420
ttgactagtc cacgcatggc tgaagcatga ggaaactcat cacaggactc attttcctta     480
aaatttagac ttgtacagta aagacttcaa cttgaccttc ctcagactga gggctgttcc     540
cagagtatac atcaagtcac tgaggtagga caaaaggttg ctacagtcct attattttac     600
agttattata agtgtactgg aactctaaaa agaacttgtt tttataatgt tattctatac     660
aattatttat aatacaatat acaaataatg tatttagccc aggaaatgac caacctgatg     720
tgtgttatga cccatctgag cctcccatga ccacagtttt taaaataaga ttaagaactg     780
aagactggtg ggggctcata aacaatatga gtaaagtgtt agccaaaata aaacaaaaaa     840
aaaagggcgg cc                                                         852
```

<210> SEQ ID NO 2
<211> LENGTH: 30

```
<212> TYPE: DNA
<213> ORGANISM: Homo sapiens

<400> SEQUENCE: 2
atgacaaacc cacagtcaat atcatactga                                    30

<210> SEQ ID NO 3
<211> LENGTH: 9
<212> TYPE: PRT
<213> ORGANISM: Homo sapiens

<400> SEQUENCE: 3

Met Thr Asn Pro Gln Ser Ile Ser Tyr
 1               5

<210> SEQ ID NO 4
<211> LENGTH: 60
<212> TYPE: DNA
<213> ORGANISM: Homo sapiens

<400> SEQUENCE: 4
atgggcaaaa gctggaagca ttctaaatac caaaggacat cattagttaa caaatgctag    60

<210> SEQ ID NO 5
<211> LENGTH: 19
<212> TYPE: PRT
<213> ORGANISM: Homo sapiens

<400> SEQUENCE: 5

Met Gly Lys Ser Trp Lys His Ser Lys Tyr Gln Arg Thr Ser Leu Val
 1               5                  10                  15

Asn Lys Cys

<210> SEQ ID NO 6
<211> LENGTH: 12
<212> TYPE: DNA
<213> ORGANISM: Homo sapiens

<400> SEQUENCE: 6
atgctagact aa                                                       12

<210> SEQ ID NO 7
<211> LENGTH: 3
<212> TYPE: PRT
<213> ORGANISM: Homo sapiens

<400> SEQUENCE: 7

Met Leu Asp
 1

<210> SEQ ID NO 8
<211> LENGTH: 33
<212> TYPE: DNA
<213> ORGANISM: Homo sapiens

<400> SEQUENCE: 8
atgggagcag ctttgccaac ccctgcaaag tga                                33

<210> SEQ ID NO 9
<211> LENGTH: 10
<212> TYPE: PRT
<213> ORGANISM: Homo sapiens

<400> SEQUENCE: 9
```

Met Gly Ala Ala Leu Pro Thr Pro Ala Lys
 1               5                  10

<210> SEQ ID NO 10
<211> LENGTH: 15
<212> TYPE: DNA
<213> ORGANISM: Homo sapiens

<400> SEQUENCE: 10
atggctgaag catga                                                    15

<210> SEQ ID NO 11
<211> LENGTH: 4
<212> TYPE: PRT
<213> ORGANISM: Homo sapiens

<400> SEQUENCE: 11

Met Ala Glu Ala
 1

<210> SEQ ID NO 12
<211> LENGTH: 42
<212> TYPE: DNA
<213> ORGANISM: Homo sapiens

<400> SEQUENCE: 12
atgaggaaac tcatcacagg actcattttc cttaaaattt ag                      42

<210> SEQ ID NO 13
<211> LENGTH: 13
<212> TYPE: PRT
<213> ORGANISM: Homo sapiens

<400> SEQUENCE: 13

Met Arg Lys Leu Ile Thr Gly Leu Ile Phe Leu Lys Ile
 1               5                  10

<210> SEQ ID NO 14
<211> LENGTH: 42
<212> TYPE: DNA
<213> ORGANISM: Homo sapiens

<400> SEQUENCE: 14
atgttattct atacaattat ttataataca atatacaaat aa                      42

<210> SEQ ID NO 15
<211> LENGTH: 13
<212> TYPE: PRT
<213> ORGANISM: Homo sapiens

<400> SEQUENCE: 15

Met Leu Phe Tyr Thr Ile Ile Tyr Asn Thr Ile Tyr Lys
 1               5                  10

<210> SEQ ID NO 16
<211> LENGTH: 63
<212> TYPE: DNA
<213> ORGANISM: Homo sapiens

<400> SEQUENCE: 16
atgtatttag cccaggaaat gaccaacctg atgtgtgtta tgacccatct gagcctccca   60
tga                                                                 63

```
<210> SEQ ID NO 17
<211> LENGTH: 20
<212> TYPE: PRT
<213> ORGANISM: Homo sapiens

<400> SEQUENCE: 17

Met Tyr Leu Ala Gln Glu Met Thr Asn Leu Met Cys Val Met Thr His
 1               5                  10                  15

Leu Ser Leu Pro
         20

<210> SEQ ID NO 18
<211> LENGTH: 45
<212> TYPE: DNA
<213> ORGANISM: Homo sapiens

<400> SEQUENCE: 18
atgaccaacc tgatgtgtgt tatgacccat ctgagcctcc catga                45

<210> SEQ ID NO 19
<211> LENGTH: 14
<212> TYPE: PRT
<213> ORGANISM: Homo sapiens

<400> SEQUENCE: 19

Met Thr Asn Leu Met Cys Val Met Thr His Leu Ser Leu Pro
 1               5                  10

<210> SEQ ID NO 20
<211> LENGTH: 33
<212> TYPE: DNA
<213> ORGANISM: Homo sapiens

<400> SEQUENCE: 20
atgtgtgtta tgacccatct gagcctccca tga                             33

<210> SEQ ID NO 21
<211> LENGTH: 10
<212> TYPE: PRT
<213> ORGANISM: Homo sapiens

<400> SEQUENCE: 21

Met Cys Val Met Thr His Leu Ser Leu Pro
 1               5                  10

<210> SEQ ID NO 22
<211> LENGTH: 24
<212> TYPE: DNA
<213> ORGANISM: Homo sapiens

<400> SEQUENCE: 22
atgacccatc tgagcctccc atga                                       24

<210> SEQ ID NO 23
<211> LENGTH: 7
<212> TYPE: PRT
<213> ORGANISM: Homo sapiens

<400> SEQUENCE: 23

Met Thr His Leu Ser Leu Pro
 1               5

<210> SEQ ID NO 24
```

```
<211> LENGTH: 106
<212> TYPE: DNA
<213> ORGANISM: Homo sapiens

<400> SEQUENCE: 24
atgaccacag tttttaaaat aagattaaga actgaagact ggtgggggct cataaacaat     60
atgagtaaag tgttagccaa aataaaacaa aaaaaaaagg gcggcc                   106

<210> SEQ ID NO 25
<211> LENGTH: 35
<212> TYPE: PRT
<213> ORGANISM: Homo sapiens

<400> SEQUENCE: 25

Met Thr Thr Val Phe Lys Ile Arg Leu Arg Thr Glu Asp Trp Trp Gly
 1               5                  10                  15

Leu Ile Asn Asn Met Ser Lys Val Leu Ala Lys Ile Lys Gln Lys Lys
            20                  25                  30

Lys Gly Gly
        35

<210> SEQ ID NO 26
<211> LENGTH: 1096
<212> TYPE: DNA
<213> ORGANISM: Homo sapiens

<400> SEQUENCE: 26
tcgacccacg cgtccgggca tgccaggcc ggctgggctg cagagcgccg gcacgggtcc     60
acgcctcggg tgacgggctt ccaggatgtt cgggcgcggg gcggcccatc cgcatccccc    120
aacaccccca cctccggcct gagcctccca gcgccggggg aaccacctcc tgtccgctgt    180
tgctggcccg catcctagca gcggcctgac gccctcccca ccctggcatg ccccctgac    240 ctgggacgat gagcatacga ctggggagcc cagtggaggc gccctcccga agcgccactg    300
cccatgctga ccacccagcc ctccggctgc tgatgtcatg agtaacacca ctgtgcccaa    360 tgcccccag gccaacagcg actccatggt gggctatgtg ttgggccct tcttcctcat     420 caccctggtc ggggtggtgg tggctgtggt aatgtatgta cagaagaaaa agcgggtgga    480
ccggctgcgc catcacctgc tccccatgta cagctatgac ccagctgagg aactgcatga    540
ggctgagcag gagctgctct ctgacatggg agacccaag gtggtacatg gctggcagag    600
tggctaccag cacaagcgga tgccactgct ggatgtcaag acgtgacctg accccttgc    660 cccaccttc agagcctggg gtcctggact gcctggggcc ctgccatctg cttccctgc     720 tgtcacctgg ctccccctgc tgggtgctgg gtctccattt ctccctccac ccaccctcag    780
cagcatctgc ttcccatgcc ctcaccatca cctcactgcc ccaggcctt ctgcccttg    840 tgggtgttga gctcaccgcc cacccacagg cactcatagg aagaggcttt ccttctggga    900 tggcggcgc tggtagacac ctttgctttc tctagccctc ctgggctggg cttgggccca    960
aatccccagg caggctttgg agttgttcc atggtgatgg ggccagatgt atagtattca   1020
gtatatattt tgtaaataaa atgttttgtg gctaaaaaa aaaaaaaaaa aaaaaaaaa    1080 aaaaaaagg gcggcc                                                  1096

<210> SEQ ID NO 27
<211> LENGTH: 54
<212> TYPE: DNA
<213> ORGANISM: Homo sapiens
```

-continued

```
<400> SEQUENCE: 27
atggccaggc cggctgggct gcagagcgcc ggcacgggtc cacgcctcgg gtga          54

<210> SEQ ID NO 28
<211> LENGTH: 17
<212> TYPE: PRT
<213> ORGANISM: Homo sapiens

<400> SEQUENCE: 28

Met Ala Arg Pro Ala Gly Leu Gln Ser Ala Gly Thr Gly Pro Arg Leu
 1               5                  10                  15

Gly

<210> SEQ ID NO 29
<211> LENGTH: 57
<212> TYPE: DNA
<213> ORGANISM: Homo sapiens

<400> SEQUENCE: 29
atgttcgggc gcggggcggc ccatccgcat cccccaacac ccccacctcc ggcctga      57

<210> SEQ ID NO 30
<211> LENGTH: 18
<212> TYPE: PRT
<213> ORGANISM: Homo sapiens

<400> SEQUENCE: 30

Met Phe Gly Arg Gly Ala Ala His Pro His Pro Thr Pro Pro Pro
 1               5                  10                  15

Pro Ala

<210> SEQ ID NO 31
<211> LENGTH: 12
<212> TYPE: DNA
<213> ORGANISM: Homo sapiens

<400> SEQUENCE: 31
atgccccctt ga                                                        12

<210> SEQ ID NO 32
<211> LENGTH: 3
<212> TYPE: PRT
<213> ORGANISM: Homo sapiens

<400> SEQUENCE: 32

Met Pro Pro
 1

<210> SEQ ID NO 33
<211> LENGTH: 93
<212> TYPE: DNA
<213> ORGANISM: Homo sapiens

<400> SEQUENCE: 33
atgagcatac gactggggag cccagtggag gcgccctccc gaagcgccac tgcccatgct   60
gaccacccag ccctccggct gctgatgtca tga                                93

<210> SEQ ID NO 34
<211> LENGTH: 30
<212> TYPE: PRT
<213> ORGANISM: Homo sapiens
```

```
<400> SEQUENCE: 34

Met Ser Ile Arg Leu Gly Ser Pro Val Glu Ala Pro Ser Arg Ser Ala
1               5                   10                  15

Thr Ala His Ala Asp His Pro Ala Leu Arg Leu Leu Met Ser
            20                  25                  30

<210> SEQ ID NO 35
<211> LENGTH: 30
<212> TYPE: DNA
<213> ORGANISM: Homo sapiens

<400> SEQUENCE: 35
atgctgacca cccagccctc cggctgctga                                    30

<210> SEQ ID NO 36
<211> LENGTH: 9
<212> TYPE: PRT
<213> ORGANISM: Homo sapiens

<400> SEQUENCE: 36

Met Leu Thr Thr Gln Pro Ser Gly Cys
1               5

<210> SEQ ID NO 37
<211> LENGTH: 309
<212> TYPE: DNA
<213> ORGANISM: Homo sapiens

<400> SEQUENCE: 37
atgagtaaca ccactgtgcc caatgccccc caggccaaca gcgactccat ggtgggctat    60
gtgttggggc ccttcttcct catcaccctg gtcggggtgg tggtggctgt ggtaatgtat   120
gtacagaaga aaaagcgggt ggaccggctg cgccatcacc tgctccccat gtacagctat   180
gacccagctg aggaactgca tgaggctgag caggagctgc tctctgacat gggagacccc   240
aaggtggtac atggctggca gagtggctac cagcacaagc ggatgccact gctggatgtc   300
aagacgtga                                                          309

<210> SEQ ID NO 38
<211> LENGTH: 102
<212> TYPE: PRT
<213> ORGANISM: Homo sapiens

<400> SEQUENCE: 38

Met Ser Asn Thr Thr Val Pro Asn Ala Pro Gln Ala Asn Ser Asp Ser
1               5                   10                  15

Met Val Gly Tyr Val Leu Gly Pro Phe Phe Leu Ile Thr Leu Val Gly
            20                  25                  30

Val Val Val Ala Val Val Met Tyr Val Gln Lys Lys Arg Val Asp
        35                  40                  45

Arg Leu Arg His His Leu Leu Pro Met Tyr Ser Tyr Asp Pro Ala Glu
    50                  55                  60

Glu Leu His Glu Ala Glu Gln Glu Leu Leu Ser Asp Met Gly Asp Pro
65                  70                  75                  80

Lys Val Val His Gly Trp Gln Ser Gly Tyr Gln His Lys Arg Met Pro
                85                  90                  95

Leu Leu Asp Val Lys Thr
                100
```

<210> SEQ ID NO 39
<211> LENGTH: 93
<212> TYPE: DNA
<213> ORGANISM: Homo sapiens

<400> SEQUENCE: 39

```
atgcccccca ggccaacagc gactccatgg tgggctatgt gttggggccc ttcttcctca    60
tcaccctggt cggggtggtg gtggctgtgg taa                                 93
```

<210> SEQ ID NO 40
<211> LENGTH: 30
<212> TYPE: PRT
<213> ORGANISM: Homo sapiens

<400> SEQUENCE: 40

Met Pro Pro Arg Pro Thr Ala Thr Pro Trp Trp Ala Met Cys Trp Gly
1               5                   10                  15

Pro Ser Ser Ser Ser Pro Trp Ser Gly Trp Trp Trp Leu Trp
            20                  25                  30

<210> SEQ ID NO 41
<211> LENGTH: 261
<212> TYPE: DNA
<213> ORGANISM: Homo sapiens

<400> SEQUENCE: 41

```
atggtgggct atgtgttggg gcccttcttc ctcatcaccc tggtcggggt ggtggtggct    60
gtggtaatgt atgtacagaa gaaaaagcgg gtggaccggc tgcgccatca cctgctcccc   120
atgtacagct atgacccagc tgaggaactg catgaggctg agcaggagct gctctctgac   180
atgggagacc ccaaggtggt acatggctgg cagagtggct accagcacaa gcggatgcca   240
ctgctggatg tcaagacgtg a                                             261
```

<210> SEQ ID NO 42
<211> LENGTH: 72
<212> TYPE: PRT
<213> ORGANISM: Homo sapiens

<400> SEQUENCE: 42

Met Val Gly Tyr Val Leu Gly Pro Phe Phe Leu Ile Thr Leu Val Gly
1               5                   10                  15

Val Val Val Ala Val Val Met Tyr Val Gln Lys Lys Lys Arg Val Asp
            20                  25                  30

Arg Leu Arg His His Leu Leu Pro Met Tyr Ser Tyr Asp Pro Ala Glu
            35                  40                  45

Glu Leu His Glu Ala Glu Gln Glu Leu Leu Ser Asp Met Gly Asp Pro
    50                  55                  60

Lys Val Val His Gly Trp Gln Ser
65                  70

<210> SEQ ID NO 43
<211> LENGTH: 57
<212> TYPE: DNA
<213> ORGANISM: Homo sapiens

<400> SEQUENCE: 43

```
atgtgttggg gcccttcttc ctcatcaccc tggtcggggt ggtggtggct gtggtaa       57
```

<210> SEQ ID NO 44
<211> LENGTH: 18

```
<212> TYPE: PRT
<213> ORGANISM: Homo sapiens

<400> SEQUENCE: 44

Met Cys Trp Gly Pro Ser Ser Ser Pro Trp Ser Gly Trp Trp Trp
 1               5                  10                  15

Leu Trp

<210> SEQ ID NO 45
<211> LENGTH: 195
<212> TYPE: DNA
<213> ORGANISM: Homo sapiens

<400> SEQUENCE: 45
atgtatgtac agaagaaaaa gcgggtggac cggctgcgcc atcacctgct ccccatgtac      60
agctatgacc cagctgagga actgcatgag gctgagcagg agctgctctc tgacatggga     120
gaccccaagg tggtacatgg ctggcagagt ggctaccagc acaagcggat gccactgctg     180
gatgtcaaga cgtga                                                      195

<210> SEQ ID NO 46
<211> LENGTH: 64
<212> TYPE: PRT
<213> ORGANISM: Homo sapiens

<400> SEQUENCE: 46

Met Tyr Val Gln Lys Lys Lys Arg Val Asp Arg Leu Arg His His Leu
 1               5                  10                  15

Leu Pro Met Tyr Ser Tyr Asp Pro Ala Glu Glu Leu His Glu Ala Glu
                20                  25                  30

Gln Glu Leu Leu Ser Asp Met Gly Asp Pro Lys Val Val His Gly Trp
            35                  40                  45

Gln Ser Gly Tyr Gln His Lys Arg Met Pro Leu Leu Asp Val Lys Thr
        50                  55                  60

<210> SEQ ID NO 47
<211> LENGTH: 480
<212> TYPE: DNA
<213> ORGANISM: Homo sapiens

<400> SEQUENCE: 47
atgtacagaa gaaaagcgg gtggaccggc tgcgccatca cctgctcccc atgtacagct      60
atgacccagc tgaggaactg catgaggctg agcaggagct gctctctgac atgggagacc     120
ccaaggtggt acatggctgg cagagtggct accagcacaa gcggatgcca ctgctggatg     180
tcaagacgtg acctgacccc cttgccccac ccttcagagc tgggtgtcct ggactgcctg     240
gggccctgcc atctgcttcc cctgctgtca cctggctccc cctgctgggt gctgggtctc     300
catttctccc tccacccacc ctcagcagca tctgcttccc atgccctcac catcacctca     360 ctgccccag gccttctgcc ctttgtgggt gttgagctca ccgccacccc acaggcactc     420
ataggaagag gctttccttc tgggatggcg gcggctggta gacacctttg ctttctctag     480

<210> SEQ ID NO 48
<211> LENGTH: 159
<212> TYPE: PRT
<213> ORGANISM: Homo sapiens

<400> SEQUENCE: 48

Met Tyr Arg Arg Lys Ser Gly Trp Thr Gly Cys Ala Ile Thr Cys Ser
```

```
  1               5                   10                  15
Pro Cys Thr Ala Met Thr Gln Leu Arg Asn Cys Met Arg Leu Ser Arg
                20                  25                  30

Ser Cys Ser Leu Thr Trp Glu Thr Pro Arg Trp Tyr Met Ala Gly Arg
                35                  40                  45

Val Ala Thr Ser Thr Ser Gly Cys His Cys Trp Met Ser Arg Arg Asp
 50                 55                  60

Leu Thr Pro Leu Pro His Pro Ser Glu Pro Gly Val Leu Asp Cys Leu
 65                 70                  75                  80

Gly Pro Cys His Leu Leu Pro Leu Leu Ser Pro Gly Ser Pro Cys Trp
                85                  90                  95

Val Leu Gly Leu His Phe Ser Leu His Pro Pro Ser Ala Ala Ser Ala
                100                 105                 110

Ser His Ala Leu Thr Ile Thr Ser Leu Pro Pro Gly Leu Leu Pro Phe
                115                 120                 125

Val Gly Val Glu Leu Thr Ala His Pro Gln Ala Leu Ile Gly Arg Gly
                130                 135                 140

Phe Pro Ser Gly Met Ala Ala Gly Arg His Leu Cys Phe Leu
145                 150                 155
```

<210> SEQ ID NO 49
<211> LENGTH: 141
<212> TYPE: DNA
<213> ORGANISM: Homo sapiens

<400> SEQUENCE: 49

```
atgtacagct atgacccagc tgaggaactg catgaggctg agcaggagct gctctctgac      60
atgggagacc ccaaggtggt acatggctgg cagagtggct accagcacaa gcggatgcca     120
ctgctggatg tcaagacgtg a                                               141
```

<210> SEQ ID NO 50
<211> LENGTH: 46
<212> TYPE: PRT
<213> ORGANISM: Homo sapiens

<400> SEQUENCE: 50

```
Met Tyr Ser Tyr Asp Pro Ala Glu Glu Leu His Glu Ala Glu Gln Glu
 1               5                  10                  15

Leu Leu Ser Asp Met Gly Asp Pro Lys Val Val His Gly Trp Gln Ser
                20                  25                  30

Gly Tyr Gln His Lys Arg Met Pro Leu Leu Asp Val Lys Thr
                35                  40                  45
```

<210> SEQ ID NO 51
<211> LENGTH: 420
<212> TYPE: DNA
<213> ORGANISM: Homo sapiens

<400> SEQUENCE: 51

```
atgacccagc tgaggaactg catgaggctg agcaggagct gctctctgac atgggagacc      60
ccaaggtggt acatggctgg cagagtggct accagcacaa gcggatgcca ctgctggatg     120
tcaagacgtg acctgacccc cttgccccac ccttcagagc ctggggtcct ggactgcctg     180
gggccctgcc atctgcttcc cctgctgtca cctggctccc cctgctgggt gctgggtctc     240
catttctccc tccaccccacc ctcagcagca tctgcttccc atgccctcac catcacctca     300
ctgcccccag gccttctgcc ctttgtgggt gttgagctca ccgcccaccc acaggcactc     360
```

-continued

```
ataggaagag gctttccttc tgggatggcg gcggctggta gacacctttg ctttctctag    420
```

<210> SEQ ID NO 52
<211> LENGTH: 139
<212> TYPE: PRT
<213> ORGANISM: Homo sapiens

<400> SEQUENCE: 52

```
Met Thr Gln Leu Arg Asn Cys Met Arg Leu Ser Arg Ser Cys Ser Leu
 1               5                   10                  15

Thr Trp Glu Thr Pro Arg Trp Tyr Met Ala Gly Arg Val Ala Thr Ser
            20                  25                  30

Thr Ser Gly Cys His Cys Trp Met Ser Arg Arg Asp Leu Thr Pro Leu
        35                  40                  45

Pro His Pro Ser Glu Pro Gly Val Leu Asp Cys Leu Gly Pro Cys His
    50                  55                  60

Leu Leu Pro Leu Leu Ser Pro Gly Ser Pro Cys Trp Val Leu Gly Leu
65                  70                  75                  80

His Phe Ser Leu His Pro Pro Ser Ala Ala Ser Ala Ser His Ala Leu
                85                  90                  95

Thr Ile Thr Ser Leu Pro Pro Gly Leu Leu Pro Phe Val Gly Val Glu
            100                 105                 110

Leu Thr Ala His Pro Gln Ala Leu Ile Gly Arg Gly Phe Pro Ser Gly
        115                 120                 125

Met Ala Ala Gly Arg His Leu Cys Phe Leu
    130                 135
```

<210> SEQ ID NO 53
<211> LENGTH: 399
<212> TYPE: DNA
<213> ORGANISM: Homo sapiens

<400> SEQUENCE: 53

```
atgaggctga gcaggagctg ctctctgaca tgggagaccc caaggtggta catggctggc    60
agagtggcta ccagcacaag cggatgccac tgctggatgt caagacgtga cctgaccccc   120
ttgccccacc cttcagagcc tggggtcctg gactgcctgg ggccctgcca tctgcttccc   180
ctgctgtcac ctggctcccc ctgctgggtg ctgggtctcc atttctccct ccacccaccc   240
tcagcagcat ctgcttccca tgccctcacc atcacctcac tgcccccagg ccttctgccc   300
tttgtgggtg ttgagctcac cgcccaccca caggcactca taggaagagg ctttccttct   360
gggatggcgg cggctggtag acacctttgc tttctctag                          399
```

<210> SEQ ID NO 54
<211> LENGTH: 132
<212> TYPE: PRT
<213> ORGANISM: Homo sapiens

<400> SEQUENCE: 54

```
Met Arg Leu Ser Arg Ser Cys Ser Leu Thr Trp Glu Thr Pro Arg Trp
 1               5                   10                  15

Tyr Met Ala Gly Arg Val Ala Ser Thr Ser Gly Cys His Cys Trp
            20                  25                  30

Met Ser Arg Arg Asp Leu Thr Pro Leu Pro His Pro Ser Glu Pro Gly
        35                  40                  45

Val Leu Asp Cys Leu Gly Pro Cys His Leu Leu Pro Leu Leu Ser Pro
    50                  55                  60
```

Gly Ser Pro Cys Trp Val Leu Gly Leu His Phe Ser Leu His Pro Pro
65                  70                  75                  80

Ser Ala Ala Ser Ala Ser His Ala Leu Thr Ile Thr Ser Leu Pro Pro
            85                  90                  95

Gly Leu Leu Pro Phe Val Gly Val Glu Leu Thr Ala His Pro Gln Ala
            100                 105                 110

Leu Ile Gly Arg Gly Phe Pro Ser Gly Met Ala Ala Gly Arg His
            115                 120                 125

Leu Cys Phe Leu
        130

<210> SEQ ID NO 55
<211> LENGTH: 81
<212> TYPE: DNA
<213> ORGANISM: Homo sapiens

<400> SEQUENCE: 55
atgggagacc ccaaggtggt acatggctgg cagagtggct accagcacaa gcggatgcca      60
ctgctggatg tcaagacgtg a                                               81

<210> SEQ ID NO 56
<211> LENGTH: 26
<212> TYPE: PRT
<213> ORGANISM: Homo sapiens

<400> SEQUENCE: 56

Met Gly Asp Pro Lys Val Val His Gly Trp Gln Ser Gly Tyr Gln His
1               5                   10                  15

Lys Arg Met Pro Leu Leu Asp Val Lys Thr
            20                  25

<210> SEQ ID NO 57
<211> LENGTH: 348
<212> TYPE: DNA
<213> ORGANISM: Homo sapiens

<400> SEQUENCE: 57
atggctggca gagtggctac cagcacaagc ggatgccact gctggatgtc aagacgtgac      60
ctgaccccct tgccccaccc ttcagagcct ggggtcctgg actgctgggg ccctgccat     120 ctgcttcccc tgctgtcacc tggctccccc tgctgggtgc tgggtctcca tttctccctc     180
cacccaccct cagcagcatc tgcttcccat gccctcacca tcacctcact gccccaggc      240 cttctgccct tgtgggtgt tgagctcacc gcccacccac aggcactcat aggaagaggc      300
tttccttctg ggatggcggc ggctggtaga cacctttgct ttctctag                  348

<210> SEQ ID NO 58
<211> LENGTH: 115
<212> TYPE: PRT
<213> ORGANISM: Homo sapiens

<400> SEQUENCE: 58

Met Ala Gly Arg Val Ala Thr Ser Thr Ser Gly Cys His Cys Trp Met
1               5                   10                  15

Ser Arg Arg Asp Leu Thr Pro Leu Pro His Pro Ser Glu Pro Gly Val
            20                  25                  30

Leu Asp Cys Leu Gly Pro Cys His Leu Leu Pro Leu Leu Ser Pro Gly
            35                  40                  45

Ser Pro Cys Trp Val Leu Gly Leu His Phe Ser Leu His Pro Pro Ser
        50                  55                  60

Ala Ala Ser Ala Ser His Ala Leu Thr Ile Thr Ser Leu Pro Gly
65              70                  75                  80

Leu Leu Pro Phe Val Gly Val Glu Leu Thr Ala His Pro Gln Ala Leu
                85                  90                  95

Ile Gly Arg Gly Phe Pro Ser Gly Met Ala Ala Ala Gly Arg His Leu
            100                 105                 110

Cys Phe Leu
        115

<210> SEQ ID NO 59
<211> LENGTH: 27
<212> TYPE: DNA
<213> ORGANISM: Homo sapiens

<400> SEQUENCE: 59
atgccactgc tggatgtcaa gacgtga                                          27

<210> SEQ ID NO 60
<211> LENGTH: 8
<212> TYPE: PRT
<213> ORGANISM: Homo sapiens

<400> SEQUENCE: 60

Met Pro Leu Leu Asp Val Lys Thr
1               5

<210> SEQ ID NO 61
<211> LENGTH: 303
<212> TYPE: DNA
<213> ORGANISM: Homo sapiens

<400> SEQUENCE: 61
atgtcaagac gtgacctgac ccccttgccc caccttcag agcctggggt cctggactgc       60
ctggggccct gccatctgct tcccctgctg tcacctggct cccctgctg ggtgctgggt      120 ctccatttct ccctccaccc accctcagca gcatctgctt cccatgccct caccatcacc     180
tcactgcccc caggccttct gccctttgtg ggtgttgagc tcaccgccca cccacaggca     240
ctcataggaa gaggctttcc ttctgggatg gcggcggctg gtagacacct ttgctttctc     300
tag                                                                  303

<210> SEQ ID NO 62
<211> LENGTH: 100
<212> TYPE: PRT
<213> ORGANISM: Homo sapiens

<400> SEQUENCE: 62

Met Ser Arg Arg Asp Leu Thr Pro Leu Pro His Pro Ser Glu Pro Gly
1               5                   10                  15

Val Leu Asp Cys Leu Gly Pro Cys His Leu Leu Pro Leu Leu Ser Pro
                20                  25                  30

Gly Ser Pro Cys Trp Val Leu Gly Leu His Phe Ser Leu His Pro Pro
            35                  40                  45

Ser Ala Ala Ser Ala Ser His Ala Leu Thr Ile Thr Ser Leu Pro Pro
        50                  55                  60

Gly Leu Leu Pro Phe Val Gly Val Glu Leu Thr Ala His Pro Gln Ala
65                  70                  75                  80

Leu Ile Gly Arg Gly Phe Pro Ser Gly Met Ala Ala Ala Gly Arg His
                85                  90                  95

Leu Cys Phe Leu
            100

<210> SEQ ID NO 63
<211> LENGTH: 84
<212> TYPE: DNA
<213> ORGANISM: Homo sapiens

<400> SEQUENCE: 63
atgccctcac catcacctca ctgcccccag gccttctgcc ctttgtgggt gttgagctca      60
ccgcccaccc acaggcactc atag                                            84

<210> SEQ ID NO 64
<211> LENGTH: 27
<212> TYPE: PRT
<213> ORGANISM: Homo sapiens

<400> SEQUENCE: 64

Met Pro Ser Pro Ser Pro His Cys Pro Gln Ala Phe Cys Pro Leu Trp
 1               5                  10                  15

Val Leu Ser Ser Pro Pro Thr His Arg His Ser
             20                  25

<210> SEQ ID NO 65
<211> LENGTH: 36
<212> TYPE: DNA
<213> ORGANISM: Homo sapiens

<400> SEQUENCE: 65
atggcggcgg ctggtagaca cctttgcttt ctctag                               36

<210> SEQ ID NO 66
<211> LENGTH: 11
<212> TYPE: PRT
<213> ORGANISM: Homo sapiens

<400> SEQUENCE: 66

Met Ala Ala Ala Gly Arg His Leu Cys Phe Leu
 1               5                  10

<210> SEQ ID NO 67
<211> LENGTH: 24
<212> TYPE: DNA
<213> ORGANISM: Homo sapiens

<400> SEQUENCE: 67
atggtgatgg ggccagatgt atag                                            24

<210> SEQ ID NO 68
<211> LENGTH: 7
<212> TYPE: PRT
<213> ORGANISM: Homo sapiens

<400> SEQUENCE: 68

Met Val Met Gly Pro Asp Val
 1               5

<210> SEQ ID NO 69
<211> LENGTH: 18
<212> TYPE: DNA
<213> ORGANISM: Homo sapiens

<400> SEQUENCE: 69
atggggccag atgtatag                                                18

<210> SEQ ID NO 70
<211> LENGTH: 5
<212> TYPE: PRT
<213> ORGANISM: Homo sapiens

<400> SEQUENCE: 70

Met Gly Pro Asp Val
 1               5

<210> SEQ ID NO 71
<211> LENGTH: 33
<212> TYPE: DNA
<213> ORGANISM: Homo sapiens

<400> SEQUENCE: 71
atgtatagta ttcagtatat attttgtaaa taa                                33

<210> SEQ ID NO 72
<211> LENGTH: 10
<212> TYPE: PRT
<213> ORGANISM: Homo sapiens

<400> SEQUENCE: 72

Met Tyr Ser Ile Gln Tyr Ile Phe Cys Lys
 1               5                  10

<210> SEQ ID NO 73
<211> LENGTH: 15
<212> TYPE: DNA
<213> ORGANISM: Homo sapiens

<400> SEQUENCE: 73
atgttttgtg gctaa                                                    15

<210> SEQ ID NO 74
<211> LENGTH: 4
<212> TYPE: PRT
<213> ORGANISM: Homo sapiens

<400> SEQUENCE: 74

Met Phe Cys Gly
 1

<210> SEQ ID NO 75
<211> LENGTH: 1825
<212> TYPE: DNA
<213> ORGANISM: Homo sapiens

<400> SEQUENCE: 75
tcgacccacg cgtccgtctt attccaaaat gttgagatac tggggagaga taccaatatc    60
atcaagccag accaacagaa gttccttcga tttgctccca cgggagttcc gtctggtgga   120
agtccatgac ccacccctgc accaaccctc agccaacaag ccgaagcccc ccactatgct   180
ggacatcccc tcagagccat gtagtctcac catccatacg attcagttga ttcagcacaa   240
ccgacgtctt cgcaacctta ttgccacagc tcaggcccag aatcagcagc agacagaagg   300
tgtaaaaact gaagagagtg aacctcttcc ctcgtgccct gggtcacctc ctctccctga   360
tgacctcctg cctttagatt gtaagaatcc caatgcacca ttccagatcc ggcacagtga   420

```
cccagagagt gacttttatc gtgggaaagg ggaacctgtg actgaactca gctggcactc      480
ctgtcggcag ctcctctacc aggcagtggc acaatcctg gcccacgcgg gctttgactg       540
tgctaatgag agtgtcctgg agaccctaac tgatgtggca catgagtatt gccttaagtt      600
taccaagttg ctgcgttttg ctgtggaccg ggaggcccgg ctgggacaga ctccttttcc      660
tgatgtgatg gagcaggtat tccatgaagt gggtattggc agtgtgctct ccctccagaa      720
gttctggcag caccgcatca aggactatca cagttacatg ctacagatta gtaagcaact      780
ctctgaagaa tatgaaagga ttgtcaatcc tgagaaggcc acagaggacg ctaaacctgt      840
gaagatcaag gaggaacctg tgagcgacat cacttttcct gtcagtgagg agctggaggc      900
tgaccttgct tctggagacc agtcactgcc tatgggagtg cttggggctc agagcgaacg      960
cttcccatct aacctggagg ttgaagcttc accacaggct tcaagtgcag aggtaaatgc     1020
ttctcctctt tggaatctgg cccatgtgaa atggagcct caagaaagtg aagaggcaa      1080 tgtctctggg catggtgtgc tgggcagtga tgtcttcgag gagcctatgt caggcatgag     1140
tgaagctggg attcctcaga gccctgatga ctcagatagc agctatggtt cccactccac     1200
tgacagcctc atgggtcct cccctgtttt caaccagcgc tgcaagaaga ggatgaggaa     1260
aatataaaag gaaagaggg agatgttttg tccagaccta ctagacccaa cagaaaaggt     1320
tagctgacta cagcagaccc tttgcagcag tagttttaac attgacttca catattcaga     1380
agtgattcta aaggactgtg gcacatagaa atgtattttg ctgagctgta caacaggatg     1440
gcacaaaatc ctgctgatag aaataagtgt aaccggccag gcacagtggc tcatgcctgt     1500
aatcccagca ttttgggagg cccaggtggg tggatcatct gaggtcagga gttcgagacc     1560
agcctgacca acatggaaaa aaccccatct ctactaaaaa tacaaaatta gccgggtgtg     1620
gtggcacatg cctgtaatcc cagctactca ggaaggctga ggcaggagaa ctgcttgaac     1680
ctgggaggtg gaggttgtgg tgagccgaga ctccagcctg gcaacaaga gtgaaactcc     1740 gtctcaaaaa taaataaata aataaaagaa aaaaaaaaaa aaaaaaaaaa aaaaaaaaaa     1800
aaaaaaaaaa aaaaaagggg cggcc                                          1825
```

<210> SEQ ID NO 76
<211> LENGTH: 1239
<212> TYPE: DNA
<213> ORGANISM: Homo sapiens

<400> SEQUENCE: 76

```
atgttgagat actggggaga gataccaata tcatcaagcc agaccaacag aagttccttc       60
gatttgctcc cacgggagtt ccgtctggtg gaagtccatg acccacccct gcaccaaccc      120
tcagccaaca agccgaagcc ccccactatg ctggacatcc cctcagagcc atgtagtctc      180
accatccata cgattcagtt gattcagcac aaccgacgtc ttcgcaacct tattgccaca      240
gctcaggccc agaatcagca gcagacagaa ggtgtaaaaa ctgaagagag tgaacctctt      300
ccctcgtgcc ctgggtcacc tcctctccct gatgacctcc tgcctttaga ttgtaagaat      360
cccaatgcac cattccagat ccggcacagt gacccagaga gtgacttta cgtgggaaa       420 ggggaacctg tgactgaact cagctggcac tcctgtcggc agctcctcta ccaggcagtg      480
gccacaatcc tggcccacgc gggctttgac tgtgctaatg agagtgtcct ggagaccctaa    540 actgatgtgg cacatgagta ttgccttaag tttaccaagt tgctgcgttt tgctgtggac      600
cgggaggccc ggctgggaca gactcctttt cctgatgtga tggagcaggt attccatgaa      660
```

```
gtgggtattg gcagtgtgct ctccctccag aagttctggc agcaccgcat caaggactat    720
cacagttaca tgctacagat tagtaagcaa ctctctgaag aatatgaaag gattgtcaat    780
cctgagaagg ccacagagga cgctaaacct gtgaagatca aggaggaacc tgtgagcgac    840 atcactttc  ctgtcagtga ggagctggag gctgaccttg cttctggaga ccagtcactg    900
cctatgggag tgcttggggc tcagagcgaa cgcttcccat ctaacctgga ggttgaagct    960
tcaccacagg cttcaagtgc agaggtaaat gcttctcctc tttggaatct ggcccatgtg   1020
aaaatggagc tcaagaaag  tgaagaaggc aatgtctctg gcatggtgt  gctgggcagt   1080 gatgtcttcg aggagcctat gtcaggcatg agtgaagctg ggattcctca gagccctgat   1140
gactcagata gcagctatgg ttcccactcc actgacagcc tcatggggtc ctcccctgtt   1200
ttcaaccagc gctgcaagaa gaggatgagg aaaatataa                          1239
```

<210> SEQ ID NO 77
<211> LENGTH: 412
<212> TYPE: PRT
<213> ORGANISM: Homo sapiens

<400> SEQUENCE: 77

```
Met Leu Arg Tyr Trp Gly Glu Ile Pro Ile Ser Ser Ser Gln Thr Asn
 1               5                  10                  15

Arg Ser Ser Phe Asp Leu Leu Pro Arg Glu Phe Arg Leu Val Glu Val
                20                  25                  30

His Asp Pro Pro Leu His Gln Pro Ser Ala Asn Lys Pro Lys Pro Pro
            35                  40                  45

Thr Met Leu Asp Ile Pro Ser Glu Pro Cys Ser Leu Thr Ile His Thr
        50                  55                  60

Ile Gln Leu Ile Gln His Asn Arg Arg Leu Arg Asn Leu Ile Ala Thr
65                  70                  75                  80

Ala Gln Ala Gln Asn Gln Gln Thr Glu Gly Val Lys Thr Glu Glu
                85                  90                  95

Ser Glu Pro Leu Pro Ser Cys Pro Gly Ser Pro Pro Leu Pro Asp Asp
                100                 105                 110

Leu Leu Pro Leu Asp Cys Lys Asn Pro Asn Ala Pro Phe Gln Ile Arg
            115                 120                 125

His Ser Asp Pro Glu Ser Asp Phe Tyr Arg Gly Lys Gly Glu Pro Val
        130                 135                 140

Thr Glu Leu Ser Trp His Ser Cys Arg Gln Leu Leu Tyr Gln Ala Val
145                 150                 155                 160

Ala Thr Ile Leu Ala His Ala Gly Phe Asp Cys Ala Asn Glu Ser Val
                165                 170                 175

Leu Glu Thr Leu Thr Asp Val Ala His Glu Tyr Cys Leu Lys Phe Thr
            180                 185                 190

Lys Leu Leu Arg Phe Ala Val Asp Arg Glu Ala Arg Leu Gly Gln Thr
        195                 200                 205

Pro Phe Pro Asp Val Met Glu Gln Val Phe His Glu Val Gly Ile Gly
    210                 215                 220

Ser Val Leu Ser Leu Gln Lys Phe Trp Gln His Arg Ile Lys Asp Tyr
225                 230                 235                 240

His Ser Tyr Met Leu Gln Ile Ser Lys Gln Leu Ser Glu Tyr Glu
                245                 250                 255

Arg Ile Val Asn Pro Glu Lys Ala Thr Glu Asp Ala Lys Pro Val Lys
            260                 265                 270
```

```
Ile Lys Glu Glu Pro Val Ser Asp Ile Thr Phe Pro Val Ser Glu Glu
            275                 280                 285

Leu Glu Ala Asp Leu Ala Ser Gly Asp Gln Ser Leu Pro Met Gly Val
            290                 295                 300

Leu Gly Ala Gln Ser Glu Arg Phe Pro Ser Asn Leu Glu Val Glu Ala
305                 310                 315                 320

Ser Pro Gln Ala Ser Ser Ala Glu Val Asn Ala Ser Pro Leu Trp Asn
                325                 330                 335

Leu Ala His Val Lys Met Glu Pro Gln Glu Ser Glu Glu Gly Asn Val
            340                 345                 350

Ser Gly His Gly Val Leu Gly Ser Asp Val Phe Glu Glu Pro Met Ser
            355                 360                 365

Gly Met Ser Glu Ala Gly Ile Pro Gln Ser Pro Asp Asp Ser Asp Ser
370                 375                 380

Ser Tyr Gly Ser His Ser Thr Asp Ser Leu Met Gly Ser Ser Pro Val
385                 390                 395                 400

Phe Asn Gln Arg Cys Lys Lys Arg Met Arg Lys Ile
                405                 410

<210> SEQ ID NO 78
<211> LENGTH: 105
<212> TYPE: DNA
<213> ORGANISM: Homo sapiens

<400> SEQUENCE: 78
atgacccacc cctgcaccaa ccctcagcca acaagccgaa gcccccccact atgctggaca     60 tcccctcaga gccatgtagt ctcaccatcc atacgattca gttga                    105

<210> SEQ ID NO 79
<211> LENGTH: 34
<212> TYPE: PRT
<213> ORGANISM: Homo sapiens

<400> SEQUENCE: 79

Met Thr His Pro Cys Thr Asn Pro Gln Pro Thr Ser Arg Ser Pro Pro
  1               5                  10                  15

Leu Cys Trp Thr Ser Pro Gln Ser His Val Val Ser Pro Ser Ile Arg
             20                  25                  30

Phe Ser

<210> SEQ ID NO 80
<211> LENGTH: 1092
<212> TYPE: DNA
<213> ORGANISM: Homo sapiens

<400> SEQUENCE: 80
atgctggaca tcccctcaga gccatgtagt ctcaccatcc atacgattca gttgattcag     60
cacaaccgac gtcttcgcaa ccttattgcc acagctcagg cccagaatca gcagcagaca    120
gaaggtgtaa aaactgaaga gagtgaacct cttccctcgt gccctgggtc acctcctctc    180
cctgatgacc tcctgccttt agattgtaag aatcccaatg caccattcca gatccggcac    240
agtgacccag agagtgactt ttatcgtggg aaagggaac ctgtgactga actcagctgg    300
cactcctgtc ggcagctcct ctaccaggca gtggccacaa tcctggccca cgcgggcttt    360
gactgtgcta atgagagtgt cctggagacc taactgatg tggcacatga gtattgcctt    420
aagtttacca agttgctgcg ttttgctgtg daccgggagg cccggctggg acagactcct    480
```

```
tttcctgatg tgatggagca ggtattccat gaagtgggta ttggcagtgt gctctccctc      540
cagaagttct ggcagcaccg catcaaggac tatcacagtt acatgctaca gattagtaag      600
caactctctg aagaatatga aaggattgtc aatcctgaga aggccacaga ggacgctaaa      660
cctgtgaaga tcaaggagga acctgtgagc gacatcactt ttcctgtcag tgaggagctg      720
gaggctgacc ttgcttctgg agaccagtca ctgcctatgg gagtgcttgg ggctcagagc      780
gaacgcttcc catctaacct ggaggttgaa gcttcaccac aggcttcaag tgcagaggta      840
aatgcttctc ctctttggaa tctggcccat gtgaaaatgg agcctcaaga agtgaagaa       900 ggcaatgtct ctgggcatgg tgtgctgggc agtgatgtct tcgaggagcc tatgtcaggc      960
atgagtgaag ctgggattcc tcagagccct gatgactcag atagcagcta tggttcccac     1020
tccactgaca gcctcatggg gtcctcccct gttttcaacc agcgctgcaa gaagaggatg     1080
aggaaaatat aa                                                          1092
```

<210> SEQ ID NO 81
<211> LENGTH: 363
<212> TYPE: PRT
<213> ORGANISM: Homo sapiens

<400> SEQUENCE: 81

```
Met Leu Asp Ile Pro Ser Glu Pro Cys Ser Leu Thr Ile His Thr Ile
 1               5                  10                  15

Gln Leu Ile Gln His Asn Arg Arg Leu Arg Asn Leu Ile Ala Thr Ala
            20                  25                  30

Gln Ala Gln Asn Gln Gln Gln Thr Glu Gly Val Lys Thr Glu Glu Ser
        35                  40                  45

Glu Pro Leu Pro Ser Cys Pro Gly Ser Pro Pro Leu Pro Asp Asp Leu
    50                  55                  60

Leu Pro Leu Asp Cys Lys Asn Pro Asn Ala Pro Phe Gln Ile Arg His
65                  70                  75                  80

Ser Asp Pro Glu Ser Asp Phe Tyr Arg Gly Lys Gly Glu Pro Val Thr
                85                  90                  95

Glu Leu Ser Trp His Ser Cys Arg Gln Leu Leu Tyr Gln Ala Val Ala
            100                 105                 110

Thr Ile Leu Ala His Ala Gly Phe Asp Cys Ala Asn Glu Ser Val Leu
        115                 120                 125

Glu Thr Leu Thr Asp Val Ala His Glu Tyr Cys Leu Lys Phe Thr Lys
    130                 135                 140

Leu Leu Arg Phe Ala Val Asp Arg Glu Ala Arg Leu Gly Gln Thr Pro
145                 150                 155                 160

Phe Pro Asp Val Met Glu Gln Val Phe His Glu Val Gly Ile Gly Ser
                165                 170                 175

Val Leu Ser Leu Gln Lys Phe Trp Gln His Arg Ile Lys Asp Tyr His
            180                 185                 190

Ser Tyr Met Leu Gln Ile Ser Lys Gln Leu Ser Glu Glu Tyr Glu Arg
        195                 200                 205

Ile Val Asn Pro Glu Lys Ala Thr Glu Asp Ala Lys Pro Val Lys Ile
    210                 215                 220

Lys Glu Glu Pro Val Ser Asp Ile Thr Phe Pro Val Ser Glu Glu Leu
225                 230                 235                 240

Glu Ala Asp Leu Ala Ser Gly Asp Gln Ser Leu Pro Met Gly Val Leu
                245                 250                 255

Gly Ala Gln Ser Glu Arg Phe Pro Ser Asn Leu Glu Val Glu Ala Ser
```

-continued

```
                    260                 265                 270
    Pro Gln Ala Ser Ser Ala Glu Val Asn Ala Ser Pro Leu Trp Asn Leu
                275                 280                 285

Ala His Val Lys Met Glu Pro Gln Glu Ser Glu Glu Gly Asn Val Ser
                290                 295                 300

Gly His Gly Val Leu Gly Ser Asp Val Phe Glu Glu Pro Met Ser Gly
    305                 310                 315                 320

Met Ser Glu Ala Gly Ile Pro Gln Ser Pro Asp Asp Ser Asp Ser Ser
                    325                 330                 335

Tyr Gly Ser His Ser Thr Asp Ser Leu Met Gly Ser Ser Pro Val Phe
                    340                 345                 350

Asn Gln Arg Cys Lys Lys Arg Met Arg Lys Ile
                    355                 360

<210> SEQ ID NO 82
<211> LENGTH: 18
<212> TYPE: DNA
<213> ORGANISM: Homo sapiens

<400> SEQUENCE: 82
atgacctcct gcctttag                                                    18

<210> SEQ ID NO 83
<211> LENGTH: 5
<212> TYPE: PRT
<213> ORGANISM: Homo sapiens

<400> SEQUENCE: 83

Met Thr Ser Cys Leu
  1               5

<210> SEQ ID NO 84
<211> LENGTH: 69
<212> TYPE: DNA
<213> ORGANISM: Homo sapiens

<400> SEQUENCE: 84
atgcaccatt ccagatccgg cacagtgacc cagagagtga cttttatcgt gggaaagggg    60
aacctgtga                                                             69

<210> SEQ ID NO 85
<211> LENGTH: 22
<212> TYPE: PRT
<213> ORGANISM: Homo sapiens

<400> SEQUENCE: 85

Met His His Ser Arg Ser Gly Thr Val Thr Gln Arg Val Thr Phe Ile
  1               5                  10                  15

Val Gly Lys Gly Asn Leu
                20

<210> SEQ ID NO 86
<211> LENGTH: 24
<212> TYPE: DNA
<213> ORGANISM: Homo sapiens

<400> SEQUENCE: 86
atgagagtgt cctggagacc ctaa                                            24

<210> SEQ ID NO 87
```

-continued

<211> LENGTH: 7
<212> TYPE: PRT
<213> ORGANISM: Homo sapiens

<400> SEQUENCE: 87

Met Arg Val Ser Trp Arg Pro
1               5

<210> SEQ ID NO 88
<211> LENGTH: 96
<212> TYPE: DNA
<213> ORGANISM: Homo sapiens

<400> SEQUENCE: 88
atgtggcaca tgagtattgc cttaagttta ccaagttgct gcgttttgct gtggaccggg      60
aggcccggct gggacagact ccttttcctg atgtga                               96

<210> SEQ ID NO 89
<211> LENGTH: 31
<212> TYPE: PRT
<213> ORGANISM: Homo sapiens

<400> SEQUENCE: 89

Met Trp His Met Ser Ile Ala Leu Ser Leu Pro Ser Cys Cys Val Leu
1               5                   10                  15

Leu Trp Thr Gly Arg Pro Gly Trp Asp Arg Leu Leu Phe Leu Met
            20                  25                  30

<210> SEQ ID NO 90
<211> LENGTH: 87
<212> TYPE: DNA
<213> ORGANISM: Homo sapiens

<400> SEQUENCE: 90
atgagtattg ccttaagttt accaagttgc tgcgttttgc tgtggaccgg gaggcccggc      60
tgggacagac tccttttcct gatgtga                                         87

<210> SEQ ID NO 91
<211> LENGTH: 28
<212> TYPE: PRT
<213> ORGANISM: Homo sapiens

<400> SEQUENCE: 91

Met Ser Ile Ala Leu Ser Leu Pro Ser Cys Cys Val Leu Leu Trp Thr
1               5                   10                  15

Gly Arg Pro Gly Trp Asp Arg Leu Leu Phe Leu Met
            20                  25

<210> SEQ ID NO 92
<211> LENGTH: 600
<212> TYPE: DNA
<213> ORGANISM: Homo sapiens

<400> SEQUENCE: 92
atggagcagg tattccatga agtgggtatt ggcagtgtgc tctccctcca gaagttctgg      60
cagcaccgca tcaaggacta tcacagttac atgctacaga ttagtaagca actctctgaa     120
gaatatgaaa ggattgtcaa tcctgagaag gccacagagg acgctaaacc tgtgaagatc     180
aaggaggaac tgtgagcga catcactttt cctgtcagtg aggagctgga ggctgacctt     240
gcttctggag accagtcact gcctatggga gtgcttgggg ctcagagcga acgcttccca     300

-continued

```
tctaacctgg aggttgaagc ttcaccacag gcttcaagtg cagaggtaaa tgcttctcct    360
ctttggaatc tggcccatgt gaaaatggag cctcaagaaa gtgaagaagg caatgtctct    420

gggcatggtg tgctgggcag tgatgtcttc gaggagccta tgtcaggcat gagtgaagct    480
gggattcctc agagccctga tgactcagat agcagctatg gttcccactc cactgacagc    540
ctcatggggt cctcccctgt tttcaaccag cgctgcaaga agaggatgag gaaaatataa    600
```

```

<210> SEQ ID NO 93
<211> LENGTH: 199
<212> TYPE: PRT
<213> ORGANISM: Homo sapiens

<400> SEQUENCE: 93

Met Glu Gln Val Phe His Glu Val Gly Ile Gly Ser Val Leu Ser Leu
 1               5                  10                  15

Gln Lys Phe Trp Gln His Arg Ile Lys Asp Tyr His Ser Tyr Met Leu
            20                  25                  30

Gln Ile Ser Lys Gln Leu Ser Glu Glu Tyr Glu Arg Ile Val Asn Pro
        35                  40                  45

Glu Lys Ala Thr Glu Asp Ala Lys Pro Val Lys Ile Lys Glu Glu Pro
    50                  55                  60

Val Ser Asp Ile Thr Phe Pro Val Ser Glu Glu Leu Glu Ala Asp Leu
65                  70                  75                  80

Ala Ser Gly Asp Gln Ser Leu Pro Met Gly Val Leu Gly Ala Gln Ser
                85                  90                  95

Glu Arg Phe Pro Ser Asn Leu Glu Val Glu Ala Ser Pro Gln Ala Ser
            100                 105                 110

Ser Ala Glu Val Asn Ala Ser Pro Leu Trp Asn Leu Ala His Val Lys
        115                 120                 125

Met Glu Pro Gln Glu Ser Glu Glu Gly Asn Val Ser Gly His Gly Val
    130                 135                 140

Leu Gly Ser Asp Val Phe Glu Glu Pro Met Ser Gly Met Ser Glu Ala
145                 150                 155                 160

Gly Ile Pro Gln Ser Pro Asp Asp Ser Asp Ser Ser Tyr Gly Ser His
                165                 170                 175

Ser Thr Asp Ser Leu Met Gly Ser Ser Pro Val Phe Asn Gln Arg Cys
            180                 185                 190

Lys Lys Arg Met Arg Lys Ile
        195
```

```

<210> SEQ ID NO 94
<211> LENGTH: 159
<212> TYPE: DNA
<213> ORGANISM: Homo sapiens

<400> SEQUENCE: 94
atgaagtggg tattggcagt gtgctctccc tccagaagtt ctggcagcac cgcatcaagg     60
actatcacag ttacatgcta cagattagta agcaactctc tgaagaatat gaaaggattg    120
tcaatcctga gaaggccaca gaggacgcta aacctgtga                           159
```

```

<210> SEQ ID NO 95
<211> LENGTH: 52
<212> TYPE: PRT
<213> ORGANISM: Homo sapiens

<400> SEQUENCE: 95

```

```
Met Lys Trp Val Leu Ala Val Cys Ser Pro Ser Arg Ser Ser Gly Ser
1               5                   10                  15

Thr Ala Ser Arg Thr Ile Thr Val Thr Cys Tyr Arg Leu Val Ser Asn
            20                  25                  30

Ser Leu Lys Asn Met Lys Gly Leu Ser Ile Leu Arg Arg Pro Gln Arg
        35                  40                  45

Thr Leu Asn Leu
    50
```

<210> SEQ ID NO 96
<211> LENGTH: 510
<212> TYPE: DNA
<213> ORGANISM: Homo sapiens

<400> SEQUENCE: 96

```
atgctacaga ttagtaagca actctctgaa gaatatgaaa ggattgtcaa tcctgagaag      60
gccacagagg acgctaaacc tgtgaagatc aaggaggaac ctgtgagcga catcactttt     120
cctgtcagtg aggagctgga ggctgacctt gcttctggag accagtcact gcctatggga     180
gtgcttgggg ctcagagcga acgcttccca tctaacctgg aggttgaagc ttcaccacag     240
gcttcaagtg cagaggtaaa tgcttctcct ctttggaatc tggcccatgt gaaaatggag     300
cctcaagaaa gtgaagaagg caatgtctct gggcatggtg tgctgggcag tgatgtcttc     360
gaggagccta tgtcaggcat gagtgaagct gggattcctc agagccctga tgactcagat     420
agcagctatg gttcccactc cactgacagc ctcatggggt cctcccctgt tttcaaccag     480
cgctgcaaga gaggatgag gaaaatataa                                       510
```

<210> SEQ ID NO 97
<211> LENGTH: 169
<212> TYPE: PRT
<213> ORGANISM: Homo sapiens

<400> SEQUENCE: 97

```
Met Leu Gln Ile Ser Lys Gln Leu Ser Glu Glu Tyr Glu Arg Ile Val
1               5                   10                  15

Asn Pro Glu Lys Ala Thr Glu Asp Ala Lys Pro Val Lys Ile Lys Glu
            20                  25                  30

Glu Pro Val Ser Asp Ile Thr Phe Pro Val Ser Glu Glu Leu Glu Ala
        35                  40                  45

Asp Leu Ala Ser Gly Asp Gln Ser Leu Pro Met Gly Val Leu Gly Ala
    50                  55                  60

Gln Ser Glu Arg Phe Pro Ser Asn Leu Glu Val Glu Ala Ser Pro Gln
65                  70                  75                  80

Ala Ser Ser Ala Glu Val Asn Ala Ser Pro Leu Trp Asn Leu Ala His
                85                  90                  95

Val Lys Met Glu Pro Gln Glu Ser Glu Gly Asn Val Ser Gly His
                100                 105                 110

Gly Val Leu Gly Ser Asp Val Phe Glu Glu Pro Met Ser Gly Met Ser
            115                 120                 125

Glu Ala Gly Ile Pro Gln Ser Pro Asp Asp Ser Asp Ser Ser Tyr Gly
        130                 135                 140

Ser His Ser Thr Asp Ser Leu Met Gly Ser Ser Pro Val Phe Asn Gln
145                 150                 155                 160

Arg Cys Lys Lys Arg Met Arg Lys Ile
                165
```

<210> SEQ ID NO 98
<211> LENGTH: 51
<212> TYPE: DNA
<213> ORGANISM: Homo sapiens

<400> SEQUENCE: 98

```
atgaaaggat tgtcaatcct gagaaggcca cagaggacgc taaacctgtg a          51
```

<210> SEQ ID NO 99
<211> LENGTH: 16
<212> TYPE: PRT
<213> ORGANISM: Homo sapiens

<400> SEQUENCE: 99

```
Met Lys Gly Leu Ser Ile Leu Arg Arg Pro Gln Arg Thr Leu Asn Leu
 1               5                  10                  15
```

<210> SEQ ID NO 100
<211> LENGTH: 336
<212> TYPE: DNA
<213> ORGANISM: Homo sapiens

<400> SEQUENCE: 100

```
atgggagtgc ttggggctca gagcgaacgc ttcccatcta acctggaggt tgaagcttca    60
ccacaggctt caagtgcaga ggtaaatgct tctcctcttt ggaatctggc ccatgtgaaa   120
atggagcctc aagaaagtga agaaggcaat gtctctgggc atggtgtgct gggcagtgat   180
gtcttcgagg agcctatgtc aggcatgagt gaagctggga ttcctcagag ccctgatgac   240
tcagatagca gctatggttc ccactccact gacagcctca tggggtcctc ccctgttttc   300
aaccagcgct gcaagaagag gatgaggaaa atataa                            336
```

<210> SEQ ID NO 101
<211> LENGTH: 111
<212> TYPE: PRT
<213> ORGANISM: Homo sapiens

<400> SEQUENCE: 101

```
Met Gly Val Leu Gly Ala Gln Ser Glu Arg Phe Pro Ser Asn Leu Glu
 1               5                  10                  15

Val Glu Ala Ser Pro Gln Ala Ser Ser Ala Glu Val Asn Ala Ser Pro
             20                  25                  30

Leu Trp Asn Leu Ala His Val Lys Met Glu Pro Gln Glu Ser Glu Glu
         35                  40                  45

Gly Asn Val Ser Gly His Gly Val Leu Gly Ser Asp Val Phe Glu Glu
     50                  55                  60

Pro Met Ser Gly Met Ser Glu Ala Gly Ile Pro Gln Ser Pro Asp Asp
 65                  70                  75                  80

Ser Asp Ser Ser Tyr Gly Ser His Ser Thr Asp Ser Leu Met Gly Ser
                 85                  90                  95

Ser Pro Val Phe Asn Gln Arg Cys Lys Lys Arg Met Arg Lys Ile
            100                 105                 110
```

<210> SEQ ID NO 102
<211> LENGTH: 33
<212> TYPE: DNA
<213> ORGANISM: Homo sapiens

<400> SEQUENCE: 102

```
atgcttctcc tctttggaat ctggcccatg tga                               33
```

<210> SEQ ID NO 103
<211> LENGTH: 10
<212> TYPE: PRT
<213> ORGANISM: Homo sapiens

<400> SEQUENCE: 103

Met Leu Leu Leu Phe Gly Ile Trp Pro Met
1               5                   10

<210> SEQ ID NO 104
<211> LENGTH: 216
<212> TYPE: DNA
<213> ORGANISM: Homo sapiens

<400> SEQUENCE: 104
atggagcctc aagaaagtga agaaggcaat gtctctgggc atggtgtgct gggcagtgat      60
gtcttcgagg agcctatgtc aggcatgagt gaagctggga ttcctcagag ccctgatgac     120
tcagatagca gctatggttc ccactccact gacagcctca tggggtcctc ccctgttttc     180
aaccagcgct gcaagaagag gatgaggaaa atataa                               216

<210> SEQ ID NO 105
<211> LENGTH: 71
<212> TYPE: PRT
<213> ORGANISM: Homo sapiens

<400> SEQUENCE: 105

Met Glu Pro Gln Glu Ser Glu Glu Gly Asn Val Ser Gly His Gly Val
1               5                   10                  15

Leu Gly Ser Asp Val Phe Glu Glu Pro Met Ser Gly Met Ser Glu Ala
                20                  25                  30

Gly Ile Pro Gln Ser Pro Asp Asp Ser Asp Ser Ser Tyr Gly Ser His
            35                  40                  45

Ser Thr Asp Ser Leu Met Gly Ser Ser Pro Val Phe Asn Gln Arg Cys
        50                  55                  60

Lys Lys Arg Met Arg Lys Ile
65                  70

<210> SEQ ID NO 106
<211> LENGTH: 60
<212> TYPE: DNA
<213> ORGANISM: Homo sapiens

<400> SEQUENCE: 106
atgtctctgg gcatggtgtg ctgggcagtg atgtcttcga ggagcctatg tcaggcatga      60

<210> SEQ ID NO 107
<211> LENGTH: 19
<212> TYPE: PRT
<213> ORGANISM: Homo sapiens

<400> SEQUENCE: 107

Met Ser Leu Gly Met Val Cys Trp Ala Val Met Ser Ser Arg Ser Leu
1               5                   10                  15

Cys Gln Ala

<210> SEQ ID NO 108
<211> LENGTH: 48
<212> TYPE: DNA
<213> ORGANISM: Homo sapiens

<400> SEQUENCE: 108
atggtgtgct gggcagtgat gtcttcgagg agcctatgtc aggcatga        48

<210> SEQ ID NO 109
<211> LENGTH: 15
<212> TYPE: PRT
<213> ORGANISM: Homo sapiens

<400> SEQUENCE: 109

Met Val Cys Trp Ala Val Met Ser Ser Arg Ser Leu Cys Gln Ala
1               5                   10                  15

<210> SEQ ID NO 110
<211> LENGTH: 30
<212> TYPE: DNA
<213> ORGANISM: Homo sapiens

<400> SEQUENCE: 110
atgtcttcga ggagcctatg tcaggcatga        30

<210> SEQ ID NO 111
<211> LENGTH: 9
<212> TYPE: PRT
<213> ORGANISM: Homo sapiens

<400> SEQUENCE: 111

Met Ser Ser Arg Ser Leu Cys Gln Ala
1               5

<210> SEQ ID NO 112
<211> LENGTH: 141
<212> TYPE: DNA
<213> ORGANISM: Homo sapiens

<400> SEQUENCE: 112
atgtcaggca tgagtgaagc tgggattcct cagagccctg atgactcaga tagcagctat        60
ggttcccact ccactgacag cctcatgggg tcctcccctg ttttcaacca gcgctgcaag       120
aagaggatga ggaaaatata a       141

<210> SEQ ID NO 113
<211> LENGTH: 46
<212> TYPE: PRT
<213> ORGANISM: Homo sapiens

<400> SEQUENCE: 113

Met Ser Gly Met Ser Glu Ala Gly Ile Pro Gln Ser Pro Asp Asp Ser
1               5                   10                  15

Asp Ser Ser Tyr Gly Ser His Ser Thr Asp Ser Leu Met Gly Ser Ser
                20                  25                  30

Pro Val Phe Asn Gln Arg Cys Lys Lys Arg Met Arg Lys Ile
            35                  40                  45

<210> SEQ ID NO 114
<211> LENGTH: 132
<212> TYPE: DNA
<213> ORGANISM: Homo sapiens

<400> SEQUENCE: 114
atgagtgaag ctgggattcc tcagagccct gatgactcag atagcagcta tggttcccac        60
tccactgaca gcctcatggg gtcctcccct gttttcaacc agcgctgcaa gaagaggatg       120

-continued aggaaaatat aa                                                                              132

<210> SEQ ID NO 115
<211> LENGTH: 43
<212> TYPE: PRT
<213> ORGANISM: Homo sapiens

<400> SEQUENCE: 115

Met Ser Glu Ala Gly Ile Pro Gln Ser Pro Asp Ser Asp Ser Ser
1               5                   10                  15

Tyr Gly Ser His Ser Thr Asp Ser Leu Met Gly Ser Ser Pro Val Phe
            20                  25                  30

Asn Gln Arg Cys Lys Lys Arg Met Arg Lys Ile
        35                  40

<210> SEQ ID NO 116
<211> LENGTH: 90
<212> TYPE: DNA
<213> ORGANISM: Homo sapiens

<400> SEQUENCE: 116
atgactcaga tagcagctat ggttcccact ccactgacag cctcatgggg tcctcccctg       60
ttttcaacca gcgctgcaag aagaggatga                                       90

<210> SEQ ID NO 117
<211> LENGTH: 29
<212> TYPE: PRT
<213> ORGANISM: Homo sapiens

<400> SEQUENCE: 117

Met Thr Gln Ile Ala Ala Met Val Pro Thr Pro Leu Thr Ala Ser Trp
1               5                   10                  15

Gly Pro Pro Leu Phe Ser Thr Ser Ala Ala Arg Arg Gly
            20                  25

<210> SEQ ID NO 118
<211> LENGTH: 72
<212> TYPE: DNA
<213> ORGANISM: Homo sapiens

<400> SEQUENCE: 118
atggttccca ctccactgac agcctcatgg ggtcctcccc tgttttcaac cagcgctgca       60
agaagaggat ga                                                          72

<210> SEQ ID NO 119
<211> LENGTH: 23
<212> TYPE: PRT
<213> ORGANISM: Homo sapiens

<400> SEQUENCE: 119

Met Val Pro Thr Pro Leu Thr Ala Ser Trp Gly Pro Pro Leu Phe Ser
1               5                   10                  15

Thr Ser Ala Ala Arg Arg Gly
            20

<210> SEQ ID NO 120
<211> LENGTH: 57
<212> TYPE: DNA
<213> ORGANISM: Homo sapiens

<400> SEQUENCE: 120

```
atgggtcct cccctgtttt caaccagcgc tgcaagaaga ggatgaggaa aatataa        57
```

<210> SEQ ID NO 121
<211> LENGTH: 18
<212> TYPE: PRT
<213> ORGANISM: Homo sapiens

<400> SEQUENCE: 121

Met Gly Ser Ser Pro Val Phe Asn Gln Arg Cys Lys Lys Arg Met Arg
 1               5                  10                  15

Lys Ile

<210> SEQ ID NO 122
<211> LENGTH: 15
<212> TYPE: DNA
<213> ORGANISM: Homo sapiens

<400> SEQUENCE: 122

```
atgaggaaaa tataa                                                    15
```

<210> SEQ ID NO 123
<211> LENGTH: 4
<212> TYPE: PRT
<213> ORGANISM: Homo sapiens

<400> SEQUENCE: 123

Met Arg Lys Ile
 1

<210> SEQ ID NO 124
<211> LENGTH: 45
<212> TYPE: DNA
<213> ORGANISM: Homo sapiens

<400> SEQUENCE: 124

```
atgttttgtc cagacctact agacccaaca gaaaaggtta gctga                   45
```

<210> SEQ ID NO 125
<211> LENGTH: 14
<212> TYPE: PRT
<213> ORGANISM: Homo sapiens

<400> SEQUENCE: 125

Met Phe Cys Pro Asp Leu Leu Asp Pro Thr Glu Lys Val Ser
 1               5                  10

<210> SEQ ID NO 126
<211> LENGTH: 132
<212> TYPE: DNA
<213> ORGANISM: Homo sapiens

<400> SEQUENCE: 126

```
atgtattttg ctgagctgta caacaggatg gcacaaaatc ctgctgatag aaataagtgt   60
aaccggccag gcacagtggc tcatgcctgt aatcccagca ttttgggagg cccaggtggg  120
tggatcatct ga                                                      132
```

<210> SEQ ID NO 127
<211> LENGTH: 43
<212> TYPE: PRT
<213> ORGANISM: Homo sapiens

<400> SEQUENCE: 127

Met Tyr Phe Ala Glu Leu Tyr Asn Arg Met Ala Gln Asn Pro Ala Asp
1               5                   10                  15

Arg Asn Lys Cys Asn Arg Pro Gly Thr Val Ala His Ala Cys Asn Pro
            20                  25                  30

Ser Ile Leu Gly Gly Pro Gly Gly Trp Ile Ile
        35                  40

<210> SEQ ID NO 128
<211> LENGTH: 105
<212> TYPE: DNA
<213> ORGANISM: Homo sapiens

<400> SEQUENCE: 128
atggcacaaa atcctgctga tagaaataag tgtaaccggc caggcacagt ggctcatgcc      60
tgtaatccca gcattttggg aggcccaggt gggtggatca tctga                     105

<210> SEQ ID NO 129
<211> LENGTH: 34
<212> TYPE: PRT
<213> ORGANISM: Homo sapiens

<400> SEQUENCE: 129

Met Ala Gln Asn Pro Ala Asp Arg Asn Lys Cys Asn Arg Pro Gly Thr
1               5                   10                  15

Val Ala His Ala Cys Asn Pro Ser Ile Leu Gly Gly Pro Gly Gly Trp
            20                  25                  30

Ile Ile

<210> SEQ ID NO 130
<211> LENGTH: 75
<212> TYPE: DNA
<213> ORGANISM: Homo sapiens

<400> SEQUENCE: 130
atgcctgtaa tcccagcatt ttgggaggcc caggtgggtg gatcatctga ggtcaggagt      60
tcgagaccag cctga                                                      75

<210> SEQ ID NO 131
<211> LENGTH: 24
<212> TYPE: PRT
<213> ORGANISM: Homo sapiens

<400> SEQUENCE: 131

Met Pro Val Ile Pro Ala Phe Trp Glu Ala Gln Val Gly Gly Ser Ser
1               5                   10                  15

Glu Val Arg Ser Ser Arg Pro Ala
            20

<210> SEQ ID NO 132
<211> LENGTH: 39
<212> TYPE: DNA
<213> ORGANISM: Homo sapiens

<400> SEQUENCE: 132
atggaaaaaa ccccatctct actaaaaata caaaattag                            39

<210> SEQ ID NO 133
<211> LENGTH: 12
<212> TYPE: PRT
<213> ORGANISM: Homo sapiens

```
<400> SEQUENCE: 133

Met Glu Lys Thr Pro Ser Leu Leu Lys Ile Gln Asn
1               5                   10

<210> SEQ ID NO 134
<211> LENGTH: 33
<212> TYPE: DNA
<213> ORGANISM: Homo sapiens

<400> SEQUENCE: 134
atgcctgtaa tcccagctac tcaggaaggc tga                                  33

<210> SEQ ID NO 135
<211> LENGTH: 10
<212> TYPE: PRT
<213> ORGANISM: Homo sapiens

<400> SEQUENCE: 135

Met Pro Val Ile Pro Ala Thr Gln Glu Gly
1               5                   10

<210> SEQ ID NO 136
<211> LENGTH: 542
<212> TYPE: DNA
<213> ORGANISM: Homo sapiens

<400> SEQUENCE: 136
tcgacccacg cgtccgggac aatagtgtag gttatggatg gaggtgtcgg tactaaattg     60
aataacgagt aaataatctt acttgggtag agatggcctt tgccaacaaa gtgaactgtt    120
ttggttgttt taaactcatg aagtatgggt tcagtggaaa tgtttggaac tctgaaggat    180
ttagacaagg ttttgaaaag gataatcatg ggttagaagg aagtgtttga agtcactttt    240
gaaagttagt tttgggccag cacggtagct cacccttgta atcccagcac tttgggaggc    300
tgaggtgggt agattacttg agcccaggaa ttcaagacca gcctgggcaa catggtgaaa    360
ccctgtttct ataaaaaata atctgggctt tgtagcatat gcctgtggtc ccagctactg    420
aggaggctga ggtgggagga ttgcttgagc ccaggaggca gaggttgcag tgagccaagg    480
tcacgtcact gcactctagc ctgggcaaca gagtaagaca aaaaaaaaaa aaagggcgg     540 cc                                                                  542

<210> SEQ ID NO 137
<211> LENGTH: 39
<212> TYPE: DNA
<213> ORGANISM: Homo sapiens

<400> SEQUENCE: 137
atggatggag gtgtcggtac taaattgaat aacgagtaa                            39

<210> SEQ ID NO 138
<211> LENGTH: 12
<212> TYPE: PRT
<213> ORGANISM: Homo sapiens

<400> SEQUENCE: 138

Met Asp Gly Gly Val Gly Thr Lys Leu Asn Asn Glu
1               5                   10

<210> SEQ ID NO 139
<211> LENGTH: 24
```

```
<212> TYPE: DNA
<213> ORGANISM: Homo sapiens

<400> SEQUENCE: 139
atggaggtgt cggtactaaa ttga                                          24

<210> SEQ ID NO 140
<211> LENGTH: 7
<212> TYPE: PRT
<213> ORGANISM: Homo sapiens

<400> SEQUENCE: 140

Met Glu Val Ser Val Leu Asn
1               5

<210> SEQ ID NO 141
<211> LENGTH: 138
<212> TYPE: DNA
<213> ORGANISM: Homo sapiens

<400> SEQUENCE: 141
atggcctttg ccaacaaagt gaactgtttt ggttgttttta aactcatgaa gtatgggttc    60
agtggaaatg tttggaactc tgaaggattt agacaaggtt ttgaaaagga taatcatggg   120
ttagaaggaa gtgtttga                                                 138

<210> SEQ ID NO 142
<211> LENGTH: 45
<212> TYPE: PRT
<213> ORGANISM: Homo sapiens

<400> SEQUENCE: 142

Met Ala Phe Ala Asn Lys Val Asn Cys Phe Gly Cys Phe Lys Leu Met
1               5                   10                  15

Lys Tyr Gly Phe Ser Gly Asn Val Trp Asn Ser Glu Gly Phe Arg Gln
            20                  25                  30

Gly Phe Glu Lys Asp Asn His Gly Leu Glu Gly Ser Val
        35                  40                  45

<210> SEQ ID NO 143
<211> LENGTH: 93
<212> TYPE: DNA
<213> ORGANISM: Homo sapiens

<400> SEQUENCE: 143
atgaagtatg ggttcagtgg aaatgtttgg aactctgaag gatttagaca aggttttgaa    60
aaggataatc atgggttaga aggaagtgtt tga                                 93

<210> SEQ ID NO 144
<211> LENGTH: 30
<212> TYPE: PRT
<213> ORGANISM: Homo sapiens

<400> SEQUENCE: 144

Met Lys Tyr Gly Phe Ser Gly Asn Val Trp Asn Ser Glu Gly Phe Arg
1               5                   10                  15

Gln Gly Phe Glu Lys Asp Asn His Gly Leu Glu Gly Ser Val
            20                  25                  30

<210> SEQ ID NO 145
<211> LENGTH: 72
<212> TYPE: DNA
```

<213> ORGANISM: Homo sapiens

<400> SEQUENCE: 145
atgggttcag tggaaatgtt tggaactctg aaggatttag acaaggtttt gaaaaggata      60
atcatgggtt ag                                                         72

<210> SEQ ID NO 146
<211> LENGTH: 23
<212> TYPE: PRT
<213> ORGANISM: Homo sapiens

<400> SEQUENCE: 146

Met Gly Ser Val Glu Met Phe Gly Thr Leu Lys Asp Leu Asp Lys Val
1               5                   10                  15

Leu Lys Arg Ile Ile Met Gly
            20

<210> SEQ ID NO 147
<211> LENGTH: 57
<212> TYPE: DNA
<213> ORGANISM: Homo sapiens

<400> SEQUENCE: 147
atgtttggaa ctctgaagga tttagacaag gttttgaaaa ggataatcat gggttag         57

<210> SEQ ID NO 148
<211> LENGTH: 18
<212> TYPE: PRT
<213> ORGANISM: Homo sapiens

<400> SEQUENCE: 148

Met Phe Gly Thr Leu Lys Asp Leu Asp Lys Val Leu Lys Arg Ile Ile
1               5                   10                  15

Met Gly

<210> SEQ ID NO 149
<211> LENGTH: 30
<212> TYPE: DNA
<213> ORGANISM: Homo sapiens

<400> SEQUENCE: 149
atggtgaaac cctgtttcta taaaaaataa                                      30

<210> SEQ ID NO 150
<211> LENGTH: 9
<212> TYPE: PRT
<213> ORGANISM: Homo sapiens

<400> SEQUENCE: 150

Met Val Lys Pro Cys Phe Tyr Lys Lys
1               5

<210> SEQ ID NO 151
<211> LENGTH: 75
<212> TYPE: DNA
<213> ORGANISM: Homo sapiens

<400> SEQUENCE: 151
atgcctgtgg tcccagctac tgaggaggct gaggtgggag gattgcttga gcccaggagg      60
cagaggttgc agtga                                                      75

<210> SEQ ID NO 152
<211> LENGTH: 24
<212> TYPE: PRT
<213> ORGANISM: Homo sapiens

<400> SEQUENCE: 152

Met Pro Val Val Pro Ala Thr Glu Glu Ala Glu Val Gly Gly Leu Leu
1               5                   10                  15

Glu Pro Arg Arg Gln Arg Leu Gln
            20

<210> SEQ ID NO 153
<211> LENGTH: 771
<212> TYPE: DNA
<213> ORGANISM: Homo sapiens

<400> SEQUENCE: 153

```
tcgacccacg cgtccgcaaa acctaaatag aagttgttgt taccgtgtgc caatgtgtcc      60
catgtgggtt gtgccaggta gagaaacagg aagtcaatca tctgtgacag tctctattct     120
gtcgttttgc tccttggtat ttgatttgca ctatatttag ttgaagcctg ttcactgttt     180
aaaaccggag gtatcttcaa aggcatggag acctggttcc agtaaatgtc ccaccagtgg     240
ggtatagaaa gcatgctcat gaccctgccg tgtcgtctga ggtacccgtt cttatcctag     300
tggttcagga agagaaaacg cagtttgcac tttcaagaca gcttctctaa ggctggcatg     360
ttatctcctt gctttgcttt tgccgttttt aaaatgtgta attgttccag cattccaatg     420
gtcttgtgca tagcagggga ctgtaaccaa aaataaacat gtatttgtgt aattggtttg     480
aagaagtctt gaatagctct ttactgtctt acttggggtt gataagattt gagtgtttgc     540
aattttttac taaatgtagc tccaaagtct taaatggctt gtttgttctt aaactgttaa     600
ttgatgaaac tgtgcataag tttacaatgt actaacttat tttgcttatt atatatagtg     660
ttttattgga aattgtaacc acacacttca gcatgatgaa aataaagatt agtgtttcca     720
tttaaataaa tgttttatcc tcccataaaa aaaaaaaaa aaagggcggc c                771
```

<210> SEQ ID NO 154
<211> LENGTH: 108
<212> TYPE: DNA
<213> ORGANISM: Homo sapiens

<400> SEQUENCE: 154

```
atgtgtccca tgtgggttgt gccaggtaga gaaacaggaa gtcaatcatc tgtgacagtc      60
tctattctgt cgttttgctc cttggtattt gatttgcact atatttag                   108
```

<210> SEQ ID NO 155
<211> LENGTH: 35
<212> TYPE: PRT
<213> ORGANISM: Homo sapiens

<400> SEQUENCE: 155

Met Cys Pro Met Trp Val Val Pro Gly Arg Glu Thr Gly Ser Gln Ser
1               5                   10                  15

Ser Val Thr Val Ser Ile Leu Ser Phe Cys Ser Leu Val Phe Asp Leu
            20                  25                  30

His Tyr Ile
        35

<210> SEQ ID NO 156
<211> LENGTH: 99

```
<212> TYPE: DNA
<213> ORGANISM: Homo sapiens

<400> SEQUENCE: 156
atgtgggttg tgccaggtag agaaacagga agtcaatcat ctgtgacagt ctctattctg      60
tcgttttgct ccttggtatt tgatttgcac tatatttag                              99

<210> SEQ ID NO 157
<211> LENGTH: 32
<212> TYPE: PRT
<213> ORGANISM: Homo sapiens

<400> SEQUENCE: 157

Met Trp Val Val Pro Gly Arg Glu Thr Gly Ser Gln Ser Ser Val Thr
 1               5                  10                  15

Val Ser Ile Leu Ser Phe Cys Ser Leu Val Phe Asp Leu His Tyr Ile
            20                  25                  30

<210> SEQ ID NO 158
<211> LENGTH: 21
<212> TYPE: DNA
<213> ORGANISM: Homo sapiens

<400> SEQUENCE: 158
atggagacct ggttccagta a                                                 21

<210> SEQ ID NO 159
<211> LENGTH: 6
<212> TYPE: PRT
<213> ORGANISM: Homo sapiens

<400> SEQUENCE: 159

Met Glu Thr Trp Phe Gln
 1               5

<210> SEQ ID NO 160
<211> LENGTH: 75
<212> TYPE: DNA
<213> ORGANISM: Homo sapiens

<400> SEQUENCE: 160
atgtcccacc agtggggtat agaaagcatg ctcatgaccc tgccgtgtcg tctgaggtac      60
ccgttcttat cctag                                                        75

<210> SEQ ID NO 161
<211> LENGTH: 24
<212> TYPE: PRT
<213> ORGANISM: Homo sapiens

<400> SEQUENCE: 161

Met Ser His Gln Trp Gly Ile Glu Ser Met Leu Met Thr Leu Pro Cys
 1               5                  10                  15

Arg Leu Arg Tyr Pro Phe Leu Ser
            20

<210> SEQ ID NO 162
<211> LENGTH: 48
<212> TYPE: DNA
<213> ORGANISM: Homo sapiens

<400> SEQUENCE: 162
atgctcatga ccctgccgtg tcgtctgagg taccgttcct tatcctag                    48
```

<210> SEQ ID NO 163
<211> LENGTH: 15
<212> TYPE: PRT
<213> ORGANISM: Homo sapiens

<400> SEQUENCE: 163

Met Leu Met Thr Leu Pro Cys Arg Leu Arg Tyr Pro Phe Leu Ser
1               5                   10                  15

<210> SEQ ID NO 164
<211> LENGTH: 42
<212> TYPE: DNA
<213> ORGANISM: Homo sapiens

<400> SEQUENCE: 164
atgaccctgc cgtgtcgtct gaggtacccg ttcttatcct ag                          42

<210> SEQ ID NO 165
<211> LENGTH: 13
<212> TYPE: PRT
<213> ORGANISM: Homo sapiens

<400> SEQUENCE: 165

Met Thr Leu Pro Cys Arg Leu Arg Tyr Pro Phe Leu Ser
1               5                   10

<210> SEQ ID NO 166
<211> LENGTH: 99
<212> TYPE: DNA
<213> ORGANISM: Homo sapiens

<400> SEQUENCE: 166
atgttatctc cttgctttgc tttttgccgt tttaaaatgt gtaattgttc cagcattcca      60
atggtcttgt gcatagcagg ggactgtaac caaaaataa                             99

<210> SEQ ID NO 167
<211> LENGTH: 32
<212> TYPE: PRT
<213> ORGANISM: Homo sapiens

<400> SEQUENCE: 167

Met Leu Ser Pro Cys Phe Ala Phe Cys Arg Phe Lys Met Cys Asn Cys
1               5                   10                  15

Ser Ser Ile Pro Met Val Leu Cys Ile Ala Gly Asp Cys Asn Gln Lys
                20                  25                  30

<210> SEQ ID NO 168
<211> LENGTH: 63
<212> TYPE: DNA
<213> ORGANISM: Homo sapiens

<400> SEQUENCE: 168
atgtgtaatt gttccagcat tccaatggtc ttgtgcatag caggggactg taaccaaaaa      60
taa                                                                    63

<210> SEQ ID NO 169
<211> LENGTH: 20
<212> TYPE: PRT
<213> ORGANISM: Homo sapiens

<400> SEQUENCE: 169

Met Cys Asn Cys Ser Ser Ile Pro Met Val Leu Cys Ile Ala Gly Asp
1               5                   10                  15

Cys Asn Gln Lys
            20

<210> SEQ ID NO 170
<211> LENGTH: 39
<212> TYPE: DNA
<213> ORGANISM: Homo sapiens

<400> SEQUENCE: 170
atggtcttgt gcatagcagg ggactgtaac caaaaataa                               39

<210> SEQ ID NO 171
<211> LENGTH: 12
<212> TYPE: PRT
<213> ORGANISM: Homo sapiens

<400> SEQUENCE: 171

Met Val Leu Cys Ile Ala Gly Asp Cys Asn Gln Lys
1               5                   10

<210> SEQ ID NO 172
<211> LENGTH: 177
<212> TYPE: DNA
<213> ORGANISM: Homo sapiens

<400> SEQUENCE: 172
atgtatttgt gtaattggtt tgaagaagtc ttgaatagct ctttactgtc ttacttgggg        60
ttgataagat ttgagtgttt gcaatttttt actaaatgta gctccaaagt cttaaatggc       120
ttgtttgttc ttaaactgtt aattgatgaa actgtgcata agtttacaat gtactaa          177

<210> SEQ ID NO 173
<211> LENGTH: 58
<212> TYPE: PRT
<213> ORGANISM: Homo sapiens

<400> SEQUENCE: 173

Met Tyr Leu Cys Asn Trp Phe Glu Glu Val Leu Asn Ser Ser Leu Leu
1               5                   10                  15

Ser Tyr Leu Gly Leu Ile Arg Phe Glu Cys Leu Gln Phe Phe Thr Lys
            20                  25                  30

Cys Ser Lys Val Leu Asn Gly Leu Phe Val Leu Lys Leu Leu Ile
        35                  40                  45

Asp Glu Thr Val His Lys Phe Thr Met Tyr
    50                  55

<210> SEQ ID NO 174
<211> LENGTH: 27
<212> TYPE: DNA
<213> ORGANISM: Homo sapiens

<400> SEQUENCE: 174
atggcttgtt tgttcttaaa ctgttaa                                            27

<210> SEQ ID NO 175
<211> LENGTH: 8
<212> TYPE: PRT
<213> ORGANISM: Homo sapiens

<400> SEQUENCE: 175

Met Ala Cys Leu Phe Leu Asn Cys
1               5

<210> SEQ ID NO 176
<211> LENGTH: 75
<212> TYPE: DNA
<213> ORGANISM: Homo sapiens

<400> SEQUENCE: 176
atgaaactgt gcataagttt acaatgtact aacttatttt gcttattata tatagtgttt    60
tattggaaat tgtaa                                                     75

<210> SEQ ID NO 177
<211> LENGTH: 24
<212> TYPE: PRT
<213> ORGANISM: Homo sapiens

<400> SEQUENCE: 177

Met Lys Leu Cys Ile Ser Leu Gln Cys Thr Asn Leu Phe Cys Leu Leu
1               5                   10                  15

Tyr Ile Val Phe Tyr Trp Lys Leu
            20

<210> SEQ ID NO 178
<211> LENGTH: 33
<212> TYPE: DNA
<213> ORGANISM: Homo sapiens

<400> SEQUENCE: 178
atgatgaaaa taaagattag tgtttccatt taa                                 33

<210> SEQ ID NO 179
<211> LENGTH: 10
<212> TYPE: PRT
<213> ORGANISM: Homo sapiens

<400> SEQUENCE: 179

Met Met Lys Ile Lys Ile Ser Val Ser Ile
1               5                   10

<210> SEQ ID NO 180
<211> LENGTH: 30
<212> TYPE: DNA
<213> ORGANISM: Homo sapiens

<400> SEQUENCE: 180
atgaaaataa agattagtgt ttccatttaa                                     30

<210> SEQ ID NO 181
<211> LENGTH: 9
<212> TYPE: PRT
<213> ORGANISM: Homo sapiens

<400> SEQUENCE: 181

Met Lys Ile Lys Ile Ser Val Ser Ile
1               5

<210> SEQ ID NO 182
<211> LENGTH: 42
<212> TYPE: DNA
<213> ORGANISM: Homo sapiens

<400> SEQUENCE: 182

```
atgttttatc ctcccataaa aaaaaaaaa aaaagggcgg cc                          42
```

<210> SEQ ID NO 183
<211> LENGTH: 14
<212> TYPE: PRT
<213> ORGANISM: Homo sapiens

<400> SEQUENCE: 183

Met Phe Tyr Pro Pro Ile Lys Lys Lys Lys Lys Arg Ala Ala
 1               5                  10

<210> SEQ ID NO 184
<211> LENGTH: 1669
<212> TYPE: DNA
<213> ORGANISM: Homo sapiens

<400> SEQUENCE: 184

```
tcgacccacg cgtccgcagg cagtgactgc cttcggcttt ttttctgctg actaagatct      60
cctatagaga gctacaacaa tgcccaaaag aaagccaaag agaagatctg ccaggttgtc     120
tgctatgctt gtgccagtta caccagaggt gaagcctaaa agaacatcaa gttcaaggaa     180
aatgaagaca aaaagtgata tgatggaaga aaacatagat acaagtgccc aagcagttgc     240
tgaaaccaag caagaagcag ttgttgaaga agactacaat gaaaatgcta aaaatggaga     300
agccaaaatt acagaggcac cagcttctga aaaagaaatt gtggaagtaa agaagaaaa      360
tattgaagat gccacagaaa agggaggaga aagaaagaa gcagtggcag cagaagtaaa     420
aaatgaagaa gaagatcaga agaagatga agaagatcaa acgaagaga aaggggaagc      480
tggaaaagaa gacaaagatg aaaaggggga gaagatggga aaagaggata aaatggaaaa     540
tgagaaagga gaagatgcaa agagaaga agatggaaaa aaaggtgaag acggaaaagg     600
aaatggagaa gatggaaaag agaaggaga agatgaaaaa gaggaagaag acagaaaga      660
aacaggagtt ggaaaagaga atgaagatgg aaaagagaag ggagataaaa aagagggaa     720
agatgtaaaa gtcaaagaag atgaaaaaga gagagaagat ggaaaagaag atgaaggtgg     780
aaatgaggaa gaagctggaa agagaaaga agatttaaaa gaagaggaag aaggaaaaga     840
ggaagatgag atcaaagaag atgatggaaa aaagaggag ccacagagta ttgttttaaaa     900
ctgccctatg tagtttcata atttggtaac atgtaccttc atgttgtaaa gttaatagag     960
ataaatattt ttatcaaaaa ttttataaac acagcctttc tttagcattg atttaatttc    1020
agaacatctt catattgatt attagccata agtttctaa catgaaacat ttatctataa    1080
attttgtgat tatagtagtg aatacatag aaaaaaatat gctttcaact ttgtgagtga    1140
atttcgtgtt gtgtaagtta tatgtcaaat ctttgaattt taattttact ccttttatac    1200
atgtgataat ttcataaagt gagggatccc aaaaaaagag tttcatccca acattcttgt    1260
tctgcaggtt gcttttataa agaaggtgaa ctattttcat gtaatgttaa gagttaaact    1320
tatctttccc aaatataact ttattattag cttgggaaaa atgaaattgt attcccattt    1380
ttaaaataaa tacaaatgtt tatttcagaa gggcagtttt gattatatgt gaatacacaa    1440
attttactgg atttatctta ataaaagac tctgacgatg attgtgtttt gttatatctt    1500
caaaaatata gctagtgaaa tattgtgctt aattttttc tattgtgtta ttcatgaaaa    1560
tatttaatat tcactgacat aaaattaata taagtaaaa ttcaccatt taattataat    1620
aaaaataaag tatataattc aaaaaaaaaa aaaaaaaaa agggcggcc                1669
```

<210> SEQ ID NO 185

```
<211> LENGTH: 819
<212> TYPE: DNA
<213> ORGANISM: Homo sapiens

<400> SEQUENCE: 185
atgcccaaaa gaaagccaaa gagaagatct gccaggttgt ctgctatgct tgtgccagtt      60
acaccagagg tgaagcctaa agaacatca agttcaagga aaatgaagac aaaaagtgat     120
atgatggaag aaaacataga tacaagtgcc caagcagttg ctgaaaccaa gcaagaagca     180
gttgttgaag aagactacaa tgaaaatgct aaaaatggag aagccaaaat tacagaggca     240
ccagcttctg aaaaagaaat tgtggaagta aagaagaaa atattgaaga tgccacagaa      300
aagggaggag aaaagaaaga agcagtggca gcagaagtaa aaatgaaga agaagatcag      360 aaagaagatg aagaagatca aaacgaagag aaggggaag ctggaaaaga agacaaagat      420
gaaaaggggg aagaagatgg aaaagaggat aaaaatggaa atgagaaagg agaagatgca     480
aaagagaaag aagatggaaa aaaggtgaaa gacggaaaag gaaatggaga agatggaaaa     540
gagaaaggag aagatgaaaa agaggaagaa gacagaaaag aaacaggagt tggaaaagag     600
aatgaagatg gaaaagagaa gggagataaa aagaggggaa agatgtaaa agtcaaagaa      660 gatgaaaaag agagagaaga tggaaaagaa gatgaaggtg gaaatgagga agaagctgga     720
aaagagaaag aagatttaaa agaagaggaa gaggaaaag aggaagatga gatcaaagaa      780
gatgatggaa aaaagagga gccacagagt attgttttaa                           819

<210> SEQ ID NO 186
<211> LENGTH: 272
<212> TYPE: PRT
<213> ORGANISM: Homo sapiens

<400> SEQUENCE: 186
```

Met Pro Lys Arg Lys Pro Lys Arg Arg Ser Ala Arg Leu Ser Ala Met
1               5                   10                  15

Leu Val Pro Val Thr Pro Glu Val Lys Pro Lys Arg Thr Ser Ser Ser
            20                  25                  30

Arg Lys Met Lys Thr Lys Ser Asp Met Met Glu Glu Asn Ile Asp Thr
        35                  40                  45

Ser Ala Gln Ala Val Ala Glu Thr Lys Gln Glu Ala Val Val Glu Glu
    50                  55                  60

Asp Tyr Asn Glu Asn Ala Lys Asn Gly Glu Ala Lys Ile Thr Glu Ala
65                  70                  75                  80

Pro Ala Ser Glu Lys Glu Ile Val Glu Val Lys Glu Glu Asn Ile Glu
                85                  90                  95

Asp Ala Thr Glu Lys Gly Gly Glu Lys Lys Glu Ala Val Ala Ala Glu
            100                 105                 110

Val Lys Asn Glu Glu Glu Asp Gln Lys Glu Asp Glu Glu Asp Gln Asn
        115                 120                 125

Glu Glu Lys Gly Glu Ala Gly Lys Glu Asp Lys Asp Glu Lys Gly Glu
    130                 135                 140

Glu Asp Gly Lys Glu Asp Lys Asn Gly Asn Glu Lys Gly Glu Asp Ala
145                 150                 155                 160

Lys Glu Lys Glu Asp Gly Lys Lys Gly Glu Asp Gly Lys Gly Asn Gly
                165                 170                 175

Glu Asp Gly Lys Glu Lys Gly Glu Asp Glu Lys Glu Glu Asp Arg
            180                 185                 190

Lys Glu Thr Gly Val Gly Lys Glu Asn Glu Asp Gly Lys Glu Lys Gly

```
                    195                 200                 205
Asp Lys Lys Glu Gly Lys Asp Val Lys Val Lys Glu Asp Glu Lys Glu
            210                 215                 220

Arg Glu Asp Gly Lys Glu Asp Glu Gly Gly Asn Glu Glu Glu Ala Gly
225                 230                 235                 240

Lys Glu Lys Glu Asp Leu Lys Glu Glu Glu Gly Lys Glu Glu Asp
                245                 250                 255

Glu Ile Lys Glu Asp Asp Gly Lys Lys Glu Glu Pro Gln Ser Ile Val
                260                 265                 270

<210> SEQ ID NO 187
<211> LENGTH: 774
<212> TYPE: DNA
<213> ORGANISM: Homo sapiens

<400> SEQUENCE: 187
atgcttgtgc cagttacacc agaggtgaag cctaaaagaa catcaagttc aaggaaaatg      60
aagacaaaaa gtgatatgat ggaagaaaac atagatacaa gtgcccaagc agttgctgaa     120
accaagcaag aagcagttgt tgaagaagac tacaatgaaa atgctaaaaa tggagaagcc     180
aaaattacag aggcaccagc ttctgaaaaa gaaattgtgg aagtaaaaga gaaaatatt      240 gaagatgcca cagaaaaggg aggagaaaag aagaagcag tggcagcaga agtaaaaaat     300
gaagaagaag atcagaaaga agatgaagaa gatcaaaacg aagagaaagg ggaagctgga     360
aaagaagaca aagtgaaaaa aggggaagaa gatggaaaag aggataaaaa tggaaatgag     420
aaaggagaag atgcaaaaga gaagaagat ggaaaaaaag gtgaagacgg aaaaggaaat     480
ggagaagatg gaaagagaa aggagaagat gaaaaagagg aagaagacag aaaagaaaca     540
ggagttggaa aagagaatga agatggaaaa gagaagggag ataaaaaga ggggaaagat     600 gtaaaagtca aagaagatga aaagagaga gaagatggaa aagaagatga aggtggaaat     660
gaggaagaag ctggaaaaga gaagaagat ttaaaagaag aggaagaagg aaaagaggaa     720
gatgagatca aagaagatga tggaaaaaaa gaggagccac agagtattgt ttaa           774

<210> SEQ ID NO 188
<211> LENGTH: 257
<212> TYPE: PRT
<213> ORGANISM: Homo sapiens

<400> SEQUENCE: 188

Met Leu Val Pro Val Thr Pro Glu Val Lys Pro Lys Arg Thr Ser Ser
1               5                   10                  15

Ser Arg Lys Met Lys Thr Lys Ser Asp Met Met Glu Glu Asn Ile Asp
                20                  25                  30

Thr Ser Ala Gln Ala Val Ala Glu Thr Lys Gln Glu Ala Val Val Glu
            35                  40                  45

Glu Asp Tyr Asn Glu Asn Ala Lys Asn Gly Glu Ala Lys Ile Thr Glu
        50                  55                  60

Ala Pro Ala Ser Glu Lys Glu Ile Val Glu Val Lys Glu Glu Asn Ile
65                  70                  75                  80

Glu Asp Ala Thr Glu Lys Gly Gly Glu Lys Lys Glu Ala Val Ala Ala
                85                  90                  95

Glu Val Lys Asn Glu Glu Glu Asp Gln Lys Glu Asp Glu Glu Asp Gln
            100                 105                 110

Asn Glu Glu Lys Gly Glu Ala Gly Lys Glu Asp Lys Asp Glu Lys Gly
        115                 120                 125
```

Glu Glu Asp Gly Lys Glu Asp Lys Asn Gly Asn Glu Lys Gly Glu Asp
            130                 135                 140

Ala Lys Glu Lys Glu Asp Gly Lys Lys Gly Glu Asp Gly Lys Gly Asn
145                 150                 155                 160

Gly Glu Asp Gly Lys Glu Lys Gly Glu Asp Glu Lys Glu Glu Glu Asp
                165                 170                 175

Arg Lys Glu Thr Gly Val Gly Lys Glu Asn Glu Asp Gly Lys Glu Lys
                180                 185                 190

Gly Asp Lys Lys Glu Gly Lys Asp Val Lys Val Lys Glu Asp Glu Lys
            195                 200                 205

Glu Arg Glu Asp Gly Lys Glu Asp Glu Gly Asn Glu Glu Glu Ala
        210                 215                 220

Gly Lys Glu Lys Glu Asp Leu Lys Glu Glu Glu Gly Lys Glu Glu
225                 230                 235                 240

Asp Glu Ile Lys Glu Asp Asp Gly Lys Lys Glu Pro Gln Ser Ile
                245                 250                 255

Val

<210> SEQ ID NO 189
<211> LENGTH: 717
<212> TYPE: DNA
<213> ORGANISM: Homo sapiens

<400> SEQUENCE: 189

```
atgaagacaa aaagtgatat gatggaagaa acatagata caagtgccca agcagttgct    60
gaaaccaagc aagaagcagt tgttgaagaa gactacaatg aaaatgctaa aatggagaa   120 gccaaaatta cagaggcacc agcttctgaa aaagaaattg tggaagtaaa agaagaaaat   180
attgaagatg ccacagaaaa gggaggagaa aagaaagaag cagtggcagc agaagtaaaa   240
aatgaagaag aagatcagaa agaagatgaa gaagatcaaa acgaagagaa aggggaagct   300
ggaaaagaag acaaagatga aaaggggaa gaagatggaa aagaggataa aaatggaaat   360
gagaaaggag aagatgcaaa agagaaagaa gatggaaaaa aaggtgaaga cggaaaagga   420
aatggagaag atggaaaaga gaagggagaa gatgaaaaag aggaagaaga cagaaaagaa   480
acaggagttg aaaagagaa tgaagatgga aagagaaagg gagataaaaa agagggaaa    540 gatgtaaaag tcaaagaaga tgaaaaagag agagaagatg gaaaagaaga tgaaggtgga   600
aatgaggaag aagctggaaa agagaaagaa gatttaaaag aagaggaaga aggaaaagag   660
gaagatgaga tcaaagaaga tgatggaaaa aagaggagc cacagagtat tgttttaa    717
```

<210> SEQ ID NO 190
<211> LENGTH: 238
<212> TYPE: PRT
<213> ORGANISM: Homo sapiens

<400> SEQUENCE: 190

Met Lys Thr Lys Ser Asp Met Met Glu Glu Asn Ile Asp Thr Ser Ala
  1               5                  10                  15

Gln Ala Val Ala Glu Thr Lys Gln Glu Ala Val Val Glu Glu Asp Tyr
            20                  25                  30

Asn Glu Asn Ala Lys Asn Gly Glu Ala Lys Ile Thr Glu Ala Pro Ala
        35                  40                  45

Ser Glu Lys Glu Ile Val Glu Val Lys Glu Glu Asn Ile Glu Asp Ala
    50                  55                  60

```
Thr Glu Lys Gly Gly Glu Lys Glu Ala Val Ala Ala Glu Val Lys
 65                  70                  75                  80

Asn Glu Glu Glu Asp Gln Lys Glu Asp Glu Glu Asp Gln Asn Glu Glu
                 85                  90                  95

Lys Gly Glu Ala Gly Lys Glu Asp Lys Asp Glu Lys Gly Glu Glu Asp
            100                 105                 110

Gly Lys Glu Asp Lys Asn Gly Asn Glu Lys Gly Glu Asp Ala Lys Glu
        115                 120                 125

Lys Glu Asp Gly Lys Lys Gly Glu Asp Gly Lys Gly Asn Gly Glu Asp
    130                 135                 140

Gly Lys Glu Lys Gly Glu Asp Glu Lys Glu Glu Glu Asp Arg Lys Glu
145                 150                 155                 160

Thr Gly Val Gly Lys Glu Asn Glu Asp Gly Lys Glu Lys Gly Asp Lys
                165                 170                 175

Lys Glu Gly Lys Asp Val Lys Val Lys Glu Asp Glu Lys Glu Arg Glu
            180                 185                 190

Asp Gly Lys Glu Asp Glu Gly Gly Asn Glu Glu Glu Ala Gly Lys Glu
        195                 200                 205

Lys Glu Asp Leu Lys Glu Glu Glu Glu Gly Lys Glu Glu Asp Glu Ile
    210                 215                 220

Lys Glu Asp Asp Gly Lys Lys Glu Glu Pro Gln Ser Ile Val
225                 230                 235

<210> SEQ ID NO 191
<211> LENGTH: 699
<212> TYPE: DNA
<213> ORGANISM: Homo sapiens

<400> SEQUENCE: 191
atgatggaag aaaacataga tacaagtgcc caagcagttg ctgaaaccaa gcaagaagca      60
gttgttgaag aagactacaa tgaaaatgct aaaaatggag aagccaaaat tacagaggca     120
ccagcttctg aaaagaaat tgtggaagta aagaagaaa atattgaaga tgccacagaa       180
aagggaggag aaaagaaaga agcagtggca gcagaagtaa aaaatgaaga agaagatcag     240
aaagaagatg aagaagatca aaacgaagag aaggggaag ctggaaaaga agacaaagat      300 gaaaagggg aagaagatgg aaaagaggat aaaaatggaa atgagaaagg agaagatgca     360
aaagagaaag aagatggaaa aaaggtgaa gacggaaaag gaaatggaga gatggaaaa       420 gagaaggag aagatgaaaa agaggaagaa gacagaaaag aaacaggagt tggaaaagag      480
aatgaagatg gaaagagaa gggagataaa aagagggga agatgtaaa agtcaaagaa        540 gatgaaaag agagagaaga tggaaaagaa gatgaaggtg gaaatgagga gaagctgga      600 aaagagaaag aagatttaaa agaagaggaa gaggaaaaag aggaagatga gatcaaagaa     660
gatgatggaa aaaagagga gccacagagt attgtttaa                             699

<210> SEQ ID NO 192
<211> LENGTH: 232
<212> TYPE: PRT
<213> ORGANISM: Homo sapiens

<400> SEQUENCE: 192

Met Met Glu Glu Asn Ile Asp Thr Ser Ala Gln Ala Val Ala Glu Thr
  1               5                  10                  15

Lys Gln Glu Ala Val Val Glu Glu Asp Tyr Asn Glu Asn Ala Lys Asn
                 20                  25                  30
```

Gly Glu Ala Lys Ile Thr Glu Ala Pro Ala Ser Glu Lys Glu Ile Val
            35                  40                  45

Glu Val Lys Glu Glu Asn Ile Glu Asp Ala Thr Glu Lys Gly Gly Glu
 50                  55                  60

Lys Lys Glu Ala Val Ala Ala Glu Val Lys Asn Glu Glu Asp Gln
 65                  70                  75                  80

Lys Glu Asp Glu Glu Asp Gln Asn Glu Glu Lys Gly Glu Ala Gly Lys
                 85                  90                  95

Glu Asp Lys Asp Glu Lys Gly Glu Glu Asp Gly Lys Glu Asp Lys Asn
                100                 105                 110

Gly Asn Glu Lys Gly Glu Asp Ala Lys Glu Lys Glu Asp Gly Lys Lys
            115                 120                 125

Gly Glu Asp Gly Lys Gly Asn Gly Glu Asp Gly Lys Glu Lys Gly Glu
        130                 135                 140

Asp Glu Lys Glu Glu Glu Asp Arg Lys Glu Thr Gly Val Gly Lys Glu
145                 150                 155                 160

Asn Glu Asp Gly Lys Glu Lys Gly Asp Lys Lys Glu Gly Lys Asp Val
                165                 170                 175

Lys Val Lys Glu Asp Glu Lys Glu Arg Glu Asp Gly Lys Glu Asp Glu
            180                 185                 190

Gly Gly Asn Glu Glu Glu Ala Gly Lys Glu Lys Glu Asp Leu Lys Glu
        195                 200                 205

Glu Glu Glu Gly Lys Glu Glu Asp Glu Ile Lys Glu Asp Asp Gly Lys
    210                 215                 220

Lys Glu Glu Pro Gln Ser Ile Val
225                 230

<210> SEQ ID NO 193
<211> LENGTH: 696
<212> TYPE: DNA
<213> ORGANISM: Homo sapiens

<400> SEQUENCE: 193
atggaagaaa acatagatac aagtgcccaa gcagttgctg aaaccaagca agaagcagtt      60
gttgaagaag actacaatga aaatgctaaa aatggagaag ccaaaattac agaggcacca     120
gcttctgaaa agaaattgt ggaagtaaaa gaagaaaata ttgaagatgc cacagaaaag     180
ggaggagaaa agaaagaagc agtggcagca gaagtaaaaa atgaagaaga agatcagaaa     240
gaagatgaag aagatcaaaa cgaagagaaa ggggaagctg gaaaagaaga caaagatgaa     300
aaagggaag aagatggaaa agaggataaa aatggaaatg agaaggaga gatgcaaaa     360
gagaaagaag atgaaaaaa aggtgaagac ggaaaaggaa atggagaaga tggaaaagag     420
aaggagaag atgaaaaaga ggaagaagac agaaaagaaa caggagttgg aaaagagaat     480
gaagatggaa aagagaaggg agataaaaaa gaggggaaag atgtaaaagt caagaagat     540
gaaaagaga gagaagatgg aaaagaagat gaagtggaa atgaggaaga agctggaaaa     600
gagaaagaag atttaaaaga gaggaagaa ggaaaagagg aagatgagat caagaagat     660
gatggaaaaa agaggagcc acagagtatt gtttaa                                696

<210> SEQ ID NO 194
<211> LENGTH: 231
<212> TYPE: PRT
<213> ORGANISM: Homo sapiens

<400> SEQUENCE: 194

```
Met Glu Glu Asn Ile Asp Thr Ser Ala Gln Ala Val Ala Glu Thr Lys
 1               5                  10                  15

Gln Glu Ala Val Val Glu Glu Asp Tyr Asn Glu Asn Ala Lys Asn Gly
            20                  25                  30

Glu Ala Lys Ile Thr Glu Ala Pro Ala Ser Glu Lys Glu Ile Val Glu
        35                  40                  45

Val Lys Glu Glu Asn Ile Glu Asp Ala Thr Glu Lys Gly Gly Glu Lys
 50                  55                  60

Lys Glu Ala Val Ala Glu Val Lys Asn Glu Glu Glu Asp Gln Lys
 65                  70                  75                  80

Glu Asp Glu Glu Asp Gln Asn Glu Gly Lys Gly Ala Gly Lys Glu
                85                  90                  95

Asp Lys Asp Glu Lys Gly Glu Glu Asp Gly Lys Glu Asp Lys Asn Gly
            100                 105                 110

Asn Glu Lys Gly Glu Asp Ala Lys Glu Lys Glu Asp Gly Lys Lys Gly
        115                 120                 125

Glu Asp Gly Lys Gly Asn Gly Glu Asp Gly Lys Glu Lys Gly Glu Asp
    130                 135                 140

Glu Lys Glu Glu Glu Asp Arg Lys Glu Thr Gly Val Gly Lys Glu Asn
145                 150                 155                 160

Glu Asp Gly Lys Glu Lys Gly Asp Lys Lys Gly Lys Asp Val Lys
            165                 170                 175

Val Lys Glu Asp Glu Lys Glu Arg Glu Asp Gly Lys Glu Asp Glu Gly
            180                 185                 190

Gly Asn Glu Glu Glu Ala Gly Lys Glu Lys Glu Asp Leu Lys Glu Glu
            195                 200                 205

Glu Glu Gly Lys Glu Glu Asp Glu Ile Lys Glu Asp Asp Gly Lys Lys
    210                 215                 220

Glu Glu Pro Gln Ser Ile Val
225                 230
```

<210> SEQ ID NO 195
<211> LENGTH: 72
<212> TYPE: DNA
<213> ORGANISM: Homo sapiens

<400> SEQUENCE: 195
atgaaaatgc taaaaatgga gaagccaaaa ttacagaggc accagcttct gaaaaagaaa     60
ttgtggaagt aa                                                         72

<210> SEQ ID NO 196
<211> LENGTH: 23
<212> TYPE: PRT
<213> ORGANISM: Homo sapiens

<400> SEQUENCE: 196

```
Met Lys Met Leu Lys Met Glu Lys Pro Lys Leu Gln Arg His Gln Leu
 1               5                  10                  15

Leu Lys Lys Lys Leu Trp Lys
            20
```

<210> SEQ ID NO 197
<211> LENGTH: 66
<212> TYPE: DNA
<213> ORGANISM: Homo sapiens

<400> SEQUENCE: 197

```
atgctaaaaa tgagaagcc aaaattacag aggcaccagc ttctgaaaaa gaaattgtgg      60
aagtaa                                                                66
```

<210> SEQ ID NO 198
<211> LENGTH: 21
<212> TYPE: PRT
<213> ORGANISM: Homo sapiens

<400> SEQUENCE: 198

```
Met Leu Lys Met Glu Lys Pro Lys Leu Gln Arg His Gln Leu Leu Lys
1               5                   10                  15

Lys Lys Leu Trp Lys
            20
```

<210> SEQ ID NO 199
<211> LENGTH: 57
<212> TYPE: DNA
<213> ORGANISM: Homo sapiens

<400> SEQUENCE: 199

```
atggagaagc caaaattaca gaggcaccag cttctgaaaa agaaattgtg gaagtaa         57
```

<210> SEQ ID NO 200
<211> LENGTH: 18
<212> TYPE: PRT
<213> ORGANISM: Homo sapiens

<400> SEQUENCE: 200

```
Met Glu Lys Pro Lys Leu Gln Arg His Gln Leu Leu Lys Lys Lys Leu
1               5                   10                  15

Trp Lys
```

<210> SEQ ID NO 201
<211> LENGTH: 51
<212> TYPE: DNA
<213> ORGANISM: Homo sapiens

<400> SEQUENCE: 201

```
atgccacaga aagggagga gaaaagaaag aagcagtggc agcagaagta a                51
```

<210> SEQ ID NO 202
<211> LENGTH: 16
<212> TYPE: PRT
<213> ORGANISM: Homo sapiens

<400> SEQUENCE: 202

```
Met Pro Gln Lys Arg Glu Glu Lys Arg Lys Lys Gln Trp Gln Gln Lys
1               5                   10                  15
```

<210> SEQ ID NO 203
<211> LENGTH: 306
<212> TYPE: DNA
<213> ORGANISM: Homo sapiens

<400> SEQUENCE: 203

```
atgaagaaga agatcagaaa gaagatgaag aagatcaaaa cgaagagaaa ggggaagctg     60 gaaagaaga caaagatgaa aaagggggaag aagatggaaa agaggataaa aatggaaatg    120
agaaaggaga gatgcaaaa gagaaagaag atgaaaaaga aggtgaagac ggaaaaggaa    180
atggagaaga tggaaaagag aaaggagaag atgaaaaaga ggaagaagac agaaaagaaa    240
caggagttgg aaaagagaat gaagatggaa aagagaaggg agataaaaaa gaggggaaag    300
```

```
atgtaa                                                             306
```

<210> SEQ ID NO 204
<211> LENGTH: 101
<212> TYPE: PRT
<213> ORGANISM: Homo sapiens

<400> SEQUENCE: 204

Met Lys Lys Lys Ile Arg Lys Lys Met Lys Lys Ile Lys Thr Lys Arg
1               5                   10                  15

Lys Gly Lys Leu Glu Lys Lys Thr Lys Met Lys Lys Gly Lys Lys Met
                20                  25                  30

Glu Lys Arg Ile Lys Met Glu Met Arg Lys Glu Lys Met Gln Lys Arg
            35                  40                  45

Lys Lys Met Glu Lys Lys Val Lys Thr Glu Lys Glu Met Glu Lys Met
        50                  55                  60

Glu Lys Arg Lys Glu Lys Met Lys Lys Arg Lys Lys Thr Glu Lys Lys
65                  70                  75                  80

Gln Glu Leu Glu Lys Arg Met Lys Met Glu Lys Arg Arg Glu Ile Lys
                85                  90                  95

Lys Arg Gly Lys Met
            100

<210> SEQ ID NO 205
<211> LENGTH: 282
<212> TYPE: DNA
<213> ORGANISM: Homo sapiens

<400> SEQUENCE: 205

```
atgaagaaga tcaaaacgaa gagaaagggg aagctggaaa agaagacaaa gatgaaaaag    60
gggaagaaga tggaaaagag gataaaaatg gaaatgagaa aggagaagat gcaaaagaga   120
aagaagatgg aaaaaaaggt gaagacggaa aaggaaatgg agaagatgga aaagagaaag   180
gagaagatga aaaagaggaa gaagacagaa aagaaacagg agttggaaaa gagaatgaag   240
atggaaaaga gaagggagat aaaaaagagg ggaaagatgt aa                      282
```

<210> SEQ ID NO 206
<211> LENGTH: 93
<212> TYPE: PRT
<213> ORGANISM: Homo sapiens

<400> SEQUENCE: 206

Met Lys Lys Ile Lys Thr Lys Arg Lys Gly Lys Leu Glu Lys Lys Thr
1               5                   10                  15

Lys Met Lys Lys Gly Lys Lys Met Glu Lys Arg Ile Lys Met Glu Met
                20                  25                  30

Arg Lys Glu Lys Met Gln Lys Arg Lys Lys Met Glu Lys Lys Val Lys
            35                  40                  45

Thr Glu Lys Glu Met Glu Lys Met Glu Lys Arg Lys Glu Lys Met Lys
        50                  55                  60

Lys Arg Lys Lys Thr Glu Lys Lys Gln Glu Leu Glu Lys Arg Met Lys
65                  70                  75                  80

Met Glu Lys Arg Arg Glu Ile Lys Lys Arg Gly Lys Met
                85                  90

<210> SEQ ID NO 207
<211> LENGTH: 231

<212> TYPE: DNA
<213> ORGANISM: Homo sapiens

<400> SEQUENCE: 207

```
atgaaaaagg ggaagaagat ggaaaagagg ataaaaatgg aaatgagaaa ggagaagatg      60
caaaagagaa agaagatgga aaaaaaggtg aagacggaaa aggaaatgga gaagatggaa     120
aagagaaagg agaagatgaa aaagaggaag aagacagaaa agaaacagga gttggaaaag    180
agaatgaaga tggaaaagag aagggagata aaaagaggg gaaagatgta a               231
```

<210> SEQ ID NO 208
<211> LENGTH: 76
<212> TYPE: PRT
<213> ORGANISM: Homo sapiens

<400> SEQUENCE: 208

```
Met Lys Lys Gly Lys Lys Met Glu Lys Arg Ile Lys Met Glu Met Arg
 1               5                  10                  15

Lys Glu Lys Met Gln Lys Arg Lys Lys Met Glu Lys Lys Val Lys Thr
                20                  25                  30

Glu Lys Glu Met Glu Lys Met Glu Lys Arg Lys Glu Lys Met Lys Lys
            35                  40                  45

Arg Lys Lys Thr Glu Lys Lys Gln Glu Leu Glu Lys Arg Met Lys Met
        50                  55                  60

Glu Lys Arg Arg Glu Ile Lys Lys Arg Gly Lys Met
65                  70                  75
```

<210> SEQ ID NO 209
<211> LENGTH: 213
<212> TYPE: DNA
<213> ORGANISM: Homo sapiens

<400> SEQUENCE: 209

```
atggaaaaga ggataaaaat ggaaatgaga aaggagaaga tgcaaaagag aaagaagatg      60
gaaaaaaagg tgaagacgga aaaggaaatg gagaagatgg aaaagagaaa ggagaagatg    120
aaaaagagga agaagacaga aaagaaacag gagttggaaa agagaatgaa gatggaaaag    180
agaagggaga taaaaagag gggaaagatg taa                                   213
```

<210> SEQ ID NO 210
<211> LENGTH: 70
<212> TYPE: PRT
<213> ORGANISM: Homo sapiens

<400> SEQUENCE: 210

```
Met Glu Lys Arg Ile Lys Met Glu Met Arg Lys Glu Lys Met Gln Lys
 1               5                  10                  15

Arg Lys Lys Met Glu Lys Val Lys Thr Glu Lys Glu Met Glu Lys
                20                  25                  30

Met Glu Lys Arg Lys Glu Lys Met Lys Lys Arg Lys Lys Thr Glu Lys
            35                  40                  45

Lys Gln Glu Leu Glu Lys Arg Met Lys Met Glu Lys Arg Arg Glu Ile
        50                  55                  60

Lys Lys Arg Gly Lys Met
65                  70
```

<210> SEQ ID NO 211
<211> LENGTH: 195
<212> TYPE: DNA

-continued

```
<213> ORGANISM: Homo sapiens

<400> SEQUENCE: 211
atggaaatga gaaaggagaa gatgcaaaag agaaagaaga tggaaaaaaa ggtgaagacg      60
gaaaaggaaa tggagaagat ggaaaagaga aggagaagaa tgaaaagag  gaagaagaca     120 gaaaagaaac aggagttgga aaagagaatg aagatggaaa agagaaggga gataaaaaag    180
aggggaaaga tgtaa                                                     195

<210> SEQ ID NO 212
<211> LENGTH: 64
<212> TYPE: PRT
<213> ORGANISM: Homo sapiens

<400> SEQUENCE: 212

Met Glu Met Arg Lys Glu Lys Met Gln Lys Arg Lys Lys Met Glu Lys
  1               5                  10                  15

Lys Val Lys Thr Glu Lys Glu Met Glu Lys Met Glu Lys Arg Lys Glu
             20                  25                  30

Lys Met Lys Lys Arg Lys Lys Thr Glu Lys Lys Gln Glu Leu Glu Lys
         35                  40                  45

Arg Met Lys Met Glu Lys Arg Arg Glu Ile Lys Lys Arg Gly Lys Met
     50                  55                  60

<210> SEQ ID NO 213
<211> LENGTH: 189
<212> TYPE: DNA
<213> ORGANISM: Homo sapiens

<400> SEQUENCE: 213
atgagaaagg agaagatgca aaagagaaag aagatggaaa aaaggtgaa  gacggaaaag     60 gaaatggaga gatggaaaa gagaaaggag aagatgaaaa agaggaagaa gacagaaaag    120
aaacaggagt tggaaaagag aatgaagatg gaaaagagaa gggagataaa aaagagggga   180
aagatgtaa                                                            189

<210> SEQ ID NO 214
<211> LENGTH: 62
<212> TYPE: PRT
<213> ORGANISM: Homo sapiens

<400> SEQUENCE: 214

Met Arg Lys Glu Lys Met Gln Lys Arg Lys Lys Met Glu Lys Lys Val
  1               5                  10                  15

Lys Thr Glu Lys Glu Met Glu Lys Met Glu Lys Arg Lys Glu Lys Met
             20                  25                  30

Lys Lys Arg Lys Lys Thr Glu Lys Lys Gln Glu Leu Glu Lys Arg Met
         35                  40                  45

Lys Met Glu Lys Arg Arg Glu Ile Lys Lys Arg Gly Lys Met
     50                  55                  60

<210> SEQ ID NO 215
<211> LENGTH: 174
<212> TYPE: DNA
<213> ORGANISM: Homo sapiens

<400> SEQUENCE: 215
atgcaaaaga gaaagaagat ggaaaaaaag gtgaagacgg aaaaggaaat ggagaagatg      60
gaaaagagaa aggagaagat gaaaagagg aagaagacag aaaagaaaca ggagttggaa     120
```

```
aagagaatga agatggaaaa gagaagggag ataaaaaaga ggggaaagat gtaa        174
```

<210> SEQ ID NO 216
<211> LENGTH: 57
<212> TYPE: PRT
<213> ORGANISM: Homo sapiens

<400> SEQUENCE: 216

```
Met Gln Lys Arg Lys Met Glu Lys Val Lys Thr Glu Lys Glu
 1               5                  10                 15

Met Glu Lys Met Glu Lys Arg Lys Glu Lys Met Lys Lys Arg Lys Lys
                20                  25                  30

Thr Glu Lys Lys Gln Glu Leu Glu Lys Arg Met Lys Met Glu Lys Arg
            35                  40                  45

Arg Glu Ile Lys Lys Arg Gly Lys Met
        50                  55
```

<210> SEQ ID NO 217
<211> LENGTH: 156
<212> TYPE: DNA
<213> ORGANISM: Homo sapiens

<400> SEQUENCE: 217

```
atggaaaaaa aggtgaagac ggaaaaggaa atggagaaga tggaaaagag aaaggagaag    60
atgaaaaaga ggaagaagac agaaaagaaa caggagttgg aaaagagaat gaagatggaa   120
aagagaaggg agataaaaaa gaggggaaag atgtaa                             156
```

<210> SEQ ID NO 218
<211> LENGTH: 51
<212> TYPE: PRT
<213> ORGANISM: Homo sapiens

<400> SEQUENCE: 218

```
Met Glu Lys Lys Val Lys Thr Glu Lys Glu Met Glu Lys Met Glu Lys
 1               5                  10                  15

Arg Lys Glu Lys Met Lys Lys Arg Lys Lys Thr Glu Lys Lys Gln Glu
                20                  25                  30

Leu Glu Lys Arg Met Lys Met Glu Lys Arg Arg Glu Ile Lys Lys Arg
            35                  40                  45

Gly Lys Met
    50
```

<210> SEQ ID NO 219
<211> LENGTH: 126
<212> TYPE: DNA
<213> ORGANISM: Homo sapiens

<400> SEQUENCE: 219

```
atggagaaga tggaaaagag aaaggagaag atgaaaaaga ggaagaagac agaaaagaaa    60
caggagttgg aaaagagaat gaagatggaa aagagaaggg agataaaaaa gaggggaaag   120
atgtaa                                                              126
```

<210> SEQ ID NO 220
<211> LENGTH: 41
<212> TYPE: PRT
<213> ORGANISM: Homo sapiens

<400> SEQUENCE: 220

Met Glu Lys Met Glu Lys Arg Lys Glu Lys Met Lys Lys Arg Lys Lys
1               5                   10                  15

Thr Glu Lys Lys Gln Glu Leu Glu Lys Arg Met Lys Met Glu Lys Arg
            20                  25                  30

Arg Glu Ile Lys Lys Arg Gly Lys Met
            35                  40

<210> SEQ ID NO 221
<211> LENGTH: 117
<212> TYPE: DNA
<213> ORGANISM: Homo sapiens

<400> SEQUENCE: 221
atggaaaaga gaaggagaa gatgaaaaag aggaagaaga cagaaaagaa acaggagttg     60 gaaagagaa tgaagatgga aaagagaagg gagataaaaa agaggggaaa gatgtaa      117

<210> SEQ ID NO 222
<211> LENGTH: 38
<212> TYPE: PRT
<213> ORGANISM: Homo sapiens

<400> SEQUENCE: 222

Met Glu Lys Arg Lys Glu Lys Met Lys Lys Arg Lys Lys Thr Glu Lys
1               5                   10                  15

Lys Gln Glu Leu Glu Lys Arg Met Lys Met Glu Lys Arg Arg Glu Ile
            20                  25                  30

Lys Lys Arg Gly Lys Met
            35

<210> SEQ ID NO 223
<211> LENGTH: 96
<212> TYPE: DNA
<213> ORGANISM: Homo sapiens

<400> SEQUENCE: 223 atgaaaaga ggaagaagac agaaaagaaa caggagttgg aaaagagaat gaagatggaa     60
aagagaaggg agataaaaaa gagggggaaag atgtaa                             96

<210> SEQ ID NO 224
<211> LENGTH: 31
<212> TYPE: PRT
<213> ORGANISM: Homo sapiens

<400> SEQUENCE: 224

Met Lys Lys Arg Lys Lys Thr Glu Lys Lys Gln Glu Leu Glu Lys Arg
1               5                   10                  15

Met Lys Met Glu Lys Arg Arg Glu Ile Lys Lys Arg Gly Lys Met
            20                  25                  30

<210> SEQ ID NO 225
<211> LENGTH: 48
<212> TYPE: DNA
<213> ORGANISM: Homo sapiens

<400> SEQUENCE: 225
atgaagatgg aaagagaag ggagataaaa aagagggaa agatgtaa                   48

<210> SEQ ID NO 226
<211> LENGTH: 15
<212> TYPE: PRT
<213> ORGANISM: Homo sapiens

```
<400> SEQUENCE: 226

Met Lys Met Glu Lys Arg Arg Glu Ile Lys Lys Arg Gly Lys Met
1               5                   10                  15

<210> SEQ ID NO 227
<211> LENGTH: 42
<212> TYPE: DNA
<213> ORGANISM: Homo sapiens

<400> SEQUENCE: 227
atggaaaaga aagggagat aaaaaagagg ggaaagatgt aa                           42

<210> SEQ ID NO 228
<211> LENGTH: 13
<212> TYPE: PRT
<213> ORGANISM: Homo sapiens

<400> SEQUENCE: 228

Met Glu Lys Arg Arg Glu Ile Lys Lys Arg Gly Lys Met
1               5                   10

<210> SEQ ID NO 229
<211> LENGTH: 78
<212> TYPE: DNA
<213> ORGANISM: Homo sapiens

<400> SEQUENCE: 229
atgaaaaaga gagagaagat ggaaaagaag atgaaggtgg aaatgaggaa gaagctggaa        60
aagagaaaga agatttaa                                                     78

<210> SEQ ID NO 230
<211> LENGTH: 25
<212> TYPE: PRT
<213> ORGANISM: Homo sapiens

<400> SEQUENCE: 230

Met Lys Lys Arg Glu Lys Met Glu Lys Lys Met Lys Val Glu Met Arg
1               5                   10                  15

Lys Lys Leu Glu Lys Arg Lys Lys Ile
            20                  25

<210> SEQ ID NO 231
<211> LENGTH: 60
<212> TYPE: DNA
<213> ORGANISM: Homo sapiens

<400> SEQUENCE: 231
atggaaaaga agatgaaggt ggaaatgagg aagaagctgg aaaagagaaa gaagatttaa        60

<210> SEQ ID NO 232
<211> LENGTH: 19
<212> TYPE: PRT
<213> ORGANISM: Homo sapiens

<400> SEQUENCE: 232

Met Glu Lys Lys Met Lys Val Glu Met Arg Lys Lys Leu Glu Lys Arg
1               5                   10                  15

Lys Lys Ile

<210> SEQ ID NO 233
<211> LENGTH: 48
```

```
<212> TYPE: DNA
<213> ORGANISM: Homo sapiens

<400> SEQUENCE: 233
atgaaggtgg aaatgaggaa gaagctggaa aagagaaaga agatttaa              48

<210> SEQ ID NO 234
<211> LENGTH: 15
<212> TYPE: PRT
<213> ORGANISM: Homo sapiens

<400> SEQUENCE: 234
```

Met Lys Val Glu Met Arg Lys Lys Leu Glu Lys Arg Lys Lys Ile
 1               5                  10                  15

```
<210> SEQ ID NO 235
<211> LENGTH: 36
<212> TYPE: DNA
<213> ORGANISM: Homo sapiens

<400> SEQUENCE: 235
atgaggaaga agctggaaaa gagaaagaag atttaa                           36

<210> SEQ ID NO 236
<211> LENGTH: 11
<212> TYPE: PRT
<213> ORGANISM: Homo sapiens

<400> SEQUENCE: 236
```

Met Arg Lys Lys Leu Glu Lys Arg Lys Lys Ile
 1               5                  10

```
<210> SEQ ID NO 237
<211> LENGTH: 84
<212> TYPE: DNA
<213> ORGANISM: Homo sapiens

<400> SEQUENCE: 237
atgagatcaa agaagatgat ggaaaaaaag aggagccaca gagtattgtt taaaactgcc   60
ctatgtagtt tcataatttg gtaa                                         84

<210> SEQ ID NO 238
<211> LENGTH: 27
<212> TYPE: PRT
<213> ORGANISM: Homo sapiens

<400> SEQUENCE: 238
```

Met Arg Ser Lys Lys Met Met Glu Lys Lys Arg Ser His Arg Val Leu
 1               5                  10                  15
Phe Lys Thr Ala Leu Cys Ser Phe Ile Ile Trp
            20                  25

```
<210> SEQ ID NO 239
<211> LENGTH: 69
<212> TYPE: DNA
<213> ORGANISM: Homo sapiens

<400> SEQUENCE: 239
atgatggaaa aaagaggag ccacagagta ttgtttaaaa ctgccctatg tagtttcata    60
atttggtaa                                                          69

<210> SEQ ID NO 240
```

```
<211> LENGTH: 22
<212> TYPE: PRT
<213> ORGANISM: Homo sapiens

<400> SEQUENCE: 240

Met Met Glu Lys Lys Arg Ser His Arg Val Leu Phe Lys Thr Ala Leu
1               5                   10                  15

Cys Ser Phe Ile Ile Trp
            20

<210> SEQ ID NO 241
<211> LENGTH: 66
<212> TYPE: DNA
<213> ORGANISM: Homo sapiens

<400> SEQUENCE: 241
atggaaaaaa agaggagcca cagagtattg tttaaaactg ccctatgtag tttcataatt      60
tggtaa                                                                66

<210> SEQ ID NO 242
<211> LENGTH: 21
<212> TYPE: PRT
<213> ORGANISM: Homo sapiens

<400> SEQUENCE: 242

Met Glu Lys Lys Arg Ser His Arg Val Leu Phe Lys Thr Ala Leu Cys
1               5                   10                  15

Ser Phe Ile Ile Trp
            20

<210> SEQ ID NO 243
<211> LENGTH: 75
<212> TYPE: DNA
<213> ORGANISM: Homo sapiens

<400> SEQUENCE: 243
atgtaccttc atgttgtaaa gttaatagag ataaatattt ttatcaaaaa ttttataaac      60
acagcctttc tttag                                                      75

<210> SEQ ID NO 244
<211> LENGTH: 24
<212> TYPE: PRT
<213> ORGANISM: Homo sapiens

<400> SEQUENCE: 244

Met Tyr Leu His Val Val Lys Leu Ile Glu Ile Asn Ile Phe Ile Lys
1               5                   10                  15

Asn Phe Ile Asn Thr Ala Phe Leu
            20

<210> SEQ ID NO 245
<211> LENGTH: 75
<212> TYPE: DNA
<213> ORGANISM: Homo sapiens

<400> SEQUENCE: 245
atgaaacatt tatctataaa tttttgtgatt atagtagtgg aatacataga aaaaaatatg     60
ctttcaactt tgtga                                                      75

<210> SEQ ID NO 246
<211> LENGTH: 24
```

```
<212> TYPE: PRT
<213> ORGANISM: Homo sapiens

<400> SEQUENCE: 246

Met Lys His Leu Ser Ile Asn Phe Val Ile Ile Val Val Glu Tyr Ile
  1               5                  10                  15

Glu Lys Asn Met Leu Ser Thr Leu
             20

<210> SEQ ID NO 247
<211> LENGTH: 18
<212> TYPE: DNA
<213> ORGANISM: Homo sapiens

<400> SEQUENCE: 247
atgctttcaa ctttgtga                                                 18

<210> SEQ ID NO 248
<211> LENGTH: 5
<212> TYPE: PRT
<213> ORGANISM: Homo sapiens

<400> SEQUENCE: 248

Met Leu Ser Thr Leu
  1               5

<210> SEQ ID NO 249
<211> LENGTH: 15
<212> TYPE: DNA
<213> ORGANISM: Homo sapiens

<400> SEQUENCE: 249
atgtcaaatc tttga                                                    15

<210> SEQ ID NO 250
<211> LENGTH: 4
<212> TYPE: PRT
<213> ORGANISM: Homo sapiens

<400> SEQUENCE: 250

Met Ser Asn Leu
  1

<210> SEQ ID NO 251
<211> LENGTH: 81
<212> TYPE: DNA
<213> ORGANISM: Homo sapiens

<400> SEQUENCE: 251
atgttaagag ttaaacttat ctttcccaaa tataacttta ttattagctt gggaaaaatg   60
aaattgtatt cccattttta a                                             81

<210> SEQ ID NO 252
<211> LENGTH: 26
<212> TYPE: PRT
<213> ORGANISM: Homo sapiens

<400> SEQUENCE: 252

Met Leu Arg Val Lys Leu Ile Phe Pro Lys Tyr Asn Phe Ile Ile Ser
  1               5                  10                  15

Leu Gly Lys Met Lys Leu Tyr Ser His Phe
             20                  25
```

```
<210> SEQ ID NO 253
<211> LENGTH: 24
<212> TYPE: DNA
<213> ORGANISM: Homo sapiens

<400> SEQUENCE: 253
atgaaattgt attcccattt ttaa                                          24

<210> SEQ ID NO 254
<211> LENGTH: 7
<212> TYPE: PRT
<213> ORGANISM: Homo sapiens

<400> SEQUENCE: 254

Met Lys Leu Tyr Ser His Phe
1               5

<210> SEQ ID NO 255
<211> LENGTH: 27
<212> TYPE: DNA
<213> ORGANISM: Homo sapiens

<400> SEQUENCE: 255
atgtttattt cagaagggca gttttga                                       27

<210> SEQ ID NO 256
<211> LENGTH: 8
<212> TYPE: PRT
<213> ORGANISM: Homo sapiens

<400> SEQUENCE: 256

Met Phe Ile Ser Glu Gly Gln Phe
1               5

<210> SEQ ID NO 257
<211> LENGTH: 90
<212> TYPE: DNA
<213> ORGANISM: Homo sapiens

<400> SEQUENCE: 257
atgattgtgt tttgttatat cttcaaaaat atagctagtg aaatattgtg cttaattttt   60
ttctattgtg ttattcatga aaatatttaa                                    90

<210> SEQ ID NO 258
<211> LENGTH: 29
<212> TYPE: PRT
<213> ORGANISM: Homo sapiens

<400> SEQUENCE: 258

Met Ile Val Phe Cys Tyr Ile Phe Lys Asn Ile Ala Ser Glu Ile Leu
1               5                   10                  15

Cys Leu Ile Phe Phe Tyr Cys Val Ile His Glu Asn Ile
            20                  25

<210> SEQ ID NO 259
<211> LENGTH: 24
<212> TYPE: DNA
<213> ORGANISM: Homo sapiens

<400> SEQUENCE: 259
atgaaaatat ttaatattca ctga                                          24
```

<210> SEQ ID NO 260
<211> LENGTH: 7
<212> TYPE: PRT
<213> ORGANISM: Homo sapiens

<400> SEQUENCE: 260

Met Lys Ile Phe Asn Ile His
 1               5

<210> SEQ ID NO 261
<211> LENGTH: 1182
<212> TYPE: DNA
<213> ORGANISM: Homo sapiens

<400> SEQUENCE: 261

| | | | | | |
|---|---|---|---|---|---|
| tcgacccacg | cgtccgtgat | aaataactta | taggtgatag | tgataattcc | tgattccaag | 60 |
| aatgccatct | gataaaaaag | aatagaaatg | gaaagtggga | ctgagaggga | gtcagcaggc | 120 |
| atgctgcggt | ggcggtcact | ccctctgcca | ctatcccag | ggaaggaaag | gctccgccat | 180 |
| ttgggaaagt | ggtttctacg | tcactggaca | ccggttctga | gcattagttt | gagaactcgt | 240 |
| tcccgaatgt | gctttcctcc | ctctcccctg | cccacctcaa | gtttaataaa | taaggttgta | 300 |
| cttttcttac | tataaaataa | atgtctgtaa | ctgctgtgca | ctgctgtaaa | cttgttagag | 360 |
| aaaaaaataa | cctgcatgtg | ggctcctcag | ttattgagtt | tttgtgatcc | tatctcagtc | 420 |
| tgggggggaa | cattctcaag | aggtgaaata | caagaaagcc | ttttttcttt | ggatcttttc | 480 |
| ccgagattca | aatctccgat | ttcccatttg | ggggcaagtt | tttttcttca | ccttcaatat | 540 |
| gagaattcag | cgaacttgaa | agaaaaatca | tctgtgagtt | ccttcaggtt | ctcactcata | 600 |
| gtcatgatcc | ttcagaggga | atatgcactg | gcgagtttaa | agtaagggct | atgatatttg | 660 |
| atggtcccaa | agtacggcag | ctgcaaaaag | tagtggaagg | aaattgtcta | cgtgtcttgg | 720 |
| aaaaattagt | taggaatttg | gatgggtaaa | aggtaccctt | gccttactcc | atcttatttt | 780 |
| cttagccccc | tttgagtgtt | ttaactggtt | tcatgtccta | gtaggaagtg | cattctccat | 840 |
| cctcatcctc | tgccctccca | ggaagtcagt | gattgtcttt | tgggcttcc | cctccaaagg | 900 |
| accttctgca | gtggaagtgc | cacatccagt | tcttttcttt | tgttgctgct | gtgtttagat | 960 |
| aattgaagag | atctttgtgc | cacacaggat | ttttttttt | ttttaagaaa | aacctataga | 1020 |
| tgaaaaatta | ctaatgaaac | tgtgtgtacg | tgtctgtgcg | tgcaacataa | aaatacagta | 1080 |
| gcacctaagg | agcttgaatc | ttggttcctg | taaaatttca | aattgatgtg | gtattaataa | 1140 |
| aaaaaaaaaa | aacccaaaaa | aaaaaaaaa | aaagggcgg | cc | | 1182 |

<210> SEQ ID NO 262
<211> LENGTH: 24
<212> TYPE: DNA
<213> ORGANISM: Homo sapiens

<400> SEQUENCE: 262
atgccatctg ataaaaaaga atag                                            24

<210> SEQ ID NO 263
<211> LENGTH: 7
<212> TYPE: PRT
<213> ORGANISM: Homo sapiens

<400> SEQUENCE: 263

Met Pro Ser Asp Lys Lys Glu
 1               5

```
<210> SEQ ID NO 264
<211> LENGTH: 228
<212> TYPE: DNA
<213> ORGANISM: Homo sapiens

<400> SEQUENCE: 264
atggaaagtg ggactgagag ggagtcagca ggcatgctgc ggtggcggtc actccctctg      60
ccactatccc cagggaagga aaggctccgc catttgggaa agtggtttct acgtcactgg     120
acaccggttc tgagcattag tttgagaact cgttcccgaa tgtgctttcc tccctctccc     180
ctgcccacct caagtttaat aaataaggtt gtacttttct tactataa                  228

<210> SEQ ID NO 265
<211> LENGTH: 75
<212> TYPE: PRT
<213> ORGANISM: Homo sapiens

<400> SEQUENCE: 265

Met Glu Ser Gly Thr Glu Arg Glu Ser Ala Gly Met Leu Arg Trp Arg
1               5                   10                  15

Ser Leu Pro Leu Pro Leu Ser Pro Gly Lys Glu Arg Leu Arg His Leu
            20                  25                  30

Gly Lys Trp Phe Leu Arg His Trp Thr Pro Val Leu Ser Ile Ser Leu
        35                  40                  45

Arg Thr Arg Ser Arg Met Cys Phe Pro Pro Ser Pro Leu Pro Thr Ser
    50                  55                  60

Ser Leu Ile Asn Lys Val Val Leu Phe Leu Leu
65                  70                  75

<210> SEQ ID NO 266
<211> LENGTH: 195
<212> TYPE: DNA
<213> ORGANISM: Homo sapiens

<400> SEQUENCE: 266
atgctgcggt ggcggtcact ccctctgcca ctatccccag ggaaggaaag gctccgccat      60
ttgggaaagt ggtttctacg tcactggaca ccggttctga gcattagttt gagaactcgt     120
tcccgaatgt gctttcctcc ctctcccctg cccacctcaa gtttaataaa taaggttgta     180
cttttcttac tataa                                                     195

<210> SEQ ID NO 267
<211> LENGTH: 64
<212> TYPE: PRT
<213> ORGANISM: Homo sapiens

<400> SEQUENCE: 267

Met Leu Arg Trp Arg Ser Leu Pro Leu Pro Leu Ser Pro Gly Lys Glu
1               5                   10                  15

Arg Leu Arg His Leu Gly Lys Trp Phe Leu Arg His Trp Thr Pro Val
            20                  25                  30

Leu Ser Ile Ser Leu Arg Thr Arg Ser Arg Met Cys Phe Pro Pro Ser
        35                  40                  45

Pro Leu Pro Thr Ser Ser Leu Ile Asn Lys Val Val Leu Phe Leu Leu
    50                  55                  60

<210> SEQ ID NO 268
<211> LENGTH: 69
<212> TYPE: DNA
```

<213> ORGANISM: Homo sapiens

<400> SEQUENCE: 268

```
atgtgctttc ctccctctcc cctgcccacc tcaagtttaa taaataaggt tgtacttttc      60
ttactataa                                                              69
```

<210> SEQ ID NO 269
<211> LENGTH: 21
<212> TYPE: PRT
<213> ORGANISM: Homo sapiens

<400> SEQUENCE: 269

```
Met Cys Phe Pro Pro Ser Pro Leu Pro Thr Ser Ser Leu Ile Asn Lys
1               5                   10                  15

Val Val Leu Phe Leu
            20
```

<210> SEQ ID NO 270
<211> LENGTH: 87
<212> TYPE: DNA
<213> ORGANISM: Homo sapiens

<400> SEQUENCE: 270

```
atgtctgtaa ctgctgtgca ctgctgtaaa cttgttagag aaaaaaataa cctgcatgtg      60
ggctcctcag ttattgagtt tttgtga                                          87
```

<210> SEQ ID NO 271
<211> LENGTH: 28
<212> TYPE: PRT
<213> ORGANISM: Homo sapiens

<400> SEQUENCE: 271

```
Met Ser Val Thr Ala Val His Cys Cys Lys Leu Val Arg Glu Lys Asn
1               5                   10                  15

Asn Leu His Val Gly Ser Ser Val Ile Glu Phe Leu
            20                  25
```

<210> SEQ ID NO 272
<211> LENGTH: 270
<212> TYPE: DNA
<213> ORGANISM: Homo sapiens

<400> SEQUENCE: 272

```
atgtgggctc ctcagttatt gagttttgt gatcctatct cagtctgggg gggaacattc       60
tcaagaggtg aaatacaaga aagcctttt ttcttggatc ttttcccgag attcaaatct      120
ccgatttccc atttgggggc aagtttttt cttcaccttc aatatgagaa ttcagcgaac      180
ttgaaagaaa aatcatctgt gagttccttc aggttctcac tcatagtcat gatccttcag      240
agggaatatg cactggcgag tttaaagtaa                                       270
```

<210> SEQ ID NO 273
<211> LENGTH: 89
<212> TYPE: PRT
<213> ORGANISM: Homo sapiens

<400> SEQUENCE: 273

```
Met Trp Ala Pro Gln Leu Leu Ser Phe Cys Asp Pro Ile Ser Val Trp
1               5                   10                  15

Gly Gly Thr Phe Ser Arg Gly Glu Ile Gln Glu Ser Leu Phe Phe Leu
            20                  25                  30
```

```
Asp Leu Phe Pro Arg Phe Lys Ser Pro Ile Ser His Leu Gly Ala Ser
            35                  40                  45

Phe Phe Leu His Leu Gln Tyr Glu Asn Ser Ala Asn Leu Lys Glu Lys
     50                  55                  60

Ser Ser Val Ser Ser Phe Arg Phe Ser Leu Ile Val Met Ile Leu Gln
 65                  70                  75                  80

Arg Glu Tyr Ala Leu Ala Ser Leu Lys
                85
```

<210> SEQ ID NO 274
<211> LENGTH: 21
<212> TYPE: DNA
<213> ORGANISM: Homo sapiens

<400> SEQUENCE: 274
atgagaattc agcgaacttg a                                           21

<210> SEQ ID NO 275
<211> LENGTH: 6
<212> TYPE: PRT
<213> ORGANISM: Homo sapiens

<400> SEQUENCE: 275

```
Met Arg Ile Gln Arg Thr
 1               5
```

<210> SEQ ID NO 276
<211> LENGTH: 42
<212> TYPE: DNA
<213> ORGANISM: Homo sapiens

<400> SEQUENCE: 276
atgatccttc agagggaata tgcactggcg agtttaaagt aa                    42

<210> SEQ ID NO 277
<211> LENGTH: 13
<212> TYPE: PRT
<213> ORGANISM: Homo sapiens

<400> SEQUENCE: 277

```
Met Ile Leu Gln Arg Glu Tyr Ala Leu Ala Ser Leu Lys
 1               5                  10
```

<210> SEQ ID NO 278
<211> LENGTH: 18
<212> TYPE: DNA
<213> ORGANISM: Homo sapiens

<400> SEQUENCE: 278
atgcactggc gagtttaa                                               18

<210> SEQ ID NO 279
<211> LENGTH: 5
<212> TYPE: PRT
<213> ORGANISM: Homo sapiens

<400> SEQUENCE: 279

```
Met His Trp Arg Val
 1               5
```

<210> SEQ ID NO 280
<211> LENGTH: 99

```
<212> TYPE: DNA
<213> ORGANISM: Homo sapiens

<400> SEQUENCE: 280
atgatatttg atggtcccaa agtacggcag ctgcaaaaag tagtggaagg aaattgtcta      60
cgtgtcttgg aaaaattagt taggaatttg gatgggtaa                            99

<210> SEQ ID NO 281
<211> LENGTH: 32
<212> TYPE: PRT
<213> ORGANISM: Homo sapiens

<400> SEQUENCE: 281

Met Ile Phe Asp Gly Pro Lys Val Arg Gln Leu Gln Lys Val Val Glu
 1               5                  10                  15

Gly Asn Cys Leu Arg Val Leu Glu Lys Leu Val Arg Asn Leu Asp Gly
            20                  25                  30

<210> SEQ ID NO 282
<211> LENGTH: 33
<212> TYPE: DNA
<213> ORGANISM: Homo sapiens

<400> SEQUENCE: 282
atggtcccaa agtacggcag ctgcaaaaag tag                                  33

<210> SEQ ID NO 283
<211> LENGTH: 10
<212> TYPE: PRT
<213> ORGANISM: Homo sapiens

<400> SEQUENCE: 283

Met Val Pro Lys Tyr Gly Ser Cys Lys Lys
 1               5                  10

<210> SEQ ID NO 284
<211> LENGTH: 54
<212> TYPE: DNA
<213> ORGANISM: Homo sapiens

<400> SEQUENCE: 284
atgggtaaaa ggtacccttg ccttactcca tcttattttc ttagccccct ttga            54

<210> SEQ ID NO 285
<211> LENGTH: 17
<212> TYPE: PRT
<213> ORGANISM: Homo sapiens

<400> SEQUENCE: 285

Met Gly Lys Arg Tyr Pro Cys Leu Thr Pro Ser Tyr Phe Leu Ser Pro
 1               5                  10                  15

Leu

<210> SEQ ID NO 286
<211> LENGTH: 15
<212> TYPE: DNA
<213> ORGANISM: Homo sapiens

<400> SEQUENCE: 286
atgaaaaatt actaa                                                      15

<210> SEQ ID NO 287
```

<211> LENGTH: 4
<212> TYPE: PRT
<213> ORGANISM: Homo sapiens

<400> SEQUENCE: 287

Met Lys Asn Tyr
 1

<210> SEQ ID NO 288
<211> LENGTH: 48
<212> TYPE: DNA
<213> ORGANISM: Homo sapiens

<400> SEQUENCE: 288
atgaaactgt gtgtacgtgt ctgtgcgtgc aacataaaaa tacagtag           48

<210> SEQ ID NO 289
<211> LENGTH: 15
<212> TYPE: PRT
<213> ORGANISM: Homo sapiens

<400> SEQUENCE: 289

Met Lys Leu Cys Val Arg Val Cys Ala Cys Asn Ile Lys Ile Gln
 1               5                  10                  15

<210> SEQ ID NO 290
<211> LENGTH: 12
<212> TYPE: DNA
<213> ORGANISM: Homo sapiens

<400> SEQUENCE: 290
atgtggtatt aa                                                  12

<210> SEQ ID NO 291
<211> LENGTH: 3
<212> TYPE: PRT
<213> ORGANISM: Homo sapiens

<400> SEQUENCE: 291

Met Trp Tyr
 1

<210> SEQ ID NO 292
<211> LENGTH: 1965
<212> TYPE: DNA
<213> ORGANISM: Homo sapiens

<400> SEQUENCE: 292
tcgacccacg cgtccggagg agagagagtg aacagggagc ggggcttttg tctgttggtc      60
tccctggact gaagagaggg agaatagaag cccaagacta agattctcaa aatggtttat     120
tacccagaac tctttgtctg ggtcagtcaa gaaccatttc caaacaagga catggaggga     180
aggcttccta aggaagact tcctgtccca aggaagtga accgcaagaa gaacgatgag      240
acaaacgctg cctccctgac tccactgggc agcagtgaac tccgctcccc aagaatcagt     300
tacctccact ttttttaatc gtaacacctc catttgtatt acatatggtg tatgggtatt     360
gatgaggtca tggtatcata tatgggatt ttttctgtgt aaatcatcaa gtataagaag      420
aaactatggg actctgagcc ttgctttaga gaatttacag tggacaaata ggtgtcatca     480
aaccagtttt taatcattct gactcaagtg aaaacgctca gaatttcaca ctgtgaatcc     540
cgtttacaac ccttacaggt gggccttcag gcctggttcg ctacaacaat gtcttccaca     600

```
actcaaactc ccaccgcgct cacacaaccg gtccactcct gccttttcac tcacacagct      660
cccgactgct tcttgcagag gctgagagtc ccccccccac cttttttttc atttagatgt      720
aacaaaccta gtagtttatg ttcatcaatt gtctgtatat ctctatattt tatccatgta      780
ctcttttgat gtatagaagt agtttgaaac tcattgtttc cttgtggtaa gtgaccgaga      840
tgctgccaca ggacctgaga cactgatgaa tggtgctatt ttggactttc aacatgctcc      900
ttggcgaggt agctctgatg gagttatttt ttatttccat gttctaagaa ggtgttggta      960
ctctgtttcc cttgaatgtt gttctctaga ctggattgac ttgttttcct tgtgtcttca     1020
gtgtggcttt cttcctcagt gttgtaggtt gagcgaatgc taccagagtg tgagagacca     1080
ttgtctcgtt ggctggcgct cacggacatg cagtcacggt agcgggagca atcacaaaac     1140
tgtaatttac ttaccaaatc tcttcctttc cgtagcctcg cctgcctgac ttagagaaag     1200
aaaagcaata attttacagg cattttgagg tgtctctttg ggttctttct gtttgaaagg     1260
atatttgtcg aaaaaaagag caaaaccgtt ttaaataaac tcccctggaa aaaaaccca     1320 aaacactggc atactgagtg ggaatatgaa aatgacacct tttccaaata ttaaattgga     1380
aaacaaggtc tacaaaatca tgatactttt ttaaaaggca gagcattctt ttttcggcaa     1440
ttttgataag caaggtgtag atttacattt ttgtccttgc tcccaacgaa atggataaac     1500
aaaaataaat taccatctac tcatggaatg ttgttgtgtt agccagtctg aaagcccacc     1560
ttaattttta taactgtc tttagctctt cttttgacag gcaggcctt gttctgaact     1620 gtttcgcttc tgactgttaa acaccgatga cgcatgcact gcacttcttc gttttcttct     1680
tgctccccca ttggcctgag tttcttgtgc attactcctc tccctccttc gttagaatag     1740
gtgtatcagc tgtgtaaata gagcaagaaa acagtattct gcatctgtgg catttatgta     1800
gagttgcagt tgtgtactgc tgaaaatgca ggcttttgta acagtgtgat ctttactgat     1860
gcactcatga caagtaccca atgtatttta gctattttag tagtatttgt tcaataaata     1920
cgcaagctgt aaggtaaaaa aaaaaaaaaa aaaaaagggg cggcc                    1965

<210> SEQ ID NO 293
<211> LENGTH: 207
<212> TYPE: DNA
<213> ORGANISM: Homo sapiens

<400> SEQUENCE: 293
atggtttatt acccagaact ctttgtctgg gtcagtcaag aaccatttcc aaacaaggac       60
atggagggaa ggcttcctaa gggaagactt cctgtcccaa aggaagtgaa ccgcaagaag      120
aacgatgaga caaacgctgc ctccctgact ccactgggca gcagtgaact ccgctcccca      180
agaatcagtt acctccactt tttttaa                                          207

<210> SEQ ID NO 294
<211> LENGTH: 68
<212> TYPE: PRT
<213> ORGANISM: Homo sapiens

<400> SEQUENCE: 294

Met Val Tyr Tyr Pro Glu Leu Phe Val Trp Val Ser Gln Glu Pro Phe
1               5                   10                  15

Pro Asn Lys Asp Met Glu Gly Arg Leu Pro Lys Gly Arg Leu Pro Val
                20                  25                  30

Pro Lys Glu Val Asn Arg Lys Lys Asn Asp Glu Thr Asn Ala Ala Ser
            35                  40                  45
```

Leu Thr Pro Leu Gly Ser Ser Glu Leu Arg Ser Pro Arg Ile Ser Tyr
    50                  55                  60

Leu His Phe Phe
65

<210> SEQ ID NO 295
<211> LENGTH: 147
<212> TYPE: DNA
<213> ORGANISM: Homo sapiens

<400> SEQUENCE: 295
atggagggaa ggcttcctaa gggaagactt cctgtcccaa aggaagtgaa ccgcaagaag    60
aacgatgaga caaacgctgc ctccctgact ccactgggca gcagtgaact ccgctcccca   120
agaatcagtt acctccactt tttttaa                                       147

<210> SEQ ID NO 296
<211> LENGTH: 48
<212> TYPE: PRT
<213> ORGANISM: Homo sapiens

<400> SEQUENCE: 296

Met Glu Gly Arg Leu Pro Lys Gly Arg Leu Pro Val Pro Lys Glu Val
1               5                   10                  15

Asn Arg Lys Lys Asn Asp Glu Thr Asn Ala Ala Ser Leu Thr Pro Leu
            20                  25                  30

Gly Ser Ser Glu Leu Arg Ser Pro Arg Ile Ser Tyr Leu His Phe Phe
        35                  40                  45

<210> SEQ ID NO 297
<211> LENGTH: 24
<212> TYPE: DNA
<213> ORGANISM: Homo sapiens

<400> SEQUENCE: 297
atgagacaaa cgctgcctcc ctga                                           24

<210> SEQ ID NO 298
<211> LENGTH: 7
<212> TYPE: PRT
<213> ORGANISM: Homo sapiens

<400> SEQUENCE: 298

Met Arg Gln Thr Leu Pro Pro
1               5

<210> SEQ ID NO 299
<211> LENGTH: 18
<212> TYPE: DNA
<213> ORGANISM: Homo sapiens

<400> SEQUENCE: 299
atggtgtatg ggtattga                                                  18

<210> SEQ ID NO 300
<211> LENGTH: 5
<212> TYPE: PRT
<213> ORGANISM: Homo sapiens

<400> SEQUENCE: 300

Met Val Tyr Gly Tyr
1               5

```
<210> SEQ ID NO 301
<211> LENGTH: 51
<212> TYPE: DNA
<213> ORGANISM: Homo sapiens

<400> SEQUENCE: 301
atgggtattg atgaggtcat ggtatcatat atgggatttt ttctgtgta a        51

<210> SEQ ID NO 302
<211> LENGTH: 16
<212> TYPE: PRT
<213> ORGANISM: Homo sapiens

<400> SEQUENCE: 302

Met Gly Ile Asp Glu Val Met Val Ser Tyr Met Gly Phe Phe Ser Val
 1               5                  10                  15

<210> SEQ ID NO 303
<211> LENGTH: 132
<212> TYPE: DNA
<213> ORGANISM: Homo sapiens

<400> SEQUENCE: 303
atgaggtcat ggtatcatat atgggatttt ttctgtgta aatcatcaag tataagaaga     60
aactatggga ctctgagcct tgctttagag aatttacagt ggacaaatag gtgtcatcaa   120
accagttttt aa                                                       132

<210> SEQ ID NO 304
<211> LENGTH: 43
<212> TYPE: PRT
<213> ORGANISM: Homo sapiens

<400> SEQUENCE: 304

Met Arg Ser Trp Tyr His Ile Trp Asp Phe Phe Leu Cys Lys Ser Ser
 1               5                  10                  15

Ser Ile Arg Arg Asn Tyr Gly Thr Leu Ser Leu Ala Leu Glu Asn Leu
                20                  25                  30

Gln Trp Thr Asn Arg Cys His Gln Thr Ser Phe
        35                  40

<210> SEQ ID NO 305
<211> LENGTH: 33
<212> TYPE: DNA
<213> ORGANISM: Homo sapiens

<400> SEQUENCE: 305
atggtatcat atatgggatt tttttctgtg taa                                33

<210> SEQ ID NO 306
<211> LENGTH: 10
<212> TYPE: PRT
<213> ORGANISM: Homo sapiens

<400> SEQUENCE: 306

Met Val Ser Tyr Met Gly Phe Phe Ser Val
 1               5                  10

<210> SEQ ID NO 307
<211> LENGTH: 21
<212> TYPE: DNA
<213> ORGANISM: Homo sapiens
```

<400> SEQUENCE: 307
atgggatttt tttctgtgta a                                              21

<210> SEQ ID NO 308
<211> LENGTH: 6
<212> TYPE: PRT
<213> ORGANISM: Homo sapiens

<400> SEQUENCE: 308

Met Gly Phe Phe Ser Val
 1               5

<210> SEQ ID NO 309
<211> LENGTH: 12
<212> TYPE: DNA
<213> ORGANISM: Homo sapiens

<400> SEQUENCE: 309
atgggactct ga                                                        12

<210> SEQ ID NO 310
<211> LENGTH: 3
<212> TYPE: PRT
<213> ORGANISM: Homo sapiens

<400> SEQUENCE: 310

Met Gly Leu
 1

<210> SEQ ID NO 311
<211> LENGTH: 201
<212> TYPE: DNA
<213> ORGANISM: Homo sapiens

<400> SEQUENCE: 311
atgtcttcca caactcaaac tcccaccgcg ctcacacaac cggtccactc ctgccttttc     60
actcacacag ctcccgactg cttcttgcag aggctgagag tccccccccc acctttttt    120 tcatttagat gtaacaaacc tagtagttta tgttcatcaa ttgtctgtat atctctatat   180
tttatccatg tactcttttg a                                             201

<210> SEQ ID NO 312
<211> LENGTH: 66
<212> TYPE: PRT
<213> ORGANISM: Homo sapiens

<400> SEQUENCE: 312

Met Ser Ser Thr Thr Gln Thr Pro Thr Ala Leu Thr Gln Pro Val His
 1               5                  10                  15

Ser Cys Leu Phe Thr His Thr Ala Pro Asp Cys Phe Leu Gln Arg Leu
                20                  25                  30

Arg Val Pro Pro Pro Pro Phe Phe Ser Phe Arg Cys Asn Lys Pro Ser
            35                  40                  45

Ser Leu Cys Ser Ser Ile Val Cys Ile Ser Leu Tyr Phe Ile His Val
        50                  55                  60

Leu Phe
65

<210> SEQ ID NO 313
<211> LENGTH: 93
<212> TYPE: DNA

<213> ORGANISM: Homo sapiens

<400> SEQUENCE: 313
atgttcatca attgtctgta tatctctata ttttatccat gtactctttt gatgtataga    60
agtagtttga aactcattgt ttccttgtgg taa    93

<210> SEQ ID NO 314
<211> LENGTH: 30
<212> TYPE: PRT
<213> ORGANISM: Homo sapiens

<400> SEQUENCE: 314

Met Phe Ile Asn Cys Leu Tyr Ile Ser Ile Phe Tyr Pro Cys Thr Leu
1               5                   10                  15

Leu Met Tyr Arg Ser Ser Leu Lys Leu Ile Val Ser Leu Trp
            20                  25                  30

<210> SEQ ID NO 315
<211> LENGTH: 21
<212> TYPE: DNA
<213> ORGANISM: Homo sapiens

<400> SEQUENCE: 315
atgtactctt ttgatgtata g    21

<210> SEQ ID NO 316
<211> LENGTH: 6
<212> TYPE: PRT
<213> ORGANISM: Homo sapiens

<400> SEQUENCE: 316

Met Tyr Ser Phe Asp Val
1               5

<210> SEQ ID NO 317
<211> LENGTH: 42
<212> TYPE: DNA
<213> ORGANISM: Homo sapiens

<400> SEQUENCE: 317
atgtatagaa gtagtttgaa actcattgtt tccttgtggt aa    42

<210> SEQ ID NO 318
<211> LENGTH: 13
<212> TYPE: PRT
<213> ORGANISM: Homo sapiens

<400> SEQUENCE: 318

Met Tyr Arg Ser Ser Leu Lys Leu Ile Val Ser Leu Trp
1               5                   10

<210> SEQ ID NO 319
<211> LENGTH: 27
<212> TYPE: DNA
<213> ORGANISM: Homo sapiens

<400> SEQUENCE: 319
atgctgccac aggacctgag acactga    27

<210> SEQ ID NO 320
<211> LENGTH: 8
<212> TYPE: PRT
<213> ORGANISM: Homo sapiens

<400> SEQUENCE: 320

Met Leu Pro Gln Asp Leu Arg His
1               5

<210> SEQ ID NO 321
<211> LENGTH: 324
<212> TYPE: DNA
<213> ORGANISM: Homo sapiens

<400> SEQUENCE: 321
atgaatggtg ctattttgga ctttcaacat gctccttggc gaggtagctc tgatggagtt      60 atttttatt tccatgttct aagaaggtgt tggtactctg tttcccttga atgttgttct      120
ctagactgga ttgacttgtt ttccttgtgt cttcagtgtg gctttcttcc tcagtgttgt      180
aggttgagcg aatgctacca gagtgtgaga gaccattgtc tcgttggctg gcgctcacgg      240
acatgcagtc acggtagcgg gagcaatcac aaaactgtaa tttacttacc aaatctcttc      300
ctttccgtag cctcgcctgc ctga                                            324

<210> SEQ ID NO 322
<211> LENGTH: 107
<212> TYPE: PRT
<213> ORGANISM: Homo sapiens

<400> SEQUENCE: 322

Met Asn Gly Ala Ile Leu Asp Phe Gln His Ala Pro Trp Arg Gly Ser
1               5                   10                  15

Ser Asp Gly Val Ile Phe Tyr Phe His Val Leu Arg Arg Cys Trp Tyr
            20                  25                  30

Ser Val Ser Leu Glu Cys Cys Ser Leu Asp Trp Ile Asp Leu Phe Ser
        35                  40                  45

Leu Cys Leu Gln Cys Gly Phe Leu Pro Gln Cys Cys Arg Leu Ser Glu
    50                  55                  60

Cys Tyr Gln Ser Val Arg Asp His Cys Leu Val Gly Trp Arg Ser Arg
65                  70                  75                  80

Thr Cys Ser His Gly Ser Gly Ser Asn His Lys Thr Val Ile Tyr Leu
                85                  90                  95

Pro Asn Leu Phe Leu Ser Val Ala Ser Pro Ala
            100                 105

<210> SEQ ID NO 323
<211> LENGTH: 78
<212> TYPE: DNA
<213> ORGANISM: Homo sapiens

<400> SEQUENCE: 323
atggtgctat tttggacttt caacatgctc cttggcgagg tagctctgat ggagttattt      60
tttatttcca tgttctaa                                                   78

<210> SEQ ID NO 324
<211> LENGTH: 25
<212> TYPE: PRT
<213> ORGANISM: Homo sapiens

<400> SEQUENCE: 324

Met Val Leu Phe Trp Thr Phe Asn Met Leu Leu Gly Glu Val Ala Leu
1               5                   10                  15

Met Glu Leu Phe Phe Ile Ser Met Phe

<210> SEQ ID NO 325
<211> LENGTH: 54
<212> TYPE: DNA
<213> ORGANISM: Homo sapiens

<400> SEQUENCE: 325
atgctccttg gcgaggtagc tctgatggag ttatttttta tttccatgtt ctaa        54

<210> SEQ ID NO 326
<211> LENGTH: 17
<212> TYPE: PRT
<213> ORGANISM: Homo sapiens

<400> SEQUENCE: 326

Met Leu Leu Gly Glu Val Ala Leu Met Glu Leu Phe Phe Ile Ser Met
 1               5                  10                  15

Phe

<210> SEQ ID NO 327
<211> LENGTH: 30
<212> TYPE: DNA
<213> ORGANISM: Homo sapiens

<400> SEQUENCE: 327
atggagttat tttttatttc catgttctaa                                    30

<210> SEQ ID NO 328
<211> LENGTH: 9
<212> TYPE: PRT
<213> ORGANISM: Homo sapiens

<400> SEQUENCE: 328

Met Glu Leu Phe Phe Ile Ser Met Phe
 1               5

<210> SEQ ID NO 329
<211> LENGTH: 24
<212> TYPE: DNA
<213> ORGANISM: Homo sapiens

<400> SEQUENCE: 329
atgttgttct ctagactgga ttga                                          24

<210> SEQ ID NO 330
<211> LENGTH: 7
<212> TYPE: PRT
<213> ORGANISM: Homo sapiens

<400> SEQUENCE: 330

Met Leu Phe Ser Arg Leu Asp
 1               5

<210> SEQ ID NO 331
<211> LENGTH: 66
<212> TYPE: DNA
<213> ORGANISM: Homo sapiens

<400> SEQUENCE: 331
atgctaccag agtgtgagag accattgtct cgttggctgg cgctcacgga catgcagtca   60
cggtag                                                              66

<210> SEQ ID NO 332
<211> LENGTH: 21
<212> TYPE: PRT
<213> ORGANISM: Homo sapiens

<400> SEQUENCE: 332

Met Leu Pro Glu Cys Glu Arg Pro Leu Ser Arg Trp Leu Ala Leu Thr
1               5                   10                  15

Asp Met Gln Ser Arg
            20

<210> SEQ ID NO 333
<211> LENGTH: 15
<212> TYPE: DNA
<213> ORGANISM: Homo sapiens

<400> SEQUENCE: 333
atgcagtcac ggtag                                                    15

<210> SEQ ID NO 334
<211> LENGTH: 4
<212> TYPE: PRT
<213> ORGANISM: Homo sapiens

<400> SEQUENCE: 334

Met Gln Ser Arg
1

<210> SEQ ID NO 335
<211> LENGTH: 69
<212> TYPE: DNA
<213> ORGANISM: Homo sapiens

<400> SEQUENCE: 335
atgaaaatga cacctttttcc aaatattaaa ttggaaaaca aggtctacaa aatcatgata    60
cttttttaa                                                           69

<210> SEQ ID NO 336
<211> LENGTH: 22
<212> TYPE: PRT
<213> ORGANISM: Homo sapiens

<400> SEQUENCE: 336

Met Lys Met Thr Pro Phe Pro Asn Ile Lys Leu Glu Asn Lys Val Tyr
1               5                   10                  15

Lys Ile Met Ile Leu Phe
            20

<210> SEQ ID NO 337
<211> LENGTH: 63
<212> TYPE: DNA
<213> ORGANISM: Homo sapiens

<400> SEQUENCE: 337
atgacccttt tccaaatat taaattggaa aacaaggtct acaaaatcat gatacttttt    60
taa                                                                 63

<210> SEQ ID NO 338
<211> LENGTH: 20
<212> TYPE: PRT
<213> ORGANISM: Homo sapiens

```
<400> SEQUENCE: 338

Met Thr Pro Phe Pro Asn Ile Lys Leu Glu Asn Lys Val Tyr Lys Ile
 1               5                  10                  15
Met Ile Leu Phe
        20

<210> SEQ ID NO 339
<211> LENGTH: 15
<212> TYPE: DNA
<213> ORGANISM: Homo sapiens

<400> SEQUENCE: 339
atgatacttt tttaa                                                        15

<210> SEQ ID NO 340
<211> LENGTH: 4
<212> TYPE: PRT
<213> ORGANISM: Homo sapiens

<400> SEQUENCE: 340

Met Ile Leu Phe
 1

<210> SEQ ID NO 341
<211> LENGTH: 18
<212> TYPE: DNA
<213> ORGANISM: Homo sapiens

<400> SEQUENCE: 341
atggataaac aaaaataa                                                     18

<210> SEQ ID NO 342
<211> LENGTH: 5
<212> TYPE: PRT
<213> ORGANISM: Homo sapiens

<400> SEQUENCE: 342

Met Asp Lys Gln Lys
 1               5

<210> SEQ ID NO 343
<211> LENGTH: 42
<212> TYPE: DNA
<213> ORGANISM: Homo sapiens

<400> SEQUENCE: 343
atggaatgtt gttgtgttag ccagtctgaa agcccacctt aa                          42

<210> SEQ ID NO 344
<211> LENGTH: 13
<212> TYPE: PRT
<213> ORGANISM: Homo sapiens

<400> SEQUENCE: 344

Met Glu Cys Cys Cys Val Ser Gln Ser Glu Ser Pro Pro
 1               5                  10

<210> SEQ ID NO 345
<211> LENGTH: 15
<212> TYPE: DNA
<213> ORGANISM: Homo sapiens

<400> SEQUENCE: 345
```

```
atgttgttgt gttag                                                  15

<210> SEQ ID NO 346
<211> LENGTH: 4
<212> TYPE: PRT
<213> ORGANISM: Homo sapiens

<400> SEQUENCE: 346

Met Leu Leu Cys
  1

<210> SEQ ID NO 347
<211> LENGTH: 111
<212> TYPE: DNA
<213> ORGANISM: Homo sapiens

<400> SEQUENCE: 347
atgacgcatg cactgcactt cttcgttttc ttcttgctcc cccattggcc tgagtttctt    60
gtgcattact cctctccctc cttcgttaga ataggtgtat cagctgtgta a            111

<210> SEQ ID NO 348
<211> LENGTH: 36
<212> TYPE: PRT
<213> ORGANISM: Homo sapiens

<400> SEQUENCE: 348

Met Thr His Ala Leu His Phe Phe Val Phe Phe Leu Leu Pro His Trp
  1               5                  10                  15

Pro Glu Phe Leu Val His Tyr Ser Ser Pro Ser Phe Val Arg Ile Gly
             20                  25                  30

Val Ser Ala Val
         35

<210> SEQ ID NO 349
<211> LENGTH: 87
<212> TYPE: DNA
<213> ORGANISM: Homo sapiens

<400> SEQUENCE: 349
atgcactgca cttcttcgtt ttcttcttgc tcccccattg gcctgagttt cttgtgcatt    60
actcctctcc ctccttcgtt agaatag                                       87

<210> SEQ ID NO 350
<211> LENGTH: 28
<212> TYPE: PRT
<213> ORGANISM: Homo sapiens

<400> SEQUENCE: 350

Met His Cys Thr Ser Ser Phe Ser Ser Cys Ser Pro Ile Gly Leu Ser
  1               5                  10                  15

Phe Leu Cys Ile Thr Pro Leu Pro Pro Ser Leu Glu
             20                  25

<210> SEQ ID NO 351
<211> LENGTH: 24
<212> TYPE: DNA
<213> ORGANISM: Homo sapiens

<400> SEQUENCE: 351
atgcaggctt ttgtaacagt gtga                                          24
```

<210> SEQ ID NO 352
<211> LENGTH: 7
<212> TYPE: PRT
<213> ORGANISM: Homo sapiens

<400> SEQUENCE: 352

Met Gln Ala Phe Val Thr Val
 1               5

<210> SEQ ID NO 353
<211> LENGTH: 12
<212> TYPE: DNA
<213> ORGANISM: Homo sapiens

<400> SEQUENCE: 353
atgcactcat ga                                                            12

<210> SEQ ID NO 354
<211> LENGTH: 3
<212> TYPE: PRT
<213> ORGANISM: Homo sapiens

<400> SEQUENCE: 354

Met His Ser
 1

<210> SEQ ID NO 355
<211> LENGTH: 51
<212> TYPE: DNA
<213> ORGANISM: Homo sapiens

<400> SEQUENCE: 355
atgacaagta cccaatgtat tttagctatt ttagtagtat ttgttcaata a                  51

<210> SEQ ID NO 356
<211> LENGTH: 16
<212> TYPE: PRT
<213> ORGANISM: Homo sapiens

<400> SEQUENCE: 356

Met Thr Ser Thr Gln Cys Ile Leu Ala Ile Leu Val Val Phe Val Gln
 1               5                  10                  15

<210> SEQ ID NO 357
<211> LENGTH: 57
<212> TYPE: DNA
<213> ORGANISM: Homo sapiens

<400> SEQUENCE: 357
atgtatttta gctattttag tagtatttgt tcaataaata cgcaagctgt aaggtaa            57

<210> SEQ ID NO 358
<211> LENGTH: 18
<212> TYPE: PRT
<213> ORGANISM: Homo sapiens

<400> SEQUENCE: 358

Met Tyr Phe Ser Tyr Phe Ser Ser Ile Cys Ser Ile Asn Thr Gln Ala
 1               5                  10                  15

Val Arg

<210> SEQ ID NO 359
<211> LENGTH: 2702
<212> TYPE: DNA

<213> ORGANISM: Homo sapiens

<400> SEQUENCE: 359

| | | | | | |
|---|---|---|---|---|---|
| tcgacccacg | cgtccgggaa | cgtacgtccc | agccctcttt | agctacttag | cgcctctggg | 60 |
| cccgagaaca | cctgctcctt | ggctcagtct | ggcgccaccg | gcatcacgga | actgtacttc | 120 |
| ccagagacgt | cacaccggga | gacttccgat | tcccgctctt | gagattggac | tctcacgtgc | 180 |
| aggagccagt | cctcgctggg | ctctagcggg | cttctgatgg | aggagctact | cctctgggag | 240 |
| gacagaaatt | agcagcagcc | tctgtcacca | tccaaagatt | acaacccatg | aaaccattga | 300 |
| gtttgtgcct | tgtatcagaa | agcaaaggag | aatgaaaaag | cacagctaac | attgcttgag | 360 |
| gatctaggcg | attaattctt | tagactgtca | tcatgggtat | cccgaggact | aatgagtttt | 420 |
| gtgggaagat | cataagtaat | gaagttcttc | actgatttga | agttgcgggg | acacaaaaat | 480 |
| tgtcattgat | ggttatgctc | ttttccaccg | tctttgcttc | agtttcaaac | ttggatctcc | 540 |
| ggtatggagg | ggactatgat | tcttttgcag | atgttgtaca | aaaattcttt | gaatcactgt | 600 |
| ttgcttgtaa | tatatgccca | tatgttgtat | tagatggagg | atgtgacatt | tcagataaaa | 660 |
| agcttacaac | tttaaaggat | agagctagag | agaagatcca | gatggcccat | tccctttctg | 720 |
| ttggtgggag | tgggtatgta | tgtcccttac | tcatccggga | agtattcata | caggttttga | 780 |
| tcaagctgcg | ggtgtgtttt | gtccagtgct | tttcagaagc | agatcgggac | attatgacac | 840 |
| ttgctaacca | ttggaattgc | cctgtgttat | catcagatag | tgacttttgc | attttttgacc | 900 |
| tgaaaactgg | gttttgccca | ttgaatagct | ttcagtggag | aaatatgaac | actattaagg | 960 |
| gcacacaaaa | ctatatccct | gccaaatgct | tttcccttga | tgcattctgc | catcacttca | 1020 |
| gcaatatgaa | taaagctcta | ctacctctct | ttgcggtgct | atgtgaaat | gaccatgtta | 1080 |
| atctacccat | catggagaca | ttcttaagta | agcgcgtct | cctcttgga | gctaccagtt | 1140 |
| ctaaagggag | gagacaccac | cgaatcctgg | gacttctgaa | ttggttgtct | cattttgcca | 1200 |
| accctaccga | agcactagat | aatgttctga | atacctccc | aaaaaaggat | cgagaaaatg | 1260 |
| ttaaggaact | tctctgctgt | tccatggaag | aataccaaca | gtcccaggtg | aagctacagg | 1320 |
| acttcttcca | gtgtggtact | tatgtctgtc | cagatgcctt | gaatcttggt | ttaccagaat | 1380 |
| gggtattagt | ggctttagct | aaaggccagc | tatctccttt | catcagtgat | gctttggtcc | 1440 |
| taagacggac | cattcttccc | acacaggtgg | aaaacatgca | gcaaccaaat | gcccacagaa | 1500 |
| tatctcagcc | catcaggcaa | atcatctatg | ggcttctttt | aaatgcctca | ccacatctgg | 1560 |
| acaagacatc | ctggaatgca | ttgcctcctc | agcctctagc | tttcagtgaa | gtggaaagga | 1620 |
| ttaataaaaa | tatcagaacc | tcaatcattg | atgcagtaga | actggccaag | gatcattctg | 1680 |
| acttaagcag | attgactgag | ctctccttga | ggaggcggca | gatgcttctg | ttagaaaccc | 1740 |
| tgaaggtgaa | acagaccatt | ctggagccaa | tccctacttc | actgaagttg | cccattgctg | 1800 |
| tcagttgcta | ctggttgcag | cacaccgaga | ccaaagcaaa | gctacatcat | ctacaatcct | 1860 |
| tactgctcac | aatgctagtg | gggcccttga | ttgccataat | caacagccct | ggaaatgtgg | 1920 |
| accctgtacc | caggcaggct | cagtgtcttg | ctcctcgcta | gttggtaaaa | ggtaaggaag | 1980 |
| agctgcagga | agatggtgct | aagatgttgt | atgcagagtt | ccaaagagtg | aaggcgcaga | 2040 |
| cacggctggg | cacaagactg | gacttagaca | cagctcacat | cttctgtcag | tggcagtcct | 2100 |
| gtctccagat | ggggatgtat | ctcaaccagc | tgctgtccac | tcctctccca | gagccagacc | 2160 |
| taactcgact | gtacagtgga | agcctggtgc | acggactatg | ccagcaactg | ctagcatcga | 2220 |
| cctctgtaga | aagtctcctg | agcatatgtc | ctgaggctaa | gcaactttat | gaatatctat | 2280 |

```
tcaatgccca caaggtcata tgcccccgct gaaatattcc taccaaaagg tagatcaaat      2340
tcaaaaaaaa aaaggcagaa gaaacagaat accagctgtt ctaagaacag agggagaacc      2400
actgcacaca ccaagtgttg gtatgaggga acaaccggt ttgggttgtt aatggttgaa       2460
aacttagagg aacatagtga ggcctccaac attgaataaa actcagtttg catcaaacta     2520
gatgtattta atataatcct tacttaaaat tcttccgtta ccaccttga aacaattagc       2580 tttttcttta ggactgacct gttagggat aaacatcaca ataatctgaa ttccaagtta      2640
ttttgtattt tgttttttaat aaatacaacc tgatttaaga aaaaaaaaa aaagggcgg       2700 cc                                                                    2702
```

<210> SEQ ID NO 360
<211> LENGTH: 36
<212> TYPE: DNA
<213> ORGANISM: Homo sapiens

<400> SEQUENCE: 360

```
atggaggagc tactcctctg ggaggacaga aattag                                36
```

<210> SEQ ID NO 361
<211> LENGTH: 11
<212> TYPE: PRT
<213> ORGANISM: Homo sapiens

<400> SEQUENCE: 361

```
Met Glu Glu Leu Leu Leu Trp Glu Asp Arg Asn
 1               5                  10
```

<210> SEQ ID NO 362
<211> LENGTH: 48
<212> TYPE: DNA
<213> ORGANISM: Homo sapiens

<400> SEQUENCE: 362

```
atgaaaccat tgagtttgtg ccttgtatca gaaagcaaag gagaatga                   48
```

<210> SEQ ID NO 363
<211> LENGTH: 15
<212> TYPE: PRT
<213> ORGANISM: Homo sapiens

<400> SEQUENCE: 363

```
Met Lys Pro Leu Ser Leu Cys Leu Val Ser Glu Ser Lys Gly Glu
 1               5                  10                  15
```

<210> SEQ ID NO 364
<211> LENGTH: 18
<212> TYPE: DNA
<213> ORGANISM: Homo sapiens

<400> SEQUENCE: 364

```
atgaaaaagc acagctaa                                                    18
```

<210> SEQ ID NO 365
<211> LENGTH: 5
<212> TYPE: PRT
<213> ORGANISM: Homo sapiens

<400> SEQUENCE: 365

```
Met Lys Lys His Ser
 1               5
```

<210> SEQ ID NO 366
<211> LENGTH: 63
<212> TYPE: DNA
<213> ORGANISM: Homo sapiens

<400> SEQUENCE: 366
atgggtatcc cgaggactaa tgagttttgt gggaagatca taagtaatga agttcttcac    60
tga                                                                 63

<210> SEQ ID NO 367
<211> LENGTH: 20
<212> TYPE: PRT
<213> ORGANISM: Homo sapiens

<400> SEQUENCE: 367

Met Gly Ile Pro Arg Thr Asn Glu Phe Cys Gly Lys Ile Ile Ser Asn
 1               5                  10                  15

Glu Val Leu His
            20

<210> SEQ ID NO 368
<211> LENGTH: 24
<212> TYPE: DNA
<213> ORGANISM: Homo sapiens

<400> SEQUENCE: 368
atgagttttg tgggaagatc ataa                                           24

<210> SEQ ID NO 369
<211> LENGTH: 7
<212> TYPE: PRT
<213> ORGANISM: Homo sapiens

<400> SEQUENCE: 369

Met Ser Phe Val Gly Arg Ser
 1               5

<210> SEQ ID NO 370
<211> LENGTH: 51
<212> TYPE: DNA
<213> ORGANISM: Homo sapiens

<400> SEQUENCE: 370
atgaagttct tcactgattt gaagttgcgg ggacacaaaa attgtcattg a             51

<210> SEQ ID NO 371
<211> LENGTH: 16
<212> TYPE: PRT
<213> ORGANISM: Homo sapiens

<400> SEQUENCE: 371

Met Lys Phe Phe Thr Asp Leu Lys Leu Arg Gly His Lys Asn Cys His
 1               5                  10                  15

<210> SEQ ID NO 372
<211> LENGTH: 1473
<212> TYPE: DNA
<213> ORGANISM: Homo sapiens

<400> SEQUENCE: 372
atggttatgc tcttttccac cgtctttgct tcagtttcaa acttggatct ccggtatgga    60

-continued

```
ggggactatg attcttttgc agatgttgta caaaaattct ttgaatcact gtttgcttgt        120
aatatatgcc catatgttgt attagatgga ggatgtgaca tttcagataa aaagcttaca        180
actttaaagg atagagctag agagaagatc cagatggccc attcccttc tgttggtggg         240 agtgggtatg tatgtcccttt actcatccgg gaagtattca tacaggtttt gatcaagctg       300
cgggtgtgtt ttgtccagtg cttttcagaa gcagatcggg acattatgac acttgctaac       360
cattggaatt gccctgtgtt atcatcagat agtgactttt gcattttga cctgaaaact        420 gggttttgcc cattgaatag ctttcagtgg agaaatatga acactattaa gggcacacaa       480
aactatatcc ctgccaaatg cttttccctt gatgcattct gccatcactt cagcaatatg      540
aataaagctc tactacctct ctttgcggtg ctatgtggaa atgaccatgt taatctaccc       600
atcatggaga cattcttaag taaagcgcgt cttcctcttg gagctaccag ttctaaaggg       660
aggagacacc accgaatcct gggacttctg aattggttgt ctcattttgc caaccctacc       720
gaagcactag ataatgttct gaaataccttc ccaaaaaagg atcgagaaaa tgttaaggaa      780
cttctctgct gttccatgga agaataccaa cagtcccagg tgaagctaca ggacttcttc      840
cagtgtggta cttatgtctg tccagatgcc ttgaatcttg gtttaccaga atgggtatta      900
gtggctttag ctaaaggcca gctatctcct ttcatcagtg atgctttggt cctaagacgg       960
accattcttc ccacacaggt ggaaaacatg cagcaaccaa atgcccacag aatatctcag      1020
cccatcaggc aaatcatcta tgggcttctt ttaaatgcct caccacatct ggacaagaca      1080
tcctggaatg cattgcctcc tcagcctcta gctttcagtg aagtggaaag gattaataaa      1140
aatatcagaa cctcaatcat tgatgcagta gaactggcca aggatcattc tgacttaagc      1200
agattgactg agctctcctt gaggaggcgg cagatgcttc tgttagaaac cctgaaggtg      1260
aaacagacca ttctggagcc aatccctact tcactgaagt tgcccattgc tgtcagttgc      1320
tactggttgc agcacaccga gaccaaagca aagctacatc atctacaatc cttactgctc      1380
acaatgctag tggggccctt gattgccata atcaacagcc tggaaatgt ggaccctgta       1440 cccaggcagg ctcagtgtct tgctcctcgc tag                                    1473
```

<210> SEQ ID NO 373
<211> LENGTH: 490
<212> TYPE: PRT
<213> ORGANISM: Homo sapiens

<400> SEQUENCE: 373

```
Met Val Met Leu Phe Ser Thr Val Phe Ala Ser Val Ser Asn Leu Asp
  1               5                  10                  15

Leu Arg Tyr Gly Gly Asp Tyr Asp Ser Phe Ala Asp Val Gln Lys
             20                  25                  30

Phe Phe Glu Ser Leu Phe Ala Cys Asn Ile Cys Pro Tyr Val Val Leu
         35                  40                  45

Asp Gly Gly Cys Asp Ile Ser Asp Lys Lys Leu Thr Thr Leu Lys Asp
     50                  55                  60

Arg Ala Arg Glu Lys Ile Gln Met Ala His Ser Leu Ser Val Gly Gly
 65                  70                  75                  80

Ser Gly Tyr Val Cys Pro Leu Leu Ile Arg Glu Val Phe Ile Gln Val
                 85                  90                  95

Leu Ile Lys Leu Arg Val Cys Phe Val Gln Cys Phe Ser Glu Ala Asp
            100                 105                 110

Arg Asp Ile Met Thr Leu Ala Asn His Trp Asn Cys Pro Val Leu Ser
        115                 120                 125
```

```
Ser Asp Ser Asp Phe Cys Ile Phe Asp Leu Lys Thr Gly Phe Cys Pro
    130                 135                 140

Leu Asn Ser Phe Gln Trp Arg Asn Met Asn Thr Ile Lys Gly Thr Gln
145                 150                 155                 160

Asn Tyr Ile Pro Ala Lys Cys Phe Ser Leu Asp Ala Phe Cys His His
                165                 170                 175

Phe Ser Asn Met Asn Lys Ala Leu Leu Pro Leu Phe Ala Val Leu Cys
            180                 185                 190

Gly Asn Asp His Val Asn Leu Pro Ile Met Glu Thr Phe Leu Ser Lys
        195                 200                 205

Ala Arg Leu Pro Leu Gly Ala Thr Ser Ser Lys Gly Arg Arg His His
    210                 215                 220

Arg Ile Leu Gly Leu Leu Asn Trp Leu Ser His Phe Ala Asn Pro Thr
225                 230                 235                 240

Glu Ala Leu Asp Asn Val Leu Lys Tyr Leu Pro Lys Lys Asp Arg Glu
                245                 250                 255

Asn Val Lys Glu Leu Leu Cys Cys Ser Met Glu Glu Tyr Gln Gln Ser
            260                 265                 270

Gln Val Lys Leu Gln Asp Phe Phe Gln Cys Gly Thr Tyr Val Cys Pro
        275                 280                 285

Asp Ala Leu Asn Leu Gly Leu Pro Glu Trp Val Leu Val Ala Leu Ala
    290                 295                 300

Lys Gly Gln Leu Ser Pro Phe Ile Ser Asp Ala Leu Val Leu Arg Arg
305                 310                 315                 320

Thr Ile Leu Pro Thr Gln Val Glu Asn Met Gln Gln Pro Asn Ala His
                325                 330                 335

Arg Ile Ser Gln Pro Ile Arg Gln Ile Ile Tyr Gly Leu Leu Leu Asn
            340                 345                 350

Ala Ser Pro His Leu Asp Lys Thr Ser Trp Asn Ala Leu Pro Pro Gln
        355                 360                 365

Pro Leu Ala Phe Ser Glu Val Glu Arg Ile Asn Lys Asn Ile Arg Thr
    370                 375                 380

Ser Ile Ile Asp Ala Val Glu Leu Ala Lys Asp His Ser Asp Leu Ser
385                 390                 395                 400

Arg Leu Thr Glu Leu Ser Leu Arg Arg Gln Met Leu Leu Leu Glu
                405                 410                 415

Thr Leu Lys Val Lys Gln Thr Ile Leu Glu Pro Ile Pro Thr Ser Leu
            420                 425                 430

Lys Leu Pro Ile Ala Val Ser Cys Tyr Trp Leu Gln His Thr Glu Thr
        435                 440                 445

Lys Ala Lys Leu His His Leu Gln Ser Leu Leu Leu Thr Met Leu Val
    450                 455                 460

Gly Pro Leu Ile Ala Ile Ile Asn Ser Pro Gly Asn Val Asp Pro Val
465                 470                 475                 480

Pro Arg Gln Ala Gln Cys Leu Ala Pro Arg
                485                 490

<210> SEQ ID NO 374
<211> LENGTH: 1467
<212> TYPE: DNA
<213> ORGANISM: Homo sapiens

<400> SEQUENCE: 374
atgctctttt ccaccgtctt tgcttcagtt tcaaacttgg atctccggta tggaggggac    60
```

-continued

```
tatgattctt tgcagatgt tgtacaaaaa ttctttgaat cactgtttgc ttgtaatata    120
tgcccatatg ttgtattaga tggaggatgt gacatttcag ataaaaagct tacaacttta   180
aaggatagag ctagagagaa gatccagatg gcccattccc tttctgttgg tgggagtggg   240
tatgtatgtc ccttactcat ccgggaagta ttcatacagg ttttgatcaa gctgcgggtg   300
tgttttgtcc agtgcttttc agaagcagat cgggacatta tgacacttgc taaccattgg   360
aattgccctg tgttatcatc agatagtgac ttttgcattt ttgacctgaa aactgggttt   420
tgcccattga atagctttca gtggagaaat atgaacacta ttaagggcac acaaaactat   480
atccctgcca aatgcttttc ccttgatgca ttctgccatc acttcagcaa tatgaataaa   540
gctctactac ctctctttgc ggtgctatgt ggaaatgacc atgttaatct acccatcatg   600
gagacattct taagtaaagc gcgtcttcct cttggagcta ccagttctaa agggaggaga   660
caccaccgaa tcctgggact tctgaattgg ttgtctcatt ttgccaaccc taccgaagca   720
ctagataatg ttctgaaata cctcccaaaa aaggatcgag aaaatgttaa ggaacttctc   780
tgctgttcca tggaagaata ccaacagtcc caggtgaagc tacaggactt cttccagtgt   840
ggtacttatg tctgtccaga tgccttgaat cttggtttac cagaatgggt attagtggct   900
ttagctaaag gccagctatc tcctttcatc agtgatgctt tggtcctaag acggaccatt   960
cttcccacac aggtggaaaa catgcagcaa ccaaatgccc acagaatatc tcagcccatc  1020
aggcaaatca tctatgggct tcttttaaat gcctcaccac atctggacaa gacatcctgg  1080
aatgcattgc ctcctcagcc tctagctttc agtgaagtgg aaaggattaa taaaaatatc  1140
agaacctcaa tcattgatgc agtagaactg gccaaggatc attctgactt aagcagattg  1200
actgagctct ccttgaggag gcggcagatg cttctgttag aaaccctgaa ggtgaaacag  1260
accattctgg agccaatccc tacttcactg aagttgccca ttgctgtcag ttgctactgg  1320
ttgcagcaca ccgagaccaa agcaaagcta catcatctac aatccttact gctcacaatg  1380
ctagtggggc ccttgattgc cataatcaac agccctggaa atgtggaccc tgtacccagg  1440
caggctcagt gtcttgctcc tcgctag                                      1467
```

<210> SEQ ID NO 375
<211> LENGTH: 488
<212> TYPE: PRT
<213> ORGANISM: Homo sapiens

<400> SEQUENCE: 375

```
Met Leu Phe Ser Thr Val Phe Ala Ser Val Ser Asn Leu Asp Leu Arg
  1               5                  10                  15

Tyr Gly Gly Asp Tyr Asp Ser Phe Ala Asp Val Val Gln Lys Phe Phe
             20                  25                  30

Glu Ser Leu Phe Ala Cys Asn Ile Cys Pro Tyr Val Val Leu Asp Gly
         35                  40                  45

Gly Cys Asp Ile Ser Asp Lys Lys Leu Thr Thr Leu Lys Asp Arg Ala
     50                  55                  60

Arg Glu Lys Ile Gln Met Ala His Ser Leu Ser Val Gly Gly Ser Gly
 65                  70                  75                  80

Tyr Val Cys Pro Leu Leu Ile Arg Glu Val Phe Ile Gln Val Leu Ile
                 85                  90                  95

Lys Leu Arg Val Cys Phe Val Gln Cys Phe Ser Glu Ala Asp Arg Asp
            100                 105                 110

Ile Met Thr Leu Ala Asn His Trp Asn Cys Pro Val Leu Ser Ser Asp
```

115                 120                 125
    Ser Asp Phe Cys Ile Phe Asp Leu Lys Thr Gly Phe Cys Pro Leu Asn
    130                 135                 140

Ser Phe Gln Trp Arg Asn Met Asn Thr Ile Lys Gly Thr Gln Asn Tyr
145                 150                 155                 160

Ile Pro Ala Lys Cys Phe Ser Leu Asp Ala Phe Cys His His Phe Ser
                    165                 170                 175

Asn Met Asn Lys Ala Leu Leu Pro Leu Phe Ala Val Leu Cys Gly Asn
                    180                 185                 190

Asp His Val Asn Leu Pro Ile Met Glu Thr Phe Leu Ser Lys Ala Arg
                    195                 200                 205

Leu Pro Leu Gly Ala Thr Ser Ser Lys Gly Arg Arg His His Arg Ile
    210                 215                 220

Leu Gly Leu Leu Asn Trp Leu Ser His Phe Ala Asn Pro Thr Glu Ala
225                 230                 235                 240

Leu Asp Asn Val Leu Lys Tyr Leu Pro Lys Lys Asp Arg Glu Asn Val
                    245                 250                 255

Lys Glu Leu Leu Cys Cys Ser Met Glu Glu Tyr Gln Gln Ser Gln Val
                    260                 265                 270

Lys Leu Gln Asp Phe Phe Gln Cys Gly Thr Tyr Val Cys Pro Asp Ala
                    275                 280                 285

Leu Asn Leu Gly Leu Pro Glu Trp Val Leu Val Ala Leu Ala Lys Gly
    290                 295                 300

Gln Leu Ser Pro Phe Ile Ser Asp Ala Leu Val Leu Arg Arg Thr Ile
305                 310                 315                 320

Leu Pro Thr Gln Val Glu Asn Met Gln Gln Pro Asn Ala His Arg Ile
                    325                 330                 335

Ser Gln Pro Ile Arg Gln Ile Ile Tyr Gly Leu Leu Leu Asn Ala Ser
                    340                 345                 350

Pro His Leu Asp Lys Thr Ser Trp Asn Ala Leu Pro Pro Gln Pro Leu
                    355                 360                 365

Ala Phe Ser Glu Val Glu Arg Ile Asn Lys Asn Ile Arg Thr Ser Ile
    370                 375                 380

Ile Asp Ala Val Glu Leu Ala Lys Asp His Ser Asp Leu Ser Arg Leu
385                 390                 395                 400

Thr Glu Leu Ser Leu Arg Arg Gln Met Leu Leu Leu Glu Thr Leu
                    405                 410                 415

Lys Val Lys Gln Thr Ile Leu Glu Pro Ile Pro Thr Ser Leu Lys Leu
                    420                 425                 430

Pro Ile Ala Val Ser Cys Tyr Trp Leu Gln His Thr Glu Thr Lys Ala
                    435                 440                 445

Lys Leu His His Leu Gln Ser Leu Leu Leu Thr Met Leu Val Gly Pro
                    450                 455                 460

Leu Ile Ala Ile Ile Asn Ser Pro Gly Asn Val Asp Pro Val Pro Arg
    465                 470                 475                 480

Gln Ala Gln Cys Leu Ala Pro Arg
                    485

<210> SEQ ID NO 376
<211> LENGTH: 90
<212> TYPE: DNA
<213> ORGANISM: Homo sapiens

<400> SEQUENCE: 376

```
atgggggga ctatgattct tttgcagatg ttgtacaaaa attctttgaa tcactgtttg    60
cttgtaatat atgcccatat gttgtattag                                    90
```

<210> SEQ ID NO 377
<211> LENGTH: 29
<212> TYPE: PRT
<213> ORGANISM: Homo sapiens

<400> SEQUENCE: 377

```
Met Glu Gly Thr Met Ile Leu Leu Gln Met Leu Tyr Lys Asn Ser Leu
 1               5                  10                  15

Asn His Cys Leu Leu Val Ile Tyr Ala His Met Leu Tyr
            20                  25
```

<210> SEQ ID NO 378
<211> LENGTH: 78
<212> TYPE: DNA
<213> ORGANISM: Homo sapiens

<400> SEQUENCE: 378

```
atgattcttt tgcagatgtt gtacaaaaat tctttgaatc actgtttgct tgtaatatat    60
gcccatatgt tgtattag                                                 78
```

<210> SEQ ID NO 379
<211> LENGTH: 25
<212> TYPE: PRT
<213> ORGANISM: Homo sapiens

<400> SEQUENCE: 379

```
Met Ile Leu Leu Gln Met Leu Tyr Lys Asn Ser Leu Asn His Cys Leu
 1               5                  10                  15

Leu Val Ile Tyr Ala His Met Leu Tyr
            20                  25
```

<210> SEQ ID NO 380
<211> LENGTH: 63
<212> TYPE: DNA
<213> ORGANISM: Homo sapiens

<400> SEQUENCE: 380

```
atgttgtaca aaaattcttt gaatcactgt ttgcttgtaa tatatgccca tatgttgtat    60
tag                                                                 63
```

<210> SEQ ID NO 381
<211> LENGTH: 20
<212> TYPE: PRT
<213> ORGANISM: Homo sapiens

<400> SEQUENCE: 381

```
Met Leu Tyr Lys Asn Ser Leu Asn His Cys Leu Leu Val Ile Tyr Ala
 1               5                  10                  15

His Met Leu Tyr
            20
```

<210> SEQ ID NO 382
<211> LENGTH: 33
<212> TYPE: DNA
<213> ORGANISM: Homo sapiens

<400> SEQUENCE: 382

```
atgcccatat gttgtattag atggaggatg tga                                33
```

<210> SEQ ID NO 383
<211> LENGTH: 10
<212> TYPE: PRT
<213> ORGANISM: Homo sapiens

<400> SEQUENCE: 383

Met Pro Ile Cys Cys Ile Arg Trp Arg Met
 1               5                  10

<210> SEQ ID NO 384
<211> LENGTH: 12
<212> TYPE: DNA
<213> ORGANISM: Homo sapiens

<400> SEQUENCE: 384
atgttgtatt ag                                                          12

<210> SEQ ID NO 385
<211> LENGTH: 3
<212> TYPE: PRT
<213> ORGANISM: Homo sapiens

<400> SEQUENCE: 385

Met Leu Tyr
 1

<210> SEQ ID NO 386
<211> LENGTH: 42
<212> TYPE: DNA
<213> ORGANISM: Homo sapiens

<400> SEQUENCE: 386
atggaggatg tgacatttca gataaaaagc ttacaacttt aa                         42

<210> SEQ ID NO 387
<211> LENGTH: 13
<212> TYPE: PRT
<213> ORGANISM: Homo sapiens

<400> SEQUENCE: 387

Met Glu Asp Val Thr Phe Gln Ile Lys Ser Leu Gln Leu
 1               5                  10

<210> SEQ ID NO 388
<211> LENGTH: 1260
<212> TYPE: DNA
<213> ORGANISM: Homo sapiens

<400> SEQUENCE: 388
atggcccatt ccctttctgt tggtgggagt gggtatgtat gtcccttact catccgggaa      60
gtattcatac aggttttgat caagctgcgg gtgtgttttg tccagtgctt ttcagaagca     120
gatcgggaca ttatgacact tgctaaccat tggaattgcc ctgtgttatc atcagatagt     180
gacttttgca tttttgacct gaaaactggg ttttgcccat gaatagctt tcagtggaga      240
aatatgaaca ctattaaggg cacacaaaac tatatccctg ccaaatgctt ttcccttgat     300
gcattctgcc atcacttcag caatatgaat aaagctctac tacctctctt tgcggtgcta     360
tgtggaaatg accatgttaa tctacccatc atggagacat tcttaagtaa agcgcgtctt     420
cctcttggag ctaccagttc taagggagg agacaccacc gaatcctggg acttctgaat     480
tggttgtctc attttgccaa ccctaccgaa gcactagata atgttctgaa atacctccca     540

```
aaaaaggatc gagaaaatgt taaggaactt ctctgctgtt ccatggaaga ataccaacag    600
tcccaggtga agctacagga cttcttccag tgtggtactt atgtctgtcc agatgccttg    660
aatcttggtt taccagaatg ggtattagtg gctttagcta aaggccagct atctcctttc    720
atcagtgatg ctttggtcct aagacggacc attcttccca cacaggtgga aaacatgcag    780
caaccaaatg cccacagaat atctcagccc atcaggcaaa tcatctatgg gcttctttta    840
aatgcctcac acatctggaa caagacatcc tggaatgcat tgcctcctca gcctctagct    900
ttcagtgaag tggaaaggat taataaaaat atcagaacct caatcattga tgcagtagaa    960
ctggccaagg atcattctga cttaagcaga ttgactgagc tctccttgag gaggcggcag   1020
atgcttctgt tagaacccct gaaggtgaaa cagaccattc tggagccaat ccctacttca   1080
ctgaagttgc ccattgctgt cagttgctac tggttgcagc acaccgagac caaagcaaag   1140
ctacatcatc tacaatcctt actgctcaca atgctagtgg ggcccttgat tgccataatc   1200
aacagccctg gaaatgtgga ccctgtaccc aggcaggctc agtgtcttgc tcctcgctag   1260
```

`<210>` SEQ ID NO 389
`<211>` LENGTH: 419
`<212>` TYPE: PRT
`<213>` ORGANISM: Homo sapiens

`<400>` SEQUENCE: 389

```
Met Ala His Ser Leu Ser Val Gly Gly Ser Gly Tyr Val Cys Pro Leu
 1               5                  10                  15

Leu Ile Arg Glu Val Phe Ile Gln Val Leu Ile Lys Leu Arg Val Cys
            20                  25                  30

Phe Val Gln Cys Phe Ser Glu Ala Asp Arg Asp Ile Met Thr Leu Ala
        35                  40                  45

Asn His Trp Asn Cys Pro Val Leu Ser Ser Asp Ser Asp Phe Cys Ile
    50                  55                  60

Phe Asp Leu Lys Thr Gly Phe Cys Pro Leu Asn Ser Phe Gln Trp Arg
65                  70                  75                  80

Asn Met Asn Thr Ile Lys Gly Thr Gln Asn Tyr Ile Pro Ala Lys Cys
                85                  90                  95

Phe Ser Leu Asp Ala Phe Cys His His Phe Ser Asn Met Asn Lys Ala
            100                 105                 110

Leu Leu Pro Leu Phe Ala Val Leu Cys Gly Asn Asp His Val Asn Leu
        115                 120                 125

Pro Ile Met Glu Thr Phe Leu Ser Lys Ala Arg Leu Pro Leu Gly Ala
    130                 135                 140

Thr Ser Ser Lys Gly Arg Arg His His Arg Ile Leu Gly Leu Leu Asn
145                 150                 155                 160

Trp Leu Ser His Phe Ala Asn Pro Thr Glu Ala Leu Asp Asn Val Leu
                165                 170                 175

Lys Tyr Leu Pro Lys Lys Asp Arg Glu Asn Val Lys Glu Leu Leu Cys
            180                 185                 190

Cys Ser Met Glu Glu Tyr Gln Gln Ser Gln Val Lys Leu Gln Asp Phe
        195                 200                 205

Phe Gln Cys Gly Thr Tyr Val Cys Pro Asp Ala Leu Asn Leu Gly Leu
    210                 215                 220

Pro Glu Trp Val Leu Val Ala Leu Ala Lys Gly Gln Leu Ser Pro Phe
225                 230                 235                 240

Ile Ser Asp Ala Leu Val Leu Arg Arg Thr Ile Leu Pro Thr Gln Val
```

```
                    245                 250                 255
Glu Asn Met Gln Gln Pro Asn Ala His Arg Ile Ser Gln Pro Ile Arg
            260                 265                 270

Gln Ile Ile Tyr Gly Leu Leu Leu Asn Ala Ser Pro His Leu Asp Lys
            275                 280                 285

Thr Ser Trp Asn Ala Leu Pro Pro Gln Pro Leu Ala Phe Ser Glu Val
        290                 295                 300

Glu Arg Ile Asn Lys Asn Ile Arg Thr Ser Ile Ile Asp Ala Val Glu
305                 310                 315                 320

Leu Ala Lys Asp His Ser Asp Leu Ser Arg Leu Thr Glu Leu Ser Leu
                325                 330                 335

Arg Arg Arg Gln Met Leu Leu Leu Glu Thr Leu Lys Val Lys Gln Thr
            340                 345                 350

Ile Leu Glu Pro Ile Pro Thr Ser Leu Lys Leu Pro Ile Ala Val Ser
            355                 360                 365

Cys Tyr Trp Leu Gln His Thr Glu Thr Lys Ala Lys Leu His His Leu
        370                 375                 380

Gln Ser Leu Leu Leu Thr Met Leu Val Gly Pro Leu Ile Ala Ile Ile
385                 390                 395                 400

Asn Ser Pro Gly Asn Val Asp Pro Val Pro Arg Gln Ala Gln Cys Leu
                405                 410                 415

Ala Pro Arg

<210> SEQ ID NO 390
<211> LENGTH: 45
<212> TYPE: DNA
<213> ORGANISM: Homo sapiens

<400> SEQUENCE: 390
atgtatgtcc cttactcatc cgggaagtat tcatacaggt tttga                45

<210> SEQ ID NO 391
<211> LENGTH: 14
<212> TYPE: PRT
<213> ORGANISM: Homo sapiens

<400> SEQUENCE: 391

Met Tyr Val Pro Tyr Ser Ser Gly Lys Tyr Ser Tyr Arg Phe
1               5                   10

<210> SEQ ID NO 392
<211> LENGTH: 108
<212> TYPE: DNA
<213> ORGANISM: Homo sapiens

<400> SEQUENCE: 392 atgtcccctta ctcatccggg aagtattcat acaggttttg atcaagctgc gggtgtgttt    60
tgtccagtgc ttttcagaag cagatcggga cattatgaca cttgctaa                108

<210> SEQ ID NO 393
<211> LENGTH: 35
<212> TYPE: PRT
<213> ORGANISM: Homo sapiens

<400> SEQUENCE: 393

Met Ser Leu Thr His Pro Gly Ser Ile His Thr Gly Phe Asp Gln Ala
1               5                   10                  15

Ala Gly Val Phe Cys Pro Val Leu Phe Arg Ser Arg Ser Gly His Tyr
```

Asp Thr Cys
    35

<210> SEQ ID NO 394
<211> LENGTH: 1128
<212> TYPE: DNA
<213> ORGANISM: Homo sapiens

<400> SEQUENCE: 394

```
atgacacttg ctaaccattg gaattgccct gtgttatcat cagatagtga cttttgcatt      60
tttgacctga aaactgggtt tgcccattg aatagctttc agtggagaaa tatgaacact     120
attaagggca cacaaaacta tatccctgcc aaatgctttt cccttgatgc attctgccat     180
cacttcagca atatgaataa agctctacta cctctctttg cggtgctatg tggaaatgac     240
catgttaatc tacccatcat ggagacattc ttaagtaaag cgcgtcttcc tcttggagct     300
accagttcta aagggaggag acaccaccga atcctgggac ttctgaattg gttgtctcat     360
tttgccaacc ctaccgaagc actagataat gttctgaaat acctcccaaa aaaggatcga     420
gaaaatgtta aggaacttct ctgctgttcc atggaagaat accaacagtc ccaggtgaag     480
ctacaggact tcttccagtg tggtacttat gtctgtccag atgccttgaa tcttggttta     540
ccagaatggg tattagtggc tttagctaaa ggccagctat ctcctttcat cagtgatgct     600
ttggtcctaa gacggaccat tcttcccaca caggtggaaa acatgcagca accaaatgcc     660
cacagaatat ctcagcccat caggcaaatc atctatgggc ttctttaaa tgcctcacca      720
catctggaca agacatcctg gaatgcattg cctcctcagc ctctagcttt cagtgaagtg     780
gaaaggatta ataaaaatat cagaacctca atcattgatg cagtagaact ggccaaggat     840
cattctgact taagcagatt gactgagctc tccttgagga ggcggcagat gcttctgtta     900
gaaaccctga aggtgaaaca gaccattctg gagccaatcc ctacttcact gaagttgccc     960
attgctgtca gttgctactg gttgcagcac accgagacca aagcaaagct acatcatcta    1020
caatccttac tgctcacaat gctagtgggg cccttgattg ccataatcaa cagccctgga    1080
aatgtggacc ctgtacccag gcaggctcag tgtcttgctc ctcgctag              1128
```

<210> SEQ ID NO 395
<211> LENGTH: 375
<212> TYPE: PRT
<213> ORGANISM: Homo sapiens

<400> SEQUENCE: 395

Met Thr Leu Ala Asn His Trp Asn Cys Pro Val Leu Ser Ser Asp Ser
 1               5                  10                  15

Asp Phe Cys Ile Phe Asp Leu Lys Thr Gly Phe Cys Pro Leu Asn Ser
            20                  25                  30

Phe Gln Trp Arg Asn Met Asn Thr Ile Lys Gly Thr Gln Asn Tyr Ile
        35                  40                  45

Pro Ala Lys Cys Phe Ser Leu Asp Ala Phe Cys His His Phe Ser Asn
    50                  55                  60

Met Asn Lys Ala Leu Leu Pro Leu Phe Ala Val Leu Cys Gly Asn Asp
65                  70                  75                  80

His Val Asn Leu Pro Ile Met Glu Thr Phe Leu Ser Lys Ala Arg Leu
                85                  90                  95

Pro Leu Gly Ala Thr Ser Ser Lys Gly Arg Arg His His Arg Ile Leu
            100                 105                 110

Gly Leu Leu Asn Trp Leu Ser His Phe Ala Asn Pro Thr Glu Ala Leu
            115                 120                 125

Asp Asn Val Leu Lys Tyr Leu Pro Lys Lys Asp Arg Glu Asn Val Lys
    130                 135                 140

Glu Leu Leu Cys Cys Ser Met Glu Glu Tyr Gln Gln Ser Gln Val Lys
145                 150                 155                 160

Leu Gln Asp Phe Phe Gln Cys Gly Thr Tyr Val Cys Pro Asp Ala Leu
                165                 170                 175

Asn Leu Gly Leu Pro Glu Trp Val Leu Val Ala Leu Ala Lys Gly Gln
            180                 185                 190

Leu Ser Pro Phe Ile Ser Asp Ala Leu Val Leu Arg Arg Thr Ile Leu
        195                 200                 205

Pro Thr Gln Val Glu Asn Met Gln Gln Pro Asn Ala His Arg Ile Ser
    210                 215                 220

Gln Pro Ile Arg Gln Ile Ile Tyr Gly Leu Leu Leu Asn Ala Ser Pro
225                 230                 235                 240

His Leu Asp Lys Thr Ser Trp Asn Ala Leu Pro Pro Gln Pro Leu Ala
                245                 250                 255

Phe Ser Glu Val Glu Arg Ile Asn Lys Asn Ile Arg Thr Ser Ile Ile
            260                 265                 270

Asp Ala Val Glu Leu Ala Lys Asp His Ser Asp Leu Ser Arg Leu Thr
        275                 280                 285

Glu Leu Ser Leu Arg Arg Arg Gln Met Leu Leu Leu Glu Thr Leu Lys
    290                 295                 300

Val Lys Gln Thr Ile Leu Glu Pro Ile Pro Thr Ser Leu Lys Leu Pro
305                 310                 315                 320

Ile Ala Val Ser Cys Tyr Trp Leu Gln His Thr Glu Thr Lys Ala Lys
                325                 330                 335

Leu His His Leu Gln Ser Leu Leu Leu Thr Met Leu Val Gly Pro Leu
            340                 345                 350

Ile Ala Ile Ile Asn Ser Pro Gly Asn Val Asp Pro Val Pro Arg Gln
        355                 360                 365

Ala Gln Cys Leu Ala Pro Arg
    370                 375

<210> SEQ ID NO 396
<211> LENGTH: 1017
<212> TYPE: DNA
<213> ORGANISM: Homo sapiens

<400> SEQUENCE: 396
atgaacacta ttaagggcac acaaaactat atccctgcca aatgcttttc ccttgatgca      60
ttctgccatc acttcagcaa tatgaataaa gctctactac ctctctttgc ggtgctatgt     120
ggaaatgacc atgttaatct acccatcatg agacattct taagtaaagc gcgtcttcct     180
cttggagcta ccagttctaa agggaggaga caccaccgaa tcctgggact ctgaattgg      240 ttgtctcatt ttgccaaccc taccgaagca ctagataatg ttctgaaata cctcccaaaa     300
aaggatcgag aaaatgttaa ggaacttctc tgctgttcca tggaagaata ccaacagtcc     360
caggtgaagc tacaggactt cttccagtgt ggtacttatg tctgtccaga tgccttgaat     420
cttggtttac cagaatgggt attagtggct ttagctaaag ccagctatc cctttcatc      480 agtgatgctt tggtcctaag acggaccatt cttcccacac aggtggaaaa catgcagcaa     540
ccaaatgccc acagaatatc tcagcccatc aggcaaatca tctatgggct tctttttaaat    600

```
gcctcaccac atctggacaa gacatcctgg aatgcattgc ctcctcagcc tctagctttc    660
agtgaagtgg aaaggattaa taaaaatatc agaacctcaa tcattgatgc agtagaactg    720
gccaaggatc attctgactt aagcagattg actgagctct ccttgaggag gcggcagatg    780
cttctgttag aaaccctgaa ggtgaaacag accattctgg agccaatccc tacttcactg    840
aagttgccca ttgctgtcag ttgctactgg ttgcagcaca ccgagaccaa agcaaagcta    900
catcatctac aatccttact gctcacaatg ctagtggggc ccttgattgc cataatcaac    960
agccctggaa atgtggaccc tgtacccagg caggctcagt gtcttgctcc tcgctag     1017
```

<210> SEQ ID NO 397
<211> LENGTH: 338
<212> TYPE: PRT
<213> ORGANISM: Homo sapiens

<400> SEQUENCE: 397

```
Met Asn Thr Ile Lys Gly Thr Gln Asn Tyr Ile Pro Ala Lys Cys Phe
 1               5                  10                  15

Ser Leu Asp Ala Phe Cys His His Phe Ser Asn Met Asn Lys Ala Leu
            20                  25                  30

Leu Pro Leu Phe Ala Val Leu Cys Gly Asn Asp His Val Asn Leu Pro
        35                  40                  45

Ile Met Glu Thr Phe Leu Ser Lys Ala Arg Leu Pro Leu Gly Ala Thr
    50                  55                  60

Ser Ser Lys Gly Arg Arg His His Arg Ile Leu Gly Leu Leu Asn Trp
65                  70                  75                  80

Leu Ser His Phe Ala Asn Pro Thr Glu Ala Leu Asp Asn Val Leu Lys
                85                  90                  95

Tyr Leu Pro Lys Lys Asp Arg Glu Asn Val Lys Glu Leu Leu Cys Cys
            100                 105                 110

Ser Met Glu Glu Tyr Gln Gln Ser Gln Val Lys Leu Gln Asp Phe Phe
        115                 120                 125

Gln Cys Gly Thr Tyr Val Cys Pro Asp Ala Leu Asn Leu Gly Leu Pro
    130                 135                 140

Glu Trp Val Leu Val Ala Leu Ala Lys Gly Gln Leu Ser Pro Phe Ile
145                 150                 155                 160

Ser Asp Ala Leu Val Leu Arg Arg Thr Ile Leu Pro Thr Gln Val Glu
                165                 170                 175

Asn Met Gln Gln Pro Asn Ala His Arg Ile Ser Gln Pro Ile Arg Gln
            180                 185                 190

Ile Ile Tyr Gly Leu Leu Leu Asn Ala Ser Pro His Leu Asp Lys Thr
        195                 200                 205

Ser Trp Asn Ala Leu Pro Pro Gln Pro Leu Ala Phe Ser Glu Val Glu
    210                 215                 220

Arg Ile Asn Lys Asn Ile Arg Thr Ser Ile Ile Asp Ala Val Glu Leu
225                 230                 235                 240

Ala Lys Asp His Ser Asp Leu Ser Arg Leu Thr Glu Leu Ser Leu Arg
                245                 250                 255

Arg Arg Gln Met Leu Leu Leu Glu Thr Leu Lys Val Lys Gln Thr Ile
            260                 265                 270

Leu Glu Pro Ile Pro Thr Ser Leu Lys Leu Pro Ile Ala Val Ser Cys
        275                 280                 285

Tyr Trp Leu Gln His Thr Glu Thr Lys Ala Lys Leu His His Leu Gln
    290                 295                 300
```

Ser Leu Leu Leu Thr Met Leu Val Gly Pro Leu Ile Ala Ile Ile Asn
305                 310                 315                 320

Ser Pro Gly Asn Val Asp Pro Val Pro Arg Gln Ala Gln Cys Leu Ala
                325                 330                 335

Pro Arg

<210> SEQ ID NO 398
<211> LENGTH: 15
<212> TYPE: DNA
<213> ORGANISM: Homo sapiens

<400> SEQUENCE: 398
atgcttttcc cttga                                                    15

<210> SEQ ID NO 399
<211> LENGTH: 4
<212> TYPE: PRT
<213> ORGANISM: Homo sapiens

<400> SEQUENCE: 399

Met Leu Phe Pro
 1

<210> SEQ ID NO 400
<211> LENGTH: 30
<212> TYPE: DNA
<213> ORGANISM: Homo sapiens

<400> SEQUENCE: 400
atgcattctg ccatcacttc agcaatatga                                    30

<210> SEQ ID NO 401
<211> LENGTH: 9
<212> TYPE: PRT
<213> ORGANISM: Homo sapiens

<400> SEQUENCE: 401

Met His Ser Ala Ile Thr Ser Ala Ile
 1               5

<210> SEQ ID NO 402
<211> LENGTH: 936
<212> TYPE: DNA
<213> ORGANISM: Homo sapiens

<400> SEQUENCE: 402
atgaataaag ctctactacc tctctttgcg gtgctatgtg aaatgaccca tgttaatcta    60
cccatcatgg agacattctt aagtaaagcg cgtcttcctc ttggagctac cagttctaaa   120
gggaggagac accaccgaat cctgggactt ctgaattggt tgtctcattt tgccaaccct   180
accgaagcac tagataatgt tctgaaatac ctcccaaaaa aggatcgaga aaatgttaag   240
gaacttctct gctgttccat ggaagaatac caacagtccc aggtgaagct acaggacttc   300
ttccagtgtg gtacttatgt ctgtccagat gccttgaatc ttggtttacc agaatgggta   360
ttagtggctt tagctaaagg ccagctatct cctttcatca gtgatgcttt ggtcctaaga   420
cggaccattc ttcccacaca ggtggaaaac atgcagcaac caaatgccca cagaatatct   480
cagcccatca gcaaatcat ctatgggctt cttttaaatg cctcaccaca tctggacaag   540
acatcctgga atgcattgcc tcctcagcct ctagctttca gtgaagtgga aaggattaat   600

```
aaaaatatca gaacctcaat cattgatgca gtagaactgg ccaaggatca ttctgactta    660
agcagattga ctgagctctc cttgaggagg cggcagatgc ttctgttaga aaccctgaag    720
gtgaaacaga ccattctgga gccaatccct acttcactga agttgcccat tgctgtcagt    780
tgctactggt tgcagcacac cgagaccaaa gcaaagctac atcatctaca atccttactg    840
ctcacaatgc tagtggggcc cttgattgcc ataatcaaca gccctggaaa tgtggaccct    900
gtacccaggc aggctcagtg tcttgctcct cgctag                              936
```

```
<210> SEQ ID NO 403
<211> LENGTH: 311
<212> TYPE: PRT
<213> ORGANISM: Homo sapiens

<400> SEQUENCE: 403

Met Asn Lys Ala Leu Leu Pro Leu Phe Ala Val Leu Cys Gly Asn Asp
 1               5                  10                  15

His Val Asn Leu Pro Ile Met Glu Thr Phe Leu Ser Lys Ala Arg Leu
                20                  25                  30

Pro Leu Gly Ala Thr Ser Ser Lys Gly Arg Arg His His Arg Ile Leu
            35                  40                  45

Gly Leu Leu Asn Trp Leu Ser His Phe Ala Asn Pro Thr Glu Ala Leu
        50                  55                  60

Asp Asn Val Leu Lys Tyr Leu Pro Lys Lys Asp Arg Glu Asn Val Lys
65                  70                  75                  80

Glu Leu Leu Cys Cys Ser Met Glu Glu Tyr Gln Gln Ser Gln Val Lys
                85                  90                  95

Leu Gln Asp Phe Phe Gln Cys Gly Thr Tyr Val Cys Pro Asp Ala Leu
            100                 105                 110

Asn Leu Gly Leu Pro Glu Trp Val Leu Val Ala Leu Ala Lys Gly Gln
        115                 120                 125

Leu Ser Pro Phe Ile Ser Asp Ala Leu Val Leu Arg Arg Thr Ile Leu
    130                 135                 140

Pro Thr Gln Val Glu Asn Met Gln Gln Pro Asn Ala His Arg Ile Ser
145                 150                 155                 160

Gln Pro Ile Arg Gln Ile Ile Tyr Gly Leu Leu Leu Asn Ala Ser Pro
                165                 170                 175

His Leu Asp Lys Thr Ser Trp Asn Ala Leu Pro Pro Gln Pro Leu Ala
            180                 185                 190

Phe Ser Glu Val Glu Arg Ile Asn Lys Asn Ile Arg Thr Ser Ile Ile
        195                 200                 205

Asp Ala Val Glu Leu Ala Lys Asp His Ser Asp Leu Ser Arg Leu Thr
    210                 215                 220

Glu Leu Ser Leu Arg Arg Arg Gln Met Leu Leu Leu Glu Thr Leu Lys
225                 230                 235                 240

Val Lys Gln Thr Ile Leu Glu Pro Ile Pro Thr Ser Leu Lys Leu Pro
                245                 250                 255

Ile Ala Val Ser Cys Tyr Trp Leu Gln His Thr Glu Thr Lys Ala Lys
            260                 265                 270

Leu His His Leu Gln Ser Leu Leu Thr Met Leu Val Gly Pro Leu
        275                 280                 285

Ile Ala Ile Ile Asn Ser Pro Gly Asn Val Asp Pro Val Pro Arg Gln
    290                 295                 300

Ala Gln Cys Leu Ala Pro Arg
305                 310
```

<210> SEQ ID NO 404
<211> LENGTH: 12
<212> TYPE: DNA
<213> ORGANISM: Homo sapiens

<400> SEQUENCE: 404
atgtggaaat ga                                                          12

<210> SEQ ID NO 405
<211> LENGTH: 3
<212> TYPE: PRT
<213> ORGANISM: Homo sapiens

<400> SEQUENCE: 405

Met Trp Lys
 1

<210> SEQ ID NO 406
<211> LENGTH: 39
<212> TYPE: DNA
<213> ORGANISM: Homo sapiens

<400> SEQUENCE: 406
atgaccatgt taatctaccc atcatggaga cattcttaa                             39

<210> SEQ ID NO 407
<211> LENGTH: 12
<212> TYPE: PRT
<213> ORGANISM: Homo sapiens

<400> SEQUENCE: 407

Met Thr Met Leu Ile Tyr Pro Ser Trp Arg His Ser
 1               5                  10

<210> SEQ ID NO 408
<211> LENGTH: 33
<212> TYPE: DNA
<213> ORGANISM: Homo sapiens

<400> SEQUENCE: 408
atgttaatct acccatcatg gagacattct taa                                   33

<210> SEQ ID NO 409
<211> LENGTH: 10
<212> TYPE: PRT
<213> ORGANISM: Homo sapiens

<400> SEQUENCE: 409

Met Leu Ile Tyr Pro Ser Trp Arg His Ser
 1               5                  10

<210> SEQ ID NO 410
<211> LENGTH: 870
<212> TYPE: DNA
<213> ORGANISM: Homo sapiens

<400> SEQUENCE: 410
atggagacat tcttaagtaa agcgcgtctt cctcttggag ctaccagttc taaagggagg      60
agacaccacc gaatcctggg acttctgaat tggttgtctc attttgccaa ccctaccgaa     120
gcactagata atgttctgaa atacctccca aaaaaggatc gagaaaatgt taaggaactt     180
ctctgctgtt ccatggaaga ataccaacag tcccaggtga agctacagga cttcttccag     240

```
tgtggtactt atgtctgtcc agatgccttg aatcttggtt taccagaatg ggtattagtg    300
gctttagcta aaggccagct atctcctttc atcagtgatg ctttggtcct aagacggacc    360
attcttccca cacaggtgga aaacatgcag caaccaaatg cccacagaat atctcagccc    420
atcaggcaaa tcatctatgg gcttcttttta aatgcctcac cacatctgga caagacatcc    480
tggaatgcat tgcctcctca gcctctagct ttcagtgaag tggaaaggat taataaaaat    540
atcagaacct caatcattga tgcagtagaa ctggccaagg atcattctga cttaagcaga    600
ttgactgagc tctccttgag gaggcggcag atgcttctgt tagaaccct gaaggtgaaa     660 cagaccattc tggagccaat ccctacttca ctgaagttgc ccattgctgt cagttgctac    720
tggttgcagc acaccgagac caaagcaaag ctacatcatc tacaatcctt actgctcaca    780
atgctagtgg ggcccttgat tgccataatc aacagccctg gaaatgtgga ccctgtaccc    840
aggcaggctc agtgtcttgc tcctcgctag                                     870
```

<210> SEQ ID NO 411
<211> LENGTH: 289
<212> TYPE: PRT
<213> ORGANISM: Homo sapiens

<400> SEQUENCE: 411

```
Met Glu Thr Phe Leu Ser Lys Ala Arg Leu Pro Leu Gly Ala Thr Ser
 1               5                  10                  15

Ser Lys Gly Arg Arg His His Arg Ile Leu Gly Leu Leu Asn Trp Leu
             20                  25                  30

Ser His Phe Ala Asn Pro Thr Glu Ala Leu Asp Asn Val Leu Lys Tyr
         35                  40                  45

Leu Pro Lys Lys Asp Arg Glu Asn Val Lys Glu Leu Leu Cys Cys Ser
 50                  55                  60

Met Glu Glu Tyr Gln Gln Ser Gln Val Lys Leu Gln Asp Phe Phe Gln
 65                  70                  75                  80

Cys Gly Thr Tyr Val Cys Pro Asp Ala Leu Asn Leu Gly Leu Pro Glu
                 85                  90                  95

Trp Val Leu Val Ala Leu Ala Lys Gly Gln Leu Ser Pro Phe Ile Ser
            100                 105                 110

Asp Ala Leu Val Leu Arg Arg Thr Ile Leu Pro Thr Gln Val Glu Asn
        115                 120                 125

Met Gln Gln Pro Asn Ala His Arg Ile Ser Gln Pro Ile Arg Gln Ile
    130                 135                 140

Ile Tyr Gly Leu Leu Leu Asn Ala Ser Pro His Leu Asp Lys Thr Ser
145                 150                 155                 160

Trp Asn Ala Leu Pro Pro Gln Pro Leu Ala Phe Ser Glu Val Glu Arg
                165                 170                 175

Ile Asn Lys Asn Ile Arg Thr Ser Ile Ile Asp Ala Val Glu Leu Ala
            180                 185                 190

Lys Asp His Ser Asp Leu Ser Arg Leu Thr Glu Leu Ser Leu Arg Arg
        195                 200                 205

Arg Gln Met Leu Leu Leu Glu Thr Leu Lys Val Lys Gln Thr Ile Leu
    210                 215                 220

Glu Pro Ile Pro Thr Ser Leu Lys Leu Pro Ile Ala Val Ser Cys Tyr
225                 230                 235                 240

Trp Leu Gln His Thr Glu Thr Lys Ala Lys Leu His His Leu Gln Ser
                245                 250                 255
```

```
Leu Leu Leu Thr Met Leu Val Gly Pro Leu Ile Ala Ile Ile Asn Ser
            260                 265                 270

Pro Gly Asn Val Asp Pro Val Pro Arg Gln Ala Gln Cys Leu Ala Pro
        275                 280                 285

Arg
```

<210> SEQ ID NO 412
<211> LENGTH: 54
<212> TYPE: DNA
<213> ORGANISM: Homo sapiens

<400> SEQUENCE: 412

```
atgttaagga acttctctgc tgttccatgg aagaatacca acagtcccag gtga        54
```

<210> SEQ ID NO 413
<211> LENGTH: 17
<212> TYPE: PRT
<213> ORGANISM: Homo sapiens

<400> SEQUENCE: 413

```
Met Leu Arg Asn Phe Ser Ala Val Pro Trp Lys Asn Thr Asn Ser Pro
  1               5                  10                  15

Arg
```

<210> SEQ ID NO 414
<211> LENGTH: 678
<212> TYPE: DNA
<213> ORGANISM: Homo sapiens

<400> SEQUENCE: 414

```
atggaagaat accaacagtc ccaggtgaag ctacaggact tcttccagtg tggtacttat     60
gtctgtccag atgccttgaa tcttggttta ccagaatggg tattagtggc tttagctaaa    120
ggccagctat ctcctttcat cagtgatgct ttggtcctaa gacggaccat tcttcccaca    180
caggtggaaa acatgcagca accaaatgcc cacagaatat ctcagcccat caggcaaatc    240
atctatgggc ttcttttaaa tgcctcacca catctggaca agacatcctg gaatgcattg    300
cctcctcagc tctagctttt cagtgaagtg gaaaggatta taaaaatat cagaaccctca    360
atcattgatg cagtagaact ggccaaggat cattctgact taagcagatt gactgagctc    420
tccttgagga ggcggcagat gcttctgtta gaaaccctga aggtgaaaca gaccattctg    480
gagccaatcc ctacttcact gaagttgccc attgctgtca gttgctactg gttgcagcac    540
accgagacca aagcaaagct acatcatcta caatccttac tgctcacaat gctagtgggg    600
cccttgattg ccataatcaa cagccctgga atgtggaccc tgtacccag gcaggctcag    660
tgtcttgctc ctcgctag                                                  678
```

<210> SEQ ID NO 415
<211> LENGTH: 225
<212> TYPE: PRT
<213> ORGANISM: Homo sapiens

<400> SEQUENCE: 415

```
Met Glu Glu Tyr Gln Gln Ser Gln Val Lys Leu Gln Asp Phe Gln
  1               5                  10                  15

Cys Gly Thr Tyr Val Cys Pro Asp Ala Leu Asn Leu Gly Leu Pro Glu
                 20                  25                  30

Trp Val Leu Val Ala Leu Ala Lys Gly Gln Leu Ser Pro Phe Ile Ser
             35                  40                  45
```

-continued

```
Asp Ala Leu Val Leu Arg Arg Thr Ile Leu Pro Thr Gln Val Glu Asn
    50                  55                  60

Met Gln Gln Pro Asn Ala His Arg Ile Ser Gln Pro Ile Arg Gln Ile
65                  70                  75                  80

Ile Tyr Gly Leu Leu Leu Asn Ala Ser Pro His Leu Asp Lys Thr Ser
                85                  90                  95

Trp Asn Ala Leu Pro Pro Gln Pro Leu Ala Phe Ser Glu Val Glu Arg
            100                 105                 110

Ile Asn Lys Asn Ile Arg Thr Ser Ile Ile Asp Ala Val Glu Leu Ala
            115                 120                 125

Lys Asp His Ser Asp Leu Ser Arg Leu Thr Glu Leu Ser Leu Arg Arg
        130                 135                 140

Arg Gln Met Leu Leu Leu Glu Thr Leu Lys Val Lys Gln Thr Ile Leu
145                 150                 155                 160

Glu Pro Ile Pro Thr Ser Leu Lys Leu Pro Ile Ala Val Ser Cys Tyr
                165                 170                 175

Trp Leu Gln His Thr Glu Thr Lys Ala Lys Leu His His Leu Gln Ser
            180                 185                 190

Leu Leu Leu Thr Met Leu Val Gly Pro Leu Ile Ala Ile Ile Asn Ser
        195                 200                 205

Pro Gly Asn Val Asp Pro Val Pro Arg Gln Ala Gln Cys Leu Ala Pro
    210                 215                 220

Arg
225

<210> SEQ ID NO 416
<211> LENGTH: 21
<212> TYPE: DNA
<213> ORGANISM: Homo sapiens

<400> SEQUENCE: 416
atgtctgtcc agatgccttg a                                             21

<210> SEQ ID NO 417
<211> LENGTH: 6
<212> TYPE: PRT
<213> ORGANISM: Homo sapiens

<400> SEQUENCE: 417

Met Ser Val Gln Met Pro
1               5

<210> SEQ ID NO 418
<211> LENGTH: 24
<212> TYPE: DNA
<213> ORGANISM: Homo sapiens

<400> SEQUENCE: 418
atgggtatta gtggctttag ctaa                                          24

<210> SEQ ID NO 419
<211> LENGTH: 7
<212> TYPE: PRT
<213> ORGANISM: Homo sapiens

<400> SEQUENCE: 419

Met Gly Ile Ser Gly Phe Ser
1               5
```

<210> SEQ ID NO 420
<211> LENGTH: 15
<212> TYPE: DNA
<213> ORGANISM: Homo sapiens

<400> SEQUENCE: 420

```
atgctttggt cctaa                                                  15
```

<210> SEQ ID NO 421
<211> LENGTH: 4
<212> TYPE: PRT
<213> ORGANISM: Homo sapiens

<400> SEQUENCE: 421

```
Met Leu Trp Ser
  1
```

<210> SEQ ID NO 422
<211> LENGTH: 486
<212> TYPE: DNA
<213> ORGANISM: Homo sapiens

<400> SEQUENCE: 422

```
atgcagcaac caaatgccca cagaatatct cagcccatca ggcaaatcat ctatgggctt    60
cttttaaatg cctcaccaca tctggacaag acatcctgga atgcattgcc tcctcagcct   120
ctagctttca gtgaagtgga aaggattaat aaaaatatca gaacctcaat cattgatgca   180
gtagaactgg ccaaggatca ttctgactta agcagattga ctgagctctc cttgaggagg   240
cggcagatgc ttctgttaga aaccctgaag gtgaaacaga ccattctgga gccaatccct   300
acttcactga agttgcccat tgctgtcagt tgctactggt tgcagcacac cgagaccaaa   360
gcaaagctac atcatctaca atccttactg ctcacaatgc tagtggggcc ttgattgcc    420
ataatcaaca gccctggaaa tgtggaccct gtacccaggc aggctcagtg tcttgctcct   480
cgctag                                                             486
```

<210> SEQ ID NO 423
<211> LENGTH: 161
<212> TYPE: PRT
<213> ORGANISM: Homo sapiens

<400> SEQUENCE: 423

```
Met Gln Gln Pro Asn Ala His Arg Ile Ser Gln Pro Ile Arg Gln Ile
  1               5                  10                  15

Ile Tyr Gly Leu Leu Leu Asn Ala Ser Pro His Leu Asp Lys Thr Ser
             20                  25                  30

Trp Asn Ala Leu Pro Pro Gln Pro Leu Ala Phe Ser Glu Val Glu Arg
         35                  40                  45

Ile Asn Lys Asn Ile Arg Thr Ser Ile Ile Asp Ala Val Glu Leu Ala
     50                  55                  60

Lys Asp His Ser Asp Leu Ser Arg Leu Thr Glu Leu Ser Leu Arg Arg
 65                  70                  75                  80

Arg Gln Met Leu Leu Leu Glu Thr Leu Lys Val Lys Gln Thr Ile Leu
                 85                  90                  95

Glu Pro Ile Pro Thr Ser Leu Lys Leu Pro Ile Ala Val Ser Cys Tyr
            100                 105                 110

Trp Leu Gln His Thr Glu Thr Lys Ala Lys Leu His His Leu Gln Ser
        115                 120                 125
```

Leu Leu Leu Thr Met Leu Val Gly Pro Leu Ile Ala Ile Ile Asn Ser
    130                 135                 140

Pro Gly Asn Val Asp Pro Val Pro Arg Gln Ala Gln Cys Leu Ala Pro
145                 150                 155                 160

Arg

<210> SEQ ID NO 424
<211> LENGTH: 54
<212> TYPE: DNA
<213> ORGANISM: Homo sapiens

<400> SEQUENCE: 424
atgcccacag aatatctcag cccatcaggc aaatcatcta tgggcttctt ttaa        54

<210> SEQ ID NO 425
<211> LENGTH: 17
<212> TYPE: PRT
<213> ORGANISM: Homo sapiens

<400> SEQUENCE: 425

Met Pro Thr Glu Tyr Leu Ser Pro Ser Gly Lys Ser Ser Met Gly Phe
 1               5                  10                  15

Phe

<210> SEQ ID NO 426
<211> LENGTH: 15
<212> TYPE: DNA
<213> ORGANISM: Homo sapiens

<400> SEQUENCE: 426
atgggcttct tttaa                                                    15

<210> SEQ ID NO 427
<211> LENGTH: 4
<212> TYPE: PRT
<213> ORGANISM: Homo sapiens

<400> SEQUENCE: 427

Met Gly Phe Phe
 1

<210> SEQ ID NO 428
<211> LENGTH: 57
<212> TYPE: DNA
<213> ORGANISM: Homo sapiens

<400> SEQUENCE: 428
atgcctcacc acatctggac aagacatcct ggaatgcatt gcctcctcag cctctag     57

<210> SEQ ID NO 429
<211> LENGTH: 18
<212> TYPE: PRT
<213> ORGANISM: Homo sapiens

<400> SEQUENCE: 429

Met Pro His His Ile Trp Thr Arg His Pro Gly Met His Cys Leu Leu
 1               5                  10                  15

Ser Leu

<210> SEQ ID NO 430
<211> LENGTH: 24
<212> TYPE: DNA

<213> ORGANISM: Homo sapiens

<400> SEQUENCE: 430
atgcattgcc tcctcagcct ctag                                          24

<210> SEQ ID NO 431
<211> LENGTH: 7
<212> TYPE: PRT
<213> ORGANISM: Homo sapiens

<400> SEQUENCE: 431

Met His Cys Leu Leu Ser Leu
 1               5

<210> SEQ ID NO 432
<211> LENGTH: 240
<212> TYPE: DNA
<213> ORGANISM: Homo sapiens

<400> SEQUENCE: 432
atgcttctgt tagaaaccct gaaggtgaaa cagaccattc tggagccaat ccctacttca    60
ctgaagttgc ccattgctgt cagttgctac tggttgcagc acaccgagac caaagcaaag   120
ctacatcatc tacaatcctt actgctcaca atgctagtgg ggcccttgat tgccataatc   180
aacagccctg gaaatgtgga ccctgtaccc aggcaggctc agtgtcttgc tcctcgctag   240

<210> SEQ ID NO 433
<211> LENGTH: 79
<212> TYPE: PRT
<213> ORGANISM: Homo sapiens

<400> SEQUENCE: 433

Met Leu Leu Glu Thr Leu Lys Val Lys Gln Thr Ile Leu Glu Pro
 1               5                  10                  15

Ile Pro Thr Ser Leu Lys Leu Pro Ile Ala Val Ser Cys Tyr Trp Leu
                20                  25                  30

Gln His Thr Glu Thr Lys Ala Lys Leu His His Leu Gln Ser Leu Leu
            35                  40                  45

Leu Thr Met Leu Val Gly Pro Leu Ile Ala Ile Asn Ser Pro Gly
        50                  55                  60

Asn Val Asp Pro Val Pro Arg Gln Ala Gln Cys Leu Ala Pro Arg
 65                  70                  75

<210> SEQ ID NO 434
<211> LENGTH: 90
<212> TYPE: DNA
<213> ORGANISM: Homo sapiens

<400> SEQUENCE: 434
atgctagtgg ggcccttgat tgccataatc aacagccctg gaaatgtgga ccctgtaccc    60
aggcaggctc agtgtcttgc tcctcgctag                                    90

<210> SEQ ID NO 435
<211> LENGTH: 29
<212> TYPE: PRT
<213> ORGANISM: Homo sapiens

<400> SEQUENCE: 435

Met Leu Val Gly Pro Leu Ile Ala Ile Asn Ser Pro Gly Asn Val
 1               5                  10                  15

Asp Pro Val Pro Arg Gln Ala Gln Cys Leu Ala Pro Arg
        20                  25

<210> SEQ ID NO 436
<211> LENGTH: 54
<212> TYPE: DNA
<213> ORGANISM: Homo sapiens

<400> SEQUENCE: 436
atgtggaccc tgtacccagg caggctcagt gtcttgctcc tcgctagttg gtaa        54

<210> SEQ ID NO 437
<211> LENGTH: 17
<212> TYPE: PRT
<213> ORGANISM: Homo sapiens

<400> SEQUENCE: 437

Met Trp Thr Leu Tyr Pro Gly Arg Leu Ser Val Leu Leu Ala Ser
1               5                   10                  15

Trp

<210> SEQ ID NO 438
<211> LENGTH: 39
<212> TYPE: DNA
<213> ORGANISM: Homo sapiens

<400> SEQUENCE: 438
atggtgctaa gatgttgtat gcagagttcc aaagagtga                         39

<210> SEQ ID NO 439
<211> LENGTH: 12
<212> TYPE: PRT
<213> ORGANISM: Homo sapiens

<400> SEQUENCE: 439

Met Val Leu Arg Cys Cys Met Gln Ser Ser Lys Glu
1               5                   10

<210> SEQ ID NO 440
<211> LENGTH: 309
<212> TYPE: DNA
<213> ORGANISM: Homo sapiens

<400> SEQUENCE: 440
atgttgtatg cagagttcca aagagtgaag gcgcagacac ggctgggcac aagactggac    60
ttagacacag ctcacatctt ctgtcagtgg cagtcctgtc tccagatggg gatgtatctc   120
aaccagctgc tgtccactcc tctcccagag ccagacctaa ctcgactgta cagtggaagc   180
ctggtgcacg gactatgcca gcaactgcta gcatcgacct ctgtagaaag tctcctgagc   240
atatgtcctg aggctaagca actttatgaa tatctattca atgcccacaa ggtcatatgc   300
ccccgctga                                                          309

<210> SEQ ID NO 441
<211> LENGTH: 102
<212> TYPE: PRT
<213> ORGANISM: Homo sapiens

<400> SEQUENCE: 441

Met Leu Tyr Ala Glu Phe Gln Arg Val Lys Ala Gln Thr Arg Leu Gly
1               5                   10                  15

Thr Arg Leu Asp Leu Asp Thr Ala His Ile Phe Cys Gln Trp Gln Ser

```
                    20                  25                  30

Cys Leu Gln Met Gly Met Tyr Leu Asn Gln Leu Leu Ser Thr Pro Leu
            35                  40                  45

Pro Glu Pro Asp Leu Thr Arg Leu Tyr Ser Gly Ser Leu Val His Gly
        50                  55                  60

Leu Cys Gln Gln Leu Leu Ala Ser Thr Ser Val Glu Ser Leu Leu Ser
65                  70                  75                  80

Ile Cys Pro Glu Ala Lys Gln Leu Tyr Glu Tyr Leu Phe Asn Ala His
                85                  90                  95

Lys Val Ile Cys Pro Arg
            100

<210> SEQ ID NO 442
<211> LENGTH: 21
<212> TYPE: DNA
<213> ORGANISM: Homo sapiens

<400> SEQUENCE: 442
atgcagagtt ccaaagagtg a                                              21

<210> SEQ ID NO 443
<211> LENGTH: 6
<212> TYPE: PRT
<213> ORGANISM: Homo sapiens

<400> SEQUENCE: 443

Met Gln Ser Ser Lys Glu
1               5

<210> SEQ ID NO 444
<211> LENGTH: 204
<212> TYPE: DNA
<213> ORGANISM: Homo sapiens

<400> SEQUENCE: 444
atggggatgt atctcaacca gctgctgtcc actcctctcc cagagccaga cctaactcga    60
ctgtacagtg gaagcctggt gcacggacta tgccagcaac tgctagcatc gacctctgta   120
gaaagtctcc tgagcatatg tcctgaggct aagcaacttt atgaatatct attcaatgcc   180
cacaaggtca tatgcccccg ctga                                         204

<210> SEQ ID NO 445
<211> LENGTH: 67
<212> TYPE: PRT
<213> ORGANISM: Homo sapiens

<400> SEQUENCE: 445

Met Gly Met Tyr Leu Asn Gln Leu Leu Ser Thr Pro Leu Pro Glu Pro
1               5                   10                  15

Asp Leu Thr Arg Leu Tyr Ser Gly Ser Leu Val His Gly Leu Cys Gln
            20                  25                  30

Gln Leu Leu Ala Ser Thr Ser Val Glu Ser Leu Leu Ser Ile Cys Pro
        35                  40                  45

Glu Ala Lys Gln Leu Tyr Glu Tyr Leu Phe Asn Ala His Lys Val Ile
    50                  55                  60

Cys Pro Arg
65

<210> SEQ ID NO 446
```

```
<211> LENGTH: 198
<212> TYPE: DNA
<213> ORGANISM: Homo sapiens

<400> SEQUENCE: 446
atgtatctca accagctgct gtccactcct ctcccagagc cagacctaac tcgactgtac      60
agtggaagcc tggtgcacgg actatgccag caactgctag catcgacctc tgtagaaagt     120
ctcctgagca tatgtcctga ggctaagcaa ctttatgaat atctattcaa tgcccacaag     180
gtcatatgcc cccgctga                                                   198

<210> SEQ ID NO 447
<211> LENGTH: 65
<212> TYPE: PRT
<213> ORGANISM: Homo sapiens

<400> SEQUENCE: 447

Met Tyr Leu Asn Gln Leu Leu Ser Thr Pro Leu Pro Glu Pro Asp Leu
  1               5                  10                  15

Thr Arg Leu Tyr Ser Gly Ser Leu Val His Gly Leu Cys Gln Gln Leu
             20                  25                  30

Leu Ala Ser Thr Ser Val Glu Ser Leu Leu Ser Ile Cys Pro Glu Ala
         35                  40                  45

Lys Gln Leu Tyr Glu Tyr Leu Phe Asn Ala His Lys Val Ile Cys Pro
     50                  55                  60

Arg
 65

<210> SEQ ID NO 448
<211> LENGTH: 57
<212> TYPE: DNA
<213> ORGANISM: Homo sapiens

<400> SEQUENCE: 448
atgccagcaa ctgctagcat cgacctctgt agaaagtctc ctgagcatat gtcctga        57

<210> SEQ ID NO 449
<211> LENGTH: 18
<212> TYPE: PRT
<213> ORGANISM: Homo sapiens

<400> SEQUENCE: 449

Met Pro Ala Thr Ala Ser Ile Asp Leu Cys Arg Lys Ser Pro Glu His
  1               5                  10                  15

Met Ser

<210> SEQ ID NO 450
<211> LENGTH: 231
<212> TYPE: DNA
<213> ORGANISM: Homo sapiens

<400> SEQUENCE: 450
atgaatatct attcaatgcc cacaaggtca tatgcccccg ctgaaatatt cctaccaaaa      60
ggtagatcaa attcaaaaaa aaaaaggcag aagaaacaga ataccagctg ttctaagaac     120
agagggagaa ccactgcaca caccaagtgt tggtatgagg gaaacaaccg gtttgggttg     180
ttaatggttg aaaacttaga ggaacatagt gaggcctcca acattgaata a              231

<210> SEQ ID NO 451
<211> LENGTH: 76
```

```
<212> TYPE: PRT
<213> ORGANISM: Homo sapiens

<400> SEQUENCE: 451

Met Asn Ile Tyr Ser Met Pro Thr Arg Ser Tyr Ala Pro Ala Glu Ile
1               5                   10                  15

Phe Leu Pro Lys Gly Arg Ser Asn Ser Lys Lys Arg Gln Lys Lys
            20                  25                  30

Gln Asn Thr Ser Cys Ser Lys Asn Arg Gly Arg Thr Thr Ala His Thr
            35                  40                  45

Lys Cys Trp Tyr Glu Gly Asn Asn Arg Phe Gly Leu Leu Met Val Glu
    50                  55                  60

Asn Leu Glu Glu His Ser Glu Ala Ser Asn Ile Glu
65                  70                  75

<210> SEQ ID NO 452
<211> LENGTH: 216
<212> TYPE: DNA
<213> ORGANISM: Homo sapiens

<400> SEQUENCE: 452
atgcccacaa ggtcatatgc ccccgctgaa atattcctac caaaaggtag atcaaattca      60
aaaaaaaaaa ggcagaagaa acagaatacc agctgttcta agaacagagg gagaaccact     120
gcacacacca gtgttggta tgagggaaac aaccggtttg ggttgttaat ggttgaaaac     180
ttagaggaac atagtgaggc ctccaacatt gaataa                              216

<210> SEQ ID NO 453
<211> LENGTH: 71
<212> TYPE: PRT
<213> ORGANISM: Homo sapiens

<400> SEQUENCE: 453

Met Pro Thr Arg Ser Tyr Ala Pro Ala Glu Ile Phe Leu Pro Lys Gly
1               5                   10                  15

Arg Ser Asn Ser Lys Lys Arg Gln Lys Lys Gln Asn Thr Ser Cys
            20                  25                  30

Ser Lys Asn Arg Gly Arg Thr Thr Ala His Thr Lys Cys Trp Tyr Glu
            35                  40                  45

Gly Asn Asn Arg Phe Gly Leu Leu Met Val Glu Asn Leu Glu Glu His
    50                  55                  60

Ser Glu Ala Ser Asn Ile Glu
65                  70

<210> SEQ ID NO 454
<211> LENGTH: 153
<212> TYPE: DNA
<213> ORGANISM: Homo sapiens

<400> SEQUENCE: 454 atgccccgc tgaaatattc ctaccaaaag gtagatcaaa ttcaaaaaaa aaaaggcaga      60
agaaacagaa taccagctgt tctaagaaca gagggagaac cactgcacac accaagtgtt    120
ggtatgaggg aaacaaccgg tttgggttgt taa                                 153

<210> SEQ ID NO 455
<211> LENGTH: 50
<212> TYPE: PRT
<213> ORGANISM: Homo sapiens
```

```
<400> SEQUENCE: 455

Met Pro Pro Leu Lys Tyr Ser Tyr Gln Lys Val Asp Gln Ile Gln Lys
 1               5                  10                  15
Lys Lys Gly Arg Arg Asn Arg Ile Pro Ala Val Leu Arg Thr Glu Gly
            20                  25                  30
Glu Pro Leu His Thr Pro Ser Val Gly Met Arg Glu Thr Thr Gly Leu
        35                  40                  45
Gly Cys
    50

<210> SEQ ID NO 456
<211> LENGTH: 30
<212> TYPE: DNA
<213> ORGANISM: Homo sapiens

<400> SEQUENCE: 456
atgagggaaa caaccggttt gggttgttaa                                    30

<210> SEQ ID NO 457
<211> LENGTH: 9
<212> TYPE: PRT
<213> ORGANISM: Homo sapiens

<400> SEQUENCE: 457

Met Arg Glu Thr Thr Gly Leu Gly Cys
 1               5

<210> SEQ ID NO 458
<211> LENGTH: 48
<212> TYPE: DNA
<213> ORGANISM: Homo sapiens

<400> SEQUENCE: 458
atggttgaaa acttagagga acatagtgag gcctccaaca ttgaataa                48

<210> SEQ ID NO 459
<211> LENGTH: 15
<212> TYPE: PRT
<213> ORGANISM: Homo sapiens

<400> SEQUENCE: 459

Met Val Glu Asn Leu Glu Glu His Ser Glu Ala Ser Asn Ile Glu
 1               5                  10                  15

<210> SEQ ID NO 460
<211> LENGTH: 15
<212> TYPE: DNA
<213> ORGANISM: Homo sapiens

<400> SEQUENCE: 460
atgtatttaa tataa                                                    15

<210> SEQ ID NO 461
<211> LENGTH: 4
<212> TYPE: PRT
<213> ORGANISM: Homo sapiens

<400> SEQUENCE: 461

Met Tyr Leu Ile
 1

<210> SEQ ID NO 462
```

```
<211> LENGTH: 979
<212> TYPE: DNA
<213> ORGANISM: Homo sapiens

<400> SEQUENCE: 462
tcgacccacg cgtccgcctg ccagcggacg acgtggtcag catcatcgag gaggtggagg      60
agaagcggaa gcggaagaag aacgcccctc ccgagcccgt gccgcccccc cgtgccgccc     120
ccgcccccac ccacgtccgc tccccgcagc ccccgccccc cgccccgct cccgcacgag      180 acgagctgcc ggactggaac gaggtgctcc cgccctggga tcgggaggag gacgaggtgt     240
acccgccagg gccgtaccac cctttcccca actacatccg gccgcggaca ctgcagccgc     300
cctcggcctt gcgccgccgc cactaccacc acgccttgcc gccttcgcgc cactatcccg     360
gccgggaggc ccaggcgcgg cgcgcgcagg aggaggcgga ggcggaggag cgccggctgc     420
aggagcagga ggagctggag aattacatcg agcacgtgct gctccggcgc ccgtgactgc     480
ccttcccgta accgccccg cgcgccccg ccgcgcgcg cgccggcgc cccctccgt           540 gttgcccgct cccctcgt gtttgcatgc gccccgccc tgcccttgg ccctgccct          600 gtccccgggc tgcgtcggga cctgccagac cccctcccg ggtcctgagc ccgaactccc      660
agagctcacc cgcgggtgac cggggccag cccaggaggg cgggtggttt gtgcgagttc      720
ccttgccacg cggggccccg gccccatcaa gtccctctgg ggacgtcccc gtcggaaacc     780
ggaaaaagca gttccagtta attgtgtgaa gtgtgtctgt ctccagccct tcgggcctcc    840
cacgagcccc tccagcctct ccaagtcgct gtgaattgac cccttctttc ctttctctgt    900
tgtaaatacc cctcacggag gaaatagttt tgctaagaaa taaaagtgac tattttaaaa    960
aaaaaaaaaa agggcggcc                                                 979

<210> SEQ ID NO 463
<211> LENGTH: 243
<212> TYPE: DNA
<213> ORGANISM: Homo sapiens

<400> SEQUENCE: 463
atgcgccccg gccctgcccc ttggccctgc ccctgtcccc gggctgcgtc gggacctgcc      60
agacccccct cccgggtcct gagcccgaac tcccagagct cacccgcggg tgaccggggg     120
ccagcccagg agggcgggtg gtttgtgcga gttcccttgc acgcggggc cccggcccca     180 tcaagtccct ctggggacgt ccccgtcgga aaccggaaaa agcagttcca gttaattgtg     240
tga                                                                   243

<210> SEQ ID NO 464
<211> LENGTH: 80
<212> TYPE: PRT
<213> ORGANISM: Homo sapiens

<400> SEQUENCE: 464
```

Met Arg Pro Gly Pro Ala Pro Trp Pro Cys Pro Cys Pro Arg Ala Ala
 1               5                  10                  15

Ser Gly Pro Ala Arg Pro Pro Ser Arg Val Leu Ser Pro Asn Ser Gln
            20                  25                  30

Ser Ser Pro Ala Gly Asp Arg Gly Pro Ala Gln Glu Gly Gly Trp Phe
        35                  40                  45

Val Arg Val Pro Leu Pro Arg Gly Ala Pro Ala Pro Ser Ser Pro Ser
    50                  55                  60

Gly Asp Val Pro Val Gly Asn Arg Lys Lys Gln Phe Gln Leu Ile Val

-continued

```
65                  70            75            80

<210> SEQ ID NO 465
<211> LENGTH: 18
<212> TYPE: DNA
<213> ORGANISM: Artificial Sequence
<220> FEATURE:
<223> OTHER INFORMATION: Ologonucleotide

<400> SEQUENCE: 465
tgtaaaacga cggccagt                                              18

<210> SEQ ID NO 466
<211> LENGTH: 18
<212> TYPE: DNA
<213> ORGANISM: Artificial Sequence
<220> FEATURE:
<223> OTHER INFORMATION: Oligonucleotide

<400> SEQUENCE: 466
caggaaacag ctatgacc                                              18
```

What is claimed is:

1. An isolated nucleic acid molecule comprising a nucleotide sequence that encodes a protective sequence product comprising:

SEQ ID NOs: 1,26,75,136,153,184,261,292,359, and 462.

2. An isolated nucleic acid molecule comprising:

SEQ ID NOs: 1,26,75,136,153,184,261,292,359, and 462.

3. An isolated nucleic acid molecule comprising a complement of the nucleic acid molecule of any one of claims 1–2.

4. An isolated nucleic acid molecule which hybridizes to the complement of the nucleic acid molecule of any one of claims 1–2 under highly stringent conditions.

5. An isolated nucleic acid molecule which hybridizes to the complement of the nucleic acid molecule of any one of claims 1–2 under moderately stringent conditions.

6. The isolated nucleic acid molecule of claim 4, wherein said isolated nucleic acid molecule encodes a protective sequence product.

7. The isolated nucleic acid molecule of claim 5, wherein said isolated nucleic acid molecule encodes a protective sequence product.

8. A vector comprising the nucleic acid of any one of claims 1–2.

9. The vector of claim 8, wherein said vector is a viral vector.

10. An expression vector comprising the nucleic acid of any one of claims 1–2 operatively associated with a regulatory nucleic acid controlling the expression of the nucleic acid in a host cell.

11. A host cell genetically engineered to contain the nucleic acid of any one of claims 1–2.

12. A host cell genetically engineered to express the nucleic acid of any one of claims 1–2 operatively associated with a regulatory nucleic acid controlling expression of the nucleic acid in said host cell.

* * * * *